US008852577B2

(12) United States Patent
Weber et al.

(10) Patent No.: US 8,852,577 B2
(45) Date of Patent: *Oct. 7, 2014

(54) **RECOMBINANT PROTEINS OF *PARAPOXVIRUS OVIS* AND PHARMACEUTICAL COMPOSITIONS THEREFROM**

(71) Applicant: AiCuris GmbH & Co. KG, Wuppertal (DE)

(72) Inventors: Olaf Weber, Wuelfrath (DE); Sonja Maria Tennagels, Siegburg (DE); Angela Siegling, Wiener Neudorf (AT); Tobias Schlapp, Goch (DE); Andrew Allan Mercer, Dunedin (NZ); Stephen Bruce Fleming, Dunedin (NZ); Hans-Dieter Volk, Berlin (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/717,640

(22) Filed: Dec. 17, 2012

(65) Prior Publication Data
US 2013/0108704 A1    May 2, 2013

Related U.S. Application Data

(63) Continuation of application No. 10/481,112, filed as application No. PCT/EP02/06440 on Jun. 12, 2002, now Pat. No. 8,357,363.

(30) Foreign Application Priority Data

Jun. 13, 2001 (NZ) ........................................ 512341

(51) Int. Cl.
| *A61K 39/155* | (2006.01) |
| *C07K 14/065* | (2006.01) |
| *C12N 15/86*  | (2006.01) |
| *C07K 14/005* | (2006.01) |
| *A61K 39/00*  | (2006.01) |
| *A61K 48/00*  | (2006.01) |
| *A61K 38/00*  | (2006.01) |

(52) U.S. Cl.
CPC ............ *C07K 14/065* (2013.01); *C07K 2319/00* (2013.01); *A61K 48/00* (2013.01); *A61K 38/00* (2013.01); *C12N 15/86* (2013.01); *A61K 2039/525* (2013.01); *C12N 2710/24222* (2013.01); *C12N 2710/24243* (2013.01); *C07K 14/005* (2013.01)
USPC ..................... 424/93.3; 424/201.1; 424/233.1

(58) Field of Classification Search
CPC combination set(s) only.
See application file for complete search history.

(56) References Cited

U.S. PATENT DOCUMENTS

| 6,752,995 B2    | 6/2004 | Johnston et al. |
| 8,357,363 B2 *  | 1/2013 | Weber et al. ................ 424/93.3 |
| 2003/0021769 A1 | 1/2003 | Weber et al. |

FOREIGN PATENT DOCUMENTS

| DE | 3504940       | 10/1985 |
| WO | WO-02/04002   | 1/2002  |
| WO | WO-03/006654  | 1/2003  |
| WO | WO-03/049683  | 6/2003  |

OTHER PUBLICATIONS

Anderson et al., Veterinary Immunol Immunopath (2001) 83:161-176.
Arshady, Biomaterials (1993) 14(1):5-15.
Burland, Methods in Molecular Biology (2000) 132:71-91.
Casal, Biotechnol Genet Eng Rev (2001) 18:73-87.
Cleland, Pharm Biotechnol (1997) 10:1-43.
Ellis, Curr Opin Biotechnol (1996) 7(6):646-652.
Fachninger et al., Journal of Virology (2000) 74(17):7943-7951.
Final Office Action (translation) for JP 2009-084654, mailed Jun. 8, 2010, 3 pages.
Fleming et al., J Virology (1997) 21:4857-4861.
Fleming et al., Virology (1993) 195:175-184.
Fleming et al., Virus Gene (2000) 21(12):85-95.
Gaudin et al., Gen Virol (1995) 76:1541-1556.
Hai et al., Vet. Immunol. Immunopathol. (1999) 72:81-86.
Haig et al., Vet Res (1998) 29:311-326.
Hanes et al., Pharm Biotechnol (1995) 6:389-412.
Henderson et al., "Genome Sequencer Industry Evolution", 2005, 12 pages.
Henikoff and Henikoff, PNAS USA (1992) 89:10915-10919.
Hughson, Curr Biol (1995) 5(3):365-374.
International Human Genome Sequencing Consortium, Nature (2001) 409:860-921.
Janes et al., Adv Drug Deliv Rev (2001) 47(1):83-97.
Mercer et al., J Gen Virology (1996) 77:1563-1568.
Mercer et al., Virology (1987) 157:1-12.
Mercer et al., Virology (1995) 212:698-704.
Mercer et al., Virology (1997) 229:193-200.
Mercer et al., Virus Genes (1996) 13(2):175-178.
Mercer et al., Virus Research (2006) 116(1-2):146-158.
Needleman and Wunsch, J Mol Biol (1970) 48:443-453.
Office Action for European Patent Application No. 02 808 241.0, mailed on May 8, 2009, 6 pages.
Proudfoot et al., J. Biochem. Chemis. (1999) 274(45):32478-32485.
Robinson et al., Archives Virology (1982) 71:43-55.
Robinson et al., Virology (1987) 157:13-23.
Roy, Intervirology (1996) 39(1-2):62-71.
Sequence alignment provided by PTO, accession No. DQ184476, Dec. 2008.

(Continued)

*Primary Examiner* — Bao Li
(74) *Attorney, Agent, or Firm* — Morrison & Foerster LLP

(57) ABSTRACT

The invention relates to polynucleotides coding for the PPVO viral genome, to fragments of the polynucleotides coding for the PPVO genome and to polynucleotides coding for individual open reading frames (ORFs) of the PPVO viral genome. The invention also relates to recombinant proteins expressed from the above mentioned polynucleotides and to fragments of said recombinant proteins, and to the use of said recombinant proteins or fragments for the preparation of pharmaceutical compositions.

10 Claims, 1 Drawing Sheet

(56) References Cited

OTHER PUBLICATIONS

Smilek et al., Proc. Natl. Acad. Sci. USA (1991) 88:9633-9637.
Sullivan et al., Virology (1994) 202:968-973.
Summons to Attend Oral Proceedings from EP 02808241.0, dated Aug. 25, 2010.
Uhlen et al., Curr Opin Biotechnol (1992) 3(4):363-369.
Vilcek et al., J Clin Microbiol (1994) 32:2225-2231.
Wang et al., J Virology (2001) 75(8):3600-3604.
VU 330 Alignment Conducted by Aug. 13, 2009, pp. 1-13.
Restriction Requirement in U.S. Appl. No. 10/481,112, dated Nov. 28, 2006.
Response to Restriction Requirement in U.S. Appl. No. 10/481,112, dated Apr. 27, 2007.
Response to Restriction Requirement in U.S. Appl. No. 10/481,112, dated Jun. 11, 2007.
Office Action in U.S. Appl. No. 10/481,112, dated Jul. 26, 2007.
Response to Office Action in U.S. Appl. No. 10/481,112, dated Jan. 25, 2008.
Office Action in U.S. Appl. No. 10/481,112, dated May 9, 2008.
Response to Office Action in U.S. Appl. No. 10/481,112, dated Oct. 1, 2008.
Office Action in U.S. Appl. No. 10/481,112, dated Dec. 23. 2008.
Response to Office Action in U.S. Appl. No. 10/481,112, dated Mary 20, 2009.
Office Action in U.S. Appl. No. 10/481,112, dated Aug. 19, 2009.
Request for Continued Examination in U.S. Appl. No. 10/481,112, dated Nov. 19, 2009.
Office Action in U.S. Appl. No. 10/481,112, dated Jan. 5, 2010.
Response to Office Action in U.S. Appl. No. 10/481,112, dated Jun. 16, 2010.
Office Action in U.S. Appl. No. 10/481,112, dated Sep. 15, 2010.
Response to Office Action in U.S. Appl. No. 10/481,112, dated Feb. 15, 2011.
Office Action in U.S. Appl. No. 10/481,112, dated Apr. 15, 2011.
Notice of Appeal filed in U.S. Appl. No. 10/481,112, dated Oct. 14, 2011.
Office Action in U.S. Appl. No. 10/481,112, dated Dec. 2, 2011.
Response to Office Action in U.S. Appl. No. 10/481,112, dated May 1, 2012.
Supplemental Response to Office Action in U.S. Appl. No. 10/481,112, dated May 18, 2012.
Office Action in U.S. Appl. No. 10/481,112, dated Jul. 5, 2012.
Response to Office Action in U.S. Appl. No. 10/481,112, dated Sep. 4, 2012.
Extended European Search Report for EP13 175 420, dated Aug. 6, 2013, 9 pages.
Friederichs, "Investigations to Identify the Effective Immunostimulatory Component(s) of Baypamun," Thesis dated Jul. 9, 2001, Technical University of Dresden, 284 pages, (partial English translation included).
Knolle et al., "Local control of the immune response in the liver," Immunol Rev (2000) 174:21-34.
Knolle et al., "Control of immune responses by scavenger liver endothelial cells," Swiss Med Wkly (2003) 133:501-506.
Letter regarding response to Office Action in Canadian Application No. 2510049, dated Dec. 12, 2013, 29 pages.
Maranon et al., "Dendritic cells cross-present HIV antigens from live as well as apoptotic infected CD4+ T lymphocytes," Proc Natl Acad Sci USA (2004) 101(16):6092-6097.

\* cited by examiner

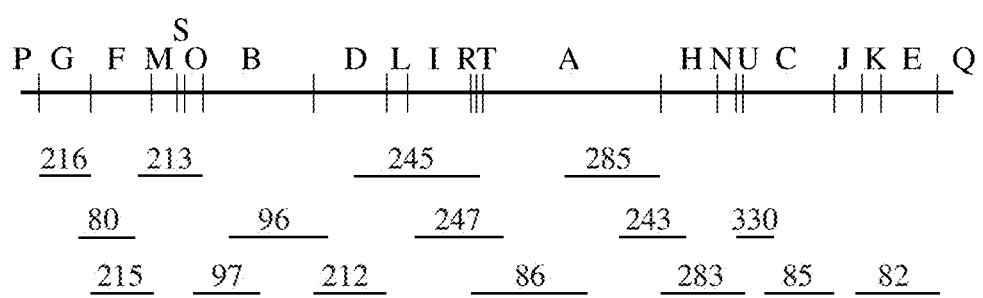

RECOMBINANT PROTEINS OF *PARAPOXVIRUS OVIS* AND PHARMACEUTICAL COMPOSITIONS THEREFROM

CROSS-REFERENCE TO RELATED APPLICATIONS

This application is a continuation of U.S. patent application Ser. No. 10/481,112, filed 11 Jun. 2004, now allowed, which is a U.S. National Phase Application of International Patent Application No. PCT/EP2002/006440, having an international filing date of 12 Jun. 2002, which claims priority to New Zealand Patent Application No. 512341 filed 13 Jun. 2001. The contents of each of these applications are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 584212002201Seqlist.txt, date recorded: 17 Dec. 2012, size: 234,735 bytes).

FIELD OF THE INVENTION

The present invention relates to polynucleotides and recombinant proteins of Parapoxvirus ovis (PPVO) and their use, alone or in combination with other substances, for the manufacture of pharmaceutical compositions.

BACKGROUND OF THE INVENTION

It is known that latent and chronically persistent viral infections can be activated or reactivated by immunosuppression, or conversely that the immune system suppresses acute diseases which may be caused by a latent virus (for example a latent herpes virus infection recurs as a result of immunosuppression in the form of lip vesicles in cases of stress or the administration of cortisone). It is also known that chronically persistent latent viral infections can only be treated with difficulty or not at all using conventional low-molecular-weight antiviral substances.

It was demonstrated that class I restricted cytotoxic T cells were capable of inhibiting hepatocellular HBV gene expression in HBV-transgenic mice, and that this process was caused by TNF-α and IFN-γ.

It is also known that in the case of chronically persistent viral infections a superinfection with another virus can produce antiviral effects against the chronically persistent virus. The dependence of this effect on interferons such as IFN-γ, as well as other cytokines and chemokines, such as TNF-α, which are secreted by T cells, natural killer cells and macrophages, has been demonstrated.

BAYPAMUN®, a pharmaceutical product for inducing "paraspecific immunity", i.e., a pharmaceutical product for inducing the unspecific immune system, is used therapeutically, metaphylactically and prophylactically for the treatment of animals in need. BAYPAMUN® is manufactured from chemically inactivated PPVO strain D1701 (see German Patent DE3504940). The inactivated PPVO induces in animals non-specific protection against infections with the most diverse types of pathogens. It is assumed that this protection is mediated via various mechanisms in the body's own defense system. These mechanisms include the induction of interferons, the activation of natural killer cells, the induction of "colony-stimulating activity" (CSA) and the stimulation of lymphocyte proliferation. Earlier investigations of the mechanism of action demonstrated the stimulation of interleukin-2 and interferon-α.

The processes for the production of the above-mentioned pharmaceutical compositions are based on the replication of the virus in cultures of suitable host cells.

One aspect of the invention relates to the use of particle-like structures comprising recombinant proteins of the invention. These particle-like structures can be, e.g., fusion proteins, protein-coated particles or virus-like particles.

Methods to produce fusion proteins, protein-coated particles or virus-like particles comprising recombinant proteins of the invention are well known to persons skilled in the art: Casal (*Biotechnol. Genet. Eng. Rev.* (2001) 18:73-87) describes the use of baculovirus expression systems for the generation of virus-like particles. Ellis (*Curr. Opin. Biotechnol.* (1996) 7(6):646-652) presents methods to produce virus-like particles and the application of suitable adjuvants. Roy (*Intervirology* (1996) 39(1-2):62-71) presents genetically engineered particulate virus-like structures and their use as vaccine delivery systems. Methods to produce fusion proteins are also well known to the person skilled in the art (Gaudin, et al., *Gen. Virol.* (1995) 76:1541-1556; Hughson, *Curr. Biol.* (1995) 5(3):365-374; Uhlen, et al., *Curr. Opin. Biotechnol.* (1992) 3(4):363-369). Known to the person skilled in the art is also the preparation of protein-coated micro- and nano-spheres (Arshady, *Biomaterials* (1993) 14(1):5-15). Proteins can be attached to biodegradable microspheres (Cleland, *Pharm Biotechnol.* (1997) 10:1-43) or attached to other polymer microspheres (Hanes, et al., *Pharm. Biotechnol.* (1995) 6:389-412) such as, e.g., polysaccharides (Janes, et al., *Adv. Drug Deliv. Rev.* (2001) 47(1):83-97).

PPVO NZ2 is another Parapoxvirus strain that exhibits immunostimulatory effects when administered in inactivated form to mammals.

The closest prior art describes the construction of an expression library representing about 95% of the PPVO NZ2 genome using the Vaccina lister virus to create recombinant viruses comprising the complete Vaccina lister genome and various fragments of the PPVO genome (Mercer, et al., *Virology*, (1997) 229:193-200). For the construction of the library, 16 PPVO DNA fragments with an average size of 11.4 kb were inserted into the Vaccinia lister genome. Each fragment was mapped relative to the PPVO restriction endonuclease maps but was otherwise uncharacterized (FIG. 1). It was found that a major portion of the PPVO genes were expressed in cells infected by the recombinant virus. The authors also showed that the entirety of all PPVO proteins expressed by some of the recombinant viruses of the expression library was able to provide protection against challenge with virulent PPVO. Expression of PPVO genes of the individual recombinant viruses has been demonstrated by immunofluorescence and immune precipitation (Mercer, et al., *Virology* (1997) 229:193-200).

To identify components of PPVO responsible for the vaccinating activity of PPVO, the Vaccinia lister/PPVO NZ2 expression library was applied.

Based on the above background it was desirable to develop PPVO based pharmaceutical compositions with antiviral and anti-tumor efficacy as well as with efficacy in paraimmunization and other desirable therapeutic effects. It was also desirable to obtain a pharmaceutical composition that exerts its full therapeutic effect while showing fewer side effects. It was furthermore desirable to find methods to produce PPVO based pharmaceutical compositions in large quantities and in economically advantageous manners.

These desirable effects have been achieved by the systematic use of selected recombinant proteins of PPVO alone or in combination with other recombinant proteins from PPVO for the preparation of pharmaceutical compositions for the treatment of objects in need.

SUMMARY OF THE INVENTION

The invention relates to polynucleotides coding for the PPVO viral genome, to fragments of the polynucleotides coding for the PPVO genome and to polynucleotides coding for individual open reading frames (ORFs) of the PPVO viral genome. The invention also relates to fragments of said polynucleotides of at least 15 or 30 or 100 base pairs in length. The invention also relates to recombinant proteins expressed from the above mentioned polynucleotides and to fragments of said recombinant proteins of at least 5 or 10 or 30 amino acids, and to the use of recombinant proteins or fragments for the preparation of pharmaceutical compositions.

"Fragments" of a polynucleotide, within the meaning of the invention, shall be understood as polynucleotides that have the same nucleotide sequence as contiguous parts of the full length (the original) polynucleotide.

"Active fragments", within the meaning of the invention, shall be those fragments of the PPVO genome the expression products of which have demonstrated to be pharmacologically active according to the invention, when inserted into the Vaccina lister genome and expressed in a suitable host.

Whereas the use of the complete PPVO virus for the manufacture of vaccines against PPVO challenge has been described, the present invention relates to the use of polynucleotides coding for the PPVO viral genome and selected fragments of the PPVO viral genome and of selected PPVO expression products, alone or in combination with others, for the preparation of improved pharmaceutical compositions for the treatment of various diseases.

The systematic use of selected genomic fragments of PPVO and their recombinant expression products makes it possible to produce pharmaceutical compositions which contain fewer (and may not contain any) inactive components (i.e., polynucleotides and proteins of PPVO) in addition to the active components.

These pharmaceutical compositions which contain less, or do not contain any additional inactive components are generally preferred by doctors and patients compared to the less well defined biological preparations of inactivated virus material. Furthermore, the possibility of producing the recombinant product in fermentation processes allows an economically advantageous mode of production. It is well known to persons skilled in the art that an economically advantageous mode of production can be achieved, e.g., by using rapidly growing production organisms (host organisms) which might also place low demands on the culture medium employed. Microorganisms which can advantageously be used as hosts for the production of recombinant proteins include, e.g., but are not limited to, *Escherichia coli, Bacillus* spec., *Corynebacterium* spec., *Streptomyces* spec., as well as yeasts, e.g., *Saccharomyces cerevisiae, Candida* spec., *Pichia* spec., *Hansenula* spec., and filamentous fungi, e.g., *Aspergillus* spec., *Penicillium* spec. and other suitable microorganisms.

Recombinant proteins of the invention can also be produced from cell lines expressing the proteins of interest. These cell lines can be recombinant mammalian cell lines, recombinant insect cell lines (e.g., using the baculovirus transfection system) or other suitable expression systems. Transfection can be achieved by various techniques known to the skilled person, one of which is the use or recombinant viruses such as the Vaccinia virus/PPVO recombinants (VVOVs) described in the examples.

DESCRIPTION OF THE INVENTION

The invention relates to fragments of the PPVO genome of at least 15 or 30 or 100 base pairs in length, and recombinant proteins expressed therefrom and to the use of said fragments and recombinant proteins for the preparation of pharmaceutical compositions. The invention also relates to individual genes (ORFs) of PPVO and their expression products, and their use, alone or in combination with others, for the preparation of pharmaceutical compositions.

A protein, within the meaning of the invention, is any polypeptide of at least five amino acids. A recombinant protein, within the meaning of the invention, is any protein that is expressed in a cell, to which the coding polynucleotide was introduced using recombinant DNA technology.

A polynucleotide, within the meaning of the invention, is meant to comprise, polyribonucleotides and/or polydesoxyribonucleotides.

Pharmaceutical compositions of the invention can be used as immunotherapeutic or immunoprophylactic agents for the treatment of infectious and non-infectious immunodeficiencies. They can also be used for the treatment of tumor diseases, cancer, viral infections and diseases associated therewith, such as, e.g., hepatitis, papillomatosis, herpes virus infections, liver fibrosis, for the prevention or prophylaxis of infectious diseases after stress (e.g., operations), for the prevention and prophylaxis of infectious diseases by administration prior to operations or procedures (e.g., preceding implantations of artificial limbs or dental procedures), for the prophylactic and metaphylactic treatment of non-viral infections, for the healing of wounds, and in particular for accelerating wound-healing processes and for promoting the healing of poorly healing or non-healing wounds (e.g., Ulcus cruris), for diseases such as multiple sclerosis, warts and other skin neoplasms, for allergic diseases, for preventing the onset of systemic allergies and for topical allergies and for improving well-being, e.g., in old age, for autoimmune diseases, chronic inflammatory diseases, such as, e.g., Crohn's disease, COPD and asthma. It is an object of the invention to use of polynucleotides and recombinant proteins of PPVO for the production of pharmaceutical compositions for the treatment of the above mentioned conditions and diseases in humans and animals.

The viral strains of the invention are PPVO NZ2 and homologues, such as D1701, NZ7, NZ10 and orf-11 strains. It is also possible to use polynucleotides and recombinant proteins of the progeny of these strains obtained by passaging and/or adaptation using specific cells, such as, e.g., WI-38, MRC-5 or Vero cells.

We have found that the identified recombinant proteins are effective for the treatment of viral diseases, cancer and other diseases or conditions in which a Th1 type immune response is of benefit. The results obtained also imply that PPVO gene products or parts thereof protect hepatitis virus-expressing hepatocytes (e.g., hepatitis B virus, HBV, or hepatitis C virus, HCV) from immune attack through HBV or HCV specific cytotoxic CD8+ T cells circulating in the blood because T cells will not leave the blood stream if their specific antigen is not presented by liver sinus endothelial cells (LSEC, that anatomically separate hepatocytes from T cells passing the liver with the blood). Therefore, we expect to have a recombinant protein that is derived from the ORFs 120-R3 (base pairs 122616-136025 Bp, recombinant virus VVOV82) that is able to down-modulate or prevent side effects such as necro-inflammatory liver disease when immunostimulants, e.g., cytokines or any others including the proteins described above administered to, e.g., hepatitis patients.

Considering the knowledge about the influence of a Th1 type immune induction in conditions and diseases such as latent and or chronic viral infections, proliferative diseases such as cancer and the capability of recombinant proteins that contain gene products of PPVO or parts thereof to induce a Th1 immune response or a local immune response selectively, we claim the use of polynucleotides and recombinant polypeptides of PPVO and recombinant proteins that contain gene products of PPVO or parts thereof for the manufacture of pharmaceutical compositions for use in humans and animals The recombinant proteins are made from products or parts thereof of the following open reading frames (ORFs) of PPVO NZ2: 64r-96r (recombinants VVOV 285 and VVOV 330 as well as VVOV 243 and VVOV 283), 18r-57 (recombinants VVOV 97, VVOV 96 and VVOV 245), 4r-14r (recombinant VVOV 215). The recombinant protein may also be made from gene products or parts thereof of ORFs 120-R3 (recombinant VVOV 82). The proteins may be prepared and used in any combination.

Recombinant proteins of PPVO within the meaning of the invention shall be understood as proteins that derive from PPVO and are expressed in homologous or heterologous systems other than the systems in which PPVO is naturally produced. Examples for recombinant proteins of PPVO are proteins of PPVO which are expressed using Vaccinia virus vectors and fibroblasts as host cells or baculovirus vectors and insect cells as host cells. Recombinant proteins, within the meaning of the invention, could also be produced in bacterial cells (e.g., *Escherichia coli, Bacillus* spec., *Streptomyces* spec.) or in yeast (e.g., *Saccharomyces cerevisiae, Candida* spec., *Pichia pastoris, Hansenula* spec.) systems. In these cases, polynucleotides of the PPVO genome would typically be brought into the respective host genome so that PPVO genes are expressed by the host. Recombinant proteins of PPVO could also be expressed by the object in need in the sense of a gene therapy.

Recombinant proteins, within the meaning of the invention, could also be recombinant virus particles that contain PPVO derived proteins. Recombinant proteins, within the meaning of the invention, could also be in form of viral-like particles that are formed or assembled from PPVO derived proteins. Recombinant proteins, within the meaning of the invention, could also be chimeric proteins that contain PPVO gene products.

In a preferred embodiment of the invention the recombinant proteins are attached to particle-like structures or be part of particle-like structures.

In another preferred embodiment of the invention the recombinant proteins are attached to, or part of, fusion proteins.

In another preferred embodiment of the invention the recombinant proteins are attached to, or part of, protein-coated particles.

In another preferred embodiment of the invention the recombinant proteins are attached to, or part of, virus-like particles.

Particle-like structures, such as particle-like fusion proteins, protein-coated particles or virus-like particles can be phagocytosed and processed by monocytes or macrophages. The process of phagocytosis enhances the efficacy of recombinant proteins of the invention in uses within the meaning of the invention.

A particle-like structure, within the meaning of the invention, is particulate matter in particle-like form of which the average particle size and other characteristics are suitable for medical application. Preferred particle-like structures are, e.g., fusion proteins, protein-coated particles, or virus-like particles.

Immunomodulating activity is defined as local or systemic suppression and/or stimulation and/or induction of any Th-1 or Th-2 type cytokine response or of any effector function of these cytokines, (e.g., cytolytic or antiviral activity or humoral response) or the modulation of MHC cross-presentation. Immunomodulating activity could also be the induction of apoptosis in antigen presenting cells or recruiting of antigen presenting cells.

Nucleotides and recombinant proteins of the invention can be administered at the same time or sequentially, administered with other agents and drugs, e.g., with drugs that treat the disease or are supportive, e.g., in the case of cancer therapy with antineoplastic or other anti-cancer agents or/and anti-coagulants or vitamins, pain relief and others.

The nucleotides and recombinant proteins can be administered systemically (e.g., intravenously, subcutaneously, intramuscularly, intracutaneously, intraperitoneally), locally (e.g., into a tumor) or orally (per os). The recombinant proteins or products thereof should be formulated appropriately, e.g., in a non-pyrogenic solution or suspension for i.v. use or in capsules for implantation or in capsules for per os use. Pharmaceutical compositions of the invention can be administered, e.g., oral, nasal, anal, vaginal etc., as well as parenteral administration. Pharmaceutical compositions of the invention can be in the form of suspensions, solutions, syrups, elixirs or appropriate formulations in polymers as well as liposomes.

Recombinant proteins of the invention can also be prepared with suitable recombinant cell lines and other cell lines. Alternatively, non-recombinant cell lines, such as WI-38, MRC-5, Vero cells could be infected with recombinant viruses that carry the recombinant genes using viral vectors such as, but not limited to, the Vaccina virus (e.g., Vaccina lister). In addition, other suitable viruses can be used in combination with other suitable cells (e.g., using Vaccinia virus vectors and fibroblasts as host cells or baculovirus vectors and insect cells as host cells). It is advantageous to cultivate the recombinant cell cultures in high-cell-density fermentations to achieve favorable productivity and a good overall process performance.

The invention relates to purified and isolated polynucleotides with the sequence of SEQ ID NO:1. The invention also relates to purified and isolated polynucleotides of at least 15 or 30 or 100 nucleotides which bind under stringent conditions to the polynucleotide of SEQ ID NO:1 or its complementary sequences.

Stringent conditions, within the meaning of the invention are 65° C. in a buffer containing 1 mM EDTA, 0.5 M $NaHPO_4$ (pH 7.2), 7% (w/v) SDS.

The invention also relates to purified and isolated polynucleotides which comprise the polynucleotide sequence of SEQ ID NO:1 or polynucleotide sequences encoding the same amino acid sequence and fragments of at least 15 or 30 or 100 nucleotides thereof. The invention also relates to recombinant proteins of five and more amino acids encoded by these polynucleotides.

The invention also relates to purified and isolated polynucleotides which show at least 99%, 95% or 90% or 80% sequence homology to the polynucleotides of the previous paragraph.

Homology of biological sequences, within the meaning of the invention, shall be understood as the homology between two biological sequences as calculated by the algorithm of Needleman and Wunsch. (*J. Mol. Biol.* (1970) 48:443-453) using the BLOSUM62 substitution matrix (Henikoff and Henikoff, *Proc. Natl. Acad. Sci. USA* (1992) 89:10915-10919) for proteins and penalties of +4 and −3 for identical and non-identical bases, respectively, when comparing polynucleotide sequences. For comparison of protein sequences the gap creation penalty and the gap extension penalty are 8 and 2, respectively. For comparison of polynucleotide sequences the gap creation penalty and the gap extension penalty are 20 and 3, respectively.

The invention also relates to purified and isolated polynucleotides which are active fragments of the PPVO genome, with a sequence selected from a group of sequences consisting of nucleotides 122616-136025 of SEQ ID NO:1 (PPVO insert of VVOV 82), 31003-46845 of SEQ ID NO:1 (PPVO insert of VVOV 96), 24056-33789 of SEQ ID NO:1 (PPVO insert of VVOV 97), 10264-20003 of SEQ ID NO:1 (PPVO insert of VVOV 215), 82324-92502 of SEQ ID NO:1 (PPVO insert of VVOV 243), 47952-66263 of SEQ ID NO:1 (PPVO insert of VVOV 245), 89400-103483 of SEQ ID NO:1 (PPVO insert of VVOV 283), 74804-88576 of SEQ ID NO:1 (PPVO insert of VVOV 285), and 102490-108393 of SEQ ID NO:11 (PPVO insert of VVOV 330).

The invention also relates to purified and isolated polynucleotide which encode for the same amino acid sequence as the active fragments of the PPVO genome of the previous paragraph and to polynucleotides of at least 15 or 30 or 100 nucleotides binding under stringent conditions to the above mentioned active fragments of the PPVO genome or its complementary sequence.

The invention also relates to polynucleotides with 99%, 95%, or 90%, or 80% sequence homology to sequences consisting of nucleotides 122616-136025 of SEQ ID NO:1 (PPVO insert of VVOV 82), 31003-46845 of SEQ ID NO:1 (PPVO insert of VVOV 96), 24056-33789 of SEQ ID NO:1 (PPVO insert of VVOV 97), 10264-20003 of SEQ ID NO:1 (PPVO insert of VVOV 215), 82324-92502 of SEQ ID NO:1 (PPVO insert of VVOV 243), 47952-66263 of SEQ ID NO:11 (PPVO insert of VVOV 245), 89400-103483 of SEQ ID NO:1 (PPVO insert of VVOV 283), 74804-88576 of SEQ ID NO:11 (PPVO insert of VVOV 285), and 102490-108393 of SEQ ID NO:11 (PPVO insert of VVOV 330) or the respective complementary sequences.

The invention also relates to purified and isolated polynucleotide, with a sequence of nucleotides 3 to 539 (ORF L1), 781 to 449 (ORF L2r), 1933 to 1664 (ORF L3r), 3269 to 2790 (ORF L4r), 2799 to 3851 (ORF L5), 2962 to 3753 (ORF L6), 3784 to 3122 (ORF L7r), 4341 to 4129 (ORF L8r), 4904 to 4428 (ORF 1ar), 6517 to 4970 (ORF 1r), 8042 to 6684 (ORF 2r), 9989 to 8070 (ORF 3r), 11195 to 10062 ORF 4r), 11493 to 11227 (ORF 5r), 11802 to 12038 (ORF 6), 12358 to 12080 (ORF 7r), 13980 to 12364 (ORF 8r), 14826 to 14053 (ORF 9ar), 15080 to 15394 (ORF 10), 16838 to 15423 (ORF 11r), 19021 to 16847 (ORF 12r), 19704 to 19156 (ORF 13r), 20314 to 19736 (ORF 14r), 20401 to 22101 (ORF 15), 22125 to 22940 (ORF 6), 23003 to 23866 (ORF 17), 26908 to 23873 (ORF 18r), 26926 to 27213 (ORF 19), 27626 to 27216 (ORF 20r), 29754 to 27616 (ORF 21r), 32217 to 29800 (ORF 22r), 33380 to 32418 (ORF 23r), 33602 to 33393 (ORF 24r), 34466 to 33612 (ORF 25r), 34735 to 34502 (ORF 26r), 35905 to 34739 (ORF 27r), 37194 to 35905 (ORF 28r), 37200 to 39248 (ORF 29), 41037 to 39229 (ORF 30r), 41374 to 42066 (ORF 31), 42336 to 41731 (ORF 32r), 42407 to 41997 (ORF 33r), 42410 to 43765 (ORF 34), 43770 to 43958 (ORF 35), 43980 to 44534 (ORF 36), 45727 to 44537 (ORF 37r), 45760 to 46557 (ORF 38), 46567 to 47568 (ORF 39), 47572 to 48303 (ORF 40), 48352 to 48621 (ORF 41), 49887 to 48634 (ORF 42r), 49917 to 50693 (ORF 43), 50719 to 51102 (ORF 44), 51059 to 51511 (ORF 44a), 51584 to 52591 (ORF 45), 52509 to 53066 (ORF 46), 53523 to 53023 (ORF 47r), 53607 to 57473 (ORF 48), 58070 to 57528 (ORF 49r), 57700 to 58662 (ORF 50), 59674 to 58673 (ORF 51r), 62089 to 59678 (ORF 52r), 62198 to 62881 (ORF 53), 62909 to 63862 (ORF 55), 63858 to 64271 (ORF 56), 64309 to 66831 (ORF 57), 67266 to 66799 (ORF 58r), 67803 to 67273 (ORF 58ar), 67915 to 68607 (ORF 59), 68624 to 70984 (ORF 60), 70994 to 72898 (ORF 61), 72938 to 73507 (ORF 62), 73540 to 74211 (ORF 63), 76120 to 74207 (ORF 64r), 76749 to 76186 (ORF 65r), 77698 to 76799 (ORF 66r), 79343 to 77709 (ORF 67r), 79816 to 79367 (ORF 68r), 80529 to 79858 (ORF 69r), 80774 to 80529 (ORF 70r), 82815 to 80788 (ORF 71r), 83835 to 82834 (ORF 72r), 83874 to 85583 (ORF 73), 85535 to 84402 (ORF 74r), 88096 to 85574 (ORF 75r), 87759 to 88667 (ORF 76), 88920 to 88642 (ORF 77r), 91652 to 88938 (ORF 78r), 91667 to 92674 (ORF 79), 93466 to 92681 (ORF 80r), 93761 to 93486 (ORF 81r), 94060 to 93788 (ORF 82r), 94238 to 94080 (ORF 83r), 94508 to 94242 (ORF 84r), 95571 to 94498 (ORF 85r), 96187 to 95600 (ORF 86r), 96202 to 97665 (ORF 87), 97915 to 97643 (ORF 88r), 98251 to 99537 (ORF 89), 99537 to 99974 (ORF 90), 100001 to 101140 (ORF 91), 101168 to 104650 (ORF 92), 106354 to 104795 (ORF 93r), 107947 to 106400 (ORF 94r), 108256 to 1079900RF 95r), 108719 to 108300 (ORF 96r), 109679 to 108738 (ORF 97r), 109861 to 109682 (ORF 98r), 110830 to 10033 (ORF 99r), 110208 to 110417 (ORF 100), 110469 to 110651 (ORF 100a), 110915 to 111397 (ORF 101), 111419 to 111913 (ORF 102), 111949 to 112485 (ORF 103), 112593 to 113450 (ORF 104), 113323 to 112967 ORF 105r), 113526 to 114152 (ORF 106), 114199 to 115236 (ORF 107), 115353 to 115787 (ORF 108), 115859 o 116551 (ORF 109), 116729 to 117523 (ORF 110), 117572 to 117114 (ORF 111r), 117423 to 118085 (ORF 12), 118968 to 118375 (ORF 114r), 118508 to 119119 (ORF 115), 119588 to 120202 (ORF 116), 120314 to 21231 (ORF 117), 121380 to 123920 (ORF 118), 121288 to 122256 (ORF 119), 122350 to 123924 (ORF 120), 123962 to 125566 (ORF 121), 125193 to 124591 (ORF 122r), 125689 to 123935 (ORF 123r), 123839 to 123297 ORF 123ar), 125652 to 126170 (ORF 124), 126121 to 125699 (ORF 125r), 126279 to 127769 (ORF 126), 127851 to 128408 (ORF 127), 128520 to 130076 (ORF 128), 130105 to 131700 (ORF 129), 131790 to 133283 (ORF 130), 133246 to 133920 (ORF 131), 133972 to 134370 (ORF 132), 134418 to 134693 (ORF 133a), 134402 to 134992 (ORF R1), 134853 to 134419 (ORF R2r), 135628 to 135897 (ORF R3), 136780 to 137112 ORF R4), and 137558 to 137022 (ORF R5r) of SEQ ID NO:1, which encode for the identified open reading frames (ORFs) listed in Table 7. ORFs of this paragraph of which the start position is a larger number than the stop position are coded by the complementary sequence of SEQ ID NO:1. The names of these ORFs end with the letter "r". The invention also relates to the complementary sequences of the sequences of this paragraph.

The invention also relates to polynucleotides which encode for the same amino acid sequence as encoded by the identified ORFs of the previous paragraph. The invention also relates to polynucleotides of at least 15, 30 or 100 nucleotides binding under stringent conditions to the identified ORFs. The invention also relates to polynucleotides which show at least 99%, 95% or 90% or 80% sequence homology to the sequences of the previous paragraph or which are functional variants a sequence of the previous paragraph.

A functional variant of a gene, within the meaning of the invention, shall be defined as a gene which is at least 99%, or 95%, or 90%, or 80% homologous to the first gene and which has a similar biological function as the first gene. A functional variant of a gene can also be a second gene encoding the same amino acid sequence as does the first gene (or as does a functional variant thereof), employing the degeneration of the genetic code. A functional variant of a gene can also be a polynucleotide comprising the same sequence as has said gene, however said polynucleotide being shorter (i.e., by means of deletions of one or several nucleotides at one or both ends of the polynucleotide) or said polynucleotide having additional nucleotides at one or both ends of the identical part of the polynucleotide.

A functional variant of a protein, within the meaning of the invention, shall be defined as another protein which is at least 99%, or 95%, or 90%, or 80% homologous to the first protein and which has a similar biological function as has the original protein.

The invention also relates to recombinant proteins encoded by nucleotides of the invention and parts and fragments of said proteins which are at least 5 or 7 or 10 or 30 amino acids long.

The invention also relates to recombinant proteins encoded by nucleotides of the invention and parts and fragments of said proteins which are at least 5 or 7 or 10 or 30 amino acids long, said recombinant proteins being attached to a carrier protein or to another carrier. Attaching a protein to a carrier protein can improve or strengthen the immune response to said protein, thereby enhancing the therapeutic or prophylactic effect of administering said protein to a subject.

The invention also relates to vectors containing polynucleotides of the invention and cells containing these vectors or polynucleotides of the invention.

The invention also relates to the use of recombinant proteins and polynucleotides of the invention, alone or in combination with at least one other recombinant protein or polynucleotide of the invention for the manufacture of pharmaceutical compositions.

Combinations of recombinant proteins (or polynucleotides) according to the invention, comprise
combinations of at least two recombinant proteins encoded by SEQ ID NO:1 (or combinations of at least two fragments of a polynucleotide of SEQ ID NO:1),
combinations of at least two recombinant proteins encoded by the same active fragment of the PPVO genome, i.e., two or more recombinant proteins encoded by the same VVOV of
Table 3, Table 4, Table 5, and Table 6 (or combinations of at least two fragments of the same active fragment (VVOV) of the PPVO genome),
combinations of at least two recombinant proteins, encoded by at least two distinct active fragments of the PPVO genome, i.e., from distinct VVOVs of
Table 3, Table 4, Table 5, and Table 6 (or combinations of at least two fragments of at least two distinct active fragments (VVOVs) of the PPVO genome), or
combinations of at least two distinct recombinant proteins encoded by ORFs of Table 7 (or combinations of at least two polynucleotides with the sequence of any of the ORFs listed in Table 7).

The invention also relates to the use of recombinant viruses comprising the Vaccina lister genome and selected fragments of the PPVO genome for the manufacture of pharmaceutical compositions.

The invention also relates to the use of recombinant proteins and polynucleotides of the invention for the manufacture of pharmaceutical compositions for the treatment of virus related diseases, viral infections, non-viral infections, proliferative diseases, inflammatory diseases, allergic diseases, and autoimmune diseases.

Viral infections, within the meaning of the invention, shell be understood as diseases associated with viral infections of the human or animal body, such as hepatitis, papillomatosis, herpes virus infections, liver fibrosis, HIV infections, AIDS, and influenza.

Non-viral infections, within the meaning of the invention, shell be understood as diseases associated with non-viral infections of the human or animal body, such as infections with mycobacteria, mycoplasma, amoeba, and plasmodia.

Proliferative diseases, within the meaning of the invention, shell be understood as diseases associated with proliferative disorders, such as cancer, leukemia, warts, tumor diseases, and other skin neoplasms.

Inflammatory diseases, within the meaning of the invention, shell be understood as diseases associated with acute or chronic inflammatory conditions, such as inflammation of the skin or organs, Crohn's disease, COPD, asthma, but also conditions related to the healing of wounds, e.g., Ulcus cruris, and others.

Allergic diseases, within the meaning of the invention, shell be understood as comprising both systemic and topical allergies.

Autoimmune diseases within the meaning of the invention, shell be understood as comprising systemic lupus erythematosus, Sjogren's syndrome, Hashimoto's thyroiditis, rheumatoid arthritis, and juvenile diabetes mellitus, and other autoimmune diseases.

The invention also relates to the use of recombinant viruses comprising a Vaccinia lister genome and fragments of a PPVO genome for the manufacture of pharmaceutical compositions.

The invention also relates to the use of recombinant viruses comprising a Vaccinia lister genome and at least one heterologous gene to express at least one heterologous gene in a subject, e.g., for prophylactic and/or therapeutic purposes.

The invention also relates to the use of a recombinant viruses comprising a Vaccinia lister genome and at least one heterologous gene for gene therapy.

"Gene therapy", within the meaning of the invention, shall be understood as the act of administering to a subject polynucleotides (and, if necessary, suitable adjuvants or suitable carriers) for the purpose of obtaining a prophylactic or therapeutic effect in said subject. Typically, the polynucleotides administered are expressed in the subject and the expressed gene products exert a prophylactic or therapeutic effect.

The invention also relates to
(a) a particle-like structure comprising a recombinant polypeptide encoded by an open reading frame (ORF) of the polynucleotide of SEQ ID NO:1 or functional variants of said polypeptides,
(b) the use of a particle-like structure of (a) for the preparation of a medicament,
(c) the use of a particle-like structure of (a) for the preparation of a medicament for the treatment of virus related diseases, viral infections, non-viral infections, proliferative diseases, inflammatory diseases, allergic diseases, and/or autoimmune diseases, (d) pharmaceutical compositions comprising a particle-like structure of (a), and to
(e) pharmaceutical compositions comprising a particle-like structure of (a) for the treatment of virus related diseases, viral infections, non-viral infections, proliferative diseases, inflammatory diseases, allergic diseases, and/or autoimmune diseases.

BRIEF DESCRIPTION OF THE FIGURE

FIG. 1 shows the genomic locations of the DNA fragments constituting the insertion library. The position of each DNA fragment is shown against the KpnI map of PPVO NZ2 (Mercer, et al., *Virology* (1997) 229:193-200).

EXAMPLES

Example 1

Determination of the Integrated PPVO Fragments in the Active VVOVs

DNA Preparation from Vaccinia lister/PPVO Recombinants was Performed as Follows:

BK-KL 3A cells were grown to confluency in 175 cm$^2$ flasks (Becton Dickson Labware, Heidelberg, Germany). Cells were infected with a recombinant Vaccina lister/PPVO virus (VVOV) of Mercer, et al. (*Virology* (1997) 229:193-200) at a MOI (multiplicity of infection) of 0.01-0.32 and incubated at 37° C. until 100% CPE (cytopathic effect) had been reached. The infected cells were frozen at −80° C., thawed and processed as follows, with modification to the RNA extraction method of Vilcek, et al. (*J. Clin. Microbiol.* (1994) 32:2225-2231). Using 2 ml PLG Heavy Eppendorf tubes (Eppendorf, Hamburg, Germany) 0.5 ml aliquots of cellular suspension were incubated with 100 μg Proteinase K (Roche Molecular Biochemicals, Mannheim, Germany) and 50 μl SDS (Sigma-Aldrich, Chemie GmbH, Taufkirchen, Germany) at 56° C. for 25 min 0.5 ml Roti®-Phenol/Chloroform (Carl Roth GmbH, Karlsruhe, Germany) was added and the tubes were inverted for several times. After centrifugation at 12000×g for 10 min, the upper phase was transferred into a fresh tube and two volumes of ethanol (Merck Eurolab GmbH, Darmstadt, Germany) and ⅒ volume of sodium acetate (Sigma-Aldrich, Chemie GmbH, Taufkirchen, Germany) was added. The reagents were mixed several times and stored at −80° C. for 3 h. The tubes were centrifuged at 14000×g for 30 min, the supernatant was decanted and the pellet was air-dried for 5-10 min. Finally the DNA pellet was resuspended in 30 μl nuclease free water and stored at −20° C. until used.

DNA concentration was measured spectrophotometrically on a BioPhotometer 6131 (Eppendorf, Hamburg, Germany) at 260/280 nm nm. The DNA yield of different sample preparations spanned from 100 ng/ml up to 1 μg/ml.

Polymerase Chain Reaction (PCR) of Terminal Flanking Regions of the Integrated Fragments in the Vaccinia lister/PPVO Recombinants was Performed as Follows:

Three different PCR amplification systems were used for amplifying the terminal flanking regions. Each reaction mixture of 50 μl contained 100 ng-1 μg resuspended DNA and primers (Table 1)) were added in a final concentration of 300 nM. Amplifications were carried out on a Mastercycler® gradient (Eppendorf, Hamburg, Germany).

The 3-prime flanking region of recombinant VVOV 285 had been analyzed using 2× Ready-Mix™ PCR Master Mix (1.5 mM MgCl$_2$) (AB Gene, Hamburg, Germany). 1 μl BSA (MBI Fermentas GmbH, St. Leon-Rot, Germany) was added to each reaction. Denaturation was performed at 94° C. for 3 min, followed by 30 cycles (94° C. for 30 s, 58.7° C.-65.3° C. for 30 s, 72° C. for 1 min) and 72° C. for 5 min.

The 5-prime flanking region of the PPVO insert of recombinant VVOV 285, the 3-prime flanking region of VVOV 97, and both terminal flanking regions of VVOV 215, VVOV 243, VVOV 245 were amplified using PfuTurbo® DNA Polymerase (Stratagene, Amsterdam, Netherlands). The reactions were setup with 2.5 U of enzyme, 1.5 mM MgCl$_2$ and 200 μM of each dNTP. Denaturation was performed at 94° C. for 3 min, followed by 30 cycles (94° C. for 30 s, 58.7° C.-65.3° C. for 30 s, 72° C. for 1 min) and 72° C. for 5 min.

The amplification of the 5-prime flanking region of VVOV 97 and VVOV 82, the 3-prime flanking region of VVOV 96 and VVOV 283 were performed with Platinium® Pfx DNA Polymerase (Life Technologies GmbH, Karlsruhe, Germany). A reaction of 50 μl contained 1.25 U polymerase, 1-1.5 mM MgCl$_2$ and 300 μM of each dNTP. Additional use of PCRx Enhancer Solution was necessary for amplification of the 5-prime flanking regions of VVOV 96 (1× concentrated) and the 3-prime flanking regions of VVOV 82 (2× concentrated). Denaturation was performed at 94° C. for 2 min, followed by 30 cycles (94° C. for 15 s, 54.6° C.-60.7° C. for 30 s, 68° C. for 1-2 min) and 68° C. for 5-7 min.

18 μl of each amplification product was analyzed by agarose gel electrophoresis on 1.5-2% SeaKem LE agarose (Biozym, Hessisch Oldendorf, Germany). After staining in a ethidium bromide solution for 20 min the DNA fragments were visualized on an UV transilluminator UVT-20 M/W (Herolab, Wiesloch, Germany).

The sequence of the amplified DNA-fragments were determined by standard sequencing procedures and compared to the published Vaccinia lister thymidine kinase-sequence and the genome sequence of PPVO NZ2 to determine exactly the integrated PPVO NZ2 sequences.

TABLE 1

PCR-primers, amplification and sequencing of the terminal flanking regions of the integrated fragments in the *Vaccinia lister*/PPVO NZ2 recombinants

| VVOV | Amplified terminal region of NZ2 insert | Primer name | Primers used for amplification Sequence 5' → 3' | SEQ ID NO: | Length of amplification product [bp] |
|---|---|---|---|---|---|
| VVOV 215 | 5' | VAC-P11-1 | ATTACAGTGATGCCTACATGCCG | 2 | 264 |
| | | PPVO 14r-1 | GCTGTAGTCGTGGTCCGGC | 3 | |

TABLE 1-continued

PCR-primers, amplification and sequencing of the terminal flanking regions of the integrated fragments in the Vaccinia lister/PPVO NZ2 recombinants

| VVOV | Amplified terminal region of NZ2 insert | Primer name | Sequence 5' → 3' | SEQ ID NO: | Length of amplification product [bp] |
|---|---|---|---|---|---|
|  | 3' | PPVO 4r-2 | CTTCCTAGGCTTCTACCGCACG | 4 | 402 |
|  |  | VAC-TK-1 | CGGTTTACGTTGAAATGTCCCAT | 5 |  |
| VVOV 245 | 5' | VAC-P11-1 | ATTACAGTGATGCCTACATGCCG | 2 | 553 |
|  |  | PPVO 57-1 | CTGGCCAACGACGCCTTC | 6 |  |
|  | 3' | PPVO 40-1 | TCTGGTACCCCTTGCCGG | 7 | 321 |
|  |  | VAC-TK-1 | CGGTTTACGTTGAAATGTCCCAT | 5 |  |
| VVOV 285 | 5' | VAC-P11-1 | ATTACAGTGATGCCTACATGCCG | 2 | 241 |
|  |  | PPVO 78r-5 | GAACCCGCTCTCGCTCGA | 8 |  |
|  | 3' | PPVO 64r-1 | GCCGGGCAAGTGTCTGGTC | 9 | 320 |
|  |  | VAC-TK-1 | CGGTTTACGTTGAAATGTCCCAT | 5 |  |
| VVOV 330 | 5' | VAC-P11-1 | ATTACAGTGATGCCTACATGCCG | 2 | 392 |
|  |  | PPVO 92-1 | CTCGAAGTAGCTGATGTCGCG | 10 |  |
|  | 3' | PPVO 96r-1 | AGAGCTTTACGTAGACTCTCCAAGTGTC | 11 | 462 |
|  |  | VAC-TK-1 | CGGTTTACGTTGAAATGTCCCAT | 5 |  |
| VVOV 96 | 5' | VAC-TK-fwd | ATACGGAACGGGACTATGGACG | 12 | 239 |
|  |  | PPVO 22r-3 | GCGGTGGCCATGTACGTG | 13 |  |
|  | 3' | PPVO 22r-4 | GGTTGTGGCGATGGTCGG | 14 | 1055 |
|  |  | VAC-TK-1 | CGGTTTACGTTGAAATGTCCCAT | 5 |  |
| VVOV 97 | 5' | VAC-TK-fwd | ATACGGAACGGGACTATGGACG | 12 | 309 |
|  |  | PPVO 18r-1 | CTTGATGAGCCGGACGCA | 15 |  |
|  | 3' | PPVO 25r-1 | CCGAGTTGGAGAGGAAGGAGC | 16 | 318 |
|  |  | VAC-TK-1 | CGGTTTACGTTGAAATGTCCCAT | 5 |  |
| VVOV 243 | 5' | VAC-P11-1 | ATTACAGTGATGCCTACATGCCG | 2 | 478 |
|  |  | PPVO 79-1 | CTGTTGGAGGATGAGGTCAAGGA | 17 |  |
|  | 3' | PPVO 71r-1 | CGTGCTCATGCCTGTGGAC | 18 | 269 |
|  |  | VAC-TK-1 | CGGTTTACGTTGAAATGTCCCAT | 5 |  |
| VVOV 283 | 5' |  |  |  |  |
|  | 3' | PPVO 92-4 | CGACATCCTCACCTGCAAGAAG | 19 | 234 |
|  |  | VAC-TK-1 | CGGTTTACGTTGAAATGTCCCAT | 5 |  |
| VVOV 82 | 5' | VAC-TK-fwd | ATACGGAACGGGACTATGGACG | 12 | 275 |
|  |  | PPVO 120-1 | TACAGGCAGCCCGTGACC | 20 |  |
|  | 3' | PPVO R3R4-3 | GCCGTGTGTCACGTTGATGC | 21 | 1960 |
|  |  | VAC-TK-1 | CGGTTTACGTTGAAATGTCCCAT | 5 |  |

Example 2

Induction of Interferon Gamma and Tumor Necrosis Factor Alpha by PPVO Gene Products The 16 recombinants were tested of their ability to induce tumor necrosis factor alpha (TNF-α) and interferon gamma (IFN-γ) in whole blood cultures.

Whole blood cultures containing blood and RPMI medium (Life Technologies GmbH, Karlsruhe, Germany) in the ratio of 1:5 were stimulated with the recombinant viruses. A pure Vaccinia lister and a whole PPVO preparation served as controls. All preparations were used at a final dilution of 1:10. The stimulation for the IFN-γ determination was done together with Concanavalin A (SIGMA, St. Louis, Mo.), because the virus alone does not induce IFN-γ. Then the cells were incubated for 24 h (TNF-α) and or 72 h (IFN-γ). The cytokine concentration was then determined in the cell culture supernatants by TNF-α or IFN-γ specific ELISA. These time points were found to be optimal when the experimental conditions were determined using whole PPVO as a control.

It was possible to identify 5 active recombinant viruses (VVOV 96, VVOV 97, VVOV 243, VVOV 285, and VVOV 330) that induced both TNF-α and IFN-γ secretion and, thus, could mimic the effect of the whole PPVO. The results are depicted in Table 2.

Table 2

TNF-α was determined after 24 h stimulation of blood cells with the recombinant virus or the controls, respectively. IFN-γ was determined after 72 h stimulation of blood cells with the recombinant virus or the controls. Stimulation was performed in the presence of the mitogen ConA. The relative induction in percent of the Vaccinia virus control is shown. Therefore, values greater than 100% are due to the activity of the PPVO fragments. Active PPVO fragments are in bold. The data represent mean values of three different blood donors.

| Recombinant Virus Clone or control | Interferon Induction (%) | TNF Induction (%) |
| --- | --- | --- |
| Vaccinia virus control | 100 | 100 |
| NZ-2 control | 2224 | 264 |
| VVOV 80 | 200 | 66 |
| VVOV 82 | 173 | 65 |
| VVOV 85 | 209 | 94 |
| VVOV 86 | 138 | 73 |
| VVOV 96 | 1638 | 1016 |
| VVOV 97 | 1713 | 1285 |
| VVOV 212 | 94 | 62 |
| VVOV 213 | 192 | 38 |
| VVOV 215 | 97 | 82 |
| VVOV 216 | 197 | 71 |
| VVOV 243 | 1446 | 933 |
| VVOV 245 | 98 | 45 |
| VVOV 247 | 85 | 74 |
| VVOV 283 | 115 | 78 |
| VVOV 285 | 1128 | 1127 |
| VVOV 330 | 1762 | 2135 |

Table 3

The recombinant Vaccinia lister/PPVO viruses that induce both interferon gamma and TNF-α expression are listed in column 1, the corresponding PPVO sequence in column 2 and all open reading frames (ORFs) that are completely or partially contained in the recombinant are depicted in column 3.

| Active recombinant PPVO Vaccinia virus | PPVO NZ2 Sequence [Bp] that is contained in the recombinant | PPVO NZ2 ORFs that are contained in the recombinant |
|---|---|---|
| VVOV 97 | 24056-33789 | 18r-25r |
| VVOV 96 | 31003-46845 | 22r-39 |
| VVOV 285 | 74804-88576 | 64r-76 |
| VVOV 243 | 82324-92502 | 71r-79 |
| VVOV 330 | 102490-108393 | 92-96r |

Example 3

Local Immunomodulation by PPVO Gene Products in Liver Sinus Endothelial Cells (LSEC)

We have established a new cell-based assay system that allows testing of hepatoprotective properties of recombinant PPVO proteins expressed in different systems (e.g., Vaccinia virus). This assay system uses primary murine liver cells, which play the central role in deciding whether immunity or tolerance is induced in the liver, the LSEC. The unique ability of LSEC to present exogenous antigens to CD8+ T cells on MHC class 1 molecules allows immune surveillance of hepatocytes as viral antigens released by infected hepatocytes are likely to be taken by LSEC and presented to cells of the immune system. The new assay allows to measure the ability of LSEC to interact antigen-specifically with CD8+ T cells, that are responsible for tissue destruction in necroinflammatory hepatitis.

Pure populations of LSEC are isolated from murine liver by a stepwise procedure of portal-vein perfusion with collagenase A (0.05%), mechanical dispersion and further enzymatic digestion in a rotatory waterbath for 40 min at 37° C. (245 rpm), gradient centrifugation (metrizamide 1.089 g/cm$^3$) and centrifugal elutriation using a Beckman Avanti J25I centrifuge equipped with a JE-6B rotor and a standard elutriation chamber. LSEC cell populations isolated by this method are typically around 95-99% pure as measured by uptake of endothelial cell specific substrate (acetylated low density lipoprotein). LSEC were seeded onto collagen type I coated 24 well tissue culture plates at a density of 100.000 cells per well and were further cultured in Dulbecco's modified Eagle Medium supplemented with 5% fetal calf serum (specially tested not to interfere with the assay system) and 2% glutamine. Three days after isolation, when LSEC gained a post mitotic and quiescent state, we tested for the ability of LSEC to present soluble ovalbumin to (ovalbumin-specific) CD8+ T cells. LSEC were incubated with 1 μM of ovalbumin for three hours (antigen dose and time were previously shown to be optimal for testing of substances suspected to influence antigen-presentation), washed and incubated with a CD8+ T cell hybridoma (200.000 cells/well) that recognizes the peptide SIINFEKL (SEQ ID NO:320). SIINFEKL (SEQ ID NO:320) is recognized in a H2b context and directly binds on the MHC-I molecules. Therefore, it has not to be processed by the cell. This allows to differentiate between accessory functions of LSEC (such as MHC-I expression) and antigen-processing function.

The extent of CD8+ T cell activation was measured by determining the extent of IL-2 release from T cells by specific sandwich ELISA.

Using Vaccinia virus expressed recombinant proteins derived from PPVO we have been able to attribute hepatoprotective activity to individual clones. To be able to compare different clones directly with respect to their ability to influence cross-presentation by LSEC, we used equal amounts of "infectious units".

We found that LSEC cross-present exogenous ovalbumin very efficiently on MHC class I molecules ($k^b$) to CD8+ T cells. To our surprise we found if LSEC were incubated with several recombinant PPVO proteins we observed subsequently a potent downregulation of cross-presentation by more than 60% compared to the mock-treated control that includes all but the active ingredient. Several regions within the genome of PPVO have immunoregulatory properties. Especially the region termed 82 (43% reduction) which is located at the 3' end of the genome appears to be responsible for the overall effect of PPVO on cross-presentation by LSEC. Further regions (VVOV 215, VVOV 212, VVOV 247 and VVOV 86) bear further immunoregulatory potential, although to a lesser degree (around 30% reduction in cross-presentation). It further appears that genes coding for proteins that downregulate cross-presentation are arranged in clusters. It is of interest to note that we identified two gene clusters coding for proteins that improved cross-presentation (VVOV 330, VVOV 283, VVOV 285, VVOV 97, and VVOV 96). However, for unknown reasons the downregulatory effect of the proteins mentioned above is dominant in the activity of PPVO on cross-presentation.

Our results strongly suggest that PPVO contains a mixture of different proteins that in a complementary way work to eliminate hepatocytes from hepatitis B virus while conserving hepatic integrity and avoiding long lasting damage secondary to hepatic fibrosis. As PPVO contains a gene with high homology to the anti-inflammatory agent IL-10 (located in the 5-prime region of the genome) we wondered whether the potent downregulatory effect of the clone 82 was due to expression of ovine IL-10. This assumes that there is cross-reactivity between murine and ovine IL-10 at the level of receptor recognition. We have been unable to demonstrate involvement of ovine IL-10 on the immunoregulatory potential of PPVO. Recombinant murine IL-10 did not show any influence on cross-presentation through LSEC and several monoclonal antibodies to murine and human IL-10 did not influence PPVO mediated downregulation of cross-presentation. We conclude that the immunoregulatory component of PPVO is probably not IL-10 but a new, so far not identified mediator. The data for the MHC-I cross-presentation-down-modulating recombinant virus are depicted in Table 4, those for the MHC-I cross-presentation-stimulating recombinant viruses in Table 5.

Table 4

The recombinant Vaccinia lister/PPVO virus that down-modulates the MHC-I cross presentation is designated in column 1, the corresponding PPVO sequence in column 2 and all open reading frames (ORFs) that are completely or partially contained in the recombinant are depicted in column 3.

| Active recombinant PPVO Vaccinia virus | PPVO NZ2 Sequence [Bp] that is contained in the recombinant | PPVO NZ2 ORFs that are contained in the recombinant |
| --- | --- | --- |
| VVOV 82 | 122616-136025 | 120-R3 |

Table 5

The recombinant Vaccinia lister/PPVO viruses that stimulate the MHC-I cross presentation are designated in column 1, the corresponding PPVO sequence in column 2 and all open reading frames (ORFs) that are completely or partially contained in the recombinant are depicted in column 3.

| Active recombinant PPVO Vaccinia virus | PPVO NZ2-Sequence [Bp] that is contained in the recombinant | PPVO NZ2-ORFs that are contained in the recombinant |
| --- | --- | --- |
| VVOV 97 | 24056-33789 | 18r-25r |
| VVOV 96 | 31003-46845 | 22r-39 |
| VVOV 285 | 74804-88576 | 64r-76 |
| VVOV 283 | 89.4-103483 | 78r-92 |
| VVOV 330 | 102490-108393 | 92-96r |

Example 4

Determination of the Immunostimulatory Activity of the Vaccinia lister/PPVO Recombinants in the Aujeszky Mouse Model We also tested the activity of recombinant Vaccinia lister/PPVO NZ2-viruses in the Aujeszky mouse model, a lethal challenge model of acute Suid Herpesvirus 1 disease for determining the activity of various immunostimulators (e.g., Baypamun®, CpG oligonucleotides).

a) Conditions Employed for the Mice

The NMRI mice (outbreed strain HdsWin:NMRI; female; weight: 18-20 g; obtained via Harlan/Winkelmann, Borchen, Germany) were kept in autoclavable polycarbonate crates lined with sawdust in an S2 isolation stall at 20-22° C. (atmospheric humidity: 50-60%) and subjected to an artificial day/night rhythm (illumination from 6:30 h to 18:30 h and darkness from 18:30 h to 6:30 h). They had free access to feed and water.

b) Challenge Model

Groups of mice consisting of 10 mice per group were used for the tests. All of the animals in one group were given the same test substance.

After the mice were supplied they were kept in the animal stall for 2-3 days. Then the Vaccinia lister/PPVO NZ2 recombinants were diluted with PBS (Life Technologies GmbH, Karlsruhe, Germany) to a titer equivalent of approx. $10^8$ $TCID_{50}$/ml and thermally inactivated (twice for one hour at 58° C.). Of these solutions 0.2 ml was administered per mouse intraperitoneally.

24 hours after the treatment the mice were infected with the pseudorabies virus of the Hannover H2 strain by intraperitoneal administration. For this purpose the virus was diluted in PBS to a test titer of approx. $10^4$ $TCID_{50}$/ml and 0.2 ml of this suspension was administered.

As a negative control one group of mice was treated with PBS and then infected. The mice in this group died 3-8 days after infection. A large proportion of the mice treated the Vaccinia lister/PPVO NZ2 recombinants VVOV 215, VVOV 245, VVOV 285 or VVOV 330 survived infection with the pseudorabies virus. 10 days after the infection with the virus the test was ended.

The level of induced immunostimulation was determined by comparing the number of dead mice in the PBS control group with the number of dead mice in the test groups and was quantified by the efficacy index (EI). This index indicates the percentage proportion of mice protected against the lethal effects of the Aujeszky virus infection through immune stimulation by the substance to be tested. It is calculated by means of the following formula:

$$EI=(b-a)/b\times100,$$

where b is the percentage proportion of the dead mice in the control group and a the percentage proportion of the dead mice in the test group.

A chi-square test was used for the statistical evaluation. This test reveals the minimum activity indices indicating a significant difference between the mortality rate of those mice treated with the test substance and those treated with PBS. Activity indices of ≥60% are significant where at least 5 of the mice used in tests with n=6 mice per group in the PBS control group and at least 7 of the mice used in tests with n=10 in the PBS control group do not survive the infection with the Aujeszky virus.

Altogether 3 separate tests were carried out in each case. The testing of Vaccinia lister/PPVO NZ2 recombinants in the Aujeszky mouse model shows the following:

Surprisingly, after the treatment of the mice with the Vaccinia lister/PPVO NZ2 recombinants VVOV 215, VVOV 245, VVOV 285 or VVOV 330 the average activity indices of higher than 60% demonstrated immunostimulation. By contrast all of the other Vaccinia lister/PPVO NZ2 recombinants were ineffective. The data is summarized in Table 6.

Table 6

The recombinant Vaccinia lister/PPVO viruses that protected mice from herpesvirus induced death are designated in column 1, the corresponding PPVO sequence in column 2 and all open reading frames (ORFs) that are completely or partially contained in the recombinant are depicted in column 3.

| Active recombinant PPVO Vaccinia virus | PPVO NZ2-Sequence [Bp] that is contained in the recombinant | PPVO NZ2 ORFs that are contained in the recombinant |
| --- | --- | --- |
| VVOV 215 | 10264-20003 | 4r-14r |
| VVOV 245 | 47952-66263 | 40r-57 |
| VVOV 285 | 74804-88576 | 64r-76 |
| VVOV 330 | 102490-108393 | 92-96r |

Table 7

Sequences of the Parapox ovis open reading frames. ORFs the names of which end with "r" are encoded on the complementary DNA strand. Base pair positions in the "from" and "to" column are relative to SEQ ID NO:1.

TABLE 7

| ORF | from | to | N-term | SEQ ID NO | C-term | SEQ ID NO | Comment |
|---|---|---|---|---|---|---|---|
| L1 | 3 | 539 | IRGFAG | 22 | PQKVFRL | 23 | long termal repeat (LTR)-protein, retroviral pseudoprotease |
| L2r | 781 | 449 | MSEGGRL | 24 | LLGLLFP | 25 | LTR-protein, retroviral pseudoprotease |
| L3r | 1933 | 1664 | MTVHPPK | 26 | VLPPNSL | 27 | LTR-protein, retroviral pseudoprotease |
| L4r | 3269 | 2790 | MHPSPRR | 28 | PVSHPFL | 29 | LTR-protein, retroviral pseudoprotease |
| L5 | 2799 | 3851 | MGDREGE | 30 | FEDGVKC | 31 | LTR-protein, retroviral pseudoprotease |
| L6 | 2962 | 3753 | MCTVATF | 32 | GAPRAGW | 33 | LTR-protein, similar to 134r, retroviral pseudoprotease |
| L7r | 3784 | 3122 | MTPTSRE | 34 | ARTAPPR | 35 | LTR-protein, retroviral pseudoprotease |
| L8r | 4341 | 4129 | MPGEGQY | 36 | NGGLGKI | 37 | LTR-protein, retroviral pseudoprotease |
| 1ar | 4904 | 4428 | MEFCHTE | 38 | DTAWYIS | 39 | dUTPase |
| 1r | 6517 | 4970 | MLSRESV | 40 | RAMLTRP | 41 | homolog of G1L in NZ2, Ankyrin-repeats |
| 2r | 8042 | 6684 | MFFWFWC | 42 | SGEGVPV | 43 | |
| 3r | 9989 | 8070 | MLGFWGK | 44 | VLPSVSR | 45 | involved in maturation of EEV (Extracellular Enveloped Virions) |
| 4r | 11195 | 10062 | MWPFSSI | 46 | EFCKPIN | 47 | Phospholipase D-type enzyme |
| 5r | 11493 | 11227 | MLIYGPR | 48 | RLLKDFP | 49 | homolog of B3L in NZ2 |
| 6 | 11802 | 12038 | MGVVMCG | 50 | APAGVTE | 51 | |
| 7r | 12358 | 12080 | MPVKVKQ | 52 | ASREFIV | 53 | ubiquitination protein with RING-finger-motiv (related to yeast proteins APC11 and HRT1) |
| 8r | 13980 | 12364 | MEEELTR | 54 | SPMVVFN | 55 | no Vaccinia virus homolog |
| 9ar | 14826 | 14053 | MIRIGGG | 56 | DNMRVDD | 57 | |
| 10 | 15080 | 15394 | MDGGVHK | 58 | EQMCRRQ | 59 | virion core DNA-binding phosphoprotein |
| 11r | 16838 | 15423 | MAPPVIE | 60 | AKNVITH | 61 | polyA polymerase |
| 12r | 19021 | 16847 | MLQLLKR | 62 | NNRGFRK | 63 | |
| 13r | 19704 | 19156 | MACECAS | 64 | NNCGISF | 65 | interferon resistance protein, homology to mammalian PACT (protein activator of the interferon-induced protein kinase) also called PRKRA (dsRNA dependent activator of Interferon-induced protein kinase), 13r-protein contains a dsRBD motif (double-stranded RNA binding domain) and a 'DRADA'-domain that is typical for RNA-editing enzymes) |
| 14r | 20314 | 19736 | MDEDRLR | 66 | KKGKPKS | 67 | RNA polymerase |
| 15 | 20401 | 22101 | MDFVRRK | 68 | VVLQGRA | 69 | |
| 16 | 22125 | 22940 | MVDSGTH | 70 | PENVVLL | 71 | |
| 17 | 23003 | 23866 | MASYISG | 72 | RTHTVYV | 73 | DNA polymerase |
| 18r | 26908 | 23873 | MLFEMEL | 74 | SKPVFTG | 75 | |
| 19 | 26926 | 27213 | MEPRFWG | 76 | AKVRPLV | 77 | distant homolog of the ERV1/ALR-protein-family (ERV1: yeast protein, Essential for Respiration and Vegatative growth, ALR: mammalian protein, Augmenter of Liver Regeneration) |
| 20r | 27626 | 27216 | MEAINVF | 78 | RAYEGML | 79 | |
| 21r | 29754 | 27616 | MLLYPKK | 80 | LLGDGGD | 81 | related to 12r |
| 22r | 32217 | 29800 | MLIRTTD | 82 | EAQNMQN | 83 | |
| 23r | 33380 | 32418 | MEDERLI | 84 | PSPCGGE | 85 | |
| 24r | 33602 | 33393 | MDKLYTG | 86 | FHYLKLV | 87 | |
| 25r | 34466 | 33612 | MKRAVSK | 88 | LEAPFNI | 89 | DNA binding phosphoprotein |
| 26r | 34735 | 34502 | MESRDLG | 90 | LNARRQN | 91 | |
| 27r | 35905 | 34739 | MNHFFKQ | 92 | RSLYTVL | 93 | |
| 28r | 37194 | 35905 | MDKYTDL | 94 | PEKPAAP | 95 | core protein |
| 29 | 37200 | 39248 | MENHLPD | 96 | IEAEPPF | 97 | RNA helicase |
| 30r | 41037 | 39229 | MIVLENG | 98 | RMGARPR | 99 | Zn-protease, involved in virion morphogenesis |
| 31 | 41374 | 42066 | MTFRELI | 100 | DSMASRS | 101 | late transcription factor |
| 32r | 42336 | 41731 | MRGHPAH | 102 | VAPREEL | 103 | |
| 33r | 42407 | 41997 | MASDASP | 104 | QPSSSRR | 105 | Glutaredoxin-like enzyme |
| 34 | 42410 | 43765 | MGIKNLK | 106 | PRLLKLR | 107 | |
| 35 | 43770 | 43958 | MVFPIVC | 108 | LPMLDIS | 109 | RNA polymerase |
| 36 | 43980 | 44534 | MREFGLA | 110 | AEPPWLV | 111 | |
| 37r | 45727 | 44537 | MESSKQA | 112 | TRAPPLF | 113 | core virion protein precursor |
| 38 | 45760 | 46557 | MTLRIKL | 114 | DRSLSCD | 115 | late transcription factor |

TABLE 7-continued

| ORF | from | to | N-term | SEQ ID NO | C-term | SEQ ID NO | Comment |
|---|---|---|---|---|---|---|---|
| 39 | 46567 | 47568 | MGGSVSL | 116 | YLLIVWL | 117 | |
| 40 | 47572 | 48303 | MGAAASI | 118 | TEFPPSV | 119 | virion protein, related to vaccinia F9L |
| 41 | 48352 | 48621 | MVRRVLL | 120 | LCLFSMD | 121 | |
| 42r | 49887 | 48634 | MEEKRGR | 122 | ARAMVCL | 123 | |
| 43 | 49917 | 50693 | MTNLLSL | 124 | TGAEAAP | 125 | core protein, DNA binding domain |
| 44 | 50719 | 51102 | MAAPTTP | 126 | VDVLGGR | 127 | |
| 44a | 51059 | 51511 | MDHEKYV | 128 | ATLSPGL | 129 | |
| 45 | 51584 | 52591 | MEGVEMD | 130 | RPLRGGK | 131 | polyA polymerase |
| 46 | 52509 | 53066 | MNRHNTR | 132 | SVSVVLD | 133 | RNA polymerase |
| 47r | 53523 | 53023 | MFFRRRA | 134 | GRRPPRP | 135 | |
| 48 | 53607 | 57473 | MSVVARV | 136 | EAAEEEF | 137 | RNA polymerase chain 1 |
| 49r | 58070 | 57528 | MGDKSEW | 138 | FVCDSPS | 139 | tyrosine phosphatase |
| 50 | 57700 | 58662 | MAAAPLR | 140 | ATSGVLT | 141 | |
| 51r | 59674 | 58673 | MDPPEIT | 142 | LLVTAIV | 143 | immunodominant envelope protein |
| 52r | 62089 | 59678 | MDSRESI | 144 | YMINFNN | 145 | RNA polymerase-associated transcription specificity factor (also called RAP94) |
| 53 | 62198 | 62881 | MSSWRLK | 146 | KAAACKK | 147 | late transcription factor |
| 55 | 62909 | 63862 | MRALHLS | 148 | NSEQVNG | 149 | topoisomerase I |
| 56 | 63858 | 64271 | MDEALRV | 150 | FIRAAVA | 151 | |
| 57 | 64309 | 66831 | MDAPSLD | 152 | LYVFSKR | 153 | mRNA capping enzyme |
| 58r | 67266 | 66799 | MEPSAMR | 154 | DVQHVDL | 155 | virion protein |
| 58ar | 67803 | 67273 | MAGFSQS | 156 | TTCVPPQ | 157 | |
| 59 | 67915 | 68607 | MATPANA | 158 | FSFYSEN | 159 | Uracil DNA glycosylase |
| 60 | 68624 | 70984 | MAAPICD | 160 | IEDVENK | 161 | ATPase, involved in DNA replication |
| 61 | 70994 | 72898 | MNSDVIK | 162 | EVSVVNI | 163 | early transcription factor |
| 62 | 72938 | 73507 | MSTFRQT | 164 | ASPAAKN | 165 | RNA polymerase |
| 63 | 73540 | 74211 | MRTYTSL | 166 | WGAAVTR | 167 | NTP pyrophosphohydrolase |
| 64r | 76120 | 74207 | MTSAHAA | 168 | VDPASIA | 169 | virion NTPase |
| 65r | 76749 | 76186 | MEGRARF | 170 | RFCNYCP | 171 | |
| 66r | 77698 | 76799 | MKTDCAS | 172 | KLKLLLQ | 173 | mRNA capping enzyme |
| 67r | 79343 | 77709 | MNNSVVS | 174 | AEKVTAQ | 175 | rifampicin resistance, virion membrane |
| 68r | 79816 | 79367 | MKRIALS | 176 | MALKSLI | 177 | late transactivator protein |
| 69r | 80529 | 79858 | MNLRMCG | 178 | AACSLDL | 179 | late transactivator protein |
| 70r | 80774 | 80529 | MGDNVWF | 180 | VLGLEQA | 181 | thioredoxin-like protein |
| 71r | 82815 | 80788 | MESPACA | 182 | NMCDVLC | 183 | major core protein |
| 72r | 83835 | 82834 | MDLRRRF | 184 | VDNTGTS | 185 | core protein |
| 73 | 83874 | 85583 | MEESVAV | 186 | LLNYGCG | 187 | RNA-polymerase |
| 74r | 85535 | 84402 | MDRLRTC | 188 | AEAAESA | 189 | |
| 75r | 88096 | 85574 | MVSVMRK | 190 | QEFYPQP | 191 | early transcription factor |
| 76 | 87759 | 88667 | MFQPVPD | 192 | SACRASP | 193 | |
| 77r | 88920 | 88642 | MRPCYVT | 194 | TRGTQTG | 195 | |
| 78r | 91652 | 88938 | MTAPNVH | 196 | AVSFDSE | 197 | major core protein |
| 79 | 91667 | 92674 | MTAVPVT | 198 | VRKLNLI | 199 | |
| 80r | 93466 | 92681 | MASEKMA | 200 | DLDGGMC | 201 | virion protein |
| 81r | 93761 | 93486 | MGLLDAL | 202 | RFSAASS | 203 | virion membrane protein |
| 82r | 94060 | 93788 | MDIFETL | 204 | DIELTAR | 205 | virion membrane protein |
| 83r | 94238 | 94080 | MVSDYDP | 206 | HFVHSVI | 207 | |
| 84r | 94508 | 94242 | MFLDSDT | 208 | DMPFSVV | 209 | |
| 85r | 95571 | 94498 | MGDTVSK | 210 | KTINVSR | 211 | |
| 86r | 96187 | 95600 | MESYFSY | 212 | EDLFFAE | 213 | virion membrane protein |
| 87 | 96202 | 97665 | MFGGVQV | 214 | GRDLAAV | 215 | RNA helicase |
| 88r | 97915 | 97643 | MSAVKAK | 216 | PLRDLAR | 217 | Zn-finger protein |
| 89 | 98251 | 99537 | MTSESDL | 218 | AIARAQP | 219 | DNA polymerase processivity factor |
| 90 | 99537 | 99974 | MIVAAFD | 220 | NYVLRTN | 221 | |
| 91 | 100001 | 101140 | MLALFEF | 222 | LKELLGP | 223 | intermediate transcription factor |
| 92 | 101168 | 104650 | MEQALGY | 224 | SLFSPED | 225 | RNA polymerase b-chain |
| 93r | 106354 | 104795 | MESDNAL | 226 | GQHAAIW | 227 | A-type inclusion body/Fusion peptide |
| 94r | 107947 | 106400 | MEKLVSD | 228 | GRSGAIW | 229 | A-type inclusion body/Fusion peptide |
| 95r | 108256 | 107990 | MDENDGE | 230 | QTGYSRY | 231 | viral fusion protein |
| 96r | 108719 | 108300 | MDAVSAL | 232 | LFLKSIL | 233 | |
| 97r | 109679 | 108738 | MADAPLV | 234 | RELRANE | 235 | RNA polymerase subunit |
| 98r | 109861 | 109682 | MEEDLNE | 236 | MGQASSA | 237 | |
| 99r | 110830 | 110033 | MDVVQEV | 238 | ADSDGGN | 239 | ATPase |
| 100 | 110208 | 110417 | MRSWFWQ | 240 | PLTGMCL | 241 | |
| 100a | 110469 | 110651 | MRPKSVG | 242 | SGHTKPS | 243 | |
| 101 | 110915 | 111397 | MAHNTFE | 244 | KYFCVSD | 245 | enveloped virion glycoprotein |
| 102 | 111419 | 111913 | MGCCKVP | 246 | CMKEMHG | 247 | enveloped virion glycoprotein |
| 103 | 111949 | 112485 | MSRLQIL | 248 | RKLDVPI | 249 | |
| 104 | 112593 | 113450 | MKAVLLL | 250 | LNLNPGN | 251 | GM-CSF/IL-2 inhibition factor |
| 105r | 113323 | 112967 | MHASLSS | 252 | DETLTYR | 253 | |

TABLE 7-continued

| ORF | from | to | N-term | SEQ ID NO | C-term | SEQ ID NO | Comment |
|---|---|---|---|---|---|---|---|
| 106 | 113526 | 114152 | MEVLVII | 254 | GEFFYDE | 255 | |
| 107 | 114199 | 115236 | MPLFRKL | 256 | RDALDGL | 257 | |
| 108 | 115353 | 115787 | MACFIEL | 258 | TTFSSSE | 259 | |
| 109 | 115859 | 116551 | MSSSSSETT | 260 | TTGTSTS | 261 | |
| 110 | 116729 | 117523 | MACLRVF | 262 | CSMQTAR | 263 | GM-CSF/IL-2 inhibition factor |
| 111r | 117572 | 117114 | MAIAHTT | 264 | FRFRTPG | 265 | |
| 112 | 117423 | 118085 | MAATIQI | 266 | KRDGYSR | 267 | |
| 114r | 118968 | 118375 | MEGLMPK | 268 | RPISVQK | 269 | |
| 115 | 118508 | 119119 | MDSRRLA | 270 | LGDSDSD | 271 | |
| 116 | 119588 | 120202 | MRLILAL | 272 | PQMMRIG | 273 | |
| 117 | 120314 | 121231 | MAGFLGA | 274 | CKVEEVL | 275 | |
| 118 | 121380 | 123920 | MHLHKDP | 276 | LAFPSLA | 277 | |
| 119 | 121288 | 122256 | MANRLVF | 278 | RPMEIDG | 279 | |
| 120 | 122350 | 123924 | MENNDGN | 280 | RFLPSHK | 281 | related to 1r/G1L with Ankyrin-repeats |
| 121 | 123962 | 125566 | MDPAGQR | 282 | CSETDRW | 283 | |
| 122r | 125193 | 124591 | MSSSAAA | 284 | IAPDSRM | 285 | |
| 123r | 125689 | 123935 | MTAEASI | 286 | DPVYHKK | 287 | |
| 123ar | 123839 | 123297 | MPRTTSG | 288 | REQTEGL | 289 | |
| 124 | 125652 | 126170 | MANREEI | 290 | VRVLRRT | 291 | |
| 125r | 126121 | 125699 | MTAPTPR | 292 | AAYSLAR | 293 | |
| 126 | 126279 | 127769 | MADEREA | 294 | LACAMRK | 295 | related to 1r/G1L with Ankyrin-repeats |
| 127 | 127851 | 128408 | MSKNKIL | 296 | SYMTTKM | 297 | sheep-like Interleukin 10 |
| 128 | 128520 | 130076 | MLTRCYI | 298 | RASGLAE | 299 | related to 1r/G1L wih Ankyrin-repeats |
| 129 | 130105 | 131700 | MVGFDRR | 300 | CGRRAPE | 301 | related to 1r/G1L, with Ankyrin-repeats (NT slightly changed) |
| 130 | 131790 | 133283 | MILARAG | 302 | PDAAALS | 303 | Kinase |
| 131 | 133246 | 133920 | MPPRTPP | 304 | RPAALRA | 305 | |
| 132 | 133972 | 134370 | MKLLVGI | 306 | RPPRRRR | 307 | homolog to the sheep VEGF (Vascular Endothelial Growth Factor) |
| 133a | 134418 | 134693 | MRKKAPR | 308 | ARTAPPR | 309 | corresponds to L7r |
| R1 | 134402 | 134992 | MMRSGHA | 310 | RMHRSEL | 311 | LTR-protein (corresponds to L4r), retroviral pseudoprotease |
| R2r | 134853 | 134419 | MCTVATF | 312 | SVAPSSA | 313 | LTR-protein (corresponds to L6, 134r), retroviral pseudoprotease |
| R3 | 135628 | 135897 | MTVHPPK | 314 | VLPPNSL | 315 | LTR-protein (corresponds to L3r), retroviral pseudoprotease |
| R4 | 136780 | 137112 | MSEGGRL | 316 | LLGLLFP | 317 | LTR-protein (corresponds to L2r), retroviral pseudoprotease |
| R5r | 137558 | 137022 | IRGFAGG | 318 | PQKVFRL | 319 | LTR-protein (corresponds to L1r), retroviral pseudoprotease |

The invention claimed is:

1. A method for inducing an immunomodulatory activity in a subject, comprising administering to the subject an individual recombinant protein encoded by a polynucleotide selected from the group consisting of:

(i) a polynucleotide having the sequence consisting of nucleotide residues 31003 to 46845 of SEQ ID NO:1 (PPVO insert of VVOV 96), (ii) a polynucleotide having the sequence consisting of nucleotide residues 24056 to 33789 of SEQ ID NO:1 (PPVO insert of VVOV 97), (iii) a polynucleotide having the sequence consisting of nucleotide residues 82324 to 92502 of SEQ ID NO:1 (PPVO insert of VVOV 243), (iv) a polynucleotide having the sequence consisting of nucleotide residues 74804 to 88576 of SEQ ID NO:1 (PPVO insert of VVOV 285), and (v) a polynucleotide having the sequence consisting of nucleotide residues 102490 to 108393 of SEQ ID NO:1 (PPVO insert of VVOV 330), wherein the individual recombinam protein induces the immunomodulatory activity in the subject.

2. The method of claim 1, wherein the immunomodulatory activity results in the induction of interferon-gamma.

3. The method of claim 1, wherein the immunomodulatory activity results in the induction of tumor necrosis factor-alpha.

4. The method of claim 1, wherein the immunomodulatory activity results in the stimulation of MHC-I cross-presentation.

5. The method of claim 1, wherein the recombinant protein is attached to or is a part of a structure selected from the group consisting of: particle-like structure, fusion protein, protein coated particle, and virus-like particle.

6. A method for inducing an immunomodulatory activity in a subject, comprising administering to the subject an individual recombinant virus containing a recombinant protein encoded by a polynucleotide selected from the group consisting of:
   (i) a polynucleotide having the sequence consisting of nucleotide residues 31003 to 46845 of SEQ ID NO:1 (PPVO insert of VVOV 96),
   (ii) a polynucleotide having the sequence consisting of nucleotide residues 24056 to 33789 of SEQ ID NO:1 (PPVO insert of VVOV 97),
   (iii) a polynucleotide having the sequence consisting of nucleotide residues 82324 to 92502 of SEQ ID NO:1 (PPVO insert of VVOV 243),
   (iv) a polynucleotide having the sequence consisting of nucleotide residues 74804 to 88576 of SEQ ID NO:1 (PPVO insert of VVOV 285), and
   (v) a polynucleotide having the sequence consisting of nucleotide residues 102490 to 108393 of SEQ ID NO:1 (PPVO insert of VVOV 330),
   wherein the recombinant protein induces the immunomodulatory activity in the subject.

7. The method of claim 6 wherein the immunomodulatory activity results in the induction of interferon-gamma.

8. The method of claim 6 wherein the immunomodulatory activity results in the induction of tumor necrosis factor-alpha.

9. The method of claim 6 wherein the immunomodulatory activity results in the stimulation of MHC-I cross-presentation.

10. The method of claim 6, wherein the recombinant protein is attached to or is a part of a structure selected from the group consisting of: particle-like structure, fusion protein, protein coated particle, and virus-like particle.

* * * * *

SEQUENCE LISTING

```
<160> NUMBER OF SEQ ID NOS: 320

<210> SEQ ID NO 1
<211> LENGTH: 137560
<212> TYPE: DNA
<213> ORGANISM: Parapoxvirus ovis NZ2
<220> FEATURE:
<221> NAME/KEY: misc_feature
<222> LOCATION: (3)...(539)
<223> OTHER INFORMATION: ORF: L1
<220> FEATURE:
<221> NAME/KEY: misc_feature
<222> LOCATION: (781)...(449)
<223> OTHER INFORMATION: ORF: L2r
<220> FEATURE:
<221> NAME/KEY: misc_feature
<222> LOCATION: (1933)...(1664)
<223> OTHER INFORMATION: ORF: L3r
<220> FEATURE:
<221> NAME/KEY: misc_feature
<222> LOCATION: (3269)...(2790)
<223> OTHER INFORMATION: ORF: L4r
<220> FEATURE:
```

```
<221> NAME/KEY: misc_feature
<222> LOCATION: (2799)...(3851)
<223> OTHER INFORMATION: ORF: L5
<220> FEATURE:
<221> NAME/KEY: misc_feature
<222> LOCATION: (2962)...(3753)
<223> OTHER INFORMATION: ORF: L6
<220> FEATURE:
<221> NAME/KEY: misc_feature
<222> LOCATION: (3784)...(3122)
<223> OTHER INFORMATION: ORF: L7r
<220> FEATURE:
<221> NAME/KEY: misc_feature
<222> LOCATION: (4341)...(4129)
<223> OTHER INFORMATION: ORF: L8r
<220> FEATURE:
<221> NAME/KEY: misc_feature
<222> LOCATION: (4904)...(4428)
<223> OTHER INFORMATION: ORF: 1ar
<220> FEATURE:
<221> NAME/KEY: misc_feature
<222> LOCATION: (6517)...(4970)
<223> OTHER INFORMATION: ORF: 1r
<220> FEATURE:
<221> NAME/KEY: misc_feature
<222> LOCATION: (8042)...(6684)
<223> OTHER INFORMATION: ORF: 2r
<220> FEATURE:
<221> NAME/KEY: misc_feature
<222> LOCATION: (9989)...(8070)
<223> OTHER INFORMATION: ORF: 3r
<220> FEATURE:
<221> NAME/KEY: misc_feature
<222> LOCATION: (11195)...(10062)
<223> OTHER INFORMATION: ORF: 4r
<220> FEATURE:
<221> NAME/KEY: misc_feature
<222> LOCATION: (11493)...(11227)
<223> OTHER INFORMATION: ORF: 5r
<220> FEATURE:
<221> NAME/KEY: misc_feature
<222> LOCATION: (11802)...(12038)
<223> OTHER INFORMATION: ORF: 6
<220> FEATURE:
<221> NAME/KEY: misc_feature
<222> LOCATION: (12358)...(12080)
<223> OTHER INFORMATION: ORF: 7r
<220> FEATURE:
<221> NAME/KEY: misc_feature
<222> LOCATION: (13980)...(12364)
<223> OTHER INFORMATION: ORF: 8r
<220> FEATURE:
<221> NAME/KEY: misc_feature
<222> LOCATION: (14826)...(14053)
<223> OTHER INFORMATION: ORF: 9ar
<220> FEATURE:
<221> NAME/KEY: misc_feature
<222> LOCATION: (15080)...(15394)
<223> OTHER INFORMATION: ORF: 10
<220> FEATURE:
<221> NAME/KEY: misc_feature
<222> LOCATION: (16838)...(15423)
<223> OTHER INFORMATION: ORF: 11r
<220> FEATURE:
<221> NAME/KEY: misc_feature
<222> LOCATION: (19021)...(16847)
<223> OTHER INFORMATION: ORF: 12r
<220> FEATURE:
<221> NAME/KEY: misc_feature
<222> LOCATION: (19704)...(19156)
<223> OTHER INFORMATION: ORF: 13r
<220> FEATURE:
<221> NAME/KEY: misc_feature
<222> LOCATION: (20314)...(19736)
<223> OTHER INFORMATION: ORF: 14r
<220> FEATURE:
<221> NAME/KEY: misc_feature
<222> LOCATION: (20401)...(22101)
<223> OTHER INFORMATION: ORF: 15
```

```
<220> FEATURE:
<221> NAME/KEY: misc_feature
<222> LOCATION: (22125)...(22940)
<223> OTHER INFORMATION: ORF: 16
<220> FEATURE:
<221> NAME/KEY: misc_feature
<222> LOCATION: (23003)...(23866)
<223> OTHER INFORMATION: ORF: 17
<220> FEATURE:
<221> NAME/KEY: misc_feature
<222> LOCATION: (26908)...(23873)
<223> OTHER INFORMATION: ORF: 18r
<220> FEATURE:
<221> NAME/KEY: misc_feature
<222> LOCATION: (26926)...(27213)
<223> OTHER INFORMATION: ORF: 19
<220> FEATURE:
<221> NAME/KEY: misc_feature
<222> LOCATION: (27626)...(27216)
<223> OTHER INFORMATION: ORF: 20r
<220> FEATURE:
<221> NAME/KEY: misc_feature
<222> LOCATION: (29754)...(27616)
<223> OTHER INFORMATION: ORF: 21r
<220> FEATURE:
<221> NAME/KEY: misc_feature
<222> LOCATION: (32217)...(29800)
<223> OTHER INFORMATION: ORF: 22r
<220> FEATURE:
<221> NAME/KEY: misc_feature
<222> LOCATION: (33380)...(32418)
<223> OTHER INFORMATION: ORF: 23r
<220> FEATURE:
<221> NAME/KEY: misc_feature
<222> LOCATION: (33602)...(33393)
<223> OTHER INFORMATION: ORF: 24r
<220> FEATURE:
<221> NAME/KEY: misc_feature
<222> LOCATION: (34466)...(33612)
<223> OTHER INFORMATION: ORF: 25r
<220> FEATURE:
<221> NAME/KEY: misc_feature
<222> LOCATION: (34735)...(34502)
<223> OTHER INFORMATION: ORF: 26r
<220> FEATURE:
<221> NAME/KEY: misc_feature
<222> LOCATION: (35905)...(34739)
<223> OTHER INFORMATION: ORF: 27r
<220> FEATURE:
<221> NAME/KEY: misc_feature
<222> LOCATION: (37194)...(35905)
<223> OTHER INFORMATION: ORF: 28r
<220> FEATURE:
<221> NAME/KEY: misc_feature
<222> LOCATION: (37200)...(39248)
<223> OTHER INFORMATION: ORF: 29
<220> FEATURE:
<221> NAME/KEY: misc_feature
<222> LOCATION: (41037)...(39229)
<223> OTHER INFORMATION: ORF: 30r
<220> FEATURE:
<221> NAME/KEY: misc_feature
<222> LOCATION: (41374)...(42066)
<223> OTHER INFORMATION: ORF: 31
<220> FEATURE:
<221> NAME/KEY: misc_feature
<222> LOCATION: (42336)...(41731)
<223> OTHER INFORMATION: ORF: 32r
<220> FEATURE:
<221> NAME/KEY: misc_feature
<222> LOCATION: (42407)...(41997)
<223> OTHER INFORMATION: ORF: 33r
<220> FEATURE:
<221> NAME/KEY: misc_feature
<222> LOCATION: (42410)...(43765)
<223> OTHER INFORMATION: ORF: 34
<220> FEATURE:
<221> NAME/KEY: misc_feature
<222> LOCATION: (43770)...(43958)
```

```
<223> OTHER INFORMATION: ORF: 35
<220> FEATURE:
<221> NAME/KEY: misc_feature
<222> LOCATION: (43980)...(44534)
<223> OTHER INFORMATION: ORF: 36
<220> FEATURE:
<221> NAME/KEY: misc_feature
<222> LOCATION: (45727)...(44537)
<223> OTHER INFORMATION: ORF: 37r
<220> FEATURE:
<221> NAME/KEY: misc_feature
<222> LOCATION: (45760)...(46557)
<223> OTHER INFORMATION: ORF: 38
<220> FEATURE:
<221> NAME/KEY: misc_feature
<222> LOCATION: (46567)...(47568)
<223> OTHER INFORMATION: ORF: 39
<220> FEATURE:
<221> NAME/KEY: misc_feature
<222> LOCATION: (47572)...(48303)
<223> OTHER INFORMATION: ORF: 40
<220> FEATURE:
<221> NAME/KEY: misc_feature
<222> LOCATION: (48352)...(48621)
<223> OTHER INFORMATION: ORF: 41
<220> FEATURE:
<221> NAME/KEY: misc_feature
<222> LOCATION: (49887)...(48634)
<223> OTHER INFORMATION: ORF: 42r
<220> FEATURE:
<221> NAME/KEY: misc_feature
<222> LOCATION: (49917)...(50693)
<223> OTHER INFORMATION: ORF: 43
<220> FEATURE:
<221> NAME/KEY: misc_feature
<222> LOCATION: (50719)...(51102)
<223> OTHER INFORMATION: ORF: 44
<220> FEATURE:
<221> NAME/KEY: misc_feature
<222> LOCATION: (51059)...(51511)
<223> OTHER INFORMATION: ORF: 44a
<220> FEATURE:
<221> NAME/KEY: misc_feature
<222> LOCATION: (51584)...(52591)
<223> OTHER INFORMATION: ORF: 45
<220> FEATURE:
<221> NAME/KEY: misc_feature
<222> LOCATION: (52509)...(53066)
<223> OTHER INFORMATION: ORF: 46
<220> FEATURE:
<221> NAME/KEY: misc_feature
<222> LOCATION: (53523)...(53023)
<223> OTHER INFORMATION: ORF: 47r
<220> FEATURE:
<221> NAME/KEY: misc_feature
<222> LOCATION: (53607)...(57473)
<223> OTHER INFORMATION: ORF: 48
<220> FEATURE:
<221> NAME/KEY: misc_feature
<222> LOCATION: (58070)...(57528)
<223> OTHER INFORMATION: ORF: 49r
<220> FEATURE:
<221> NAME/KEY: misc_feature
<222> LOCATION: (57700)...(58662)
<223> OTHER INFORMATION: ORF: 50
<220> FEATURE:
<221> NAME/KEY: misc_feature
<222> LOCATION: (59674)...(58673)
<223> OTHER INFORMATION: ORF: 51r
<220> FEATURE:
<221> NAME/KEY: misc_feature
<222> LOCATION: (62089)...(59678)
<223> OTHER INFORMATION: ORF: 52r
<220> FEATURE:
<221> NAME/KEY: misc_feature
<222> LOCATION: (62198)...(62881)
<223> OTHER INFORMATION: ORF: 53
<220> FEATURE:
<221> NAME/KEY: misc_feature
```

```
<222> LOCATION: (62909)...(63862)
<223> OTHER INFORMATION: ORF: 55
<220> FEATURE:
<221> NAME/KEY: misc_feature
<222> LOCATION: (63858)...(64271)
<223> OTHER INFORMATION: ORF: 56
<220> FEATURE:
<221> NAME/KEY: misc_feature
<222> LOCATION: (64309)...(66831)
<223> OTHER INFORMATION: ORF: 57
<220> FEATURE:
<221> NAME/KEY: misc_feature
<222> LOCATION: (67266)...(66799)
<223> OTHER INFORMATION: ORF: 58r
<220> FEATURE:
<221> NAME/KEY: misc_feature
<222> LOCATION: (67803)...(67273)
<223> OTHER INFORMATION: ORF: 58ar
<220> FEATURE:
<221> NAME/KEY: misc_feature
<222> LOCATION: (67915)...(68607)
<223> OTHER INFORMATION: ORF: 59
<220> FEATURE:
<221> NAME/KEY: misc_feature
<222> LOCATION: (68624)...(70984)
<223> OTHER INFORMATION: ORF: 60
<220> FEATURE:
<221> NAME/KEY: misc_feature
<222> LOCATION: (70994)...(72898)
<223> OTHER INFORMATION: ORF: 61
<220> FEATURE:
<221> NAME/KEY: misc_feature
<222> LOCATION: (72938)...(73507)
<223> OTHER INFORMATION: ORF: 62
<220> FEATURE:
<221> NAME/KEY: misc_feature
<222> LOCATION: (73540)...(74211)
<223> OTHER INFORMATION: ORF: 63
<220> FEATURE:
<221> NAME/KEY: misc_feature
<222> LOCATION: (76120)...(74207)
<223> OTHER INFORMATION: ORF: 64r
<220> FEATURE:
<221> NAME/KEY: misc_feature
<222> LOCATION: (76749)...(76186)
<223> OTHER INFORMATION: ORF: 65r
<220> FEATURE:
<221> NAME/KEY: misc_feature
<222> LOCATION: (77698)...(76799)
<223> OTHER INFORMATION: ORF: 66r
<220> FEATURE:
<221> NAME/KEY: misc_feature
<222> LOCATION: (79343)...(77709)
<223> OTHER INFORMATION: ORF: 67r
<220> FEATURE:
<221> NAME/KEY: misc_feature
<222> LOCATION: (79816)...(79367)
<223> OTHER INFORMATION: ORF: 68r
<220> FEATURE:
<221> NAME/KEY: misc_feature
<222> LOCATION: (80529)...(79858)
<223> OTHER INFORMATION: ORF: 69r
<220> FEATURE:
<221> NAME/KEY: misc_feature
<222> LOCATION: (80774)...(80529)
<223> OTHER INFORMATION: ORF: 70r
<220> FEATURE:
<221> NAME/KEY: misc_feature
<222> LOCATION: (82815)...(80788)
<223> OTHER INFORMATION: ORF: 71r
<220> FEATURE:
<221> NAME/KEY: misc_feature
<222> LOCATION: (83835)...(82834)
<223> OTHER INFORMATION: ORF: 72r
<220> FEATURE:
<221> NAME/KEY: misc_feature
<222> LOCATION: (83874)...(85583)
<223> OTHER INFORMATION: ORF: 73
<220> FEATURE:
```

```
<221> NAME/KEY: misc_feature
<222> LOCATION: (85535)...(84402)
<223> OTHER INFORMATION: ORF: 74r
<220> FEATURE:
<221> NAME/KEY: misc_feature
<222> LOCATION: (88096)...(85574)
<223> OTHER INFORMATION: ORF: 75r
<220> FEATURE:
<221> NAME/KEY: misc_feature
<222> LOCATION: (87759)...(88667)
<223> OTHER INFORMATION: ORF: 76
<220> FEATURE:
<221> NAME/KEY: misc_feature
<222> LOCATION: (88920)...(88642)
<223> OTHER INFORMATION: ORF: 77r
<220> FEATURE:
<221> NAME/KEY: misc_feature
<222> LOCATION: (91652)...(88938)
<223> OTHER INFORMATION: ORF: 78r
<220> FEATURE:
<221> NAME/KEY: misc_feature
<222> LOCATION: (91667)...(92674)
<223> OTHER INFORMATION: ORF: 79
<220> FEATURE:
<221> NAME/KEY: misc_feature
<222> LOCATION: (93466)...(92681)
<223> OTHER INFORMATION: ORF: 80r
<220> FEATURE:
<221> NAME/KEY: misc_feature
<222> LOCATION: (93761)...(93486)
<223> OTHER INFORMATION: ORF: 81r
<220> FEATURE:
<221> NAME/KEY: misc_feature
<222> LOCATION: (94060)...(93788)
<223> OTHER INFORMATION: ORF: 82r
<220> FEATURE:
<221> NAME/KEY: misc_feature
<222> LOCATION: (94238)...(94080)
<223> OTHER INFORMATION: ORF: 83r
<220> FEATURE:
<221> NAME/KEY: misc_feature
<222> LOCATION: (94508)...(94242)
<223> OTHER INFORMATION: ORF: 84r
<220> FEATURE:
<221> NAME/KEY: misc_feature
<222> LOCATION: (95571)...(94498)
<223> OTHER INFORMATION: ORF: 85r
<220> FEATURE:
<221> NAME/KEY: misc_feature
<222> LOCATION: (96187)...(95600)
<223> OTHER INFORMATION: ORF: 86r
<220> FEATURE:
<221> NAME/KEY: misc_feature
<222> LOCATION: (96202)...(97665)
<223> OTHER INFORMATION: ORF: 87
<220> FEATURE:
<221> NAME/KEY: misc_feature
<222> LOCATION: (97915)...(97643)
<223> OTHER INFORMATION: ORF: 88r
<220> FEATURE:
<221> NAME/KEY: misc_feature
<222> LOCATION: (98251)...(99537)
<223> OTHER INFORMATION: ORF: 89
<220> FEATURE:
<221> NAME/KEY: misc_feature
<222> LOCATION: (99537)...(99974)
<223> OTHER INFORMATION: ORF: 90
<220> FEATURE:
<221> NAME/KEY: misc_feature
<222> LOCATION: (100001)...(101140)
<223> OTHER INFORMATION: ORF: 91
<220> FEATURE:
<221> NAME/KEY: misc_feature
<222> LOCATION: (101168)...(104650)
<223> OTHER INFORMATION: ORF: 92
<220> FEATURE:
<221> NAME/KEY: misc_feature
<222> LOCATION: (106354)...(104795)
<223> OTHER INFORMATION: ORF: 93r
```

```
-continued

<220> FEATURE:
<221> NAME/KEY: misc_feature
<222> LOCATION: (107947)...(106400)
<223> OTHER INFORMATION: ORF: 94r
<220> FEATURE:
<221> NAME/KEY: misc_feature
<222> LOCATION: (108256)...(107990)
<223> OTHER INFORMATION: ORF: 95r
<220> FEATURE:
<221> NAME/KEY: misc_feature
<222> LOCATION: (108719)...(108300)
<223> OTHER INFORMATION: ORF: 96r
<220> FEATURE:
<221> NAME/KEY: misc_feature
<222> LOCATION: (109679)...(108738)
<223> OTHER INFORMATION: ORF: 97r
<220> FEATURE:
<221> NAME/KEY: misc_feature
<222> LOCATION: (109861)...(109682)
<223> OTHER INFORMATION: ORF: 98r
<220> FEATURE:
<221> NAME/KEY: misc_feature
<222> LOCATION: (110830)...(110033)
<223> OTHER INFORMATION: ORF: 99r
<220> FEATURE:
<221> NAME/KEY: misc_feature
<222> LOCATION: (110208)...(110417)
<223> OTHER INFORMATION: ORF: 100
<220> FEATURE:
<221> NAME/KEY: misc_feature
<222> LOCATION: (110469)...(110651)
<223> OTHER INFORMATION: ORF: 100a
<220> FEATURE:
<221> NAME/KEY: misc_feature
<222> LOCATION: (110915)...(111397)
<223> OTHER INFORMATION: ORF: 101
<220> FEATURE:
<221> NAME/KEY: misc_feature
<222> LOCATION: (111419)...(111913)
<223> OTHER INFORMATION: ORF: 102
<220> FEATURE:
<221> NAME/KEY: misc_feature
<222> LOCATION: (111949)...(112485)
<223> OTHER INFORMATION: ORF: 103
<220> FEATURE:
<221> NAME/KEY: misc_feature
<222> LOCATION: (112593)...(113450)
<223> OTHER INFORMATION: ORF: 104
<220> FEATURE:
<221> NAME/KEY: misc_feature
<222> LOCATION: (113323)...(112967)
<223> OTHER INFORMATION: ORF: 105r
<220> FEATURE:
<221> NAME/KEY: misc_feature
<222> LOCATION: (113526)...(114152)
<223> OTHER INFORMATION: ORF: 106
<220> FEATURE:
<221> NAME/KEY: misc_feature
<222> LOCATION: (114199)...(115236)
<223> OTHER INFORMATION: ORF: 107
<220> FEATURE:
<221> NAME/KEY: misc_feature
<222> LOCATION: (115353)...(115787)
<223> OTHER INFORMATION: ORF: 108
<220> FEATURE:
<221> NAME/KEY: misc_feature
<222> LOCATION: (115859)...(116551)
```

```
<223> OTHER INFORMATION: ORF: 109
<220> FEATURE:
<221> NAME/KEY: misc_feature
<222> LOCATION: (116729)...(117523)
<223> OTHER INFORMATION: ORF: 110
<220> FEATURE:
<221> NAME/KEY: misc_feature
<222> LOCATION: (117572)...(117114)
<223> OTHER INFORMATION: ORF: 111r
<220> FEATURE:
<221> NAME/KEY: misc_feature
<222> LOCATION: (117423)...(118085)
<223> OTHER INFORMATION: ORF: 112
<220> FEATURE:
<221> NAME/KEY: misc_feature
<222> LOCATION: (118968)...(118375)
<223> OTHER INFORMATION: ORF: 114r
<220> FEATURE:
<221> NAME/KEY: misc_feature
<222> LOCATION: (118508)...(119119)
<223> OTHER INFORMATION: ORF: 115
<220> FEATURE:
<221> NAME/KEY: misc_feature
<222> LOCATION: (119588)...(120202)
<223> OTHER INFORMATION: ORF: 116
<220> FEATURE:
<221> NAME/KEY: misc_feature
<222> LOCATION: (120314)...(121231)
<223> OTHER INFORMATION: ORF: 117
<220> FEATURE:
<221> NAME/KEY: misc_feature
<222> LOCATION: (121380)...(123920)
<223> OTHER INFORMATION: ORF: 118
<220> FEATURE:
<221> NAME/KEY: misc_feature
<222> LOCATION: (121288)...(122256)
<223> OTHER INFORMATION: ORF: 119
<220> FEATURE:
<221> NAME/KEY: misc_feature
<222> LOCATION: (122350)...(123924)
<223> OTHER INFORMATION: ORF: 120
<220> FEATURE:
<221> NAME/KEY: misc_feature
<222> LOCATION: (123962)...(125566)
<223> OTHER INFORMATION: ORF: 121
<220> FEATURE:
<221> NAME/KEY: misc_feature
<222> LOCATION: (125193)...(124591)
<223> OTHER INFORMATION: ORF: 122r
<220> FEATURE:
<221> NAME/KEY: misc_feature
<222> LOCATION: (125689)...(123935)
<223> OTHER INFORMATION: ORF: 123r
<220> FEATURE:
<221> NAME/KEY: misc_feature
<222> LOCATION: (123839)...(123297)
<223> OTHER INFORMATION: ORF: 123ar
<220> FEATURE:
<221> NAME/KEY: misc_feature
<222> LOCATION: (125652)...(126170)
<223> OTHER INFORMATION: ORF: 124
<220> FEATURE:
<221> NAME/KEY: misc_feature
<222> LOCATION: (126121)...(125699)
<223> OTHER INFORMATION: ORF: 125r
<220> FEATURE:
<221> NAME/KEY: misc_feature
<222> LOCATION: (126279)...(127769)
<223> OTHER INFORMATION: ORF: 126
<220> FEATURE:
<221> NAME/KEY: misc_feature
<222> LOCATION: (127851)...(128408)
<223> OTHER INFORMATION: ORF: 127
<220> FEATURE:
<221> NAME/KEY: misc_feature
<222> LOCATION: (128520)...(130076)
<223> OTHER INFORMATION: ORF: 128
<220> FEATURE:
<221> NAME/KEY: misc_feature
```

```
<222> LOCATION: (130105)..(131700)
<223> OTHER INFORMATION: ORF: 129
<220> FEATURE:
<221> NAME/KEY: misc_feature
<222> LOCATION: (131790)..(133283)
<223> OTHER INFORMATION: ORF: 130
<220> FEATURE:
<221> NAME/KEY: misc_feature
<222> LOCATION: (133246)..(133920)
<223> OTHER INFORMATION: ORF: 131
<220> FEATURE:
<221> NAME/KEY: misc_feature
<222> LOCATION: (133972)..(134370)
<223> OTHER INFORMATION: ORF: 132
<220> FEATURE:
<221> NAME/KEY: misc_feature
<222> LOCATION: (134418)..(134693)
<223> OTHER INFORMATION: ORF: 133a
<220> FEATURE:
<221> NAME/KEY: misc_feature
<222> LOCATION: (134402)..(134992)
<223> OTHER INFORMATION: ORF: R1
<220> FEATURE:
<221> NAME/KEY: misc_feature
<222> LOCATION: (134853)..(134419)
<223> OTHER INFORMATION: ORF: R2r
<220> FEATURE:
<221> NAME/KEY: misc_feature
<222> LOCATION: (135628)..(135897)
<223> OTHER INFORMATION: ORF: R3
<220> FEATURE:
<221> NAME/KEY: misc_feature
<222> LOCATION: (136780)..(137112)
<223> OTHER INFORMATION: ORF: R4
<220> FEATURE:
<221> NAME/KEY: misc_feature
<222> LOCATION: (137558)..(137022)
<223> OTHER INFORMATION: ORF: R5r

<400> SEQUENCE: 1
ggatccgcgg cttcgcgggc ggcggccggc tcccgcggcg gctgagccgc ggtgccgcga      60
cgaacgcgga ccaggagttc ctgcgggagg agctacggca gaggctggaa ctgctgaatg     120 cttttcgagga cgggcgtccg cgggaacgcg actccgcgga ggcggcaccc cgcagccgcg     180
agacctcgct ctggagtcag ggagtcaggg agtcggagt caggagtcg ggagtcaggg       240 agtcgggagt caggagtcg ggagtcaggg agtcgggagt caggagtcg ggagtcaggg       300 agtcgggagt caggagtcg ggagtcaggg agtcgggagt caggagtcg ggagtcaggg       360 agtcgggagt caggagtcg ggagtcaggg agtcgggagt caggagtcg ggagtcaggg       420 agtcgggagg tcaggagtc gggagtcagg gaaacagaag tccaagtagt acgggtgaga      480
caggagtcag gtggtcgggt gaccgcgccg tccgagtccc gcaaaaagtt tttagactct     540
gagagaggcc gacctgcctc caacggttcc gcggaaaagt ttttataaaa agttttcggg     600
agaggccgac tgccttccaa cggttcctcc tctcgcgtgc cgcgggcggc cgctctcccg     660
cgacggtccc gccaacgcgt ttacaaagtt ttaaaagttt tcgagagagg ccgacctgtc     720
ttccaacggt tgcgcgaaaa ggttctgcgg aggtttggaa gagccgcccg ccctccgaca     780
tcctccgaaa agttttcgca aaaagttttt aaaggtttcg cgaggagttt cgagggagg     840 cgacctgcct ccgaggttcc gcgtaaacgt ttttacaaag cgtcggaggt gggggcgacc     900
tgcccttcct ctcctccgaa aagctcttga gagtgtggga gaggcggccg gccttcgcgg     960
tcgcgcgaaa aggttctgcg ggagttcgcg ggagctgacc cgccctccgc gcccctccga    1020 aaagttttg cacgaagtct tttggcgttc tcgagaggac gcctacccg acggtaacgc     1080 ggaacgtctc gggaggtcgg cctctccgct ccgcggtcg cggcggcggc ccgtctccgg    1140
```

```
aggttccgcg aaaagttttta taaaaagttt tgagggaggt accgacctcc taaagtttta    1200
cagagagttc tcgcaaaagt tttgggaggt cgacctgacc tcctaaagtt atcgaagagt    1260
tctcgcgaag agttctcgca aagagtttga gaggccgacc tgcctccaac ggttccgcgg    1320
aaaagtttta taagagtttt gagagaggtc gacctacctt ccaacggttc cgcggaaaag    1380
ttttataaga gttttgagag aggtcgacct accttccaac ggttccgcgg aaaagtttta    1440
taagagtttt gagagaggtc gacctactct ccgaggttcc gcggaaagtt ttataaaaag    1500
tttttacaaa gttttgagg gaggtcgaca cctcggatcc tccgcctcgc gtgccgcggg    1560
cggcctccaa gagttttacg gaacgttctg gagaggagag gccgacctcc caaagatttt    1620
gcggaacgtt ttggagagga ggactggcct cgaaaagatt ttacaaagag tttggaggga    1680
ggactggcct ccaacggttc cgcgaaaaag ttttgcaaga gtttggagag aggtcgacca    1740
ccctccgagg ttccgcgaaa gtgtttgcgg agagtccgag agaggcagac actgcctgcg    1800
aaaagttttc gcggacggtt gagcgggtca ccgacctccg acagtttaca aacgttttac    1860
ggagagttag agaggcagca gaccgacctc cgaacagttt agttttacaa agttttggag    1920
ggtgaactgt catcgggaaa gttttacgaa gagttttggg agaggccgac ggttagccga    1980
gcgagcgcgc gagcgagttt acgttctctc gctcgtgtgc gcgttaactc gcactggttc    2040
cctctctaac tcggagtggg cgagcgagtg gttgactcgt cctccgctct cactctgagt    2100
ggtgataact gttaaccatt aactcgtcct ccactctctc actctctcac tctgagtgag    2160
gattgacttg ttaactcgtc ctccactctc tcgctctctc gctctgagtg agtgaggatt    2220
aactgttcaa ctcgtcaact cgtcctctgc ctctcatcca agactgagtg ggtagttgac    2280
tgctcttgtt ctcttactcc gagggggtgat tgagttagca acagctactc gttctcttgt    2340
tctctcacac cgagtgagcg agtgagcaac gttacttgtt ctctcacacc gagtgagcga    2400
gtgagcaacg gttaactcgt tctctcgttc tctcgttcta ttattccgag gagtggcgag    2460
tgaggtaacg gttactgtta cttgttctct gttcccttcc tcggtgagcg gtgcgtcaac    2520
ttgttctcgt gagtgagtac ggtcacttgt tctctcgttc tctacctcga ggagtgagtc    2580
aacttgttct cgtgagtgag ttgaccgtaa ccgttcccttt acctcaagtg agtgggcggtc    2640
gcttgttctc gtgagtgggt taaccgcgtt cccttaccgg agtgagcggg cgggcgataa    2700
aaataatcaa ttgactgatt cgctcgtgag cgagcgaagg gcggcggaca agggcgcggg    2760
atgctggtct aatctactaa ggccgattac aaaaacggat gggagaccgg gagggagagg    2820
gtcacagctc cgagcggtgc atccgcgcca gctggcggcg ccactcggcc gcgggccgcg    2880
gccgcccagg ccgcgttgta gccgcccgcc accgcgacgc aggtcagctc gaactccggc    2940
ccgagcgcgc gcacgtcgta gatgtgcacg gtcgcgacgt tcagcagcag cgcgccctttg    3000
cgcagcgagg cgaaggtcgc gtgcatgccg gcggcgagcg ggtacaccgg cgagagcgtc    3060
ccgccgccgt gcgcgaccac cgccatgtgc cgcccgtcgc cgccgacggt caggcaggtc    3120
accgaggcgg agccgttcgc gcggacgggg cccgcctcca cgagggcggc cggcagcggc    3180
ggcgccgcgg ggcggaagag cccgccgagg aggaagccca gcgccaccag cgcgagcgcg    3240
ccgagcagcc tgcgcggcga ggggtgcatg cttgttggct gcggtgttgg cgtctggcgg    3300
gtggaaggcg ggtgtggggt gtccgcggct gcggcggag ggtctcgact gctaggcggt    3360
ccttttttcac tttgctccgt ggcgcctggt ccggggcaag ggctgcgcg ggcgcccggg    3420
cgggcgggcc gctaccccgc cgcgcggccc gggccgcca gcgccgcggc cagccgccgc    3480
caccgcgggc ccgccgcgcg cagcagcccc gccgccgagc gccccgcgcc gccgcgggcg    3540
```

```
cgcgccgagg ccgcggcccc gcgccgcgcc agcagcagcg gcagccgcgc gtccagcggg    3600
ccgccgcggc gcagccgccgc gcgcagcagc gccgccagcg gcagccgccc cgccgcgtcc    3660
gggcccgccg cgcgcgcgcc cgccgccagc agcgcgcgca ccagcgccgg cgagggcgcc    3720
gcgcgcggac caggtgctcc acgagcaggg tggtgagcaa ggattctcga aagtaggag     3780 tcatgtgtga cgacaaggag agacgttata ttaggcgcgt cctacttcac tttgaagatg    3840
gtgtaaagtg ttaaaacttg aacaccgttc actccaccac tgccgttacc gtgtcctgcc    3900
ccaaaagcaa ccacagtgct ttttccacca cctgttccaa atccgttcca aaagctccca    3960
tccattgttg ttagaacttt cagatgtttc tctaggttgt ttagttccac tgcaagtttc    4020
gaccattatc gttactggac atgctgttgg taatgagttt aataaccaat cataaaata    4080 gttataattt gttataaagc taataaagta gcaaacactt taatgttata ttttgcctaa    4140
ccctccgtta acaccaccat taacaccacc acttaagctt ttactaccac cactaccacc    4200
tccaacacac attcttttct ctaaaggtcc ccaaattcca cctcctgaac ttggacgttt    4260
tacagcacct ccgggtgtac ttgcgtaccc tttagaagtt ccactgtgac tgtagatatg    4320
atactgtcct tctccaggca tgattaaagt gtgttgtaat tagtgttatc tacgcaactg    4380
tgcgagactc tcgaataaaa agaagctaca ttttacaatt ttgattagct gatgtaccac    4440
gctgtatcgc ggccaccaca agcacccgat ccagtagaac caaatccaga gtcgccgcgg    4500
tcagtgttgt ccaagcagtt aacctcttga actgctgggc acgatatgcg ttcgcatatt    4560
agctgagcta tcctgtctcc cttcttaacc tcaaagtcac tgtttccaaa gttaaacagc    4620
accactccga cgttgcctcg gtagtcttcg tcgatcacgc cagcgcccac gtcgataaag    4680
tgtttgactg caaggccaga acgtggtgct atgcgtccgt agcaaccaga agggggcttt    4740
atcagaaggt cagtaaatac tacgcgactg caatgcgaag ggatgacaca gtcgtatgca    4800
ctacataggt ctaatcctgc ggcaccagga gatcctctgg ctggtatagt ggcgttttgg    4860
ctgaggcgaa caacctgaag agtttccgtg tggcagaact ccatggctag ggtggcgagc    4920
ggccgatcga ctacggggtg tacaatttac actttctcca gaaaaatcag gggcgggtca    4980
gcatggcgcg gcgcaagtcc agcagcgagt cgtacgacga gaagcacagg atggaggtca    5040
cgatctccgg cggcagggcg cacgggcaca tgaggccggc gatctgctcg gccagcgaga    5100
cgcgcagccg catcatgcag atcttgccga agagcgccgt cccgtagatg gggaactcgg    5160
ccgcgcgctc caaaaaggcg ttctgcacga agagcgcctt cgcgtcgtcc gacgcgcgca    5220
gcacgtccaa cagcgtcgcg tccgtgtggc agcgcaccgc gcgcatgctt gcgatctcct    5280
gctcgcacgc gcggatcacg gtcgcgtagt ccgccagcgc gcgctccgcc agcatgcgcg    5340
cgccctcgcc gcgcagcgcc agctcctgca cgcacagcag cgcggcctcc gagcgtcgga    5400
acacgtggcc ccattgctcg gatgtgatca gcgcgcgcgc gagcagctcc gtcggcggcc    5460
ggcgcgcgag cacggccgcc gtcgcgcgca cgttgttgcg gcgcagcatc tccgaaaccg    5520
cgcataggcc cgaggccgac atgtgctcga gctccgcgcc catgcgcacc agccggcagc    5580
aggcgccgtg gctgaacacc gccgcgcggt gcagcgcgt ctgcaggttg ttgttgcgca    5640
ggttcaggtc cagcccgcgc tcgagcacga agtccacgac gccgcgctcg cagctcccgt    5700
aggtcgccat gtagtgcagc atggtgttcc cacacgcgtc tacggcggcc gggtccacgc    5760
ctaggcccgt gagcgtgcgc accatgccct cggagatctt ggccgtgcgc gcgaggtggt    5820
gcagcgttgt gcgcccgtac gcgtccacga cgcacgcgtc cgcgcccgcg cgcagcatca    5880
```

```
tgtccacgag cgcggcggag acgccgccgg agcacagcag cgccgccagc ggcgtcaagc    5940
cgttgcagtc gcaggcgttt gggttcgcgc cgcgctcgag cagcagccgc agcacgtcct    6000
cgcggatcca ctggttcttg cgtacacgt  gcagcggcgt tacgccgtag gtgttgccct    6060
cgttcacgcg cgcgccccgcg tccagcagca gccgcgcgac ctcgagctcg cgccgtcgg    6120 ggccgcagaa agccaggaag gaggagagca cgctgtcgca gacaacgacg ctggcgtcgc    6180
agaccacgtc cgcgcccgcc tccagcatga gcgcgaccac ctccggccgc acgccgtcgt    6240
actgcacgta ggcgtgcagc ggcgtgcggc cgcaggagtc cttggctttc acgtccgcac    6300
cggcctccag cagcacgcgc acgatctccg cgcactgctc gtgccgcgcg aagtgcacgc    6360
agaggtgcag cggcgtgcgc ccgtgctcgc cgcggaagtt cacgtctgcg tcggtggcta    6420
cgagcgcgcg accgtttcg  aggtccacct gcccggactc caggtagcgg aagagcaggt    6480
ccgcgtgcgg gaccacgacg gactcccgcg agagcatggc ggcgtttaca aatattgaaa    6540
tcttttttca ctcatcttta tggcgctgaa cgcgcaataa gggtgagagt aaaaaacttc    6600
tacaaaaagc gtacaaaagg tacaaaaggt aaaaaaggcg gggcggggac gggctggggt    6660
gctgcgagct gaattggcct ctacacaggg acgccctcgc cggagccggt gagccggtag    6720
ccggcgccgc cgatcatggt caagcgctgc acgagctcgt tgcgcttgac gccggcctct    6780
gaaacgcaca ccatgtggtg gatgtaccgc tcgatgcact cgcagcgcgg gagagtggag    6840
tcaagatcgg atgcgagttg cagaatgtca tcccagagct cggagaactt gctgtacagt    6900
tctcggaggt ctctctccat tcgagccgta agagagtcag gatgcggtgt ccttcggga    6960 gtctgagcga acaccgcgaa caggctggtt atgccgtgtt ctagaataga gtggttccgc    7020
gttaatgccg cagacaaggg tcgtcgtccg cgcaacgact ggcggcagag cgctgtttgt    7080
gccgcaccgc ccattcctct ggcgatcgca tccaccgacg cagtgatcat ctgcgcgccg    7140
acgtcattgt agcgcgcgtt aaactcagta atcatgatta cgagattgca gatttcatag    7200
tagcactttt ccaagtcgac gcgcagtttc acgatctggt tgacaatctt gcacgccttt    7260
cgccgcgtct ccgccacgtt ggcgactcgg acttgcgctt cctggtcgat ggacggcgga    7320
aacacttcaa acccaaggtc gcacagttca gcggtgggga ctagcgtcac gatgatgtac    7380
tccgcatcgc cacccacttg cggcaggaag aacaccgacc gcgcggcggg aacgaccaga    7440
acgtcgcctt cctgcatgtt ggttttttaga aacttagtgt tgttcacgga gatgccggcc    7500
atgccctcgt ttttgacaca tattatggtg acgtacgcgg cgaccgtggg ggccatgtgg    7560
tggcgcatgt accactcgtc gtgccttgagt ttcagaccgt gagattcgcc aacctcgaag    7620
tgcatgttgg cgtctctgac gtagcgcgag aactcgctgc gacagattcg cgcgggcgcc    7680
cggtggaacg tcgactcgaa gagactgatg gctgtccatt cgcccacatg agtgaccacc    7740
gaagaagtgt tttcgatccg agtctcgaac accgagtcca cgagcaccgg acagttggtt    7800
ccgggcaccg tcagcaccaa gggccgcgcc tccacgggg  cgacgacga  agccacggag    7860 tcggtgtccc cgtacccgta gtcgtcgtcg gagtcgccgc ctccgtcggc ccgtcgcgc    7920 ggcctccgca gcggcatgca gccggcggtg ggaacgcact ggtttcggcc acggccgaag    7980
cggccaaaca gtctcgccag ggctgacatc cttggacggc cacaccaaaa ccaaaaaaac    8040 atatttatc  agttatttgt cgattttcac cggctcaccg agggcaggac ctcctggatc    8100
ccggacaccc ccgccaggca gcgggccgcg cgctcgcgca cccaaaagcg gtcgtagccg    8160
tgccggagca cgaaggccgc cgtggcgtgg cagtccacgc gctcgatgaa gccgtggacg    8220
gcgcggcgcg cgtagctcgc cgcgaaggcg cggaccaccg ccgagcagcg ccccgagggc    8280
```

```
gagtcgtccg tctccagcgc cagcggcatg ctcgcgatgc gcgacatcag gttggaggtc   8340
tgcgggatgt tgagctcgcg cgtggcggtc atctgcgcct cgagcccggc cttgagcacc   8400
tcgtcgcagc ggccccactc cagcgcgcag accacgcgga tctcgtaccc cttgagccgc   8460
agcgcggtct cgatgtccac ggaggtgagc accgcgctga agcgcaggcg ctcttcgtcc   8520
gcggggtcga agagcacggg gatcttaacc tccgcgctgc gcgtgacctc gcagagcgcg   8580
atcgcgagca gcccgcgcgt gagcttgctc accatgcgcg gcttgcccac ggggtacagc   8640
tggctcgcga cctcgcgcag cgggtacgcc agtcggaagc agcgcgcgtc cgcgggcacc   8700
gggctcgcgc ccgtctcctc gaggaagagc gcggcctcaa ccatgttcag cgcggagaag   8760
tgcaccgggc aggcggcgca gccgcgcgcg gcgttcgcga gcaccatctc gcgcagcccg   8820
cggaaggccg ccatgtcgca ggaggggaag atgcgcgcga gcgcggcctg gtgcgcgagc   8880
gccgcgtccg agagcgcctg cgcgccgcgg cggcgctcct cggcggcggc cgcgctctcg   8940
tccgcggaga ccacgtcttc gggcacgtcc acgcagacgc cgccccagaa ctcgcagtac   9000
tcggagaaga gcgtcgcggg cgcaaagcgc gcgaggtcca cgaaggcgac gcggttgccg   9060
agcctggaga gcagcgtgtt ctccgagatg cgcgtccagc ccttgccggc gagctccatg   9120
acctgccgcg tgtcgaagag ggagctgtag aagccgtaca cggtgatgtt ttccttgcac   9180
gtcgtcagcc acatgaggaa gtcgcgcacc accagcttcg cgcagtctcc ggagaacacg   9240
gggccggcgt tcgtcgcgat ggagttcagg cgcacggtgc cgtcactgcc gaagcggtac   9300
acgaaccagg cggccacgct gttgccagag ggcgtgtgaa cgtgtggctg cgcccaggag   9360
tcggcgctcg cggcggtgcg cacgtcgtgc gagagcacct cggtgtcggg gcgcgagtag   9420
gtgctggggt ctttgatcca gatggcgtag ctgcccacgc agcacacgtt catgaggtcg   9480
agcagcgtct gccggcgcag cggcgtgccg agccggcgca cggcgtcgtg cgagaccatg   9540
cgcaggtcgt agaggcccac gtccgagagc cactggttga gctcgtccat ggacagggcg   9600
tcgcgggggg gcgggctgtc ttcgaaggcg gcgcggagct cgggctccgt ctccgcgcgc   9660
tgccgcagga tgtccaggaa ggggctggag gagtcgggga tgtagcagtc ggggtcgtgc   9720
ctggacacta tagcgaaccg ctgcgtcgcg ggcggcgggg ctagcgcgtc ggcgcgtgcg   9780
tcgatgaagg tgcacgatat acgcacggac ttgagcgagg ggaggacgac tgcggcggcg   9840
cgcgcgccct ccgcgtcgaa gatcatcgtc tttccgtccc tcgcctttgc gagcgcgtat   9900
tctccaggca cgaggtccgt cggcggcggc tcgtcccagg cctgccggtc agggacgccg   9960
ccgcacacct ttccccagaa ccccagcatc ctccaaaata cctataagga cggccaatag  10020
cggggcttgc gggcgttcgg accttccgcg ctttaatttt aatttattgg cttgcagaac  10080
tccgagcgcc agtccgctc gaagaccgcg gacaggtcct tgacgatgtc gcccttctcg  10140
gcgttcacgc tcacgaaggc gtggtagcgg tagtgcgtgc cgtcgaggtt ggcgaccgtg  10200
aggtgcgcga aggtgtcgtc cacgatgagc agcttagtgt tgttcgcggc gtcgtcccgg  10260
ccgggtacca cgaacttgcg cacggacatg tccacgctgc cgacgccaaa gtcgtcgagg  10320
ctgcgcgcgg ccgagaccga aagcgggtcc gcgttcttcc actcggtaat gatcacgcgc  10380
acgcgcacgc cgcggttgat ggccgcgcgc agcagcgcgt caatgatctg cggccagtac  10440
tccacggcgc tggcgtgctt gatcaccggc accatcgaga gcagcgagag gtcgatgctg  10500
ttcttggcgt tctcgatgcg gtgcagcacg aggtcctcgt cgagcgtgcg gtagaagcct  10560
aggaagcgct ccggcgagtc cgagaagaat acgccgcccc cggagtggtc gaggtggaag  10620
```

-continued

```
ttcgtggccg tgggcgtgac gatggcgcag cagagccgcg tgaacggcac cttcggctcc   10680
acgatcatgg agtagaaggt gttgtagcgg ttcatgaggt cccaggccag gtgcttgttg   10740
gtggagtaga gcccgaggtt cttgatggtg acacggacc cgcccgtgag cgaggcgctt    10800
cccacgtacc agtgcccggc gtccgagagc cagaagctgc cgagaaggtt gccgacgccc   10860
tccttggtgg acaccttgac cttgtagtag ttgacgcccg cctcgcgcag ctcgtccgcg   10920
tccttgtcct tgctctgcac gtccacgagc agcgtgacgt ctacgccctc cttggcgagc   10980
gtgcagagct tgtccttgac gtcgacgccc tccttggtgg agctcaggtt gcagcagaag   11040
ctgcagatgt acaagaactt cttcgcggac tcggcgatag cggtgaagca gtcgagggtg   11100
ctcatgttgc cctgcgccaa agacgccacc tctgcgggca gcgtctccac gacgcggcag   11160
tcggcgccca gggggatgga ggagaacggc cacatttatt tatctcacaa aaataatagg   11220
gcttcaggga aagtctttta gcaggcgggc gagttcttcg agttcgctta ggagttcttc   11280
catttcttcg gaagtcagca actggagctc ggacttgatt tgaatatctt cgaggaaacc   11340
gtctagcatg ttcgccatgt cttccgggga gcactgcgcc acatcttcgg ggacaggatc   11400
gggtgtgggc attaggtctc cgcttacttg aacgtcgtcc atcatcctgt cgatgaggtc   11460
ttcgacttct agacggggtc cgtagatcag catatttggt gatggaggta gtttaaggtg   11520
cgagagttag tgttatacga ccgccaacgt gtgtttatcg cgcgtacatt ttcaataatt   11580
aacaaactcc ccttcctgcg cctgctcgag aagcagctcg tccagctcct cctgtcggcg   11640
cgcggccacg cgtctttccg cgaagagtac catcagctcc agcccacgc cgcacagacc    11700 caggacgccg aacaccaccg ccgccgagat cgacagaccc agcagcaccg acatcctcac   11760
gcgggcatcc ggctatttaa tcgttctgga aacgtattaa tatgggcgtc gtcatgtgcg   11820
ggtgtctgtt tgtgtgggcg ggctggatcg cgcgccgcgt gcgcggcctc tgcgcggcgc   11880
tgcgccagag ggtgtcgcgc gacaagggct acgtggccgt catccagacc tgcgacgacg   11940
actacttcac agaggaggag ttcgacgacg gcaagcaggt ggtcgcgctc ctgcgcgacg   12000
tctcgcgcgt ggttgccgcg cccgcgggcg tgacggaata agttaggata aggagtcgag   12060
gggagaaaaa cagcggtcac actataaact cgcgcgaggc cgattttgac gtgctcatgt   12120
ctggaagctc cgctttctgc agcgcggagc ggcacacgaa gcacacttcc gtgttggtgg   12180
gagttatgca gtggacgtgg tagccgtgcc cgcacaccat gacttggaac ggacacgcgc   12240
cgggacaggc cgcgtttatg catccttccg gcgagcgctt gttgcagatg tagcacacgt   12300
ctgagcacgc cagcgtgcag gacacggcca gcttccactg cttaaccttta acgggcatgg  12360 ctagttgaac acgaccatgg gcgagtcgcg agcctcgagt cgggggttca gggcaaaccg   12420
tttcacgccg tcaacggttc ttctctttgc aattttctct ctgcacaggc tcgtcagcgt   12480
catctcggcc aggcgcgcgt cgttgcctag gtgccgcgcg gcgtcctcga ccgtcacgcc   12540
cgtcttgccg gcctcgtcca tgagcacaat gcataccagg tgcgcgctag agcatatgac   12600
ctcctgctcg cgcccgccgg cagcggggat ggttagctcc gcgcgcccga aggccgccag   12660
cggcgccacg tcgtaggcag tgtctgctcg ggcgagcgcc gactccacgg caccgcggag   12720
cgactccggc ggcgtcagcg cggccagcgg caccggcgtg gcacggtgt acacgttcac    12780 gggcatgagc accatctccg ggtcgtggtg gccgctctct tcgccgtcgt gctccatggg   12840
ctgcggcggc ggcagcagcg ggagcagcag ccgtccggac atgagccggc gcacaaggtc   12900
gttgagcgcg gacgaggcca tcggcgggta cagctccatg ccagcttca gcgataggtg    12960 cttctcgagg ttgacgccgg tgtagacgct cttcacgatg cgcgcgaagg ccacgcgcgc   13020
```

```
gaaggccgcc agctcctcgc gcggcaggcg ctcgatgtag gagagcagca tgtcggtgtc    13080
gcacggcggc gccgcgacca ccgcgccgta gagcgccttg cccgagagct tttccagcgc    13140
ccttgcgtgc aggccgtggg tcttgagcac gtccacgtag ttcacgtaca ggcagagcgc    13200
gcgatcgagg ttgctctccg cgacgtgcgt ctcgatgcac tccacgatga gcgggcccat    13260
gcggtccttg atgaggtcta tgagcccgcc gtaggcgact cgcgcgctca tgaggcacgt    13320
gcggcagtac gccatcaggc cctcgaggtc cgcggctatc acgtcctcga ccacgttcgc    13380
cacgacgcgc tgccagagcc gcaccttgct cacgttctgg tgccgcacca tgtccacgag    13440
ctcgtcgtac gagccgccgg gctcgtgcgc gcgatcgacg atgcacctcg ccatggtgcg    13500
gctctggcgc atgagctcgt tcgtgaagcg cacgcacgcg tcctcggaga gagcgcgct    13560 caggcaggag tagcagcggt ccgcgacgag gtgcgggaag cggcactcca cgacgccgcg    13620
gccgatccgc agcacgcact cgccgtacat ctcgtccatg gcctcgcgca gacagtcgtc    13680
cagcacgtcc gcgttgtgcg cccactggat cacgcagagg tagggctcga tgttctcgcg    13740
cgcgttttcc acctcctgca ccatgtactc gagcacggtc atgtcctcgt ggatgtcggt    13800
gcccagcatg cgcccgggcg gcagccagct cttgcgcgcg atcgcctctc gcaggcacgc    13860
caccgccgtg aaggtgttga cgcggagctt ggtcagcagc cgccgcagtc gggagatgtg    13920
tgccacggag aggtccatct ccatggcctg ggcgatgagg cgcgtgagtt cctcctccat    13980
ggcggcggct ccgcgggcag atatacgcga acaacggtaa gccgtgctat ttcatttttg    14040
gacaaaaagc tagtcgtcga cgcgcatgtt gtcgaggttc cggcacagcg agagcacgtc    14100
gtcgcgcgcg cgcctccggc gcagttgatt gttcgcgcgc cgcgcgtccg cgagcgcctg    14160
tctgtacatc gcggagtccg cgtacccgtg cagcggcgag cgccgagcgc cgggcctcgg    14220
gctcgcgcgg cgcgggagcg gcgttggcgc gcgcctcgag cgccgcgcga agtgcgcctg    14280
catggccagc aggcaaccga acggcaccat gtatcggtcc atgaggcact ggctggccgc    14340
ggacggctcg cgcgggtgca tcacgccgcc gcccacgtcc tccatgacgt cgcgcagcac    14400
gcagcgcagc atggtctcca tgctgcgctg cgtgaaccgc accggggagg cgtcgacgta    14460
gaagccgtcg gccacgaagt agagcgcgtc cagcccgccg agtttctcgc cgagaccgac    14520
gaagagctcg tccacgtgcc agtccaccac cgaggccttg aagagcacca cgtgccggat    14580
gtcgtgcgag cgcgcgagct cccaggtgtc ctcgccgatg ttgctggcgt cgatgcggcc    14640
tgtcatgcgc acgctcacgc acggcgtcat cccgttcttg tagcagaact ggcgcgcgag    14700
ctcctcctgg cgtacgatgt cgaccatgct ctccatgaag gaggtggaga gcagcatcgc    14760
gccgcgcgcg gcgcgggtcg cgttttcgtc cacctccact tccatcccgc cgccgatcct    14820
aatcatctat cgtatttaaa ttttcggcgg agcagacacg cggctgctcg ctgcgcgatc    14880
gcttcagccg cggcggcgtc acgcacgcgt tgcggcggcc ggcacgcacg gacgaccgcc    14940
ggggctgttc gctgagcgag cgccgcgcc gcgtgacgcg acagtcgcag gtgggttgcc    15000
gggagtcgct cgcgcgcctt cttcgcattt cgccggaacg ccgcgtttat gtaggggatt    15060
atattttcaa cgtaactaaa tggacggggg cgtgcacaaa cggcctttca tcgtgaacgt    15120
ggatggcatg gcaaggtgc tcgtgctccg gtacttgcgg atgtgcgagg tgcccgaggc    15180
caagtgcgag gggtcgcgcg cgtcctgcgt gctcaagatg gaccctcccc gctcacccag    15240
ctgcgagcgc aggccgtctc tcccgccgtc cccccatgc cccatgcgca cgcctcccgg    15300
gtcgccgctc caggctccct tgatgcgcac gcagatgctc caggggctgt tcgacgctgc    15360
```

```
caaaaacaac ggcgagcaga tgtgccgccg ccagtaacct aggctgcgca gtacgaaagt   15420
tagtgcgtga tcacgttttt tgcaatgtcg atcacgccgt gcgtgcccgt cttgcgctcg   15480
cgctccacca cgctagtcac gggccgcgcg tccgagacta gcgaccccag catcgagcgc   15540
acggcgccct ccgcggcggg gtggcgcgtc agcagcagga acatcacgat gtgcgcggag   15600
acgccgcgcc ggctcagatc gtgcacggcg tcgccgtcca tgagcacggt gttcgagaag   15660
tacgtgaaca gagtgttgtc tcgcaccagg aaggccgagt tcgagacgct ctcgaagtcc   15720
acgatctcgt cgtcctgcac gcccatgtcc aacagcgtct gcacgagcgc gggctcgtcc   15780
aggaacacca ctgcgcgcgc gaacccgcag tccagcgcgc gcgcgtccgc ctccaacacg   15840
cgcgaggcgc cgccctccgg cggcaggaag gcgcagggca gcggcgtgcg tccgtccgcc   15900
ggcgcctccc cgagctcctc gagcgcgaag gccagcagcg tctccatgcg cgcgcgcgcc   15960
ttgtcgaagt tgtccgcgag gtcgcggatg cggtctgtct gcgagaacat cttcagcatc   16020
gccatgagct gcacgaaggg gtgcagcacg tatatgttgt ccacgagcag cgtgggcagc   16080
gcgcgcagcg tggcctgccg cacgttgaag ctgtccagga tgtgcccgcc ctcctcgtcc   16140
tgcagcacca cgtagttctt caggtagggc acgcgcagca gcacggtctg ccgccccgtg   16200
acgaagtata tcaggaaggc gaggttgatc aggaacgggc gcgcgttcgt ctgcaccatg   16260
tcgatgtcgc cgtactctat ctcggggttc agcaggtgca gggcgtacga gccgtagcac   16320
acgcaccgct tgttgtgtcg gcgcaggtgc tccttcacga gccgcttgac cacctccacc   16380
aggtccgagt gcttgtgccg cgccatcggc gcggcctcct cgggcggcgg cagcactgcg   16440
tacgagttga gcgcgcggct ggcgagcgcg cgcgcgcggg gcgcgtccac gcgccgcacc   16500
gccgcgttga ttgcaggcgt cggcgtcgtg agagagccca gcgtgcgcgt gaactcgctc   16560
acgatcacgc tctgcagctc cagcaccgtc aggatctggc ccagcttctc caggcgccgc   16620
tgcctcgaga agtactcctc gatgcgcgcg gcgatctcct tctcggagcc gcctagcttc   16680
ttgaagaagc gacgacgact ctttacaaca agagagagaa aaagcttcct atcgaagttg   16740
aggacgcggg tcatgttgcg gcgctgcgcg cgcaggagca cgcagcgctc catggagggg   16800
cgcgagccga ggtactcttc gatcacgggt ggagccatga cagctatttt ctgaacccgc   16860
gattattgta cagcgcaagc cgcgcgcaga cctgctggca cagcagcgtc gtgtttcgca   16920
tgcacacgcg cgaggactcg atcgtgcgcg cgtccggtgc ccaggcgcgc agctccatca   16980
gttcctgctc gacgaagtcc acgggctcca cgaagcgctc tgcgcagagt ccgtccgtga   17040
acgcgttgac gatctgccgc acgagcacta ccacgtccac ctgctccacg aggcgcacgc   17100
ccatggcgac gtgcacgaag aggcagcgga agagcgcgtc catggccatc tggtggtccg   17160
agcagggccc gaccgcggtc ttgcagccca gcgcgaagcg cccgatgccg cggtactgca   17220
ccatctccga gggcgagaag gagagccgct ccatcttgag cacgggcggc gggcccgccg   17280
gcagtccgcg cgcgaggtcc agcaccggcg tccaccgggg cgtgaacatg tccgggatca   17340
ggaagagccc gtagctggcc atgcgcgcga tgtcgaaggc gtggtccacg accttgttca   17400
cggcgctgtc cgcgcggttt acgcgcagcg cctgcaggat cacgtttccg gaagcgtgcc   17460
gcgtgatcgc gaggtccgcg gtcgcgtacc cgcgcaggcc cggcaccgcg tacgcggtca   17520
gacacacggc caggcgcgcg ctgtgctccg aggagaagat ctcctgctcg tagccctcct   17580
cgggctcctc gcactcgcga gggcgccgca cgtcctcgac cgagcgcagc cgcatctctc   17640
cctccgacac cagacagcca agcgactccc tcaccgccgg cgcgagcacc tccgtggcgc   17700
agagcgcgtc gtgcacgcgc ttgagtgtgt tcggcttcag cgcgtagccg aagagcagcc   17760
```

```
gcgtcatccg cgagcccgag aacgcgaagc ggcgcacgta ctcctccgcg agctcggggc   17820
ggtcgttgat ccacgaggta gagaagacgt ggtcggaggc gaagggtct gcaccaaccg    17880 cgagcagtgt ggacagaggt acggtgtcga ggaagtccac gacgtcgggg aagttctggc   17940
gcacgcaggc ctcggcgacg cgtctggtgt gcacgcacat gtcggtgacg ggcacccggt   18000
ggccggactc cacgacggac acgcagacgt cctcggtgac ggcgtccacg ggcatggtcc   18060
gcagcagctt gccgagcacg tcgccgaacc cgccctcgag cgccttgcgc cacacgaacc   18120
ccgcgtcgaa cttcccgggg aagtccgcga tcaccgaaag ctccgcgtgc gagaggttgt   18180
ccacgttgag gtaggtggcg gcgtccacga agatgggccc gaaggcgccg gtgtcggaga   18240
cgcggtctct gaggtagtcc ctggcgtagt ggaggtactc ccgcacctgg ccggcgcgga   18300
tgcgctcgag cgcgaaggcc ttcatggtct cggagcagag cacggagtgc cgcagcccgt   18360
ccagtgtgcg ccgcacgtcg tagacgccgc gcatctgcgc gagcatctcg acggcgtccg   18420
ccggcgtcgc cgccgcgagc cccggggttca ctggaggtat cctgtgttct gcagcatgc   18480 gcttgaggaa acagaggtcc agcggccgcg tggtgtacag cgcggaggcc atctcggggc   18540
gcgtctcgac gatgtcctcg atcatctcgt ccgtgaatgc cgcgttgatg ttgtgcacgc   18600
tgcgcgcgtt cacgtgcagg aggatgtcgc ccacgttgtc ggggaatcgc tcctcgatga   18660 gccgacgtc gtcctccgtg atgttcatgt agggaataca gcggcagagc agcgcgtagt    18720
ccgcgaactg cgcgatgtag ggcgtgtgga actcgatgtg tctggcgaag agcgcgccgc   18780
agcgccgccg cgagagctct tcagcaggt cctcgggcgt gacgtgctgc gggcggaaga    18840
ggtgcaggtg cgtggggtgc tcggcggcca cgcgcgcgta cagccgccgc gggaggtgtc   18900
tggggtgcac gccggcgagc acgagatcca tggcctctga ggtagacagt gcggcgaacg   18960
cgcgctcggt gccgcccgcg gcgacagcgg cgccgacaaa tctcttgagc agctgcagca   19020
tcgcgtgttt gggctttcgc ggaaggcgct tatttttaatg ttattggcgg tggccggtgc   19080
gagataaaaa ttagaactga tgccgcagtt gttgatgata tgatgattgc gctggccggc   19140
gcgagataaa aattagaagc tgatgccgca gttgttgatg aggatggtga gtgcgctgga   19200
gcaagcggtg tggcgcgcta gcttcttgct ggccccgtcg gccacggcaa cgaccttttcc   19260 ggatatcgtg atggtgcagg tgaagcgcgg acagtgatcc tctccgccag cacgcgtctc   19320
gcagaactcc agaggtctgt gtgtcatcat gcagaactcg ttgaccgcgc tgaccgggtt   19380
aagacttttg aggcgtatca cggcagactg agtcatgatg tcgatgtcgc cgccgaaaag   19440
cgtatcgcac ccagcctcgg tctccatggg ctcggtgtcg gagttttcgt cctcctcggt   19500
gggcgcggag ggcgcgcact ctacgaacca gcggggcggg tttccgtcct cacagcaaac   19560
ctcgtccgag tccagcaggc ggtacagctg gcggtttgcc tcgtgtttgg atatgccgag   19620
ctccttcgcg atttgcttgg ccggcagctt gtcgtcggat tttctgagaa gctcgaggat   19680
cagagacgcg cactcgcagg ccattgtggc gatttacggg gcgtgcgttt ttttaggatt   19740
ttggcttgcc tttcttttcg cagaacttgg gaggattgaa actcttttgg caattttttgc  19800 aggcgtactt gatcaagggc ggctcgtccg ccgagcgcgt ctggatcatc atcggcatgg   19860
tgttcttgct ctggcacgag gggcagggca ggttgaactt ctcgtcgagc acgttgaagt   19920
acccgctgta gtcgtggtcc ggcacctcct cgatgtcgta gggcacgcgc gcggccacgc   19980
acttgaccgc gaagagcagg taccgcagcg cgtcgtgctc cgcgccgctg gtcgcgcgga   20040
tctgcgcgca caggtccgcg tagtcctcgt tcgcgtccac ctccaggctg cgcttgttct   20100
```

```
tgtacgagag ccggttcttg gcgtccttcg agtactcgat gccgatgttg tgcgcgggt      20160
caaagttggt ctcgtcggtg ttcgaggtct tggtgttcac gatgttcttc agcgcgaagc      20220
gctgcgcgca gtccagcgcc catcgcgcga tgcgcgcggc ctccgccgcg tcggtgtgct      20280
tcgccgcgag gtcgcgcagc cggtcttcgt ccatcgcccg attttaggtt gggtatatta      20340
tctcaattcc gctcttccgc gggccgcggg cgcgcgcccg cggcaaatta ggcgttacaa      20400
atggacttcg tgcggcggaa gtacatgata cacgccatcg accgcaacct cgacttcatg      20460
aaggccgagg tccagcagaa ggtctccatc ttctccctcg gcacgtgct cgcgctccac       20520
tacctggtca ccgcctttcc gcaggcggtc atcaccaagg acgtgctcgc gagcacaaac      20580
ttcttcgtgt tcgtgcacat gtcgcagcgg cacgaggtct tcgacgccgt gctcaaggcg      20640
gccttcgacg cgcctcagct ctttgtgcgg gcgctctcgc ggcacttcga ggccttcgtt      20700
gccgccatcc gggcctaccg cgcgacctgc gcggagctgc tggccgacgc gcgcttcatg      20760
gaggtggctg cgcgcgcggc cgagctcgcg gaggtcattg gcgtgaacca cgacatcgcc      20820
gcgaacccgc tcttcgcgga cggcgagccc gtgcgcgacg cggagctcat tttcgcaaag      20880
accttccgca agaccgagtt ccgcgccgtc aagcgcctcg ccgtgctgcg gctgctggtc      20940
tgggccttcc tcgtgaagaa ggaccttggc ggcgagtacg cggacaacga ccgccaggac      21000
ctgtttacgc tgctgcagaa ggccgcgggg cccgtgcgcc acagcgcgct cacagagagc      21060
atccgcgagt acctcttccc cggagacagg cccagccact gggtctggct gaacgcgcgc      21120
gtggccgacg acgcagaggt gtaccgcgac cggcccgcgc gcacgctcta cgagcgcgtg      21180
ctcagctacg cgtactcaga ggtcaagcag gggcgcgtga acgccaacac gctcaagctc      21240
gtgtaccggc tcgaggacga ccccgacatc aagggtctgc tgctgcagct catctacgac      21300
gtgcccgcgg acatcgtcgg cgtcgtggac tccgcgaacg aggagtggcg gagctacttc      21360
gtgagtctgt accgcgagaa cttcgtcgac ggacgcacct tcacctcgga cgcgcgcttc      21420
cgcgacgacc tcttccgcgt ggtcgccgcc gtcgatcccg acttcttcga gcccgagcgc      21480
atccgcgagg ccttcagcgc agacgcgcgg ctgcgagagc gcttcacgga catggacctc      21540
aacaacgcct tcatgtcgca cctcatctac gactccgtgg accccgacgt cgccgccgcc      21600
gagcgcgggc tcgcactgcg cgtgcacaac gaggactccg actacttcat ccgggagtac      21660
aacacctacc tcttcctcag cgagaaggac ccgctggtgc tggaccgcgg ggcgctcacg      21720
cggctctcgg acgtccccgc cgagcgcttc cgcgacctct tcagcgacag tgtgctgcgg      21780
tacttcctgg acgcgaagct gggcacgctc gggctggtgc tcgaggacta ccgcgaggac      21840
gtggtcgccg ccatgcttcg gcacctgcgc gcgtcgagg acgtgtcttc cttcgtgacg      21900
tacgccgcgc gcaagaaccc cgcctgcgtt cccggcgtcg tgcgcgcggt cgtgagcaac      21960
ttcaaccccg cggtggtcgc ggccatgcgc cccttcctgc gcgagcacat gacgcgcgtg      22020
gacgcgctgc tggacggaat gccgcacctc tcggaggccg accgtcggta catccgccgc      22080
gtggtgctgc agggccgcgc ctgattcgcc gtcaataaat cgcgatggtg gacagcggca      22140
cgcacgacgt ggactccgcc gcgcaggagc gcacgcccaa ccagcagacc ttcttcacca      22200
aggggctcag tccgctgatg cgccacacct acatctacaa caactacgcc tacgcctgga      22260
ttcccgagac cgcgctctgg agcagccgtc tgggcgacta ccgcgtcacg gacttctacc      22320
cgatctcgct gggcatgctc aagaagttcg agttcatgtt ctcgctgctg gcggaccccg      22380
gcggcgcctg cccccgcgtac gagcccaagc tcaacaccga gttcctgaac gcggctcct       22440
tctcgggacg gtacgtgaac ccccttccacc gcttcgcggc gctgcccgag cgcgagtaca      22500
```

```
tatccttcct gctgctgagc tcggtgccca tcttcaacat cctcttctgg tttaagggcg    22560
agaccttcga cactgccaag cacagcctgc tcggcgccgt gtacaccacg cccgagcggc    22620
acatcgagct cgcgcggtac ctgcggcgca cgggcgacta caagccgctg ttcagccgcc    22680
tgggcaacga cgacacctac tcgaagccct ctctgggtt cacgcgcatc agcaaccca    22740 cgcccatcgg gcggctgccg ccctcggact tcgagacgct ggccaacctg agcaccattc    22800
tctactacac gcgctacgac ccggtgctct gtttcctggt cttctacgtg ccggggctct    22860
ccgcgaccac gaagatcacg cccggcgtgg agttcctcat ggagaagctc tcgctcgcgc    22920
ccgagaacgt ggtgctgctg tagcctcaaa cataaaatat aggcgccttt gatcgcactg    22980
cttcagttca gacagagcta agatggcttc ctacatcagc ggcgctagcg ccagcgcgaa    23040
caccgcccag gcggcgatt ctcagtaccc acagtactat tatcacacac gcacctccca    23100
aggcgacatc cgcgacgaaa gcgaaggttg cttccacacc acggacgacg agcacttgga    23160
tctgtccgac gactacctcg gcgatggcgc accacactgc ggacagagcc acaaccacag    23220
tcgcagagat ggagatcggc accgccagcg cgcaccgcgg ctctatgagg acccggtgcc    23280
cgcgaacatc atggtgccca cgctcagtct agagcagctg ctggaggaaa cctcggtcgc    23340 gggggggcctt ctcggcggca ggacagagag ggacgtggaa cagctcctgg aggagttctc    23400
cgcactctgt cccggggacc agatcaccgc gctgcgctgc atggcggcct ccttttaccg    23460
cgacgcgctg ttcgcgccgt acgcctgcat gcacctcatc gccagtcgga tgcgcgtgca    23520
ctacgcgcgc gaggtcgtgc acgtggccga ggacctcgcg gacgcgatgt ctgcgaacag    23580
cggcgtctgc ttccggcggt accgaaagcg cgtgctagag gacatgctcg cggaggagat    23640
gggcgtgtac aattacctcg cgcgcgccaa cgcggacatc tgcgaggaca acctgctatc    23700
ggccgtggag acgctgctgc ggcgcttccg tcggatgggc tgctaccgct ctctgtgcat    23760
gctcaagatc ctcgcgctgc agcacgagga cctggccggc ttcatccgcc gcagcataag    23820
aaaaacctgc aacttggcac acgcgcgcac gcacacggtt tacgtgtagt taccctgtaa    23880
agacgggctt gctcccgaac aagcgctcga agaagagcgt gcacatagcc ttattgtcca    23940
gcaagttgac tatctctgta cacagcctct tgaagtacac ctcgtacatg atccgctcgt    24000
ttttatccag tctgaaggtc ttgtcgacca cgcgctcgta ggacttcacg ttcgcgatcc    24060
ggcgccgcca ggggccctcc tcgcacacgt acgcgaagaa gtagcgctcg ccgatctcga    24120
tggcctccgc gttcgccgcg ttgtaccgcg tcactagcgc cacgttgggg ttgtcggggg    24180
acttgaagtt cttgtggtgc gttcggctca gcaggaacca gtccagcggc atgctgcgcg    24240
cctcgaactc gaaggtgagc tcgtcctcca gcgagcgcag gatctccacg cccacgttcc    24300
cggagccctc ctccgccagc gcgcggcaga gcatgtcctt gtacttgcgg atcatgagct    24360
tgtggaaggg cgccacgtcg cggcgcgtct cgctggtgcc cttgctcacg cgctcgctgc    24420
cgccgccgtc gctcaccgca aacttgatcg tggtgtactt cttcttggac tgcatgatca    24480
ggttgcagta caccgcttcg aactccacct tgaagttcgc gaagagcacg tgctcgttga    24540
tcacgcgctc cagacagcgc cccacgcgcc gcgagaacgc gatgtcggag gcgcccacct    24600
ccaggaacac ggagtcggtg tcgccgtaca cgctgcggaa gccacgcgc tccgtgcgct    24660 cgccggccac cgccgcgtcg atctctagct ccgcggcgcg gcccgcgaag gcctcgtcgc    24720
gcagcagcgg gttgtccggc gccgccgcca gcgacagccg cgtgccgcac accgacgcgc    24780
cgtctagcgt gcgctccagg tacgcgatca tggtgcgccc gatggccgtg cagctcttgg    24840
```

```
ccgaggcgta cgagaagagc gcgctgttgc ggaagcccat gagcccgtac acggagttgg   24900
ccgtgatctt gtacgtgtac tgcatcgagt tgtagatctc gcggtccacc gcggtctccg   24960
cggccttcat cagcttcttg tacttggcgc gcgcgtccag gaaggagcgc agcagcatcg   25020
ggatgatgcc cttggcctcg cggtcgaaga tggccacctc ggcgacgagc tccggcgagc   25080
gcggctcgca gggcaccgcg atgtaccgcg gcgccgggaa catccgccgg acgtccacgg   25140
ccgcgacctc cgcgtcgagc cggttgtccg agacgaccac gccgacaagc gtctccggcg   25200
acaggttcgc gtagatgcac acgttcgggt acaggctgtt gtagtcgaag atgagcacgt   25260
gcttgttgtg catcttctgc ttgggcgcca tcacgcggcc gccctcgtag aagaacttgg   25320
acttcgtgtc cgcgcgcacc atcaccgtgc ggttctccag cagcagcttc atcagcgggc   25380
ccttgatgca ggtgctcgcg cggtactcga agaccacgct ctgcggcagc aggtacgtgg   25440
acgcggcggc cgcgatcttg gtctccacgc cgtagtgcga ccagaggtag aggcagaggc   25500
aggcgtcgtg caggcagtac cgcgccatgt ccagacacac gtccagcgag tagttcgcgt   25560
acatgtccgc gaggctgacg tcgtccttgc cgaaggccac cgtgacgcgg tcgccgggcg   25620
cgcgcgccgc ggggtccgcg aggtccacgg tgaagccgtc ctcgtcgacg cgtttgtgca   25680
gcacgcggca cacgcgctcg tccacggtca cgtagttgcc ggtgctgagc acgcgagcga   25740
acacggccgc gttcccgtcg gcgtcggtgc tgcggtcgcc gcgaaagcgg accgcgtccg   25800
gccgcgcgtc ctccacgacc gcggtgcagt ggaaggcgtt cttggatatg gcgtccagct   25860
tgtaggagtc cagcttctcg gtgcgctgga tgaaggcgta caggtcgaag tagatggtcc   25920
cgttgttgtt gttgatgtgg aaggtggtgc tcgagacgcc gccgacgccc ttgtggctgg   25980
acttcgtgcg ctcgtacacg cagaagttga ctgtctcggt cccgtccggc agccggaagc   26040
ggatgtgctc gcccgtgagc agcgacagcc gcgagtccag gtaccgcagg tcgaagttgt   26100
ggccgttgaa ggtgaccacg aagtccagcg gcatctcgag caggcgcttg gccacgcgca   26160
gcagcgtcac ctcgggacac agcgtgacct ccgcgtcgaa cttcacgtcc gccgggtcca   26220
ggcagaccgg gatctcgcgc cgtgccgcct cctcgaggtc cgcgtcggag agcatatcgg   26280
agttcgtaag cgtgaatcgc cgctccgcgc cgtccttgtc caccacgcag aagctgatgt   26340
gcgagacggc gttcttgaag acggaaggaa acttttctc gaagtggcac tctatgtcga   26400
ggaagagccc cgagcgcgtc acgttgaagc gcgggatctt ctccgcgaag cacgcgccgg   26460
ggtcgtcgca gtggaagcag ttgctcccca ggtcgcgcag cagcgcgggg tccacgcggt   26520
agcacccgtc agggtcgatg tcgtgcgcca cgaagaacca ggacacgttc agaaagtcgg   26580
acatgaagac ctctggcggc gcgagcttgc gctcgctggc caccagacac agctctatct   26640
ccgagcgctg cgctccgga atcttcgccg agcgcgctac gatctcgtcg atgctgacca   26700
cggacatggg cccgagcgcg cgcgtccacg ccagcggctg ggcgatgtcg gccaccgcgt   26760
ccgcgcgcac cacgtagtaa aagtgctgca cgaagcgcag gtacacgacg gcgttgtcgg   26820
cgcggcgcgc cttgaggaag aggaaccggc tgtcattgcc gcggttctcg aaccagttca   26880
aacatttcag ctccatttca aagagcataa taacatttca tttaaatgga gcctcgcttc   26940
tggggccgcg ccatgtgggc ggtgatcttc atcgtgctgc ggcgcttcga ggagcaccgc   27000
gacctcgagc gctgcaagcg gcagctgtac gtgatctgct ccacgctgcc ctgcatcgcg   27060
tgccgacgac acgccaccgc cgccatcgag aaaaacaacg tcctctccag cgaggacccc   27120
aactacgtgt tcttcttctt catcaagctc ttcaacaacc tcgccttcga cgacagatac   27180
aagatcgacc ccgcgaaggt gcgcccgctc gtctagagca tgccctcgta cgcgcgcgag   27240
```

```
ttgtccgagt acacggtcac cgcgatgccc tcgcgcggcg tcacgtgcac gtgcatggag   27300
tccgtgatca cgaagcccac gcccgtgacc ggctcctcgc ccgcgtcgtc cgtgaagagc   27360
agcccgtggt tgaagaggta gaactcgttc tctgcgagcg aaagccgccc gcggtcgcag   27420
aggtagtaga agatgtcgta gtcgcgcacg gccagcgtga acgtggactc gctcaccacg   27480
atgtacttgt ccagctcctc cagcacggac gcggccgcgc ggcgcgcggt ggcgcggcac   27540
tgcgtcgggc actcgcacgt gtctgcagag tacaggatgc gcgttcgccc cgaggcggtc   27600
tcgagaaaaa cgttaatcgc ctccatcgcc cagaagcgac tcgaggatcg cgagcaccgt   27660
gcgcagcacg agcccgatgg tgcagaaggg aacctctccc gactccgagc actcgcggat   27720
ctccgtctcc acgcggtcgt gcacttttat ggagggagcc gtcgttccag tggcctccat   27780
cgcgacggac accaccttgg ccacgaactc gcggatcttg ctcatgcgcc ggagcacggt   27840
cacgcggaag aagacggccg cgagcaggta ctcggccacg cagctcacgg cgatgagcgc   27900
ctgcgcgtgc ctggtgttga gcacgtgcgc gtcgggcacg aagtccgaga tcttcaggtg   27960
cgagagccgc acgagcgcgt tggtgtcctt gacgccgtcg caggaaatgt tcgcgaagat   28020
gagcttctcg tagtcgagcg cctcgaccac gcgctgcgcg tccatgtgcc gctcgcccga   28080
gagcgcgcgg ctcaaagggc cccagcacac cgagcccgcg aagcaggggt ccaccacgcc   28140
gtgcatcgcc agcagcgtca cgtcggccac cgccgcgagg atggccgcgt cgtcgagctc   28200
gttcgcgggc gtcgcgcccg tcagggacgc gctgcgcagc gcggaccgc ccggcgccgc   28260 gtgccgcgcg cagaactcgc acccgcagcc cggcggcagc ggcggcttcg agagcagact   28320
tatgagcccg cccacgtgcc cgtgctcggt gatcagaagc gccaggatgc tgtcggtgct   28380
gccctctatg gcggctgtgg ccgcgctaga aggctctccc gtgacctgcc atccgcagac   28440
aaccttgagc atcttgcgct tgagctcgtt gggcgcctcc gaggccagca tcgtgcgcgg   28500
gaacgtcgcg ttgaggcgga agtcctgcag cagcttttcg agcgtcgcgg tcttggcgtg   28560
ccgccctttg cgccactcct cccccaggtg ccacatgagc tcctcggccg tgtccagcgt   28620
cggcgagacg cgggccttgg gcacgcgcgc cgcgctgcgc atcagcggct ccgaggcgcg   28680
gaagctgccg cgcgcgtgca ggcgcatgga cgcagacgag gaccgcatcg agggtctctg   28740
gtggaagctc gtcatcgtga agcgccgcgt gagcggacct acctcgtcgc gcgactcgtc   28800
gaagtccggg tcagggtccg tcgtgtcggt ctcggcgctg tgcgtgctgg gcgcgctgct   28860
gcgggcgctg cgcgtgctgc gcgtgctgcg ggtgctctgc gtgctgaagc tgcgcgagca   28920
ggagtccgcc gtgtccgctt cctcgtagtg gaagtccacg tgctcctccg gcagccggcg   28980
cgagcgcgac ttggagatgc cgaccatctt gtccgcgccg accgggcgca cgcagagcgc   29040
catcgcgccc tcgcgcaccg cctgcgcgaa ctcgcggctg gcaaccatgc tggggtttgag   29100 gaacttgatg atgttgaagt atggccactc gcagacgagc cgcgcgcagg tcgcgacgtc   29160
gtcgacgctt ctgagggccc tgttcagcgg ggggatgttg ctgccgtcgg ccagtgcgac   29220
gaggtcctcg ggggagatct cgagcttggg aatcatctcg ttcacgagcg cggggtcgat   29280
ggcgtggcag acggtctcta cctcggtgcg cgagagcttg agctgcgcgc aggccgccca   29340
cggcgcgcac gtgagcgcga acaccgcgga gactcggccc ttgccgacca tcgccacaac   29400
ctcgggctcg tagaccaggc cggccttgag cagagcctcg agcacctcta tgtcgtcggc   29460
ggcgagcagc gcgcgcctgt ggaagcacac cgcgggcatc atcttcttgc agatgccgcg   29520
ggtgctcttg agggccgtga taaggtcggg gagcctgacg tgctgcgggct ggaagaacat   29580
```

```
gacgttggcg gggctcgcgg ccaccgcctc gtcgtacacc gacatcggca ggtcgccgtg   29640
gagcccgcac ggcagcaggc tcagcagctg cgcgcgcgag agcttctcgg cgcagaagtt   29700
cttcttggcc agggcggccg ccgcgtcgcg ggccttcttg gggtataaca acatggcggg   29760
ctttaaacac gaaacaaaaa tccgggttgt aacatttcaa ttttgcatgt tctgggcctc   29820
ctcgcagagt ttctccaggc cgccggccac gatggcgtcg acgaagaggt cggcctcggt   29880
gaagcggtgg ttgccgcgca ccgccaccag gcgttctcg gtgaccacca ccgacagctg    29940
ctgcgcagcc gtgcgcaggt cgaagtgtcg gcacgcgagc ccgtggccca gagtctggtc   30000
cagcgccgcg agcacctcct ccaggctctc ctcgcggtgg ttgtagaacc acatcagcac   30060
gaagtaggcc acgtaggtgt agaggtagtg cgcgaccgcg cgggcgcgca ccagcggctg   30120
gttgcagcgc gcgaaggcca ttccgctggc gatgaggtcg tcgtccagcg tggcgtagtc   30180
gccccagttg agcgcgctga actgcacgct gtagaccgcg cgcacgaacc cggactcgag   30240
gatgtcgatc tgcgacggcg cgccccaggt caccagccgg tacacgatgc cgcgctgcat   30300
cagccgcatg aggtcgccgc cgacctcgcg caggcggtgc gtcagcgagg cgaaggccag   30360
cttccgctgc gtgtactgca ggcccacggc cacgcacccg tccgactcca ccagcacgag   30420
cttgtggtcc gtgcagccgt cgctgcgcag gccgccctcg cgcgccatca tgtcggtgac   30480
gaacatgtac ttgcgcgcgc gcggcccgac caggatgcgc ttcttgcctt ccatgcgcag   30540
caccacgtcc tctagcagcc gcgtgctgtc cacgcgctcc acctgcgggt ggatggtggg   30600
ctggtagttg tacagcagcc gcggggacca gttgtaggcg aacgcgaaga ggtgcgtgtc   30660
caggagagag atggggaaga cgccgccttc ggtggcgcgc cggaggatgg cgagcttggt   30720
ctccgcgggc agcaggctcc cggtcaccgc gccgaagaac atggggtggt tgcggaactt   30780
gagcgcgtac gcgctcagca cctcctctcg cgagaatatc gagtccgcgg ggttggagct   30840
cgcgggcagg agcacgtcct ccacgctcag cacctcgtcg atgaagggca gcaccatgtc   30900
cacgttggag gcggtgaacc actccatgtc cacggcgttg cgctccacga tcacccggat   30960
cgtctcctcg gatatgttct cggcgaaggc gctctgcagc tcgatcaggt tctcggtggc   31020
gtcgatgctg agcccgaggc gcatgccctg ttgcagcacg tcgttgatgg ggttcacgta   31080
catggccacc gccatgcacc cggccggctg cacgcgccag aggttggagt acgcggacac   31140
gtccgtgatg cgcagcgtct ccagcacgtt gtacatcgcc gcgcgcattt ccagcgtgtc   31200
cacgtacacc tccgcgtgct cgaagatgat gtcgagctcg aacgcggaca gcggcagact   31260
cacgtagatc tggcaggcgt caaagagttc ctgcgcgtac tcagagaagc acgcgtacgc   31320
gatcacgccc gcgcggttga cgatgtagtc cgccttgaac atcttcgtga ggtaggcgta   31380
cagcgaccgg caggccacgt gcggccttag ctcgtcgagc acggcgtcca gcacctcgcg   31440
gtgctgcagc acggaggggt gcaggaactg cgtgaagtcc accgcggtct catccatgaa   31500 gtcgggatg gtctcgacca ccaagcgtg gttccgcacc gcgcggaagc cggtgttcat    31560
cggcgcgatg ctgtgctggt cgtggacctc cagcaggatc tcgtagccga tctctcggca   31620
gctcagcgcc gcgcgcgcct ccgtcacgct cgcgttccgg aagaactgcc gcaggtgctc   31680
gtccgtgcgg cagagcgtga cggattgggg gatgcgggaa aggtcgcaaa gagggctgtg   31740
gacggagatg cgccgcagcg cgtggtctac gaactcaaaa ccgcgcctcg acatcgtgaa   31800
gtcgcggagg gcgtacatgt tgtaggaaca gaggcggaag aggcagtcta tgtctagcat   31860 gttgaaacg cagtacgcgt gtctgtggag gtgcgggagc atggcgggca cgacctcggt   31920
cgtgttctgg agcatggtgc atacgaggtc gggcgctgtg aggtcggggg tgacgatgag   31980
```

```
gatgcaggag ctggagaact tgctgagctc ggaggccagc cggtgaaggt tgtagtcgtg   32040
gcgctggctg aagttgctgt ttatcgtgcc cgtgaagccc atgagcgccg ccagcgtcag   32100
gtcctcgcgc tcgatggccc agatgtctag gccggaggct atcatgcagc gcaccagcgc   32160
ggcggcgcgg tcgctcgtgg ggtagctcat ggtgctgtcg gtcgtgcgaa tcagcatggg   32220
ataatgcttc atttttacgg tcggggttg cggactgtgg ggcgcacagg gcctgcgggc    32280
ggctcgtgcc ggtccgcggc gttcgccgaa cgcaggaacg ggcccatgcg cgcccaggcc   32340
atccacagcc ccgccgtcag cgccagcagc cagacgaata ccacgatcat cttttatgta   32400
gctggaactc gcgctcactc cccgccgcac ggcgacgggg agagcccaga gccgagctcc   32460
atgcgcgtgc tctgcacggt gagcgactcc acgagcttgg acacgttcat gcgcgtgttg   32520
tcgggcacca ggtgcgcgag gcgcgcgtac acgtcatcgt gcatgcgctt gctgcagcgg   32580
tccaggctcg cggagagcgc ggagactagc gcggtgtgct tcgcgtacac gaagtcgccg   32640
agacacacgg tctcgagccc gagcacgtcg gcgctctccg cgtccttgag cgccacgaat   32700
atcttctgct cctcgcgcgt catcgagcgc atgaggtagt cgtgcagccg cgagcgcgag   32760
atgagcccct gagagatctg cgggctgcgc atgaagcgcc ggcgcatcgc gcacagcagc   32820
tcctcgtcga cgacgtacat gctgtccttg atggagctct tctcgtcgat cacgagcaga   32880
ccgtcgttgg cgaccacgtt gatgaaatcg tccacgtgcc gcgcgtctat gtcgtagcgc   32940
gtgccgccgc actcgatgtg cgagggcggc gacttgagcc ggttcgcgag cgccttcacg   33000
tcggagacgt cgatgtacag cgaggactcg cgcgggacgc agccgaggat gcgcgtctcg   33060
agcggcgtga ggatgagcac gcgctcggcg ccgtcgacga gcttgccgtc gtcgggggaa   33120
aagaagttgt tctccacgat gctcgagacg aggctggcga gcacgccgtc gcggtaggcg   33180
ccgagcgcaa actcctgcac aaagggcgcg tgcagcaagt ccacgggaat gcgcatctcc   33240
acgcggcgcg cgaccgactt cttcttctgc aggtgccgcc ggtccaccat ctcgtccacg   33300
atgtccgata tgcgggagca gaggtacgcc ttgaggacgt tggcgtttac cttgttgaag   33360
atgagccgtt cgtcctccat ttaagctgct cagacgagct ttaaatagtg gaaacacagc   33420
agcacgccga tcgccgccgc tatcaggccg attagaaaaa cggtggtcca ggggacgccc   33480
ttgggcctat cgcacgccgg cttttcggtc attacggtgc gcacgatgtt taggaactcc   33540
tcgaagtcct cgtccgagtt ggagaggaag gagccgaaga cgccggtgta cagtttgtcc   33600
atttactact agatattaaa cggcgcttcc aactcctcgt cctcgaagcc cgcgccaggc   33660
tcgacgacgc ccaggccgcg cacgtcctgc tcctcgttga acgtggtctg agtctcgctc   33720
atgcgcacac acgtctgctc gccctcgaga ccgagcacgg tcagcgagca ctcgcgcggc   33780
atggtgatct tcttaaccgc gaaggtgact ttgccctcgc cgcccgagcg gtagaacacc   33840
accggcgcca ggatgagcgt cgccatctgc gcgtcgcggg ttgcgaggtt ttctatctct   33900
cgcgtcagcg gacatatctg cggctgggtg tcgtcgtcgc tggtgaactc caggagagcg   33960
ccggtcaggc ggttgagata cagacatccg gacttaaagg tgttgtcgat ggccgtttcg   34020
gtgttgaagt tgcgcagcga cggcggaacg cgagcgccgg ttttgatgtt gtcgtatatg   34080
ttctccagca gctggtagag cagcggactg gcgctcacgg gcttgaggcg accgaagtac   34140
ccgctgtcgt tctgccgctg catgtcggtc ttcttgctcg ggtagatctt aaactcgccc   34200
ttcacgacga tgagcggcga gacgagcttg atgctagac tttcgacgag acacacgttg    34260
atgttggagc agctcgggta ctgcgacgga gttagagtca cggcctcgat gaccttggtt   34320
```

```
tggctcgacg agagcgactt agcgaagttg atcgcgtcgg tgcacgacat cgcctggttc    34380
tcgccgaacc gcctggcgga cgctgcatcc tcctgctgag gagcgcggtt agacgcgacg    34440
gtggttttgg atacagcgcg tttcattatt gcggcgattt taaagtacgt gtatactttc    34500
agttttgtcg ccgagcgttc agcgcctgca tgcagaggaa gtacaggatg atggtgcacg    34560
ggatcgtggt cagcagcgat acgaagtcca tcactgtgag gacgcgcagc gccccgcgcg    34620
agcggatgcc cagcgagggc gcgccgcggc gcgcgatggt ggccccgttc gtcaccacta    34680
ccagcagcat taggatggtc gcgcccacgg cgacgcccag gtcccgcgac tccatttata    34740
gtacagtata gagcgaccgc gtcacgaact ctcggctggc caacacgcgt ccgtcgggcg    34800
ggtgtccgcc ggccttcccg cggaactccg ggacctcgaa gctggacttc gtcacgcggt    34860
acgtgtactt gccgcgccag accaggtttt ccttctggaa gacgccgtcc atggtcacgc    34920
ccgccatgaa ggcgtccttg acgatgacca gcaccgcgtc tagcttgcgc ccgttgatgt    34980
gcgtgacgaa gtccgtgccg ctgcggctcg cgcagcggat gtccacgccc gagggcaggt    35040
ccaccacgaa cacgaagcgc ttcggcgcgt agagcaccag gtccgaggac ggcgacgccg    35100
aaggcgccga ggggaactgc cggtggtcaa aagggtgcac cacgcccacg atggacgtga    35160
cgcggtcgtc cggaactgc gtcgcggcgc cgccgccgcg gtgccgcgtg accgtgcttc    35220
```
(note: line with 35220 may read "cgcggtcgtc cggaactgc gtcgcggcgc cgccgccgcg gtgccgcgtg accgtgcttc")

```
tgcccacgtc gtcgcagacc acgtgcagct ccgacacgat cggcagcagc gtggccagca    35280
tgcggtcggt ctctgtgcgc gtcgcgcagc ggtacgcgat cccgcagtgc gcgtcctgcg    35340
tgcgcccgaa gaagagcacc agcacgctcg cgtcctggtc gaagggacac acggccatca    35400
cgcccaccgg cggcggcccg tggcctgcgt acgcggagga gaactcctgc acctcgacca    35460
cggcgtcctc gcgcgcctcg ccgggcacca tcgccgccgc cggccgcagc gcccgcacgg    35520
tctgcttaac cgcacgcgcg gcggaggccg cgctcggcgc gactacgcgc acggccgcgt    35580
gcgcgcccgg cggcggcgcg gttccggcca tccagcccac cggcgagaag aacacgtcgc    35640
agacgtgcac gcccgcggcc tgcagcgcgc gcgcgagcgc gcgcacggcc tcccactcct    35700
cgcgaaaggc gctcgcgacc gcgagcgcct tcagcaccgt gtccacggag ttgacgggct    35760
tctggaagag gttctcgttg ttgtagatga actcggggag ctccacgggc actgtgaaca    35820
gcctaatctc gtgcgcgccg ctgggcgtga gccgcgtcgc gggcttgcgc acgccggcgc    35880
cgatctgctt gaagaagtgg ttcatggcgc cgccggcttc tcgggctccg gcgggagcag    35940
actatttatt cgggaggtta tcctttccga aagcacctgc acggacttcc gcgtccagcg    36000
ctccatcttc atgtactcct tcatgccgtc gctgagcacc tcgacggcct ccagcttggg    36060
cgctgtcggg tcgaagagga tgctcttgag cagcgtcatc ttcttgtccg cgaggaagcg    36120
gaagtaagtg tagatgcagc gcagcgcgcg gaagttctcc gggtgcttga tggtgcacag    36180
gatcatgaag atgcaggtga acatgccgca ctcggactcc atgagctggt tgacctcgag    36240
gttgatgcag ccgcgccgcg ccttgaagtt gtccacgaag aagcgcatga gcacgtccac    36300
gtcgcagttg cggttgtcca ggtccgcggt ctcggcgttc acgttgaagc cgtccgagaa    36360
ggagtagaag tagaagtact tgcaggggtg gaactccgag gggctgttgc cgccggagtc    36420
gtagaaggac acgagccgcg agacggtgtc gaagatgcag cacttccagt ggaacatgta    36480
gcagaagccg aacatcacgt agcgccgccc ggcgcgctcg atcttgtcct tgagcgtgag    36540
gctgaccatg ttgcagcgga agcggtccgc cttttcgtgg atggccgcgc cgttgaggaa    36600
gttcaggttg aactggccca ggtacgcgac ctcggtgccg aacgcgaagg cgccaccag    36660 actctggatg ctcacgttgc tcatccaggc gctgcggtcg ggctttatgg cgatgggcac    36720
```

```
taccttggtg ttcacgcccg tgctgacgcc cgcgcgcgcg aggtcgtcca cgttcagcgg    36780
catctgcgag aagtccacgg cctcggacac cttctcgcgc aacgagggct tgaagaagaa    36840
gcccagcggg accttccact ccagcgcgat cgcctcgcgg aagccgtagc gacccttgag    36900
gctggccagc aacgcggtct tctgcgcgac ctcgtccttc tcggtgtccg gcggcgcggc    36960
gtcgatgagc ccgcgcttcg cgaagtccag cagcgccgcc agcgggatgc acgagacgcg    37020 accgccgtc  gcggattcgt cgaagcgccg caccacgtac ccgttgcagt tggtcttgaa    37080
gttggacacg tccaggtgcg cgctgagccc caccaccgag tagatgtggc acagaaggtt    37140
ggtgaacccc agctccggga ttttgctcac cactaaatcc gtgtacttgt ccatttatca    37200
tggagaatca tctgccggac atgctgatgt ttcccaactg cgtttctgtg tttccctttg    37260
agtactcgct ggaggacgtg ttccgcctcc ccgaggagcg acggcgcgcg ttcgccatgg    37320
ccgtgttccc gctctccaag caccgctgga ggggcgcgcg gctccagcgc gacgagcgaa    37380
gcgtgtggct cagcgtcgag gaggaccgcg ggcgcgcgct ggacgagcgg aactgctcct    37440
ggctctcgga cgtggccgcg cgcatggtcg acgacgaggg ccgcgcggtc acgcccgagg    37500
cgtacgcctt catgcgcgcc gcgcccgcg cgcgcgtcgc cgagctcgcc gcggacgcgg    37560
gcgtgctagc gggccttgtc gccggcggca acgcgctgcg cgtcttctcc tcggagtcca    37620
cgcaggcgcg cgagggctgg aaggcgcgca cgtgggcgt gctcggcaac gcggcgccgc    37680
tggcgcccgt gccgctggca tcgctgcgtc cggaagtgca gcgcgagctc ttcgccgcct    37740
ggatcggccg ccgccccgtg gtgctcacgg gcggcacggg cgtggggaag acctcgcagg    37800
ttcccaagct gctgatgtgg ttcaactacc tcttcggcgg cttcgagcgc ctggacgccg    37860
tccgcgagtt cgcggagcgc ccgctcgtgc tctcgctgcc gcgcgtcacg ctggtgcgcg    37920
cgcacaccgc gacctacctc gcctcgctgg gcttcggctc ggccgacggc tccccggtct    37980
cgccgcggta cggcgccatc ccggacgccg agcggaacac ggccccgcgc gcctacgggc    38040
tcgtggtggc cactcaccgg ctcacactga ctgccatccg ccgctacgac acggtcgtag    38100
tggacgagat ccacgagcac gaccagatgg gcgacatcgt ggtcgcggtc gcgcggaaac    38160
tgggctcgaa catgcgatcg ctggtgctta tgacggccac gctcgaggac gaccgcgcgc    38220
gcctggagga gttcctggac cggcccgcct ttgtgcacat agagggcgac acgctcttcc    38280
ccatccgcga ggtctacgtg aagaacacgc aacagccgcc gctctcgcgc aagtacgcgg    38340
aggcggagct gcagaacgtg gcgcaggcgc tgggcacctt cgtccccgag cagggaaagt    38400
gcggcatcct cttcgtagcc acggtggcgc agtgcgcgct cttcgcggag accatcgagg    38460
ccaagcaccc cgggctgctg gtgcgcgtgg tgcacggaaa ggtgccctcc gtggccgcgg    38520
tgctcgagga ggtatacgcc gcggaccggc ccgcggtgct ggtttccacg ccgtacctgg    38580
agtccagcgt gaccgtgcgc accgccacgc acgtctacga cactgggcgc gtgtacgtgc    38640
ccgagccctt cggcggccgc gagacccttcg tctccaagtc catgtacacg cagcgcaagg    38700
gccgcgtggg ccgcgtggcg cccggcacct acgtgcgcgc tt cttcgacacg cggctcgcgc    38760
tgccgctgaa gcgcatcgac tccgagttcc tgcacccgta cgtgctttac gcgcgcatct    38820
tcgggctaac gctgcccgac gacctgctcg tgcagcccag cgacctcgcg ctgctgcgcc    38880
gcaccgagga gtacgtcgac ggcttcggca tcagcctctc gcgctggacg cagctgctgg    38940
accggcacta catgcacatg gtcgagtacg cgaaggtgta cgtgcgcggc gggcgcctcg    39000
ccgccgcgct ggacgccttc gagcgcaccg gcgtgatgac gcacgaggcc accgaggcca    39060
```

```
tccgcgccgt ggacatgctc gcggccgtcc taaacgtgcg caagtccaag gaccgctacc   39120
gcgcggagtg caaggtgctc ttcgggccct tcgcgggcaa aaagttcgtg gtcgccgggc   39180
ggcgtccgcc cggctcgcac gtgctcatgg tcacagaccg cgtcttcatc gaggccgagc   39240
ccccattctg aggaccacct tcttggagac gcccgagaag tcgtcggcga cgccgcggcg   39300
cgccaccaca aggcagtacg aggtcacgtg cgggcagcgc gcgatgcagc ggaaggcttc   39360
ctcctgcgac agcgagaagg cgaacacgta aaggtgtgc ggggacttca gcggcgtgtg   39420
gtccatcgag tagatgacac cgagcttctt catgcgccac ataagcgcgt tgatgtggtc   39480
ggcgcgcagc gcgcggccct tgagcacgcc gcagacgaag ctcgagcagg ccacgacgtc   39540
gtagcgcgtg ttcctgccga agaccaggtg cggcgcgccg gcggcgcgcc gcgcggccgc   39600
gcgattctcc acgatgtcct ctatggagcg ctcgctcgca aagaagtcca ggaacatgta   39660
ctggtaggcc acggccgggc gcgacttgct gaacttcatg aaggcgtccg agtccatgat   39720
ggcgtccatg tcctcagcgg cgagccggtg ctgcagccgg atgccctcga aggtgtggaa   39780
gagccgcgcg tccgcgtgca tggacagcgc gagagtgacg aagttgagaa ggtccgcgtc   39840
gccaaagcgc acgagcacgt taccgggcgt gcgcgtcttg cgcatgagcc gcgcgggcgc   39900
gccgtcgttg tggctgcggc ggcgcatttt gtcgccgggg gactcgggcg gcaggtcgat   39960
catgaccagc cggtgccgct gcgcgtcctc ggcgttgaag atcgaggacg tgaagcccgg   40020
gtacagcacc acgcagtcgc gctccgagat ggcgtgcagc acgtcgcgct tgagcccggc   40080
caccagccgc tccgcgttct cgacgaagta gttctcgtag tccaggatgt cgtgcgccat   40140
ccaggggaag ttcaggtacg cgttcatggc gtagtcctcg gcgtcgaagc agatgcgcgt   40200
gtctggcgtc gccgcgatcg gaaggtcctt gatgccgcgg agcagcccgt cgtagtcgga   40260
ctcgtccacg aaggagagca ccacaaagag gtcctcgccc acggtttcgt agtcgaagag   40320
gtggtaaagc tctcttagcg ccagcacggc gagcgcgttg tccagcgagg cgtgcacgcg   40380
cgccaggatg ctgtagaagg gcgtggccat catcacggcc ttgccgccct cgcaggcaac   40440
ggcgcgcggg aaaatgacct ccggcgtgcg cggcagccgc ccgaacgtcg cgttcagcag   40500
cgcgaccgtg gccgcgtcgc tctggcgcag gaacactacc accgagggc ccgagatgct   40560 gagcatgcgc tcgcgcatgc gcgctggcag gtccggcgtg gtcacgaggt ccgcgaagcg   40620
gccgccgttg tagaggtcgc cgccgccgag gaaggtgagc acgtcgaagc agtgcagcac   40680
ctcgttgcgg aagtagtact cgttctcgag ctccttggcg tacgcgcgta tgtccacgtt   40740
ctcgaagttt gttcgcagac cgccgccgtc gaagaaccag gacgcgagct cgcggacggc   40800
gtccgcgggc ctgttgcggc ggctcttgca ccagaagctc atgtagttgc gcgaggtgga   40860
ggcgttcgcc aggaagaagc ggtggtcgaa ggagatgagc acatgctcga gcaggtgcgc   40920
gagccccagg accgcgccca cgtcgcgccc aaaaccgaag tttgatatcc ccaggtagac   40980
gtcccgtttc atagacggcc tcaggaacac cctgacgccg ttttccaaca ctatcattct   41040
ccggtattta cttacccaaa agtagtatgg ggagaagtgt tgaacgtcc cctcgccttt   41100 ttaaatcaaa agtagacttc tcgcgcccgt gcgccaccgt cacgcgcgcg cggcgcgagt   41160
ccataccggc gatcaccgcg ctgctctgcg gtgcgtccgg ccgcgggaag agcacggtct   41220
cggagatccc gtccagctgc gcgtcggtgc gctgccgcca cgcgtgcgcg tccgcgagct   41280
cgcgcacggc cagctgcatc ttgttcgtcg gcaggaacgt gaaacgtac gccgccgcca   41340 ggaaggctgc gaagagcacg aactcaaccg cccatgacat ttagggagct gattttgttc   41400
cacgcggcga cgcacgtcgt gacgggcgac cccgaggcgc cgcggcgcgc ggcctcgctg   41460
```

```
tgccgcggct tcggcgtgga cttccgcgcg attcacgcgg agttcgcgcg gcggtacccg   41520
cgcaccgcgg ccgccgtgga gcgcgcgcag ccgctgcccg aagtcgatgc cgcctttccg   41580
ccggacgcgc gccggcaagt cgtgcggctg cgcctcgagg ctgcggcgct ggtcgtcaag   41640
gagtcgcgtg cgctatcggc ctccatgcgc ggcgtggcgg tggtcgacgg ctgctgcgtg   41700
cgcgtgtgcc gcgccaacga cgagctgcta gagttcctcg cgcggcgcta cgaccccgcg   41760
gtctaccgct acgcggaggt gccctcgccg agcgtgcgcc cgggctcgaa agtcttcgcg   41820
tgcgcgggcc gcagcgtcac ctttgcggcc gcgcaccgga gccgcatcac ggccaaccgc   41880
ccgctgcgcg tggtcgtgac cgaggcctgt gtggacggcg tgctcgcgcg cggcgccgcg   41940
gaggtcttcg accgcggctc cggcgtgctg ccccgcgcgc tgcgcgagat cttctaccgc   42000
ctcgacgagg acggctgtcc cacgggccag acgccaggct tcgcggacag tatgcgtcg    42060 cgcagctgat ctatgtccac cttttctcg tcgatctgcg ccacgaccac gaaactgcga    42120
atgtccacag cggccatggt cttggccacc gggtcgtact tgaggagcag cacgtactcg   42180
ttgccgaagt gctcggtgac ctcggtgatg agccggtaca cgcccatgcc gagcacgttc   42240
accgcaccgt ccttggcgaa gagcgagagg atgttcacgc acttcagctc catctcgccc   42300
tcgaggcgcg cgagcatgcg ccgggtgacc tcgcatactg aacaaagagg cttacctagt   42360
aagataagcg ttagcttagc gcggtcggt gacgcgtcgg aggccattta tggggatcaa    42420
aaacttaaag gcgttgctgc tcagccacgg cgcgctgacc ccgcacgagc cgggcggcga   42480
cgagcgcttc cctgccgtgt tcgtggacgg cttcagcgtc atgatgacca tggcgtactc   42540
gtgcgcggac gaagacgagt tccgcgcggc cgtcgaggag cgcgtgcagc actggatgag   42600
cgtgtccgag agcgggcgga tcgtggtctt cctcgaccgc ggcgagattc cgatcaagca   42660
gccgctgcgc gaccagcgcc gcaaagccac gcgcgaccgc gccgcgcgcc accgcgagtt   42720
catcgccgcc gcggaggcag acgcggcggc agaggccgtt ggcgcccgcg aggacaaaca   42780
ggaggacgag cacgcggagt tcgccgagga gatccgcgct gagaagcagc taaagctgca   42840
gcgcatccgc ttccagctca gcatcgccaa ccacgaggtc gttaagtcgc tgatagagtc   42900
cacgctcgcg cgcgctggcg atgccgtgga gatcgtcttc tgccgacggcg tcgacgcgga   42960 gatggtcatg tgcgcgcgcg gacgcgccga ggccgagcgt cgcgggcgct ggccgctgct   43020
cgtgaccacg gaccaggacg cgcttttgtt cacgtccacc gatcgcgacg agaagatagt   43080
gagcaccgtc tccgcctgct acgcgttcag gcccaccgag acgaccgagt acctgtgcaa   43140
acttgcggcg ctggccaacg gctgcgactt cttccccggg ctcggcggca tatgcgtgag   43200
tgtggagtcg ctgcgccgcg ccacgctttt cccggaattc tccgtgcgca acgccgccgt   43260
gagtctgtgc acgcggccca tgcggctgtc cacgcaggac gcgctggagc cagaggccgc   43320
cgccgaggtc gtggaattca tcaggcggta cgccgccggc gacgagcgca tctaccgcga   43380
ggtgccgccc ggcgcgtgct gcggacgcgc gtttgtgcgc ggagcgctcg cggccgagtg   43440
ggccgacgcg ctgccggcgg ccacgggtct gagcgtggtc gcggacatga tcgcgtgtct   43500
gcccgcgcgg cgggacccg cgcccgagga ggtagagcgg ctgctggcgc tggaggcgcg    43560
cgcgcgaggc gcgcgcgtca cggatgcgat gctcgcgcag actgcgcagc tgctgggtta   43620
cggcgcgagt gcgggcgccg acggcgcctc cgccttcgcg gtctcgggcg ccaagggcct   43680
gatgtgtcgc ctgcgcggca cggccatgtt cttcaacgcg gagtacgtgg aaattgaaag   43740
cgaacccaga ctgttaaagc tgcggtagca tggtgttccc gatcgtgtgc tcaacgtgcg   43800
```

```
gccgcgacct gtcgcacgag cggtttctgc tcatcgtgcg acagcggccg ctaaaggttg    43860
ttttgcggac ggtgcgcaac gtctgctgcc gtataaagtt gtctacacaa atagagccgc    43920
accggaacct gacggtgctg cccatgctcg acataagctg attttctttt tccgctcgta    43980
tgcgcgagtt cggactcgcg gcgcgcatgg cccgcgccat cgaggacgtg tgtccgcgcg    44040
gcgcggtgat attcgtatcc agcgccgcgt ccatgaccga ctgcctgaac ccgtcggtgt    44100
tcaagcacgc ggcgatatac gcggggcgcg tggaccgcgc gccgctgccg ccgccctcgc    44160
cggtcccggc ggaggccgtg acggagccct gtgcgataga cgccatagcg ccttacggcg    44220
cgcgcgtggt cctgctctcg gagctgctgc ggagctgcgt ggccgttcag gcctaccgcc    44280
tggcagtccc cggcgccctc gcgctcatga acctcgcggc cgacgcggcc ttcgagctcg    44340
tgggcacgcc ctacggcttt aacagcgacc gaacgtactg cttcaagctc gttgccgact    44400
gctttgctag cgtgggcgtg acaacgaaga ccaggcgcat catgggtcgc gacgtcgtgc    44460
tcagccagga cttcctggag agcggcatgt ggaccaaggt gctggactcc gccgcggagc    44520
cgccgtggct ggtctagaac agcggcggcg cgcgggtccc gagcacgggc cgcgccacct    44580
gcagccgctg ctgcagcgcg cggcactgcg cctcggcgtc ggccgtctcg gcggggtcga    44640
cgggcgtcgg agttgcggag gtggtcctga acggctgcgt gttcaccgag acgcggatgc    44700
gctccttgca ggagcgctgc tcgatgcagt tggccagcat cttcatcacg tgcaggtact    44760
ccagcaacac gaacttttcg agggtgatgc cgtcgaaggg cgacgacccc accacgccca    44820
gcgggctgga caccgcgccg tcgagcacct cgccgcggga ctccttgcgc gcgcgctcga    44880
gcaggtcctc tgtccgagcc accacactgc cgaagtcggc ggccgcgggg gcgggaacag    44940
gcgcagcagc gctgtccgcg tccgccggca tctcctcgat cttgagaccg gccgcgaact    45000
ccgaggccgc gtgcacgggc gaggcgccgc gccgcaccat gaagtcgcac agacgcgata    45060
gcgcggagga gcgcaccggc atgtcgagca ggcgctcggc ctccatctcg gcgaccgagt    45120
cggcgcacgc gtccgcgcg cccgcccgca cgagctcgtc gcagcacccc gcctccttca    45180
tgagcgcggg catgagcttg tactgcgcca tgttcaccag cccgtacttg agctcgagca    45240
ggtccgcgag ctcggaggcc atgggtcggt ttttggtgta gatgacgcgc tccacggcct    45300
ccgccatgtc cacggcctgc atgagctcgc cgacgagcac gctggccacg agcgtggcca    45360
gcgtgacgcg cacggtgggc acgcagaccg cgaagaagga ggtggagtgg gtgaagcgca    45420
tgagcgcgcc gtgcagacgc gcgaggtccg cgctgttgcc cgcgtgcacg aagcgccggc    45480
gcagccgcgc cagcgcctcc acaaggtcct ctcgcgtggt cacgcgcacg ttcgcgatgc    45540
acaggtcgtg gatcgcgttg gcgatctgcg cgcggcgctg cggcgagctg ccgggcagca    45600
gccgcgcctt ggcctcgacg tcgacggtgc tcgagagaca gccgcaggcg gcgccgcgga    45660
cgacgaactt caacaacgac tcgaacacgc gcgcgcccgc gcgggcgct tgcttggacg    45720 actccatttta ctttaaataa tttacgagat caaaataaaa tgactctgcg catcaaactc    45780
gagaagctca agcagatcgt aacttacttc tcggagttca gcgaggaggt ctcggtgaac    45840
gtggacgtcg gcgatggcct catgtacata ttcgcggcgc tgggcgggtc cgtgaacatc    45900
tggaccatcg tgccgctcag cgcgagcgtg gtatacgacg gcgatgtcag ccgcgtgttc    45960
aacctgcccg tgctcaaggt gaaggcctgt ctgtgcagct tccacccgca ctcggtggtg    46020
agcctggagc ccgacctcga ggacaacgtg tgcggctct cgagccacca cgtggtcagc    46080
gtggactgca caacgagcc cgtggcgcac cgcacgaaca ccgccatctg cctgggcatt    46140
aaccagcgca agtcctacgt gttcaacttc cggcgctacg aggagaagtg ctgcggccgc    46200
```

```
accatcgtca acctggacct gctgctgggg ttcatcaagt gcatccacca gtaccagtac   46260
atcacggtct gcttccgcga caagaagatg gtgctgcaca cgcccgggaa ggtggacaac   46320
ttcttccgcg agtactccat gaccgagtgg gcgcccgacc tcgagcgctt ctcgttcaag   46380
atccccatct cctccgtgaa caaactccgc ggcttcaaga agcgcgtggt catgttcgag   46440
tcgcgcgtgg tcatggacgc cgacgacaac atcatcggca tgctcttcac cgaccgcgtg   46500
ggcatgtacc gcgtgaacgt gttcatgtcc tttcaggacc ggtctctttc atgcgactaa   46560
atactcatgg gcgggtcggt gagcctgccc tcgcgggacc tgccgccgcc ggtgcgcacg   46620
ccggagatga acatcgtgcc cgagcgcgac ctcgcggaca cgatggcgcg cctctccacc   46680
gcagacccgc cgcagccgct gggcgtcggc gacgacgcgc gcatggccgt gctgaagacg   46740
accttccccg agttcgcgat atcgcggccc gcgacgggca tgctcgccgc gcagcgaatc   46800
aggtacgacg gcgacccgcg cgtctgctgc ggcgggttcg ggatctcgca ttactgggag   46860 aaggggggcgc gccgatcgaa cgtcgcgttc gagggcgcgg cgctgcgcac ctgcgacccc   46920
acgcgcttcg acgcgggcgc gtgcgacgcg ctgctcttcc gcgagtgcgc cgccggcggc   46980
gtcgacgcgg acttctgcgc gcactggatc aacgcggccg tgacgcggcg cacgaccgga   47040
cagtcgcgcg cgcggctgaa cgacatgttc gtgcgcgatt gccaaaacga cgccgcccgg   47100
cctcactgcg tggcctggat ccgcgcgatg cgaagcgcgc gcgcgacggc ggacgacggt   47160
ctaatagacg ccgtgctctc ggtgcagagt cccgagttca agggcaagca catgcgctgc   47220
agctacccct cgccggccac tctcgccatg gccgcgaacg tggacgagcc gcgcgagtgc   47280
tgggaccccg agtgcgtggc cgggaacgtg gacttcatgc taagcgataa ctacacgaac   47340
ctgggcttgt gtcggctctc gcgctgctcc atcggcgtca cacacctgcg gattgacgcg   47400
cgttcgcggc tgcgcatgcg gtgcgccggc gcgcttgccg ggctcacgaa ggcgcccgtg   47460
aaccagactg tcgtcgtcgg cgacaacctc gcgcgcgcct tcgagccgcg cgtggaaacg   47520
ctcagcgtgt tggcgctgtg cgtggtgtat ctgctaattg tctggctcta aatgggggcc   47580
gccgccagca ttcagaccac cgtgaccacc gtcagcgagc gcatccgcaa cgagctcgag   47640
cagagcgcga gcgctagcgc gaccgccgac tgcgacgtca ccatcgggag tctgattatc   47700
cgcaagaacc taggatgcag cgtttccgtc cggaacatgt gctcggccaa cgccggcgcg   47760
cagctggacg ccgtcatgaa ggccgtgagc agcaccttca cgacctctc gtcggaccag   47820 aaggcctacg tgcccgggct gctcacggcc gcgctcaaca tccagaccac ggtgaacacc   47880
gccgtcaagg acttcgagac gtacatgaag cagacctgca cggcggacgc ggtcgttcac   47940
aacaaaatca agatccaaaa catcgtcatg gaagagtgcg cctctctgcc agggagtccg   48000
gccacgcacc tggatttcgt gaacaccggc acggccgtgg gcaactgcgg cgtgaaggcc   48060
gtgatggacg tgctcgcgaa ggccagcacc accgtgcgca acgaccagga ggccggcaag   48120
ggctaccaga ccatcatcat cgcgatcgtg gtcgccatcc tggcggccat cttcgcctgg   48180
tacgcgcggc acatgctatt catgtccacc tccgacaaaa tcaagctcga gctcgccaag   48240
aagcccgtgg tgcactggac cacctacctg gacaccttct ttacggaatt tccgccgtcc   48300
gtctagatac gcgcaacatt gaaacattat atccacctct caaacggcgg tatggtccga   48360
cgcgtcctcc tcgagcgcgt ggacggcatc gtcgagcact cgcgcgcaga ccgacgctac   48420
ttggaggcca ttcagcgaca cctcgagggg tctacgcccg ggctgcggca gatgtggcgc   48480
ttcctctacg acctgctgct gacggtgttc gtcgtcatgt acatcgtctt ccgcctaatc   48540
```

-continued

```
gtgcgcaacc ccggcatctg cgccatcctc gcgctcgcgg ccgcggtgta ctacctgttt    48600
ttgtgtctct ttagcatgga ctgatggcga tcacagacag accatcgccc gcgcgcgcgt    48660
gaccagctcc ggcgccgcga agacgtcctg caccgggaag tcgtcgatct cgaacacgga    48720
gccgtccgcg gaccagatca cgcgcacgtt gtcgctcacc gagacctcgg tcagcgtcac    48780
gcccagcaca accgcgtcgt tggtgctcac cagcaccagc gcgccgggct ccgcgcgccg    48840
gtgcagcggc ggccccgaga ctgagcgccg ctgcacgcgg aacatgtccg cgaactgctt    48900
cgagagcaag tccaggtggt tgcggatgat ccactcgaag aagtacgcgc aaccgccgcc    48960
gccgcacagg aagcgcgaac ccgcgggcat cagcagccgc acaacgtcca tgtagcaggc    49020
ctgcggcagg ctcgcgcggt acagccgcgt cttcggcgag agcaccacca ggctggaggt    49080
gctcatctgg aagaccagct ggctaacgga gacggtgagc gtgcacgcgg gcacggaaac    49140
cacgtccagg cagatgtcgt ccagaaagat gctccgctgg tagaggtggt acaggatggc    49200
cacgatctga aaggccgtgg cgtcgctgat ggcgcagggg cggtcggcgc agcgcatctg    49260
cgcgcaggac cagcccccga aggactcgaa gcagacggtg agcatgcccg tgctcggaca    49320
gtgtggcgag cgccgacaca ccggaaagcc cacggccttg cggcagcgca ccatggtcga    49380
gagctctatc cagcagcctg cctcctcctc gcccatgccc atggctaccg gcgtgaaggc    49440
cgtgacgtcg tcgcagatgc gccgctccag aaaccccacg cccgaggagg ggtgcgcggc    49500
cggcggcgag gtgatgcgcg ccgggacgcg gctcggagcg ggctcgggag gcgagctgcg    49560
ctcgacccgg gcagtcgccg ccggccgcga tgccctgcgc gcgggcgcgc gctcgcgcaa    49620
cttgtttgac ttgctggcct cgtcgctagc gtcatcgaag cggtcgttcc tgtcgccgcg    49680
gacgtccgcc tcgtcgcccg tcggctgcgc ggcgggcgac gtgccgtccc gcgtacggcc    49740
cgcgttcggc gcgaatgtca cgcgccggtg cacgtacggc tccgtagagc ccgtgggggc    49800
gccgcgcccg cgcccgcggc ggaaggcctg ccgggacgcg ccgaagcggg cgaactcccc    49860
cttcgcccgg cccctttttt cttccatgat atttatcaca aaaaaaactt ctctaaatga    49920
ccaatctgct ttcgttggtc gacccggagg acctggcctt ctgcgccggg ttcccgtcct    49980
tcgacgagac catgctcgtg atcgcggggg cgcgagtgcg cttcccacgc tcgctgctct    50040
cgctcttcaa cgtggtgccg cgcaccatga cgcgctacga aaccgagctc gtgggcaccg    50100
agatggtggt gggcgccgtg ttcaccaccg cgtacaacgt ccgccgcaac ctaggcctcg    50160
gcgaggagcc cgtgaccatg cgcgacatcg agaagtactt cctggactcc gagaacgagg    50220
tgctcacgct catcgtgcac aacaccgact tttccgccat gagcggcgtg cgccggcgcg    50280
gcggccggcg catcgccaac cccgtcatct tccgcagcgg gtccacgccg ctgctcatcg    50340
tgatggagtc gcgcaagaag accaacatct accgcgagcg caccgcggag caggccaacg    50400
cctcctacag ggaggtcggc tcctcgctcg cgctggtcac tcggtacgcg ggtctgcagc    50460
tggttgacgt gcacacgccc agctccgtgc taacggtctc cgccgtctac ggcttcaccg    50520
aggacaaggg gctcaagaag ctgggctccg acaaggagct cgcggactac cagtccacgc    50580
cgctcaccga ccccatccgg ctcagcgact tctccaatat attcgacggc gtcaagaaga    50640
gcatccagct cacgaacgtg cccgtgccct ccaccgcgcg cgaggccgcg ccgtaggctt    50700
tcatgcgcga taaatcggat ggcggcgccg acgacgcccg cggtgcacct cacgccggtg    50760
ttcgtggagc ctacgatcgc gcactcgctg ctgcgcgcag agtcctacct cgcgatcgcg    50820
gtccttgagc tcgtgctcgc gctcgcgctc gcgctcgtct tcttccgcga cgagctaggc    50880
tcgctattcc gctgcgcgcc gcgagcgcct tcgccgctgg acgcgtacct gcaggcgagc    50940
```

```
ctcgtctgcg acggcgacgc gctgctgatc gagctgcccg agggccgggt gccggcgctc   51000
gcgctggacg ggcggcccgt cgcgttcccg gggtgcgaga gccttttgta ccgcataaat   51060
ggaccacgaa aagtacgtct tgtcgatgtt cttggaggaa gataactcct tcttctcgtt   51120
cgtcgccgcg ctgtccgatg acgaggcgct cggcgccgtg cagtccgctg ccgccctcct   51180
ggacttcctg ctctccgtgg tggtccgcgg caaggagaag ctcgccgccg cggggcacca   51240
ctacgactcc atcgcggacg gacgcgcgcg cgccgcgttc gagttccgag acctgcgcga   51300
gctggcgcag ctcttcgacc ggcggccctg cggcgtccag gaccgcgtgc gtgtgcgcga   51360
cgggcccgcg cgcgccttcg tggacgcggc actggggctc atgcgcgagc gaggcttcga   51420
cggcacgcag gccgcggagc gcgcgcgcta catcgcgccg aacgatctgc ccgcgctggg   51480
ggcaatatcg gccacgctct cgccgggtct ataacgtaaa aaatattagt aaaattctga   51540
aggtccgtgt gtttcgcggg cggccaacaa accagtcgct taaatggagg gggtggaaat   51600
ggacaagccg ctcctctact tcgacgagat cgcgggcgcg cgcgactacg acgcggcctt   51660
cgcggagaag cacgagccgc ccaagatccc cggccgcgga cagatgaagc tgctggtctg   51720
cgagctcgtg tttctcaacc ggctgcacct gcacggcatg ctcgacggca gcgtcatcgt   51780
gtacgtgggc tccgcgcccg acggcacat ctgctgcctg cactcgcact tccaggagct   51840
cggcgtctcg cttaagtggg tgctcattga cgggcgcaag cacgacccct gtctctcggg   51900
gctgcggaac gtgaccacgg tgacgcgatt cgcggacgag gcctacctcc gcgagctgcg   51960
cggcgagctg cggcgcgcca agatcgtgct catttcggac atccgctcca accgcgtgga   52020
cacagagccc accaccgcgg acctgctgcg cgactacgcg ctccagaaca ccatggtgag   52080
cgtgctcaag cccgtggcct ccagcctgaa gtggcgctgc cccttcccgg actcctggga   52140
gaaggacttc tacgtgccct gcggcaagga gatgctgcag ccgttcgcgc cgccgttctc   52200
cgcggagatg cggctgctca ccgtgtactc ggagacgcgc ccgaagctgc gtctgatcac   52260
gctcagcgac gcggtcaact atgaaaagag gatgttctac ctcaatagcg tggtccgcca   52320
gcgcgtaatt ctgaactttg actatcccaa ccaggagtac gacttctttc acatgttctg   52380
tctgctctcg tcggtggtgt gctcgtgcga atttaaatcg cccaaagaga aggtgctgag   52440
cctgcagaac cgcttcttcc gcttcctgcg catcccgccc tccatcacgc tcgggctgcg   52500
ccggcacgat gaaccgccac aacacgcggt acctggccaa gatcctctgc ctaaaggccg   52560
cggtaagaag cgacccctt gcggtggtaa gtagggacac cgtgcgcatg tacgacatcg   52620
aggtcgagta cggcgacctc gtgacggtgg tcaccgtcac gcacaaactc gagaccagcc   52680
gcaccgtctt ccaggtcttc aacgagacct ctgtcgcgta ctcgccgctg ccggacgact   52740
acggcgagcc catcgtgctc accacgtaca tgcagcgcga gcacaccaag ttcccgctct   52800
ccatgctcta catcgacgtg gtcgcctcgg acatgttccc cacgtttaag cgccccaccg   52860
aggaggaggc cgcggtggtc gcggccatgc agcgcgtggg cggcgccgc gagcccgtgc   52920 tcaagctccc gcgcatgctg gacaccgagc tcgtgtgcaa gatactgcac ctgcccgagc   52980
acccgctgcg cgtggtgcgc ttcctgcgcc gaaacatgtt cacgggcgtg gaggtcgccg   53040
accgctcggt gtccgtggtc ctcgactgac gaagggcagc acggtcagcg aggccgccgc   53100
caccaagcac agcggcagcc acgcgcgcgg gtccgccacg ggcacgaaga cgtgctggtt   53160
caggtacttc gcctggaagc gctccgcggt ggagtccacc ttggacccgc aggcgttggt   53220
gaggcgcacg accgcgtccg cgacgcgcac gtccccgagc gatatcacgc agtcagagac   53280
```

-continued

| | |
|---|---|
| gttgcacccg gcgatgttttt tcttcagcgc gcgcggcagc agcgcgtccg cgcgcttgca | 53340 |
| gggcgcgtac cagcagtagt agggcaggcg cgtgtcgcgg ccggtgtcga ccacggcctg | 53400 |
| gctgggcttg aggcacgcgc agcgctcgtc gtccgggtgc gcgtcgcaga aggcgtaaat | 53460 |
| ctcctcgtcg ggcgcgtccg gcccgggcgc ggtcggcggc gccgcgcgac ggcggaagaa | 53520 |
| catctctgaa aaatacttc gaccagaaaa cgaccaccga tcttatttca aagataaaaa | 53580 |
| tactattaat acgcactcgg agaatcatgt cggtggtggc gcgcgtgtcg tacagcctgt | 53640 |
| actcgcagag cgagataagc gccacggacg tggtcatcag ccagttgaag aacgacgagg | 53700 |
| acctgggcac ggtgaaggac ccgcgcctgg gcgcctcgga cgggtccata tgccgcacct | 53760 |
| gcgggctcac ggagatggag tgtttcgggc actggggcaa ggtgcgcatc tacgagtcct | 53820 |
| acatcgtgcg ccccgagtac atccccgagg tggtgcggct gctcaaccac ctctgcgtgc | 53880 |
| gctgcgggct gctgcgctcg cgcgacccgt acacgacgga cttggccgcg ctcagcgtgc | 53940 |
| acgagatgcg caagatgaag gaccggatga tgtccaagaa gaaggcctgc tggaacagca | 54000 |
| agtgtctgca gccgtaccag aagatcgtct tctcccaagaa gaagatctgc ttcgtgaaca | 54060 |
| aggtggacga gatacccgtc cccaacgcgc tcatctacca gaagctgacc tccatccacc | 54120 |
| gcaagttctg gccgctgctg gaggtgttcc aggaccccgc gaacctgttc tacaaggagt | 54180 |
| acatgcccgt cccgccgctg ctcatccggc cggcgatcag cttctggata gacaacatcc | 54240 |
| ccaaggagac caacgagctc acctacctgc tgggcatgat cgtgaagtac tgctccatga | 54300 |
| acgccgagga gcaggtcatc cagcgcgccg tgatcgagta cgacaacatc aagatcatct | 54360 |
| cctcgaactc gagcagcatc aacctctcct acatcatcgc gggcaagagc aacatgctgc | 54420 |
| gcagcttcgt ggtcgcgcgg cgcaaggacc agaccgcgcg ctcggtcatc gggcccgact | 54480 |
| ccgcgctctc ggtgtgcgag gtcggcatcc ccgactacat ccggaacacg ctcacgcaga | 54540 |
| aggtgttcgt gaactacctc accagcaagc gcgtgcgcgc gctgttcgag gaccgcgcgg | 54600 |
| tcaagttcta cttcaacaag cggctgcgcc agctcacgcg catcaaggag ggcaagttca | 54660 |
| tcaaggacaa gatccaccctg ctgcccggcg actgggtgga gatccccatg tccgagggca | 54720 |
| cgaacgtgat attcggccgc cagccctcgc tgcaccgaca caacgtcata tcctcgaccg | 54780 |
| cgcgcgcctc gcccggctac accatcaaga tcccgcccgg gatcgcgaac tcgcagaacg | 54840 |
| cggacttcga cggcgacgag gagtgggccg tgctcgagca gaacccccaag tccgtgatcg | 54900 |
| agcagagcgt gctcatgtac ccggtgacta tcttcaagca cgacgcgcac ggcgcgccgg | 54960 |
| tgtacgggtc catccaggac gagatcgtgg ccgcgttctc gctgttccgg caccagaacc | 55020 |
| tctcgctgga cgaggtgctg aacctgctcg ggcgctacgg gcgagacttc gcgccggagc | 55080 |
| ctggccagaa gaccttctcg ggcgccgacg tcttccgatt catgataggc gcggacataa | 55140 |
| acttcaaggg cgtgctcgag aacgggcgcg tggtggcgcc gaacgtcgac agcgacctcg | 55200 |
| tggtggccat gcgcgcaacc tcgctagcgg ggctgatcgc ggactacgcc acgaacgtgg | 55260 |
| agggcgtgcg cttcgtggac atggcctcct acgtgtacaa gcggtacctg gccatctacg | 55320 |
| gcttcggcgt gaccttccgc gacctgcgcc cggacccgag tttggttcgc cggctgcacg | 55380 |
| cgctgaacac cgagaagata gagcagatca aggacgcgta tcgcggtac ctgcaggacg | 55440 |
| tcgcggacgg gaagctggtg ccgatggcgc ccgcggacga ggccgacgcg ctggactcgc | 55500 |
| tgctggccaa cctgaccaac ctcaacgtgc gcgagatcaa cgagtacatg cgcgagacgc | 55560 |
| tggagcgcaa ccccgataac agcctgctaa agatggcgcg cgccgggtac aaggtcaacc | 55620 |
| ccacagagct catgtacctg ctgggcacct acgggcagca gcgcgtgaac ggcgccgtcg | 55680 |

```
ccgagaccaa gatatacggg cgcgtgctcc cgtacgcgtt ccccgactcc gcggacccgg    55740
aggcgcgcgg ctacatcatc aactcgctca tgaacggtct ctccggctcg cagttctact    55800
tcgcgatgct ggtggcgcgc tcgcagtcca cggacatcgt ctgcgagacc tcgcgcacgg    55860
gcacgctcgc gcgcaaggtc atcaagaaga tggaggacac ggtcgtggac gggtacggac    55920
agatcgtgag cggctcggta ctgctcaagt acgcggccaa ctacgcgaag atcccggggt    55980
ccaccaccaa gcccgtggag ctgctcttcc cgcacgagag catgacctgg ttcctggaga    56040
taagcgcgct ctggacgaag atccggcacg ggttcgtgcg catgcaccgg cagcgcctgg    56100
ccaccaagat cctggcgccg ttcaacttcc tggtcttcgt gaaaccggcg ccctcggagg    56160
cggaggcgct ctccgcgcgg gacctgtacc acatgatcca gcgcgtgatg aacgacgtgc    56220
gcgagaagta cttcttctcg ctggcgaacg tggacttcat ggagtacgtc ttcctcacgc    56280
acctgaaccc ctcgcgcgtg cgcatcacgc gcgcgaccgc cgagctcatc ttccgcaagc    56340
tgtaccagaa gctgaacgcg ctgctcggcg gcggcacgcc cgtgggcatc atgtccgcgc    56400
aggtgctctg cgagaagttc acgcagcagg cgctctcgag cttccacacc accgagaaga    56460
gcggcgccgc gaaggtgaag ctgggcttca acgagttcag caacctcatc agcatgagcc    56520
gcaaccacac cgagatagtg gcgctgaccg cgccgagcgc ggacaagctg atgccgctga    56580
aggtaaactt cgagttcgtg tgtctgggcg agctcgtgcc cgagatcgag acccggccct    56640
cgggacggcc ctccgtgcac cgcgtggaca tcacggtgca ccgcctgcgc atcaagcgcg    56700
cgcacctgac cgaggtcctg gtggacacca tcatcgagcg cttcgtgtcc ttcaacgtgc    56760
tcgtgaagga gtggggcagc gacatgaccg tggagggcga ccgcgtcacg tacacgctgc    56820
tgctgcgctt cgtggagccg gagcagctca acttccacaa gttcatgctg gtgctgcccg    56880
gcgccgcgaa caagggcaag gtgagcaggt tcaagatccc gatcaccgag accacggtct    56940
acgacgactt cgacgccgcg cgcaaggcct accgcatgaa catcgagctc atgagtctga    57000
aggagctggg gatattcgac ctcgaggacg tgaacgtggt ccccggcatg tggaacacct    57060
tcgacatatt cggcatcgag gccgcgcgcg ggcacctctg cgagagcatg ctggacacct    57120
acggcacggg cttcgactac ctgtttccct cctgcgacct gctcgcgagc ctgctctgct    57180
ccgggtacga gcccgagtcc gtaaacaagt tcaagttctg gaacgcgagc gcgctgaaga    57240
aggccacctt cggcgacggc cgcgcgctgc tgaacgcggc gctgcacaac cgcaccgacg    57300
cggtcgcgga caacagcagc tgccacttct tcagcaagac gccctgcgtg ggcacgggct    57360
actacaagta cttcgtgaac gtggagatgt tcatgcgcat ggagcgcgag atccaggcgc    57420
gcgtggcggc gcgcaagatg gaggagatcg aggaggccgc cgaggaggag ttctaggcgc    57480 gacgcgcct tactttgcga ccgtgtcacg acgacacga acggttagga cggcgagtcg    57540
cagacgaaca tttttatgag ctggtagcgg aagttggcgt tttccaggaa ggcgccgcgg    57600
aggtcccgga tctcgtagta ggttttgagg aagtacacga agcgcgcggg ctgcgtcata    57660
gtcgggttct ccgcaagccg cttgtgcatc acgtacccca tggcggcggc gccgctgcgg    57720
ttgacgccgg ccacgcagtg cacgagcgtg ggcttctgct cggcctcgag gcgcgccagc    57780
agcttcacga gcgcgggcat gatggaagcg atgttcgtcg tgtcgtcgtc tctcagcgga    57840
atgtggtacg ccgttatccc cgcgggcgtc gagtacttgg acatggtcat gttaaccaga    57900
cacttgaagt cgacgccgga gtcccccgc agcacgcgc gcgcgtcctc ggcgctgccc    57960
aagtacacgt ggtccgtgag ccgcgtcatg cccgagggca gggccagcgg cggccccgcg    58020
```

```
cgcgtgcacc gcagcaggag cctggcgtac cactcgctct tatcgcccat atttatttat    58080
atgatacaaa tggcagacgt cacaacactg acggccaacg gtctgaccct ggagttcgcg    58140
cgcgagcgcg ctctgcgcag tctgcgcgcc gcgcgcacct ccacgctggt gttcttcacg    58200
ctcacgctcg cggcctcgct gttcgtgctc tggctgcagc taaccgagtt tcccgtcttc    58260
gaggagctcg gcaagtacgc gcgcatcaag agcgcggtgc ggtcctggcg cccgctggtg    58320
gaggctaaga cagagatcga gtccgacctc ggccggcaga agaccgccga ccggcccgag    58380
ctcttcgagt tcaggtgcgt ggacttcggc aagttctacc tgccggtgag gtacagcccc    58440
acgaccttcc tgccgcaagc cgtgcgccgc ggcgcgggcg atggctggat ggtgcacaag    58500
gcggcggccg tggacctcgc cgcgcagcag ttctgcgagt ccgtgctgcg gcaccgcgcc    58560
aacaacgtca tcacatgcgg gtcagagatg atgcggctgg tgggctacag cggctacttc    58620
gaggacgacc actggtgcgc cgcgacgtcc ggcgtgctga cgtgaacgat cacacgatgg    58680
ccgtgaccag cagcccggcg atgaaccaca gcagccgcga gttcggcagc agcagcacga    58740
gcaccagcag gtacgccagg atgaagatgt cgaccacgtc cacgtcgaag agccccatga    58800
aggagaagag cggcgtggtg aggaagtaga tggcgccggg ccagaagcgc gccagccacg    58860
tggcgagcag cgaccacagg gagggcgcgc cgctgagccg cgtcttcacc tgtatgtagt    58920
actcggggta gaccacctgc tcggcgccgg agagcaccac gcgcgccaga gagagccgct    58980
tctccagcgt gaacacctcg gtgagcaggc cgctgcgcag ccctccctcc ttgatgatcg    59040
cgtcgtagag cttcttcatg ccgccgacgc tgatgatgta ggcgtctagc gagacgtcgt    59100
acccgccggg gtagaccatg agctcggggt cgccggtgcc ggggacgttg gtggccagcg    59160
cgccggtcat gtaggtctcc ttgagctgcg tcatgtacca gccgttcgcc ttcatcgcct    59220
cgatgagcgg cttcaccatc tcgggcttgc ggaaggtcat gtcgttgtcg accaccagga    59280
tgaagtcatc gtcggagtac ttggtgggga cagtgccggc cgatatgctc tcccagaggt    59340
tgaggtggtg cgctgcgcgg cgctgcatct ccttcggaca cgtggacttg cacatgtccg    59400
tgaagaagtg cgggtagtct ttggagtcca cgtctttcca ttccaccgcc ttgagcacgt    59460
ggtcgccctt ggggtgcggc gcgggaggag atggcttggg tgccggcgcg ggggccggtg    59520
cgggggctgg gcaggagag ggagcaggcg cgggttgagg cttggcgggg tcgtcggcga    59580
ggcccaccag gtacgcagc gtggggaaca cctccttggt cccgcggcct tcggcaaccc    59640
cgattatgta ggccgtgatt tcgggtggat ccatttagtt attaaaatta atcatataca    59700
actcttttat ggcggctatg gattcggcta tccagtcctt gaccgagccc acgatgcccg    59760
ccaggaacag gaagaaggcg aactccaggt ccacgcggtt cagagagtcg ctgaagtaca    59820
cgaagacgtc gctgtccggg aagaagctgc gccggaacat gttgtacccg ttgaccttgt    59880
gcgcgacgtg ctccgcgctc agcagcgtct cgtcgaaggg gtacgggtcg ctgaagcgga    59940
acacgtacat ggccgggttt gcgtagtagt acttcatggt gtttgtgacg aagaggctcg    60000
ccagcgagat gatgattttt ttcttctcga tctcgatctt gatgtggtcc tcgaagcgct    60060
tcatgttgta ggcgttggtg tcgtgcacgc ggatgagcac gcgcgagtcc gacatgatgt    60120
cctggaactc cgcgcgcgcg tcgggctct cggcgggcgt ctccgcgggc gcgccacct    60180
ccgcgcacac cgtcggccta gcgcgcggcg gcgtgcgcat gggccgcgcc cccacgcgct    60240
gcgaagcgaa aaactccacg gcgcgagcct cgcccgcgtc cgcgtacgac tccaccaggt    60300
agttgcggct gcgcgtggtg cggccgatgg tgttcagccg gtgcagctcc gcgaccagcc    60360
ggcggtagtg cgcctccagc tcctcgggca tgatggaggt gtacacctcg gtgagcagca    60420
```

```
tcacggtgtc gaagtcctcc ttgccgcaga cgcgcgtctt cacgaggaag tggtgcacag   60480
ccgtcgcgat agagagccgc agcgtggact cggtgacctc gacgctggcg tccttggtct   60540
tcttcgcgct ccgcgaggcc atgaacgaga cgaggaagtc cgcgctgctg ttgagcacga   60600
tgaccagcgc gacgatgaag ttgaggttca gcgtcttcgc ggactggaac agctcggtgg   60660
ccgacgcgtg cacgtcgagc aggttcgcgg agagccgcag gaagaacacg ccgcgcttga   60720
tctcggccgc gaagcgacgt tcgtactcct gccggcgcgc gttgatcgcg atgaggaagt   60780
tcaggatgag ccggttgatg ttgtacttca cggcccaggt ctgcgtcttc atgatggtgt   60840
cgaaggacat cacgatgttg aagatgaagc gctggctgtg cgagaagtag ctgtagggct   60900
cgctgaggaa gatggacttg ttggtcgcgg gcaccaccac gcccgcgcgc gcgccggacg   60960
cgtcggtgtt caggtccggg atgttcatgc cgcagatgcg gcagtaggcc atgccgtcct   61020
caaagtacac gaactcctcc acgaactcgt tgatcttggc gaagtagtcc acgtccacgc   61080
gcatcgcgac cgcgagccgg atctggtgct cgcagggcgg cgactcgaag cgcaccccct   61140
cgccccagcc cggcggctcg cgcacgacca gcgcggtgcg cgaggccggg cggaacttgg   61200
cgtcgcgcgc gttgagcagc gccgggaaga ggtcgcagag gtgccggctc gagaggaaca   61260
cgtacttgta cagcagccgg cgcgcgtccg cggccatggc gtccacgaag gcgcggcccc   61320
actccgcgac cgcgggctgc tcctccgcaa agttgttcgg gtagaccttg tccgtggccg   61380
cgaggaacac cttcttcacg tcgaggaagt cgcggatcac gatggggacg cgcgcgccgt   61440
cgagctcgta catgaacacg tagcgcaggt tgagcttgcg ccgcgagacc gggatgccga   61500
tgtgccgaca caggtacgcg aactcgaggt acttcttcga gaagcggatg cggtccaggt   61560
tcttggagac gtactgcagc atgttgcgca tgttgaaggg gatctcgcgc acggcgggct   61620
ccgcggcgtc gtcgaaggcg gtgcgcagat cgctggtgcg ctgtacgacc acggcttcgc   61680
cggtggcgtc gtcgtgcacc agcacgttaa cgcgccgctg ccggatgacc atgtcgaagg   61740
tgttgaagaa catctcgtac atgctgtgcc gagtgtcgtc cgcgatgcgc tcgcccaccg   61800
agaggctcgc ggtggcgtcg tcacgcacct gcttctcgaa cttgtacccg atgtaggaga   61860
atatcgagat cagcgtggcg tcgtcggcgt cggggttctg ctccatggtc gcgaagagca   61920
ggcggatgtc gtcctccgtg atcgcgtcca cgttgtacag gttgaccacg aagatggact   61980
tgttctcggc gatgaagtcc gtgtaggact tggtggccgt gttcgggtcg cgcatgtacg   62040
cgcggatctt cggcacgatg ctcgcgagga tggactccct ggaatccatt taaggacggc   62100 aagggcgcg gagaccgtct caaaactgaa atcgtataaa ctcttaaaaa atcggtattg   62160
aaagtacgca ccaccaaata aagcgtcgag gtcgggcatg tcttcgtggc gactcaaaat   62220
gagcaagtgt tcaggttcca gcagcgtcca gactctcgag gatctgcgta atcgtcttcg   62280
ctccgaggcc ttgggcaacg attgccaaga gccccgcgac gacctcttcc ccagcggcga   62340
ggagtgtctg gacatcgacg ggccctgccc ttgcgatgag gcggagcagg agatcgacca   62400
ggagcagttg cccgtgcccg aaaccgtgcc cgaaccgccg gccaagactc ctaagcgccg   62460
accagtgaag aaggataagg cagataaggc agataaggac aagtcgacca gaggcgcaaa   62520
gaaaccgtgc ccttcggacg acaaggatga cgagctcaag agcaacgacg tcgacaacaa   62580
cgaagagtcc ggcgacacag acggcggcgc gagcgcccga agcccagcg acatcgacaa   62640 cgtggacgaa atgacgacgact ccgacctcat ggtggcgttc tccaccatcc tcgcagactt   62700
caaggacctt acccaacgag tgaaagctct ttcgtccgtg ctcacggacg tgcaggcggc   62760
```

```
cggcatacgc aggagcttct cgacgctcgg caaggctctg acggaggcgg cccacatcgc    62820
caacaccgga tctaagccag tcactgcgcc tcgcaagaag aaggccgccg cctgcaagaa    62880
gtaggcgcac taaatagcga ggctcggtat gcgggcgctg cacctgtcag acggcaaact    62940 ttttttttgac aaggagctga cgcagccggt ccccgacgac aaccccgcgt acgctgtcct   63000
tgcgaagatc cggatcccac cgcacctctc ggatgtggtc gtgtacgagc aggacctcga    63060
gtctgcgcag cagggcctca tcttcgtcgg gcgcgacgcc aagggccgaa agcagtactt    63120
ctacgggcgc ggacacgtgg agcggcgcac ggccgtccgc aacgccgtgt tcgtgcgcgt    63180
gcaccgcgtc atgaacaaga taaacgcctt catcgacgac cacctcgcct ccggcagcga    63240
ggccgaggcg cagatggccg ccttcctgct catggagacg agcttcttca tccgcgtcgg    63300
caagacgcgc tacgagcgcg agagcggcac cgtgggcatg ctcacgctgc gcaacaagca    63360
cctcgccgag gccgagggcg gtgaggagat ccgcgtcgcg ttcgtgggca aggaccgagt    63420
cgcgcacgag tttgccgtgc gcgagggggca gcggctcttc gcggcgctgc gtcggctctg    63480
ggacccgggc gcgcccgaca ggctgctgtt cgaccggctg agcgagcgcc gcgtgtacac    63540
cttcatgcga cgcttcggca tccgcgtcaa ggacctgcgc acctacggcg tgaactacac    63600
cttcctgtac aacttctggt ccaacgtgcg ctcgctggag ccgcgtccct ccgtgaagtc    63660
gctcatctgc acctccgtgc ggcagaccgc cgagacggtg gggcacacgc cctcgatctc    63720
gcgcagcgcc tacatggcca ccgcggtgct cgagctcgtc agggacgcg cgttcctgga    63780 cagagtcgcc gccaccgaca cgctcgacga cttcgtggac atcgtcgtgg actatgtaaa    63840
taactctgag caggtaaatg gatgaggcgc tgcgcgtggc ggcgcgcgtc gtggacgggc    63900
tccggccgct ggacgtggcc gtgtgtctcg cgcagctgcg cggagccgcg cccgagcgcc    63960
gcttccggcg gctcgacgag tgctccgcg aggccttcct ggactttgag ttcgccggcg    64020
gggacgtggc gtcgcggtac ctctccgcgc acacgcgcga gctccgtgcg gcggagcggc    64080
gcgagcacat ggccgcgatc gcgcgctgcg tcaccgaggc cgacctggcg ctcgcagacc    64140
gcccccgggg caaggcgcgc gcggcgctgc gcgtgtgccg caaccgcgag aaagtcgcgc    64200
gcttggcgag gctgctgcgc gacgccgaga gcagcggcgc ggacttcgcc ttcatacgcg    64260
cggccgtggc gtagcaaaac gtaaaaacaa cacattccct aaatcgccat ggacgcgcca    64320
agtctcgact gcatgctcgc cgcactcgcg gcgaaggcgg cctcggtgga ccgaggcgct    64380
cccgaggacg aggtgcacca cgaagtggag ctcgtgctcg tggacccgcc gctgtccacc    64440
ctggccgcca cgctgcgcct ggcctcggag acggagtcct tcatcctctt cacggtgacc    64500
gcgctcgcca aggaggaggg caagctgcgc gcgcgcgtgc ccatgtcgcg cgtcgtcggc    64560
ctggacgtga gaacgtgca gctggtcaac gccatcgaca gcatcgtctg ggagcgcaag    64620
gcgctcgtgg aggagaccgc gctgcaggaa ggctgtctgc tgcgccactc caccgagcgg    64680 cggcaccctct tcgtggacta caagaagtac ctctcggcca tccgcgtgga gctggtaaac    64740
cgcgtgcgcg tgcgctccaa agaagtcgtc gcggacttca agttcaagta ctttctgggg    64800
tccggcgcgc aggccaagag ctcgctgctg cacgcactca accaccccaa ggtgcggccc    64860
tcgcccacgc tggagttcga ggtcgtcccc cggggcgagg ccgtgacga ggccgccgtg     64920 ctcgcggagc tgcgcgccgt ggcgaaggcg ctcttcatgg cgcccaccga cgccgtcttc    64980
ctggcgccgc cggccgagat gccggtgcgc acgctcatgc tgcagaagca ggagatcccc    65040
gcgctagacc tcgacggcct tttcgcggtc tccaagacgg acggcgtctc cgcgagcgtg    65100
tgcgtggacg aggacggcgt cttctgcgcg ttctcgcacc tcgcgtacac catccggtac    65160
```

```
ccgctcgcgc gcgaagtgca gggccggtac cggctctggt gcgaggccgt gcggcccgtg   65220
ggcgagcgcg tgtggtccat gttcgtgctg gtcgtggagg agcctgcggg cgatgaccgc   65280
gtcgcggccg tggccggcgc cgtggaggcg ctgcgcggcg tgtgtgcacg cgtcgagttc   65340
aaacctaagc gcgtggacgg gcccttctcg gcgacctccg agctggtgga gcacatcaag   65400
agcgcgctgc agacggagcc agagggcgtg gtgctcttct acgcgcgcgg agagaagtcc   65460
aagcgcgacc tcaaggtcaa gcgcgacaac acggtggacc agaccacgaa cgtgatgttc   65520
cggtacatgt ccagcgagcc catcgtcttc ggcgagggct ccaccttcct ggagttcaag   65580
cggtacagca acgaccgcgg gttccccaag gagtacggcg cggggcgcat cttcctgcgc   65640
gaggacgtgg tctaccacaa caacatctac tgcatcgagt tcacgaagac gcacctggag   65700
gtgggcctcc gcagcgtggt cgtgcccgtg aagttcatcg gcgagttctc gcaggagggg   65760
tacctgctgc ggccgcgcct ggccaaaacg gagtgctact tccgcaaccc ctcattctac   65820
gggaaccagc actcggtggt gctcgagcac actcgcgacc agctgctctc ggtggggac    65880
gtgttcgacg agagccgcat ggccgccgtc gggcagacgc tggccaacga cgccttccgc   65940
ctgaacccgg acacgcccta cttcaccaac cgacgcacgc gcgggccgct gggcgtgctc   66000
tccaactacg tgaagacgct catgatatcg ctgtactgct cgaagacctt cctgaacaac   66060
gccgagcgac gcaaggtgct ggccgtggac ttcggcaacg cgcggacct  ggagaagtac   66120
ttcttcggcg agatcgcgtc catggtggcc acggacccgg acgcgcgcgc gatcgagcgc   66180
gccatggagc gctacaaccg cctcaacgcg gggctgaagt cgcgctacta caagtttaac   66240
tacatccagg agaccatccg atccgagacc tacgtggaga gcatccgcca ggtcatgtac   66300
ttcgggcgct tcaacatcgt ggactggcag atggccatcc actactcctt ccacccgcgg   66360
cacttcgcca cggtgatgcg caacctgcgc gagctcaccg cgcccggctg caaggtgctc   66420
atcaccacca tggacgggga cttcctgtcg acgctctccg agaagaccag cttcgtgatc   66480
aaccgcaacc tgcaggagag cgaaaaacttc atgtcgatcg agcgcgtggc cgatgaccag   66540
gtcatggtct acgcgccctc gaccatggcg cagcccatga cggagtacat cgtgcgccgc   66600
gcggacatcg tcaagctctt cgcggacaac ggcttcgacc tcgtggacca cgcgaacttc   66660
gagaccgtga tccggcgcag ccgccgcttc gtcgagggcg tctcgcggct ggagacgcgg   66720
ccctccacca agaacttctt cgagctcaac cgcaacgcgc tcacggagat ggacagcacc   66780
gacgtggccg cgctgctaaa gatctacgtg ctgtacgtct tcagcaagcg gtaggcagaa   66840
ccagggcgtc gattccgcgc ccgcgccggc gcggaaggcg ttgaacagct ccgccagcca   66900
ggctgcggtc tcgcgcgcgt cgatcgggcc gccgtcgtcc ggcggcggct cgcgcgccgc   66960
gcgcaacacc agcgtctccg cgggcggcag aggctccaga gcctcgaaga ccgcgcggct   67020
cgggaacagc gcgcgcatca tgcgcgcgcg gtggccgaac accgccttga ccgcgcgcag   67080
tgccgagcgg ttgtccagcc gcagcgctcg gtcaaaacga tgcacgcgcg cgggcgcgcc   67140
gcggtggtcg cgctccacga gcacgtgccg ccacgccagc gccgcgccga cgcggtccag   67200
gctgggcgcg agcgccacca ggcttttcag cgcatgtaaa tctccgcgca tggccgacgg   67260
ctccatttac tactgcggag gaacgcacgt ggtcgcggcc gcgccgggcg ccgcgcttgt   67320
ggtgctggac gcgcccggtg cgcggcggc  ggccgcgccc gcggggcagc gcgtcttctt   67380
cgccgagtac ggcctcgaga agcgggccgg cggcccgatc acggcgcggc tgcgccgctc   67440
cgggttccgc ggcgccgcga acgcctgggc ctccgtggcg gacttcgagg ccggcggccg   67500
```

```
tccctccgcg tggacgctgc gcgcggagga ggcttcgcgc gtgccgctgc cgacggacgc    67560
ggcgctggtc ctggcctggg gcgcgcgcga ggagccgctg cgggcgtgcg tgctggcgcg    67620
cgcggcagac gcggaggcgc cggtgggcgc cgcgctcaaa gaagccgcct tcgacgcgcg    67680
ggcgccggcg gccgcgctgt tcgcggcgct gggcgcgccc gcgctcgcgc cccgctgcg    67740 ggcgcggcta gtggcgccgc cgggcgcgcc gccgcggacg cggctctgcg agaacccggc    67800
catgctgcgc gcgttcgcgg tgggctggtt cggcgcgcag ctgggcgagg cctccgaaaa    67860
tgaaaaggta tttgccgcct ttgataaggc gaggtcgtgt ttggacgacc gctgatggcg    67920
acgcccgcga acgcgcccgc gctgctcgtc gcggcgctgc gacaccgccc gtaccgcgtg    67980
gagtaccacc cggactggga gccggtcatc gagacgctgg tggacgagta cgacgcggtc    68040
gcgccctggc tgctgcgcga cgcgacgagc cccgagcccg agcgcttctt cgcgcagctg    68100
gcgaagccgc tggcggacaa gcgagtgtgc gtgtgcggca tcgacccgta cccgcgcggc    68160
ggcaccggcg tgcccttcca gtccccggac ttcagcaaga agaccatccg cgcgatcgcg    68220
agctcggtcg cgcgcacgac cggcacgcag ggctacgcga actacgacct ggacgcggtt    68280
ccgggcgtgc tgccctggaa ctactacctc tcctgccgcg agggcgagac caagagccac    68340
gcgatgtact gggagcgcat ctcgcggctg ctgctgcagc acgtggccaa gcacgtgagc    68400
gtgctctact gcatggggcg cacggacttc cagaacgtgc gcgcgcgcct ggacgtgccg    68460
gtgacgctgg tggtgggctt ccaccccgcg gcgcgcgacg ggcagttcgc gcgcgagcgg    68520
gccttcgagg tcatcaacgc cttattggag ctcaacggga agtctcaagt ggactgggcg    68580
cgaggatttt ctttttatag tgaaaattaa tccgtggtcc taaatggcgg cgcccatatg    68640
cgataactct cacgtgttcc tcctcaagcg cctgggcgtg ccgtcttcct gccggcgctc    68700
ggaggacccg cgcttcgtgg agatcctgac tcccttcgag ctctcaaact acatcgagcg    68760
gcacccggga tgctgcctct tcgagacgct gcgcgacgag gaggactgct ccgtcgtgcg    68820
cgtcttcgcg gacgtggaca tggacagcgt gctcgaggag gaggacttcg tcgcggcgct    68880
ggaggacctc atcgtggagc tcgcggcctt cttcgaccgc ttcgcgagcg gctcctgcgg    68940
caccgtgccc ggcgaggtca agcgcgccat gctcgcgaac ttctcggtca cgcgatccac    69000
ggccgagcac aagaccagct tccacctgat cttcacggag acgtacacca cgctggacac    69060
gctggtggcg gcgaagcgcc cgctgctgga cctgtgccgg cgctcggaca acgtgctgct    69120
gcgcgcgctg gacacggccg tgtaccgccg cggcgcgacg ctgcgcgtgg tgggcacgcg    69180
caagacgccg gagtcgagcg cggtccaccg catgcagtcg cccgacgacg acatcaagga    69240
ctacctgttc acgttcgtgg agctctcgga cgcgagcgtg tacttcgagc tcgcggagcg    69300
cgagcagcac acgctgagca ccgtctgctg ggagacctcc tacatcccct tcggcgacgc    69360
gatgcggcgc gtgtgccagg cggtggtcaa cgacatcgtg aacctccgcg acatcaccga    69420
ggacaacttc ctcgacacgc cgctggtcat cgactacgcg acgcgctgcg cgctgtgcaa    69480
gaagcccaag cacaagcacg cgcaccacat caccatgggc aacggctgcc tgcgcctggt    69540
caagggcggg aacgcgcaca gctgcaaggt caagatcatc cagctcgagg gcaaccggct    69600
cttcacggcc gcgcagatca tcatcgcgtc cgaggtcgtg aagctcaccg agcgcaacga    69660
ctacatcgtg tggctgaaca actcctggcg cttcagcgcg gaggagtcgc tcatcaccaa    69720
gctcatcctg gacgtgcggc actcgctgcc cgcggactac gccaacgaca tgctgtgtcc    69780
gcgcaagcgc aaggtcgtgg agaccaacat ccgcgacatg ctcgtggaca tctccgagac    69840
ggacacgcag tacgacaagc tgcccttcac gaacggcgtg ctggacctgg ccacgggcga    69900
```

```
gttcctcacc ggcgaccgcg cgaaggcctg cgtgtgcacg gtctccaccg ggtacgcctt    69960
ctcgcgcgag gagttcgcgg ccgcggcgga ctcggaggcc atgcgccggc tggtcggcgt    70020
catcgacgac atccagccgg acacgcccga gaacgccgat aaccgcgcgc tgtacgagcg    70080
cgccatgtcc agcgcgctct gcggcgccac gaagacggtc atcgtcttct tctacggcga    70140
caccatgacc ggcaagtcca cgagcaagcg tctgctcatg tccgcgctcg gcggactctt    70200
catcgagacc gggcagaccg tgctcacgga cgtgctcgac aagggcccga accccttcgt    70260
ggccaacatg cacctgcggc gcgcggtctt ctgcagcgag ctcccggact cgcctgcaa    70320 caacgcgcgc aagctgcgct ccgacaactt caagaagctg accgagccct gcatcgtggg    70380
ccggccctgc ttctccaaca agatccacaa ccgcaaccac gccaccttca tcatcgacac    70440
caactaccgc ccggtcttcg accgcgtgga caacgcgctc atgcgccgcg tggcgctggt    70500
gcgcttccgc acgcacttct cctcgtcggc cactcgcgcg gccgccgcgc acaacgtcga    70560
gtacagcgcg gtcaaggaga tggacgagag cctggacacc aagatccagc gcaactactt    70620
ccgctacgcc ttcctgcgcc tgctcgtgca gtggttcggc aagtaccacg tcccgcaggt    70680
ctcgctggcg cccacgcccg acgcggtccc cgacttcgcc ttccaccgcc gcgtggccga    70740
gctggtggtg gccagcaacg acgcgcaccg ccgcgcgatg gagtcgctgt ccaagctggg    70800
gtacgtgctc gtgggcggca acgtggccat gcccgcggac gccttccggc agcggctggc    70860
cgcgcacttc aacgcgcgcg tgcacggcgg cgacatagac gccttcatgt tcaagcacaa    70920
gaaggtcgtc aacgtaacgg aggagtacgt ggagtacgta ttcatcgaag atgtcgagaa    70980
taaatagacg ggtatgaact cggacgtgat aaagctgttc gtcgggcacg acgagtccgt    71040
gcccggcatc ctgccgcacc agctcgcgac cgtggacttc ctgatacgcc gcgttctaga    71100
cgacaacgtc agcgtgcttc tcttccacat catgggctct gggaagaccg tcatcgcgct    71160
gctgttcgcg atggtggcct cgcgcaccaa gaaggtgtac atcctggtgc caacgtgaa    71220 cgtcatgaac atattcaact acagcatggt catggtcgct aacctgttca acgcgccctt    71280
cgtggccgag aacatattcg tgtactcgac gactagtttt tattcgctaa actgcaacga    71340
cggcgtcata aactacaacg gcctcggcaa gtacgagaac tcggtcttcg tggtcgacga    71400
ggcgcacaac atcttcggga acaacaccgg cgagctcatg atggtgatca agaacaagac    71460
gcgcgtgccc ttcctgctgc tctcggcctc gccgatcacg aacacgccgc tcacgctcag    71520
cagcatcatc agcctcatgt ccgagaagga cgtggacgtc ggcgacatcg tggtgcaggg    71580
caagaaggtg ttccagatcc tgctgaacga gcacggcgtg cgcgtgatcc gcgaggtgct    71640
caaggggcgc atctcctact acgagatgcc ggacacggac atgcccgagg tgctctacca    71700
cgggcgccgc ttcctggaca cgcgcgtggt ctactgccgc atgtcgcgcc ggcaggagga    71760
cgactacctc accgtgcgcc ggctctgcaa caacgagatg ttcgagaaga acatgaacaa    71820
cgtgtccatg gcggtgctgg gcccgctgaa cctggtgaac aacctggacg tgctcttcca    71880
ggcgcaggac aaggacctgt acccgaacct gcgcatcagc aacggcgtgc tctacgggaa    71940
cgagctcacc aagctggaca tcagctgcaa gttcaagttc ttcatctcga aggtgggcgc    72000
catgcgcggg aagcacttca tctacttctc caactcgacc tacggcagcc tggtcatccg    72060
caacgtgatg ctcagcaacg ggtactcgga gttcggcggc tcgcagagca acaatccgca    72120
caccacgccc gacgggcgcg ccaagacctt cgcgatcgtg accagcaaga tgaaggcctc    72180
gctggaggag ctgctcgagg tgtacaactc cgcggagaac aacgacggtg gcaagctcat    72240
```

```
gttcctcttc tcctcgaaca tcatgtccga gtcctacacg ctcaaggagg tgcggcacat    72300
ctggttcatg accatccccg acaccttctc gcagttcaac cagatcctgg gccgcgccgt    72360
gcgcaagttc tcctacgcgg acgtggccgc gcccgtgaac gtgtacctca tggcggcggt    72420
gtactcggac ttcgacgagg acatcgtctc gctggaggac tacagcgtgg aggacatcaa    72480
cgcgctgccc ttcgacgtga agaagctctt ctacctcaag ttcaaggcca aggaaaccaa    72540
ccgcgtgtac gccatcctgc aggagctctc ggacgcgtac tccgcgcgcc cgcacccgca    72600
gctcgtggac gtggtgctgg gggagatcgt gcgccagttc ttcgcacggc actgccgcgt    72660
gcccgccgag gacgccgcgc tcgtggccgc cgtcgaggcc gttctcggca cgcgcgaggc    72720
agcggccgag tacatccgcg cgatagtgga cggacacttc ttcgtgacca acaagacctt    72780
cgggaagtgc ctgctcttcc ggcacgagcg cgacatcgtg accgtgccct tcgagctcga    72840
gcacgacccc ttcgcgtggg cgatcaactt ccgcaaggag gtcagtgtgg tgaatatata    72900
acggcaaaca taaatagaaa gactgtcctt ttgcgcgatg tcgaccttcc ggcagacggt    72960
gtacctggcg gtgacgctgc agccgcacga gctcacgctc gacttccgcg caacgtcgc    73020 ggaggcggtc atgcgcgagt acctctacaa ggagaagggc gggctcatgg ccaccgacat    73080
cgaggtctgc ctcggaaacg agatgccgct ggggcgcatc gtgaacaacg cggttgtggt    73140
ctcggtgccc tgcaacgtga ccttcaagta ctaccgcgtc ggcgacaccg tgagcggcac    73200
gctcaacgtc gaggacgaga ccaacgtctt cgtggactgc ggagacctca tctgccagct    73260
cggcaagagc tcgggcggcg tgaccttcaa cgagtccaag tactgcctcg tgcgcaacgg    73320
agtcgtctac gagcacggca gccgggtctc ggctgtgctg cgcgaggcgc gctccggacg    73380
cgagtccgcg ttcgtgttct ccgcagtgct gctggacggc gtcccgccg aggagaagga    73440 cgagaagaag gacgagggcg agaaggccgc ggaggaggaa cgcccgcga gccccgccgc    73500 caaaaactag cattattggg ccgcgcgaac cttcgataaa tgcgcacgta cacgtcgctg    73560
ctctcgaagc tgctcaagag caaccggcgg ctcgggagca cgcgcgtctt ccgcgacccg    73620
ctgcagcaca tcagcgcgac cgcctttgtg caccggcgca tcgaccggca ccggcgcgtc    73680
tccatctgcg ccgtgctcac caccaccgac gggctcgtgg tcgcgtgccg gcgccggtac    73740 tccttttgt cctccgagct cgcggagacg cgctcgcccg cgcggcgcgt gctgctcgca    73800
accaagcacg cggacgctct cgcgcgcctc ggcgccgcgc gcccgcgcga cgacgtcatg    73860
tttccgggcg gcgccccgct gtccggggag tcgccgctgg cgtgcgtgct gcgcgaggtc    73920
gaggaggaga ccgggctgcg cggcgaccag gtcagcgtgg acgagcggct gttcgtgcac    73980
gccttcatcg acgacctggt ctcgggccgc gacttcgacg cgatcatctt cacgggcgca    74040
gtcgcgcttt cgagcgcgga ggtggcgaag cagttccggc ccaacgacga ggtcaagggg    74100
ctggtcttcc tgcaccccga ggacgcggag ggcgtgggcg tgatggcgcg gctggcggcg    74160
ttcgcgcgct gcgcggcgcg cctgcgctgc tggggcgcgg ccgtcacgcg atagaggcgg    74220
ggtccaccac gtacacgagg cgcccgccgc tcacgcgcac ggtgggcggg tcgcccagcg    74280
cggtcaggaa gttcccgtcg tcgtcgaaga ggcgcccgcc gcgctcgagg aagcccttgc    74340
gcaccgtgac cagcgccgtg gaggtggagt accacacgct ctgcccgtcc gcgagccgcg    74400
ccgcgcgcgc gggcccgcgc gcgtccgccg ggcgcgccac cagcgcggac cagccggagt    74460
cgtcctccag cggcgcgaag tccgtgaagg cctcgcgcac ccactccagc gagcagcgct    74520
tgagcacgcg gaaagagctgc gtgaactgcc gggacttgtc gcggatgagg gccagcaggt    74580
cctcgtccac ggtggcggcg ccggagtcct ggcgcgcgac cacgaagtgc acgttcacgt    74640
```

```
agcggcggtc gggcggcgtc atctcgtggc tgttcaggcg caccgcgcgg cccacgatct   74700
ggcgcagcga ggcctcgttc caggtcatgt ccaggatgaa gatgtcgttg atggagagga   74760
agctgaggcc ctcggagccg ctcagcgaga acacacagac cttgatcttc tcgccgtcgg   74820
tgttgtcgca ggcgttgaag gcgtccacga gcttggcgcg cgtgtcgcgc gtgcgcgagg   74880
agaactccac gctggagacg ccgaaggcgc ggaagtagag cagcagcatc tcgatgccgg   74940
tcacgttgac gaagggctcg aagaccagac acttgcccgg cgaggccagg atgcgcaggc   75000
agacctcggt gtacttgcag ctgcgctcgc gcagctccgc gagcagcgag acgtccgcgg   75060
aggtcatgcg gtcgccgctg acgggcgcgc cgctgcggaa gagccgcatg ccgcctccg    75120 agaagacgcg gtccttgacg gcgcgcgcga agtccaggaa gagcgcggcc acggcctcgt   75180
cgtactcctg cttggagagc acggacttgt cgggcgcgtc ctcgaaggcg aaggtggccg   75240
cgatgcgccg gtacacgcgg aagaccgcgg cgccggactt gcgctccatg gcggccgcgc   75300
ggcggtaggc ctcggtctgc ttcgcggtca tgtccacgta catcatgcgc acgcgcttgc   75360
gcgcgaaggc ggcggagccg tcgacgtcgt cgaagatgga ggcctcgttg gtgactaagt   75420
acgagcacag gccgccgagc ttgtccacga ggtcctcggg gttcgcgagc gcgccgccgt   75480
tgaagagcgg cgtctgcccg accacgccgg ggcgcagcag gttcacggcc atggagaact   75540
ccttgacgct gttcaccacc ggcgtggccg tgaggcagag cagcttcccg cggcccatgg   75600
ggatgttctt cgcgaggtag ttgtacaccg tgcgcgcggg ccgctggcgc ccgtcctcct   75660
tggtcagcga catcgagatg aagttgtgga actcgtcgat gaccacgcag acgcggctgc   75720
tcgacgaggc ggtcttcatc agcgtgaaga agcggtggtg gaagcgcggg tcgtcgtagt   75780
tgatgaaggt gcacccgggc acggcctcgg gcgcgaagcg catcatcgtc gaggtccagg   75840
gctgctccac gagcgccttc ttcacgagca cgaccaccgt ccagtccgtg aagacgtcgc   75900
gcaggtgctt gagcacgtac accgcggtca cggtcttgcc cacgcccgtc tcgtggaaga   75960
gcagcagcga gtgcatgctg tccaggccca ggaacacgcg cgccacgaag agctggtagt   76020
ccttgaggcg cacggactcc tccacgcccct gcatctcgga gggcatgtgc gcggtgcgcc   76080
gcagcgcgta gtcgatgtag gccgcgtgcg cgctggtcat ggcgacggtc ggcgctcctt   76140
ttacggggtc tgtcgtctat ctattgtcgg cgcgggtctg atttaggggc agtagttaca   76200
aaaacgtttc cgctgctcgg cgcggcgttt ggaggagcgg ttgcggccgc ggcggcgcag   76260
gcgcgcgcgg cgcgtcttcg tggtgcggtg gccgaaccag cgccggtgca tgaccgggtg   76320
cgagaccgcg gccgcgcgat ccgcgctcat gcaggttgcg taggtgcggc acatgctgcg   76380
cagcacgcgc cgcgtgcgcc gctccacggc gtcgagccgc ctcgcgacga tgggaaagag   76440
ccggcgccag ccgcgcacgg cgaagagcgg gcgctcgcag accgggcgcg cgagcgcgtg   76500
gtaggcgccc agcagccgcg ggtccagcga gcgcacgtag gtctccacga agccgttgcc   76560
gaagacgatg gcctgtgcgc atagcgggtt cgtcatctcc ctcttggagg cgatggcgtc   76620
gcccacgaag gcgcgcacgc cgcagtgccg cagcaccagg cgccgccgcg ggaagtgcag   76680
gtgcgggccg agcgccgcgc gggcggcggg gatgtgcagc cgcggagaaa acgcgcgcg    76740 tccctccatg gcatctaagc gctccgtctg ttttcagtta tatcgccgcg ggcggctact   76800
gcagcagcag cttgagcttg cgctggctct cgttctcgat gctcttggac tcggaggtca   76860
tgctctcgta gagcagcgag tgcgtgacgt agagcgcctc gtacacgcgg ctggcgaagg   76920
ccacgaagcg gtccacgaac tcgctctcta cggggtcctt gagcacgcgg aagggcacgg   76980
```

```
ccagcgcgtc gcgccaggcg gcggccttgg tgcgctcgcg cacgtgcgtc acgaaggcgg    77040
cgatggccgc gcgccgcggc tcgctggcga ccatgacggc gctgtccttg agccagctgt    77100
cgctcacgca cttgaagagg cgcacggtgc cgaagaggct gcagtacacg cgcagcgcgt    77160
gcaccacgtc ggtgccgaag agcgtgggca gcttgagcac cacgaagcgc tcctgcgtga    77220
tctcgagcag cgggcgcatc accgcgaagg tgatcgcgtg gtagtcagcc acgtagaggt    77280
tgttctcggt gaggtggttg ttggagcgga tggcgccgcg ctccttgcgg tagagccggt    77340
tgcgcgcgct gaggtcgagc acgaccgcgt cggccctgcc gcgcgctctg gagcgcacgc    77400
tggtgatgcc gtgcgcctcg agcaccttct cgacgtcgcg ctcgtcgatc atgaggtcgt    77460
gcgtgtacag actcagcatc tccgtgggca tgcggttgat gtcgttcacg cgcgagcact    77520
gcaggaagta gttggtcccg taggccaggc tgggcaggtg cccgacgccg agctgcaggt    77580
ccagcgcggg cgtcgagtcg aaggtgggca gcgtcacgct gagcccctcg cggatgctgc    77640
ggcgcacggc ctccaccgcg tccatggccg atttattgga cgcacagtct gttttcattt    77700
cgcggctact gcgcagtcac cttctcggcc acgatccccg cgtcgtagct gagccggtac    77760
acctcgttgc acaccacgac catctgccgc ggcacgtaca tgagcgggtt gtgcgcctcc    77820
atgtgcgcgt tggtcacgcg caccgccagc ttgtccttgc ccctggagac gttggagttc    77880
agcgcggtgg gcgagaagaa ggtgctgggc gtaaagttga actgcagcgt gcgcacgccg    77940
ggcgtcttgc cgaggatctc gccgaagacg cgcgagactg cgctgttctc cgagtacagc    78000
acctcgttgc cgaagcgcac gtccatgcgc gcgatgacgt cgatcttgtt cttgaagtcc    78060
acgcccttga ggaaggggtc ggccacgaag aggtccttgg cgcgcgcctc cggcgagcgg    78120
ttgtcgccgt tgtacacgtt gcgctggcag gtccacacgc ccacgggcac ggaggcgtcg    78180
ccgatgttca cggagtggat ggcggtcgtg aagcggatgc gggaggtcgc gcggctgtag    78240
gcccccgtga tggcggagaa cttcttggac atgttgtaca cgacggagtt cttcctggtg    78300
gcgaacacta ggatgttcgt gtgcaggaac acgcgcatgc ccacgggcac gtcgtcgatg    78360
cgcacgaaga cgtcggtgtc ctggatggac acgacgcccg acggggggcac ctcgactatc    78420
tccgcggtct cggggaagcc ctcggggtag cagttcgaga cgatcaccat gtcctccagc    78480
aggcgctcca cgaaggccat cacgaagtcg ccctcggact gctggaagcc ggggtacgat    78540
atgaagcggt tgttggcgtc gctgagcacg ggcttcatgt acacggacag ggaggtgcac    78600
gcgtgcacgt ccgtgatcac cgcggtggtg tggttgatct gctccacgcg ccgccgcggc    78660
atctcgatga aggccgggcg cgggcacagg ttcttgacca tgtagccgat gaagctcagc    78720
tccatggagt aggggaactc cttggcgagc ttggcggcgt cgaaggtctc gtcgtagacc    78780
atgacgcagg cgacggggtt cagcgtgacc gtgaccgtga ccttgctgtc gctgagcttg    78840
agcgtgctga aggtcttgtc cgcgtcaaag ggcgtcttga tgtaggcgtg cacgcaggcg    78900
gcctccttga tgacgtcgtt gggcgagctc ccggtggaga ggtcgttgag ctcgcgcgag    78960
aagcccgaga gctccatcac gcgctcgttg tccaggcagg agtcgaacag ctcctcgccg    79020
gaggtctccc agatggtgtc cgcggcggag ttcacggcca cgtggcggat gagcttgtac    79080
gcgatgtagg gcacgtagca catcttgccc acgcccttta tctcgggcag gtccacgctc    79140
agcacgaagt tgttcatggc cgagatgtac ttgtcgcgga tctcgaaggt cacggtgacc    79200
gcgtcgctgg tggtgtccac cacgccctgc gtggtgatgt actgcggcat gtacaccgtg    79260
ggcgcgcggt ggtccgtggc gaacacgctg gcgcgccgca cggcgtcgtc gccgcccacc    79320
aggctcacca cggagttatt catttattcc ctgggaaaac cagttaaata aggctcttca    79380
```

-continued

```
gagccatgcg caccgtccgg ccgtcgggct ccaggtagca gcgcccgtag acgccctccg    79440
tggcgcgcgt ctcgttgatg agcgcgcgca cgcggtcggg gtccgcgtac atctccagcg    79500
gcagcagctc gatcttgggc tcctcgcgca gcgcgacgag gtgccggatg agcccgcga    79560 aggagtcgcg gcacaaccgc gagcagaact cgcccacggc gccgccgtcg agcgtctcca    79620
cggccagcgc ggccgtgccc acgcgctgac ggcagaacca gcacgtgccg tccgcggcgc    79680
gcagcgccag ccgctccgcg gacaccgtgt tgaagtactt cggcagcacg tactcgatgc    79740
ggcacgccgc cggcggcgcg caggccgacg cccgcggcgc ggatatgtcc acccgcgaga    79800
gcgcgatgcg cttcatgggc ggcggtggct gctatttatg tcgcccgcgg cttttcaaag    79860
gtcgagcgag cacgccgcga agcgcgcggg cgagaacacg tactcgtggc cgaactccgg    79920
gatctgcgcg gcgcgcttgc gcgcgcgcat gtgcgcgagg aagttctccc aggtgagctg    79980
gttgctgttg ttcttcgcgt agttcttcac ggtctgcgga cgcaggttgc gcgtcacgcc    80040
cgtgacctcg aagatcttgt ccaggaagaa ggagtagttg atggttttgg tgggcgtgat    80100
ctcctggcag aagaagacca gctgcttgaa tatctcgatg acctcgttga tcttctcggt    80160
gctgaggtcc agcttctcgt ttttgacctg gttgatgatc tcgaagacca gcttgtagtc    80220
cttcttgttg atcatttcgc tgtccttgag gaagctggag acgtagttgg cgtccacgtc    80280
ctcgggccgg atctggtgcc ggtccatcat cgcgcgcagg tcgcggatga cctcctccga    80340
gcactgcttg gagagcagcc gccggagcac gttccgcagg tggatgagct tgttcgacac    80400
gtggaagttg gacctcttct gcacgcggat gcccatggga aacacggtct cgcagaacag    80460
gcagaactcg tagtccgcgt cggacacgag cccgttgcgg cggcagccgc cgcacatgcg    80520
caggttcatg cttgctccag ccccagcacg cgcaggatct cgcggtccag cactttagtg    80580
tccagcgtgc gggttctaca gaactggagg aagcccgcga gcgcgcgcgc gcgccctggc    80640
tgcgagagca gcagcatgcg cgcgttctcg gggtcctcgt tgatgacgcg cgtgaggttc    80700
agcgagcacc gcgtgcagcg ccgcggcggg tcgagctcga ccgagtacgc cgcgaaccag    80760
acgttgtcgc ccatgtatta tttattaaca cagaacgtcg cacatgttgc gcgaggacat    80820
gtacgggtcg tactcctgcc cgtagatgag gatggtgcag taccgcgaga tcatgagcat    80880
ggcctcctcc atggtgagca ggtcgtcctc gaacatggcc ttgtgctgca tgtgctggct    80940
ctgcttggcg gccatcgcgg ccgcgccgtc gccgcgcagc cactcgttca gacactggcc    81000
gtcgccgccg gcgccgctct cctgcgcgaa ggtgttgcgc atggcgcgca tgagcctggc    81060
ctccctggcc gagcggctga gcacggtcat ggggtcgtag agccagggc ctgcgtccgt    81120 gaacaggatg gtgcagtacc cgttggcgaa ggcgtccgcg ccgctgcagt tgtcgatgcc    81180
gtcgccgacc ctgtagcaca ccgcggagac cagccggtac atgatgccgt tgagcatcat    81240
gtcctgcgac acctcgatgg gaatgtcgct gatcacgggc cgcatgttcg tgaagcagtc    81300
gcccgtgctg gccatgcccc cgcgccggtt caccaggaac accagcacgc cgttcgtgat    81360
cacgggcgcg cggtcgcgct cgtagaggta gccgctcgcc gcgcacacgg cggacgccac    81420
gtccgtgcgc gagaccgcgc ccatgttctg ggcgggcatg tacagcactc gcccggcctc    81480
cgcggtgcac gagaagggct gctccccgcc cacgtggatg ggcgccgtcg atgtcgtgat    81540
catcttgctg gagtccacca ccaggtaggg caccgtgtgc atggccatgt cgcccatgcc    81600
cccgatcccc gttccgaacg acggccgcga cacgctcacg agcgtcggct tgaacgagac    81660
tatggagaag atggaggcca agatctgctc ctcgtcggtc atgatggagg cgcacgaggg    81720
```

```
gtggatgatc ttcattaggg cgttgtcgat ggactcgtcg ctctcgcagt agaagacgcc   81780
catgcggagg ttcaggatgc accgccgcag gttggtgtgc agcaccgcgc gctggatctc   81840
catggacacg gagtcgccga cgccgggcat cacgatgggc gtttcctcgg tgagcttgtt   81900
caccagcagc tggtagttgt tgggtcgcac gcggctgttg tggtggagct gcgccaggag   81960
cgagaggctg tccccgttga cgaacgcgga ctcgatggcc ggcagcttta cgccaacag    82020 cgccatggcg atggggtgca cgaagccacg gagtcggac  gacttgaacg agaagagcag   82080
gtcgcccgag gagctcatgt ctttgaagtg cacggactgg aactgcgtgg cggagagcaa   82140
gttctggtag ctggacatgc tctgcaggtc gtcgatctcc ttcatctgct tgtttacgcg   82200
ggtcgagttc ctcccgtaga tgatcaccag cgggtgcgtc tggctcacgg atagccccga   82260
gtccgtcatg gcggcgcgca cgctgttcag cagatcgaac agctccgacc ggtctctgtt   82320
ctggatcccg accttgcca  tcacagacat gagctcctgg atggtcatgt tcttgtggtc   82380
tcggcgcgtg gaccgcaggt agtcggcgat catctcgccc tccttacgga tcttcatctg   82440
ccagtcgtgc atggaggtca tgcggtccac aggcatgagc acgctgtcgg aggacgactg   82500
cgcggcgctg ccggactggc gcgagccagg gcgcgcggac gacgggcgcg cggagctgcc   82560
gcggctggag gaggacctgg acctccgcga ggatcttcgc tgcgaagagc tgcgcacggg   82620
ccgctgggcg cgcgccccgg cggaaaccat gtcctcgcgg tttatgctga ggagcgagct   82680
gcagaccgcg cacgacagcg actgcttttgg aatgtgatg tggtcgcact ccaggacat    82740 gcccgcattg tcgtagcccg ggaccaagtc gaactttgca ttaaaaaaat ctgatgcgca   82800
cgcgggcgat tccatttata ccggaagttt ttatgaggtg ccggtattat ccacgcgatc   82860
tcgcagtgtg ctgggagact ctagcgtagc cacggacccc gtgagcagac gacgcaagtc   82920
gttgatggcc gactgcgtga cggacttcgc cgtctcgatg tcgcgcgtaa ggctgagcga   82980
ctcggcgttg aggtcgcgca cgctgtccgc gatgtcggcc agctccttt  tgatgaaatc   83040 cttatcatta tcggcgttga tgactttgtc cggcactcta gactctagaa ccggtgacgc   83100
ggcgggcgcc ttgatcgtcg ggcagctgga cgccgggtac tggggcggcg gcaatgattg   83160
ctgtaggaag atgggcttag cggcaggcgc cggttttgtc ggcaagggcg cgccggcgg    83220 gcactgtcgt gtagacggcg ggcacgccgg cgcggggcac gccgccggtg gcggacatgt   83280
cggcgcagtt gcgggtggac acgcgggcgc gggcgccggc gcgggacacg tcgcggcagg   83340
agccgggcac gcgggagccg gagctggagc cgggcacggc gcggcaggag ccgggcacgt   83400
cgcggcaggc gcagggcacg cgggagccgg agccgggcac gccggcgcag gaggacatgc   83460
cggcgcagcg gcaggacaga ccaccgctgt cgcggagcac gcggcaaccg gcgtggagca   83520
cgcggcgggc attacgttca gaggcgtcga ctggaccttg gcaccgcggg gcagtagcga   83580
tggcgctagg ggcgactgtc cggtggttgg acgctgcatg caggcagtcg cagatttcag   83640
acgggactgg taatacctgc ccgcttcctt caccgtgtac ttgtcgacgg agtctacctc   83700
ctcatctgga ggacatggct gctccggtgc gggaacgact gtttgaggac acttggtgaa   83760
cagactggag ctggtctccg atagcaccag tttagacttg gccaagtcgg aggcaaacct   83820
tcttctgaga tccatttaag ccttcaaaat tgaacgtgta cgccgaccgc taaatggaag   83880
aatcggtggc cgtcgagtac gcggacgagg acgaagatga gattgaggag tacgaggagg   83940
aggacgatga cgaggaggaa gagtctgccg agggcgccgc cgcctcctcg gtcagcgacg   84000
tagcgctctc tgccgccgag aagctggtgg cctcggaggt cccggacgac gcggctgccg   84060
cggacaccaa cgtgcgtcaa cgcgtcaccg cgcgcgtgga ggagcttaag gcgcgctaca   84120
```

```
cacggcggat gagtctattt gagctcaccg gaattgtagc agagagtttc aatcttctgt    84180
gtcgcgggcg gctgccgctc gtggcggacg ccgcagaccc ggcgctcgac aacgagctaa    84240
aagtggtggt tcgggagctc gaggagggcg tctgccccat cgtcatcgag aaaaacggcg    84300
agttcctctc gccgggcgac ttcgaccccg agtgcctgcg ctaccacctg acgtacatga    84360
ccgacctctg gaagtcccag gggcgcatgt agccgcggct acgccgactc ggcggcctcc    84420 gcgattttt cttttatcat gtccagcagc tcgcgcacca cgatgggcg gccgcagtac    84480 gtgatgccgt tttcggatat cacgctctgt gcgatgtcca ccagcgagcc ctcgcgctcc    84540
cagtactcgc gcgcgagcac ctccttgtac aacgcgcgt ggttggccac gtaccgcacc    84600
agcgtctgga tgttcttcac gcccacgctc ttgaggtcct gcggcgagaa cttctcgcgc    84660
agcgacacga agacgtcccg gacgagcttg ccgatctcca cgttggtctt gaactcgttg    84720
tacagcacca cgtagagctt gcacacgacc gtagcgaact tcgcgggctt gagatccttg    84780
ttctggaaga ccagcatgct gctcatcacc ttcttcatga aggccaggta cttcgcgcgg    84840
tcgccctcga cgctcacgct cccgacctcg aggtcggaca cgcagcggat tccgtgctcc    84900
gcgctctccg cggagacgcg cagcagctcc tggtactcct tgagcttctg cttgtccgtc    84960
atcagcgagt tgtcgaatac cgccaccagc ttgagcacgt agttctcgtc cgagaagacc    85020
ttgttcagac acttcaccag gaagctgtag tggctctgca ggatcttcat gaccgcgttg    85080
gcgccgctgg ctccgcggac gtgcgatatc atctccatga tcttcttaga gtcgtcgatg    85140
atctcctcgg tgtcgttgcg catgttgcgg tacattgcgt tcagcgagac cagcgtctgc    85200
gcggccagga gcacgtcgcg gaacacgcgc gcgaactcgc gcttctcctc cgcgtcggtg    85260
atgctgttgt acacggactt cgccaccgcg ttcgacttca ggaaccagaa ggagagcgcc    85320
tggtagttga agtgcttcat cagcgccagc acgtccgcct cgctcatttc cggcgcaatg    85380
gggcacaccg agctctcgag cacgggcacc atgctgacga gcgtgtccac gtccgtgtcg    85440
aagtccaggc agtccacgca gagcccggtg ccgcggctca ggtgatcgcg gctgatgtcg    85500
tagaagcgct cgtagcaggt gcggaggcgg tccatgtcgg ctgcgtttta gagagacaca    85560
cactcttgaa ttatggctgc gggtagaact cctgcagcag cgccggcgca cgcgcggagt    85620
ccggctccac tcccagcttc agcgcgcagt tcacggacca ggtcttcatg aagcggtcgg    85680
gcgcgtccgt gaccacgtgc cggaagagct tcgcgaagtg gcggctcacg gcgttgggca    85740
cggtcgcgtt gcgcacgaag gccgtgaagc gcgaggtcag cttcggcgcg aagcgcttgc    85800
cgtccacgaa gaagcccgag gtggtgagcg agagcccgtt ctcctcgcgc accacgcgtc    85860
gcgcggcctt gtgcggaaac atgctcgcga ggcgcccgct cgcgtcctgg tctaggtgga    85920
tggcgtccgt ggccgcgtcc ttgcggatgc gcaccacgtc gtgcacgatc tcctggatga    85980
ggatgcgcgt ggccgcggtc tccgccagcc gcatggggaa gtagaccatg tccccggaga    86040
tgagcacgtt cccgctagcg tttacgtagc tcactatctc ggacacggtg cgcagacgca    86100
cgatcgcgcc ttcgcagcag tgcaccacgt agtacccagc ggtggcgcgc aggcgcttgt    86160
tgtccgcctc gaagtccgcc tccaaccct cgttgaagta cttgtcgaat atgatgggca    86220
ggaaggatag ttttgactcg gtgaccacct ttccgaagtt gaggatgtac gggttcagcg    86280
cgctgcggtc gacctcttcg tcgtacacgc aggacttgaa ggtgtcggtg tgcgcctggc    86340
tgcgcaggaa gcagcacgga atgcagatgc gctgcaggcg gtggaagatg gagaggaagc    86400
ccacgctgtt gtagcgcccg tcggggtcca tgcacgaaaa catgacgccg tttccgttta    86460
```

```
cgaagacctc gcgcgtctcg gacttgaaga agttgttgct gaccttggcc atgttcgcgt    86520
ccagcgactg cacgatcacg ggcttgcggt tcttggtctt ggtgttctgg cagatgcgcg    86580
accagtacac ggtctccacc ttggtgaagt ccgaggactg cttcacgttg ttgaacatca    86640
cgctgatggc cacgatcaag aacgtgaagt acttctcgat gttcgggatg tagttcttta    86700
ccttcacgga cacgtgcgac ttcgcgagga tgatcgagat gcgcttgtcc gtggagagca    86760
ggatgttgtt ggtcgccgtc tccacgaaga tgaagctcgt ttccatgtcc agcttcatct    86820
tagacgtgat ggtcgtgttc agcgacacct tgtaggtgat gtcgcccttg acgcggtcca    86880
tctttacgtc catgctctcg atgagcttcg tgaacagact cacgtcgttc accgtgagcg    86940
tcttcccgtc gctcgagatg accaggtcgc cttccgggcc ccacaccgag aggttcagcg    87000
gctcgtccac cagcaggaag cgagtccccg tcatcgacac gaagaagtcg tccgtcttcg    87060
agagcaggat gtcgaagtcg cccacctccg ctcgcttgtc cggcgactgc tgcgcgatcg    87120
cgcggagccc ggactcgcgc aggttcgtgc ggaagatgtt gttgaacttg gtctccacgt    87180
tcatgtttag gtcgaggttc gcgaactcgc ggatgagccg ctcctcgaac ttgaggatgg    87240
agtcgttggg ctcctcgaag gagccgaact ccggcgcgga ggtgtccgcc gcgcgcgcca    87300
cccagaccac caggaagttg cacgcgtccg cgtacgcgtt gtagaggatg ccgtccgtgc    87360
ggatgagcgt tttcttttgc gtgggcgaga acgggttgaa gatggtgttg tccacgtagc    87420
tgtactccag gttgttcttg tgcgagtaca cgatgatctc gtcctgcagg cccagcaggc    87480
tccccaagta cccccttgagc tgccgcacgc gcatggtcag caagatgtgt ctgcgcacgt    87540
gctcggggtc cttctggatg tactgcttcg cgaagaagta gatcggcgag gcctcgtcca    87600
cggagtcgta cagcgatagg tacagcacgc gctcgatctc ctggtggcgc cccaccagca    87660
ccaccagctg cggcgcgacg gtgtagagca tgttcgcgcg ggcgtattta tagccggcgt    87720
taaactgaaa taaaatacgc gggtcgcgag gcagcgccat gttccagccg gtgcccgaca    87780
tggccgccga ggccgacatc gacctcgcg acgtcagcgt ggacgcgacg cgcgcgggcg    87840
cgcgcgagaa gaccgtcttc ttcgcgcgca acaagcgcat gtacccgcac cgcagcaagg    87900
acgaggagcg caagctgtcg ctgggcttct tcttgcagcg gctggacttc ctcacgtcgc    87960
gcgaggtcaa cctgcagttc cggtcgctgg acgcgctgcg caccgagaac gtcatgaaga    88020
agaacaacgt gctcgtggcg ccgtacatcc tcatcgcgac gctcgcgggg gcgcggtttcc    88080 gcatgacgga gaccatggtc gagctctact ccccgagct gtaccgcgag accagcaagc    88140
gcttccgctt ctgcgcgcag ataaaggtca tccaggactt cctgggggttc gcccacgaca    88200 gctaccacac ttacgacttc gagacgtact tcgcgttcgt ggcgctggtg ctgcgcggcg    88260
cggactctgc ggccgaggcc ttcgacgtcc gcgccgagag cgggcttgtg cgcagcctca    88320
ccgagatcac gtaccggctc tacgtgatgc agctgcgctc cgacgccgcg cagtggagcg    88380
tgagcaccgg cgccgtagtc tcgcaggcgg tgaacaccgt gctgtcggtc gtcggcgacc    88440
tcgctgcgcg cgcggaggcc gagcggctca cgcccgtgtg cgacctcgcg cgcgagaacc    88500
cgctctcgct cgaggacctg cgcaagtacg gcccgcggct gcgctcgctg ctcacgacca    88560
tggcgcgcgc gcgatccttc aagacgaacc ggcgggacaa ggacgcgctg tcccggttcst    88620 gccgactgac ggcgggccct agcccgtctg cgtgccgcgc gtcgccatag gcgtcggcgc    88680
gcgctcgccg ccggaacact cggggtcgct gaacatgtag atgagcgcga cgcctagcag    88740
caggtacatg atcatgctga tcacggtttt gaacacgacg gcggcgaacg tgttggaccg    88800
cagtcggtgc tcgcagaagt gcatgaacag gtgccgcatg aggtcgatgg ccccgttggc    88860
```

```
cacctggaaa agggcgaggc cgccgatgga cttgatcacc gtcacgtagc acggccgcat   88920
tccgacgacg ctatttactc actgtcaaaa gaaacggcgc catccgaccg gaggttgagg   88980
ttgcgcttca tgttgttcca gtacatctca ccgatgctcg agtagtacgc cgtcagccgc   89040
gatatttttt ctcgcaccag ctcgtaggcc ttctgcatct ccgcaacgcc gatctccgcg   89100
tcgcccacgt accggccgct gcggcgcacg atcagcagca gcgccttcag gttctccagc   89160
gcgatcatgt ccatgtacag cgacttcgag agctgcacga agaggttgta ccgctccagg   89220
atgctgttct tcacctcgtc cgcgatcggg actccgaaga tgcgctccgt ggtgtacacg   89280
gactgcgtga gctgcttgaa gagcgcggag atgcagcagg tcgcgcgctt gacggcgtcg   89340
agctgcttct cggagcgcgc gctcgcgatg ctcagcgcgc tgttcacgac gttgctcgtg   89400
tcgcgcacgt agcgcgtctt cagcgcgcg ttgatggcat ccgcgatctc gttgctgctc   89460
acgctcgagt cgtccgagct gcccgagacc tcgtccagca gccccgagat cgtgatgtcg   89520
ggcgagccgc cgacggtcac cagacggtcg agcaggttgc agggcatgga catgaggatg   89580
ccctcgctcg agaggcagcc ctcgtcgatc atgctctgca ggttgcgctt gaaggccgtg   89640
ttttcgggca tgaacccgtc cacgctcatg agctcgtcga ccgtgctcgc ggaaaagatg   89700
cccctcacgt tgatgcggtc cagcatgccc atgtcctgcg agcacagcac caccgactgg   89760
tcggccgtct cggcggcgtc cttggcgccg ccgtagatga tgcgcggaaa ccgccagctc   89820
gccggaaaag agaaggaggg aaaccggcac tgcgcgctcg ggcctcggta gccctgcgcg   89880
tcgcgcacgt tggtggccgt gaccatgaac tgcagcaggt cgtgcgcgga cgccatgatc   89940
ttctccacct cctccttgct gcagcagacc ttgcccaggc tgcgcgcgat gttcgttttg   90000
ctcactgagg gcgagaccgt gacggcggtg tgtcggcggc tgccgagcgt gtacgcgctc   90060
acgctaacgc ggtaccccat ggcgccgaag agcagcttca cgaagtccag gtagctctcc   90120
ttattgatgt agtgcggcgc gcccttgtct tccatcctca gcccggcgta ggccatgagc   90180
acttccttca tcgccgtctc ggggtccgag ttgcacacca gccgcagcat ctggaagaac   90240
tgcatgaagg cgcgctgcga gagcccgatg tggtggttgg gctgcgtcga ccggcgcggg   90300
aactccctgg gcgtcatggc gttgatgccc gagagcgtct ccatcacgag cgcgcccacg   90360
gtcttctggc ccatgacgcg cgggtaaaag cacacgcgga ggggctcctt gccggccgcg   90420
agcgcgtccg agagcagcga gcagtacgtg acgttgtcgt ggtcgaagag cgcgaaggtg   90480
tagcagacgg agctcatgaa gagcgagtcg gcggtgctca tggacttgaa ctccgtgtac   90540
gcgattccgt cccagaacag gctctcttccg ggcgcgatca gcggggacgc gcggtcggcg   90600
cgcatcagca tggagagcag cgtcacgtag taacggatgt tggcggaaat gtctacgaac   90660
tgcatgccgg gcgaggccac gcgcagggtc gcgcccgagg tagtgagcac ctccaggctg   90720
tccatgagcg tcacgctggg gtgcagctgc gcaaggcgcg ccagctggct ctggtagaag   90780
atggacacgg cgaggctggc cacgctgccg cgtgccatgc gcaggttttg cccgttgaag   90840
gtgagctggc gcagcgagaa cacggagtcg aagtactgga agaaggtgag caggtacttg   90900
agcggcatgg tcgtcagctc ggtatccacc tgccggcgtct gtgcgagcac gattccgttc   90960
ttggccgcgc cgtcggggat gtcgtacatg gcgtccattc tggcgcggga ggcgtcggtg   91020
agcagcgcgc gcacgttgag cagcatgagc aggtcccgcg ctagcatggt cccgtcgacc   91080
agccgggcgc gaaagccgat ctcggcgggg ccggcgatgt tggggtagat caggttcagc   91140
aggtacgtgt tgtcgaagct cagcgagggg aaggagatgg gagacttcgc cgggaggccg   91200
```

```
gtggggtagc gcacgtagcc gccgcagatg cgcgcgtgcg cctcaaagct ggtcacgcga   91260
gtcttcagca ggttgcgggt gaagggcggc acgtccttga aggactgcgt gcagatcacg   91320
gggttggcgg tgtcggtcag cttgaggttg gtgggcttaa gctccgcgaa gttggggccc   91380
agcagcacgg ggacgaggtg cgagttggcg gcgctgtcga gcaggaagtt gatgccgaac   91440
tgcttcacgg cgacctcggt ttcctcgtcg ctggcgagct tctccgcgtc ctcgaggaag   91500
agcgcgtcca gcgggtgcac gtacgtgcgg ttgacgtcgt agctgggctt gaagtccgaa   91560
cacagcgtgg ggagcacggt ggagacgagc tggaacatgt attccgcgcc ctccacatgg   91620
tgcaaggcca tgtgcacgtt tggggccgtc atttatttag tattaaatga cggccgtacc   91680
ggtaaccgat attcctggag actacgggcc gacgtccttt tcggaggaca actacccgct   91740
gaacaagcac tacgagctca ccaaaggcca gctctcgatc ctgcgcacgg tcaacgacaa   91800
gctgctcgcg cgcaccgtgc agcactcgga cggggagagc gatgagagcg aaagcgagga   91860
ggacgacatc tccagtccgc tgccgccgga cgaggaggag ccggactcgt gcgtggcccg   91920
ggtcatgccg cgggacgcgg acctggcggc gccaaaaaag gccgacggct acatcattgc   91980
cgccgagcag cagcgccagc agcgcataaa cattctggta tccgatcgag aggccgtcgt   92040
ggagcgggag ccggttcaga cgtcgttcgc gcgcgtctcg gctatcccga tccacgggga   92100
cggcgcgcgc cgcaccaccg cctccttctc cgcgaccacg ccgtcgctgg gcgccgtgtt   92160
cgacgacgcc aagcgcgtgc ggctgctgga ggaggaggtc aaggagctcc gcagaaagtg   92220
cgcgacctct caggataacg gaaacctgga gaacttcacc aaggtgctgt tcggcaaggc   92280
gccgcgcgcg agcgagctga acaagcgcgt ggtcatcgtg aactacgcca cgctgaacaa   92340
cgtgacgctg tccatggagg acctcgagaa gtgctccgac gaggaagtgg accgcatgta   92400
ctcggtcatc cggcgctaca acgagacgcg gaagaagaag atcctggtca cgaacgtggt   92460
catcatcggg atcaccgtgc tcgagcacgt gctggtgaag cttggcttct cggaggtgcg   92520
cgggctcagc gccgacctct cgtcggagct catcgacgtg gagatcggcg aggactgcga   92580
gcacatcgcg gagcgcctgg ggttcgggaa cagcccggtg ctaaacgtgg cgctcttcgt   92640
ggtaaagctg ttcgtgcgga agctgaacct gatctgatca acacatgccg ccgtcgaggt   92700
ccatggcgtt catgaggttg gaggcgcggc ggcgcgcgcc ggtggaagcg gtggaggcgc   92760
tcgaggtcgt ggagcaggga gtgttgctgg aggaggcgcg gcggcgggag ctagaagcgg   92820
aactcgaggt tccgctggtg gtgctgcggc gactcgtgcc gctcgtgccg ctcctgctag   92880
tgccagtgcc agtgccgctg cggcgtgaag taccggtgcc ggacctgccg ctggagcttt   92940
tcttgcggcc gccgttaacg ctgtcgatgc cgagcaggtc ctcgcacacc tcgccgacgg   93000
ttccctgcac gtccaacttg ccgttcttga caaccccgta cacgatcttg ccgcagttgg   93060
acacagcctg gatggtggtc tcgtcgctgt caaaggcgtt cattccgccg cacccgccgt   93120
cgttgtttct tcgagaaggc gcgcgcctgc ggcgactcct ggtgctgccg ctggaccgag   93180
ttccggagga cctggagccc gtggaccggc tgccggtcga cctggtgccg gtagtgcgct   93240
ttctggacga agaggaggag gcgcttccgc ggcgggtgga cgaactagcc tccagcgcac   93300
cggcgccgcc cacacaatcc acgtcggcgg cggcgcctcc gcgaatgacc tgctcgttgt   93360
tgagctgcgt caggagagat cgcagctgcg gcgcgatctt ctgcaaggtg ctcacgtagt   93420
cgtcgtagct gctctgcggg cgctgcgcca ttttttcgga cgccatttat tacgcggaat   93480
atctacgacg acgcagcact gaatcggttt ctcgcgacgg gagattccgc ggtcggcgcc   93540
ggtgcggggt tgtcaccggg cgacgaggta accagcgcgt ggaaggcgcg cacctggtcg   93600
```

| | |
|---|---|
| tccgtcatct tgtcctcgaa cgaggacgcg cccgggggga gcaggtcctt gttgcgcgga | 93660 |
| acggcgggcg ccgagacgca cgaccggcgg tacatcatga tgacgatgta gcacacgatc | 93720 |
| gagatgacga tcacggtcag cagcgcgtcg aggagcccca tttattacct gtatatgccc | 93780 |
| gcgtttaccg ggcggtgagc tcaatgtcgg tgttgtttag ccgggcgtac gggacgctgc | 93840 |
| cggagcactt cctgtacatg ctgaacacga acagcccgag cagcagcacg gcgcccacta | 93900 |
| tgaagcaggt tacgcacagc gcgcgccaca cgtagtcggt gacgttgttg gtgttcttgc | 93960 |
| tgaaatccac gaaggcgaag acgcaggcgg ccgtcagcag cagcacgccg catatcagca | 94020 |
| ctccggagta gtaagagctc aaggtctcga atatgtccat ttatctgagg agaaatttaa | 94080 |
| attactgaat ggacgaagtg gaatagaaac cacgagaaca cgacggactg cagcacgaag | 94140 |
| atggtgctca gcttcgtctt catgggcatg cagaagttcg cggccagcgc catacagaag | 94200 |
| atgaacacga gcaccgccgg gtcgtagtcg gacaccattt acactacgct aaaaggcata | 94260 |
| tctcggcgcg cgacgtccac gagcaccagc acgcggacgc ccgcgggcgc gccggcggcg | 94320 |
| accgcggcga gctgcccggc cgtggggttc accagcagca gtgcgcgcgc ggttcgcggg | 94380 |
| acggggtctt cgtaggccat ggtcggcgtg gacccgggac gcagcggccg cccctgtctg | 94440 |
| tcgaagaggc cctcgggaaa cgaggtgccc ggaacggcca cgacgacggt gtcgctatct | 94500 |
| agaaacattt atggtcttgg tttccacgga tcgcctcgag tagaccgcca cgaagtagaa | 94560 |
| gatgacgccc gccgcgagcg ccgccaccag gaagggcggc acgcgggca ggttcgcgga | 94620 |
| cgcgttgtcg cgcacgccgg ggtccgggtc tgcgtagccc gcgcccacgg ccttgccgca | 94680 |
| gtcggcgatc atgtgcgcgc gcgagttctg catgaccagg ctgtccacgt cgatgcggca | 94740 |
| gcccacgtag cggcaccgcg agcgctgctc gtcctggctg aagaagagcc acttgcggtc | 94800 |
| gcgcgactgg tccgtgcact cgtgcgcgcg acagacgcgc gggcccaggt acttcccgag | 94860 |
| cgtggtgccc gcgacacacg cgcactccgg cgcggcgcgg tgcgcgtcgc agtagcgccg | 94920 |
| cagcgcggag tcgccgaagg cgaaggaggc gggccgcgcc acgcgcacga actccgagca | 94980 |
| gaagcgcgcg tccatgtgct tggcgcagag cgccgcgtag gtgtccagcg ccgcgtagcg | 95040 |
| gcccgtgcgc agccaggcca tgcactcggg cgcgtcaggc tccaccgcgc agcggctggc | 95100 |
| cataacgccg tcgcagtgcg cggtcttgta cccgttcgcg aacacggacg ggcacccggg | 95160 |
| ctccggattt gtgcagcagc gcgccatggc ggcgtccgtg ggcggcgccg aggcgccgat | 95220 |
| ctcgaacgcg cacatggtgc cctggcgcag gtacggcttc gcgatctcgg gaacgtagtc | 95280 |
| tgcgcgcagc agcgagcccg ggcggaagaa gagcgagtcg cagggcgggc ctcgcacgag | 95340 |
| ccgcgcgcgg ctcgccagct ctggcgagag gaagcgcccg cactgccgg ggtccatggt | 95400 |
| cggcagcaga cagaaccgcg gccgtacggt cttcagcttc gggtcggaga aggtttctga | 95460 |
| ttcttccgcg aaggcgaagg tgtccgtggc gctcgtgtgt gtgacgcgca gcgcgtactc | 95520 |
| gcctggcgtc ggcgtgtcga gcacctccac cttggatacg gtgtccccca tttgaagacg | 95580 |
| ctatttacgc cgctgcctac tcggcgaaga ataggtcctc cgacttggcg cccgcgtaca | 95640 |
| ccgggcaggc gggcgcggcg gagcgagtgc gcacgatacc gcggccagtg aggcggaagg | 95700 |
| cgtagatggc gaacagcagg ccgagcacga tgtacatgaa agtggtggcg cccacagacc | 95760 |
| cggtcacgtg cgtcacgatg atggtgacga tggacatgat cgtgcacacg atggccatgc | 95820 |
| cggtgttgtt ggccgcgtag gggtgcatga tctgcatggc cgcacagtat ccgatgacca | 95880 |
| ggcacggcag cgggaggata agtgaggcaa tacctatcat tactagagcg agcacggggg | 95940 |

```
tggacgtcaa ggccaataca aaaatcacaa tacctgttag tatgcggata tcctcgtact   96000
ggaggacgct gtaaggcgcg atattccctc cgggcactgg cctggggtta gccgggacta   96060
gggggagtc ggcagtgccg gggtccttgg ggagaaaggc attctgctcc tccgggctga    96120
agagctcggc gtcctgaacg ccgccggcgg tgaactcgtc gttatagtaa ctaaagtagc   96180
tttccattta tatgttgaaa aatgtttgga ggcgtacagg tggacgacaa actctacgcg   96240
tacctaaaaa aactcgccgg acgcgggcgg ccgctgtgtc tgttccgcga caacggcgag   96300
ttcgtcgaag tcttcgcggg gtccgcgttc cgctttgtgc tgcccgtggg cctcttcgcg   96360
gacctgcgcg tgcgcacgcg cggcgtggcc ttcccgaaac tgcgcgactc cgcgcgcatg   96420
cgcggcgtgc gggtggacgc gcacacgctg ccctcgctgt accccaacca gcgcatcgtg   96480
gtggacgagg tgctcgcggc ccgcgaccag ttgctggccg cgggccgcgc cgtgtacgtg   96540
acgctgcatc tggcttgcgg cttcgggaag acgctgaccg cgtgccacct catcgccacg   96600
cacggccgcc gcgcgtggt gtgcgtgccc aaccgcatgc tggtgccgca gtggcgcgcg   96660
gccgtggcgg agctgcgggt gcccttcgcg gtctcctgtg acggcgcggc ctcgctgctg   96720
cgctcgggcg agctcgaccg cgccatggtg gccatcgtgg tcagccggca cttcgccaac   96780
gacgacttct gccgcgcggt gagccggcag tttgacgtgc tcgtgctcga cgagtcgcac   96840
acatacaacc tcatgaacaa caccgcggtc tcgcgcttct tgaccaagta cccgccgccc   96900
atgtgcttct tcctgaccgc gacgccgcgc acggccaacc gcatctactg caaccgcgtg   96960
gtgaacgtgt ccgtggtcag ccgcctcacc aaggtagtgc gcgtggtgga cgccttcttc   97020
gagccgtaca ccacgcccaa gatccgcacg ctcgagcgca gcctcgaggg acccccagaac  97080
aagtaccacg tcttcaccga gaagatcctc ggcgaggacg tgcaccgcaa caagctcatc   97140
gtggacaccg tggtcgcggc catggccgcg ggcgaggcgc ggcgcgtgct cgtgctcacc   97200
aagctgcgcg aacacatggt cgggctgcac gccgcgctct gcgagcgcct cggtgcggag   97260
acggtctttc tcggcgacgc caagaacagg aagacgcccg aggtcacgcg cgcactcgcg   97320
gacaaggacc gcttcgtgct cgtgtccacg gtcttcttct cgggcacggg cctggacctg   97380
cccaacctgg acgcgctcgc ggtggccgcg ccgtgctca accgcatggt catggagcag   97440
atgatcggac gcgtgtgtcg cgagtcgcac gccaacacgc gcacgctgtt cgtgttcccg   97500
gactcctccg tgcgcgcgat ccgcgacacc gtgtctgcgt ttgcgcagcg gctcgtggcg   97560
ctggcggtgg acgggctggg cttcgtccgc gagcgcgccg ccgccggcgc gaagaacgag   97620
ccggcgctgt acagcgccat cagcgggcga gatctcgcag cggtgtaagc gcggacccgc   97680
acgccgcgca cgagagcgtg ctggagcagg cgagtcccag cgacagtgtg gacagcctgt   97740
ccacgtcctt gatgctcacc agccgcgagt tgcacgacga gcacacgggg tcgctactat   97800
catcgaccac cgtggtgacg cggcggcgtc tgcgcttttt gtttccagcg gcgacatcga   97860
ccacgcctcc cttagagccc cccttcgccc ccgcctagc tttcaccgcg ctcatctttt    97920
atttatcata aaaacacgtc tgcgtacgcg ttcgcgcaca cgtcccgcaa atccgcgcgc   97980
gcgccgcagc gcgtgaagcg cgcggcgtcc gcctccgcga tccgcgcgca cggcagcggc   98040
gcgcccttct cgtccgccat cacgcgcgca gagatcccgg tggcccccag cgcgtacgac   98100
accaccacgt cgccgacgca gcggtacacg ttgccggagc cggcgaggcg gtcgaacgcg   98160
gcgccctcct ggcgcagctt gtcgaatatg cgaggaacga ggatgttaaa aatgagaacg   98220
aaatagcaga tcagcaaaaa cagcgagatc atgacctccg agagcgattt atataccttg   98280
aaagagctaa tacgacttcg ggactcgctg cacctcgcca ccggcgccgc cgtcgagcgc   98340
```

```
tacaacgcgc tcgtggagtg ggccgcgcgc acgtactgga cggtcgcggt gctgccctcc   98400
gcgccgtgcg cctccatcga gaagtactac tgcgtgtgca aacccgactg cgcgctcgag   98460
cccggcgagt actccgtgag ccggctgcac ttcggactca cgcacgcctg ggtgcgcggc   98520
gccgccttca actcggccag cggcgccgag gtcgagccgc cagaggaggt gcgtagggcc   98580
tgcgaggcgc tcgacgccgc cttcgcggac ctcaccttcg tgcgcttctc ggtcttcggc   98640
cgcgagtgga cggtcgacga cgccgtcaca gaccactcct cgcgcgacga ggtgctcgcc   98700
gcgtgcgccg cctccggcgt gcgcgtcgcg cgcacgctgc gtgtgcgcgt gcgggcggga   98760
gagtccttcg cgcgcgcaga cttcgacgcg gtgcacgccg cgctgcgcgc ggagggcgac   98820
gtcgctcgcg gcaccgcggt ctgtctcgcg ctgcgcgggt catcgcgccg ctggatagcg   98880
gaccgcgcgc ctcgatgctt catgcgcgtg cgccgcgtgg agctcgagcc cgtggacgcg   98940
cggcaccact gcccggtgct gatctccgcg cgcggcgacc gggtgctctg ccgcggcgtg   99000
gggcacctcg cggacgcgcg cgcgcgcgag gcgtcttcg tggccgtgcg caggtacccg   99060
gagtgtctgg tgctctgcga cgaggcggcc gccgcgcgg cggagtgctc gcgcgaggag   99120
gcgctgcggc tgctggtgcg ccgcttcggg cgcgacttcg ccgtcagcga ggagggctac   99180
gtcttccgcg tgcaggacat ggacttgcgc ggcgtgtccg cgcgactggg gctcgcgccc   99240
tgcgcgagcc tggaggagct gcgccgagcg gtggagcgcg accgcgcgct gatgaggcgg   99300
ctgcgcgcgg agggcgccgt gcgcctcgcg tgcgagtgcg tgggataccc gcgccagaac   99360
gcggtggagc tcataaataa tatgcgcttt caaataacgg aagaaggcgc ggtggcgaac   99420
tttgagctgg cgaacgcgag ctgtctcggc aacccgaccg cggagtccat cttcgcgagc   99480
ttcgcgcagt tcgtgccggt cttcaacgtg ctctcggcga tcgcgcgcgc gcagccatga   99540
tcgtggcggc cttcgacctt ggcacgcgca accccgcgcg caccgtgctg gaggtgctcg   99600
acggcacggt gcgcgtggtg gacgtggcca agctggactg gagccgcgac tgggagaagc   99660
gcgtgcaccg cgacgtgacc gccttccccg cgaacgtggt gctcgtggag cgccagtgca   99720
agatgtcgcc tttttctaag ttcatatact tcatacgcgg gctgctctac gacgggcggc   99780
gccgcacgcg cgtgctcgcg gtgccgccgg ccatgaccgg cagcacctac cggcagcgca   99840
agcgccgctc ggtgcgcacc ttcctcgcgc tcgcggagag cttcggcatc ctggacgccg   99900
tgcccgcgcg gaagaagctc gacgacgtcg cggacagctt caacatggcc atcaattacg   99960
tgctccgaac aaactgaaat acgactggaa cgaataagtc atgctggcgc tgttcgagtt  100020
cctgcggtcc gtgcaggact gctaccggcg caccatcttc aacttccaca tcgcgcacag  100080
cgccgaggcg ggcgatgtct acggcgtgct gcgcgaccgc attttggcgg ccacgcgctt  100140
cgaggaggta gcgccgccag ggctcgcgga cgcgctggcc aagtggtct actgcgacat  100200
aagcaccacc aagcacctgg tcaaccacgc ggccttcgcg gcgcgcgcgc ggccggcgcg  100260
gcgcggaggc agcctcgcgc agttcttcga cgtgcacgtg ggcgaggacg cggagagccg  100320
ccgcaccgcg gagatcttcg accgcgagcg ctcctcgctg gtctcgtacg tgaagaccac  100380
ggccaagcgc tgcaagatcg actacggcga gatcaagcgc accatccacg gcgggcggca  100440
gacctacttc tcggggcggc gctcggacga cttcctgagc accaccgtgc gcgcggaccc  100500
gagcaagccc tggatcaagt ccatctccaa gcagctgcgc gtggacatcc tgcaccacgc  100560
gatctgcacg cgcggcaaga gctccatcct gcagaccatc gagatcgtgc tcacgaaccg  100620
cacctgcgtg aagatattca aggactcgac catgcacata atcctctcca aggacgaccg  100680
```

```
cgagcgcggg ctcgcggacc tcgcggacaa gctcttcggg acctacgcga ccaccttccg 100740
cgtcatcgcg gccatcaccg gcaacgcctg cttcgcggcg gtggcggacg cggccgcgcg 100800
cgtggtcgcg ctcccggacg cggacgcgaa gctggcggcg gtgcgcgggc tcgcggagtg 100860
ctacggcgtg cgcaacttca aaatcggcat gttcaacctc accttcacgg gcgccatcga 100920
gcacacggtc ttcccctcgc tgatccccgc ggagagcaag atcaagttct tcaagggcaa 100980
gaagcttaac atcgtcgcgg tgcgctccac cgaggagggc cgcgagtgcg tggagcaggc 101040
gcaggcgctg ctcgcggcca tgcgcgagcg ctcccgcgcg ctcgcggccg cggacgtggc 101100
caccgcgagc gtggacttcc tcaaggagct gctggggcca tagtgaaata atactgattt 101160
cttaaatatg gagcaggcgc tcggatacaa gtttttgttg cccgacccca aggacgacgt 101220
ctactaccgc ccgctccact tccagtatga gtcatacgcc aacttcatca agcaccggct 101280
taaggacatc ctcacggtgc ggcgcacgct gctcaccttc aagaacggca ccgagtccat 101340
cgtgctcgag atcgacgacg tgaagatctc ggcgccggag ttctcgccca tcgtggccag 101400
catcaagggc cacagctacg aggcgctggt caccttcacg gtgaacatct accggcacgt 101460
gatgaccaag gacggcctca ccgttaccaa gatcaacagc tacgagggca ccgactcgca 101520
cctcgtcaag ctcccgctgc tcatcggcta cgggaacaag aacgcgctgg accctccaa 101580
gttcgtggtc ccgaacgcca tcggcggcgt cttcatcaac aagcagtcca tcgagaagct 101640
cggcatcaac atgatcgaga agataccac ctggcccaag ttccgcgccg tgaaggccaa 101700
ctccttcacg ctctccttct cctcgatctc gcccgtgcac gtgatgcccg cgcggtaccg 101760
acactacaag atcctgctcg acgtgaacca gcccgacaac ttcgtgatct cctccgcgaa 101820
gaccttcatc accgtgaacg tgatcgtgat ggtgcagttc ctcgcggacg tcacgctcga 101880
gttcgtggcg cgcaacctct gcttcgacat gccgccgag gccgcgcacc tggccaccgc 101940
gctcgtggag agcgcgaaga ccgtgcccgc gggcgcggac gtggccgagt acgtgaacgc 102000
gctcatcgcg gccgagcacg cgaagcagaa gtcgacgctg tccaaggagg agttccgcta 102060
cgagatgctc agcaacttcc tcccgcacat gcaggacagc gccaaccagc tcaagggcct 102120
gtacctgctc tcgctggtgc gcaagatggt cttctgcgtg ttcttcccga accggtaccg 102180
ggaccgcgac tcgctggtct gccaccgcgt gtacacctac gggcgctact tcgaggcgct 102240
ggccatggac gagctcgaga cctacatcgg gaacatccgc aacgacatcc tcgcgaacca 102300
caagaaccgc ggcacctgca ccgtgaacat ccacgtgctg accacgcccg gcttcaacca 102360
cgccttcgcg gcgctgctca gcggcaagtt ccgcaagtcc gacggcagct tccgcacgca 102420
cccgcactac tcctggatgc agagcatctc catcccgcgc agcgtgggct tctaccccga 102480
gcaggtcaag atctcgaaga tgttcaaggt gcgcatgtac caccccagcc agtacggctt 102540
cttctgcgcc tcggacgtgc ccgagcgcgg gccgcaggtc gggctcatct cgcagctctc 102600
cgtgctcgcc tccatctcga acatccgcac cgcggacttc gtcgagctca ccaagcgcgt 102660
ctgcgactac gtgcgctcct acccgcgcg cgacatcagc tacttcgaga ccgggttcgc 102720
ggtcaccgtc gagaacgcgc tcgtggcctc gctgaacccc gcgatcgtgg acgcgttcgt 102780
gctcgacctg cgccggcgca agcggctcgg cttcttcggg aaccgcgaga tcggcgtcgc 102840
gctcgtgcgc gaccgcatga acgaggtgcg catcaacttc ggcgcgggcc ggctcatccg 102900
cccgctgctc gtggtcgaga acggcgtgct cgtcatggac gcggaggcgg agcggctcga 102960
gcgcgacctc gccgcgatga ccttctcgga cgtgctgcgc gagttcccgc acgtgatcga 103020
gatcgtggac gtggagcagt tcagcttcag caacgtctgc gactccgtgc agcgcttccg 103080
```

```
cacgctgccg cccgaggagc gcgcgctctt cgacttctgc gacttccggg ccgagttccg   103140
cgacgggtac gtggcctcct cgctcgtggg catcaaccac aactccgcgc cgcgcgccat   103200
cctcggctgc cgcgcaggcca agcaggccat ctcctgcctg agcgcggacc tgcgcaacaa   103260
ggtcgacaac ggcatccacc tcatgttcgc ggagcggccc atcgtggtca gcaaggcgct   103320
ggagacctcc aagatcgcgg acaactgctt cgggcaccac gtcaccatcg cgctcatgtc   103380
cttccgcggc atgaaccagg aggacggcat catcctgaag cggcagttcg cggagcgcgg   103440
cgggctcgac atcctcacct gcaagaagta ccaggtcgag atcccgctcg agaacttcaa   103500
caaccgcgag cgcgtgcgct ccgcggcgta ctccaagatc gacgtcaacg gcgtggtgcg   103560
cctgaacgcc ttcctcgagc agggcgacgc catcgcgcgg aacgtgtcct cgcgcacgct   103620
cgacgacgac ttcgtcgccg acaaccagat cagcttcgac atcgcggagc ggtactcgga   103680
catctacgcc gcgcgcgtgg agcgcgtgca ggccgacctc accgacaagg tcaaggtgcg   103740
cgcgctgacc gtgcgcgagc gccgcgccat cctcggggac aagttcacca cgcgcaccag   103800
ccagaagggc acggtcgcgt acgtggccga cgagactgag ctgccctacg acgagaacgg   103860
gatcgcgccg gacgtgatca tcaactcgac ctccatcttc tcgcggaaga cgctctccat   103920
gctcatggag gtcatcctca ccacggccta cgggcacaag cccttcgccg aggacggctc   103980
caaccgcccg atctgcttcc ccagcaccaa cgagaccgac ttcgagacct acatcgagtt   104040
cgcgcggcgc tgctacgcgc tctcgcaccc cgaggccgcc gcggacgacc ccgagttcga   104100
gcaccgcgtc ttctgcgagc gcgtgctctt cgaccccgag accgacgagc ccttcgcggc   104160
gcgcgtcttc ttcgggccgc tgtactacct gcgtctgcgg cacctcacgc tggacaaggc   104220
cacggtgcgc tgccgcgggc gcaagaccaa gctcatccgg caggccaacg agggccgccg   104280
ccgcggcggc ggcatcaaga tcggcgagat ggagcgcgac tgcatgatct cgcacggcgc   104340
ggccttcacc gtcgccgaga tcctgcgcga ctccgaggag gacgcgcagg aggtgctcgt   104400
ctgcgagaac tgcggcgaca tcgcggcgcg gctcaacggc acgcacgtct gcatccgctg   104460
ctccaagatg agcctctcgc cggtgctcac cgcgcatggac tccacgcacg tgagcaaggt   104520
cttcaccacg cagatgaacg cgcgcggcat aaagatccgc gtggagttcg agaagcagga   104580 ccctgcttc tacgggactc cgaaacggtt cagcctcgcg cccgacgagt cgctgttctc   104640 gccgaggac tgaacccgcc gtcgcgaccg cgtcgcgacg actagcttat cgttcgactg   104700
atgcgaaacg cgcggcggcg ccgcgactta gcttatctcg actgatgcga acgcgcgacc   104760
tctcgcgact ttctagcttc tcagactgat gctaccatat cgcggcgtgc tggccccacc   104820
accagggctt ctcgccgtgg ctgacgcggg gctggctgcg acgcgcgctg cagtagctgc   104880
gcgcgcccca gtcgccgcgc acgtgcgccg ggggcaggct cccgtccagc gcgtgccgcg   104940
tcacctcggc gccgggccgg cggcacgtgt gcacgtccgt cttgttggag acgagcaccg   105000
cgtactgccg catggtctct atgtgatgct ccaagtgctt gcccgccatc cggttggact   105060
cgcagcacgt ttttgcttcg gctaaggttt tttctagagg ggatagtagc ttatccacgc   105120
gctcgggcag gacgcacgcg gagccgtcga accctacttt gaacgggtc accttgatgt   105180 tcccgtcgta gcggtccac agcatcctga ggtaggttgt accgtcgggg tctgggtctg   105240
tccacactct aagcttttcg ctacagcggc cgtcgtacgt aagacggtct ctacgctcgt   105300
agtagtttct gcttatgttg ttggggtctc catgctcgta gtagtataaa tcgtacgcgc   105360
ctggcttttt taagtcgttt tcgtcgttgc tgacgtgtat cacgtcggga taataggata   105420
```

```
tcctaactgc actacaatct atagtatttg gtctagtaag ctgttcgaga tcaccttgtt    105480
catcatgatc tactgatttg tacacggcac cgtcgtgttc cgacggacgt atgaatatgt    105540
ccatggtaaa cgatgtaccc actttggaaa acgtatccca tgcagtaaag catagtccgt    105600
ccattataaa ctcaggaaca ctcataacaa atcgaaatct gtgaagtttt tcgaacacca    105660
cttttacatg gtctttgtca cgaacatcat tgccgtttac ttcagacatg aattgaagga    105720
acgctaaaga gtttcttgtt tcttcatgaa tctttccatt atacgtccat ccagtttcta    105780
gaattctata tatgcttttt gcatcgaccc cgtaccacca gtacatggga actccgaaat    105840
atatagctgg gtttgagtac caatgggcaa gagtgcccat tgcgtttaaa aagtcttgac    105900
aaaaaaatgc agttttttctg tcgataactt gacttggact acgttcgtgg acatcgtaca    105960
tgtccataat tggttcattg gtaacggtta catgacccgt cattatcttt ttaacaatca    106020
taagatacag tttgcctaaa gtcgaaatat gtataacgtt aatttttaca tgttctccta    106080
acgtaattgc gttttttactt agccattcgt cgtctacaaa aatcttacga tacataggat    106140
ttctctctac gtatcttcta aagtatagat ttaccggtct accggcgaca ttagcgccat    106200
ctatagcagg agcaagctgt atgtatcgtc gtataatgtc tcgtataagc tttctgtctt    106260
ctctgggaat acacgacacg gaacttagag actggtgcca gtgtctttca accaaagact    106320
tgaacctagc aaccaacgcg ttgtcactct ccatttataa ttaaataatt atcccaactt    106380
cgtatgttaa tccttattac cagatagcac cgctccttcc tctccaccac gtactatcta    106440
aaggatacct gtaagggtaa tgtctggata acgggcgtgt gagccaagac gtgttatggt    106500
gtcttcccca ccaacggtcc acttctctaa ctaccggagt gctagacgtt gtcgatccca    106560
ctactgttgt ttctccatta cctgtaatct ttgaagcgca acaagtgtta gtctttgcca    106620
aatcttctaa cggcttaatt aggtcgttaa gtctgtcaat atccatgcac tgaggtgtat    106680
cgttaccagt ttccccaact ttgggaggaa cttcctgttt agtgtccaaa taacccataa    106740
acctgtctct aagcattctt ctgtacgtgc ttttgtcatt gtctatgtct cccaaaaacc    106800
tgtgatttac gcatccgttg tacgtaagtc tgtcccttcg ctctcgctcg ttatttccta    106860
cttcttctat tgtactgtaa tgttgatagt ccaagtaata gccactgttt tcatgatttc    106920
ttgtaaatat aatcggtgtt ttattattga catcgtgttg cctactgtac gtatcttcca    106980
tggatctagg aacttgtcta gaaaattgag gactagaaat acgccttcca aatcctggat    107040
gataaaccaa acgcaatgca ctacagtcga catcgtcact gtctctagtt atcccatcaa    107100
caactccttc tttgtgatgc tccactgttt taaagttaac tcctctgtat atgttgagtg    107160
ttaaaaaaat atccacattg aacgcagttc catattttgt tattttatcc cacgacgtat    107220
aacacaaacc atccataatg aattccggaa ccgatactac aaaattagta tcgaacttat    107280
caaacgaaat gtttactcgc ggttgtgctt cgtatttttt gtcatacaca tctgtcatgt    107340
attgtacaaa atctatagct cctctagcat cgggcatgct aacgtctgga aaatcatttt    107400
ttaactgttc tagtacgaac tgttgatttt ggtcatctct ccaccagtac attggcaatc    107460
ctatcacaag agacttattt ttataataat ttgctacaga agctatatgc cacatgaaat    107520
tatagcaaaa ataatccatc tgtatgttta aaccggtttt actagtctgc tgagagtagc    107580
tatccatgat agtgtttccc tcgccaatac ttcctgacat tattctgtaa acaaccatta    107640
acaaaaatct tcctaccgtt gttatgttgt caaaagttct tatgttttga gcactttcga    107700
gtaaccatat gttattttca aatatacttt tgtaaactgg atttctgtcc acataactct    107760
ttaaaaatag atttactgga aggccgcttg ggttatctcc ctgtataggc ggcgcttgct    107820
```

```
ttatgtattc gcgtaacaaa tctcttacaa cttttctagt tcttctaggt atacatgacc  107880
tattattcaa aggctttgtc cagttagcgt ttataaacgt tgtaaagtca ctgactagct  107940
tctccattta taattaaata attacagacg gcaacacagc ggttatctaa tatctgctgt  108000
atcctgtctg tacatctatt tttctgttga gatcaagaag agctttacgt agactctcca  108060
agtgtctttc tagtctgtct aaccggttac ctgtttctct gcagcaatca gttatagttt  108120
tgtaactgtc taacaagctt acgaggcgct cttccacact ttctttagtt ggagctccag  108180
ccgcgtacac tccgttggtt gaattgcctg tatcatcagg ctgagtcaat aggttttctc  108240
cgtcattttc atccatattg agtccaacga acacaaacga gtaagtgttc ctctatttaa  108300
agtattgatt ttagaaaaag gcaagcctcg ctgccctgat tcggcggcaa acacggttg   108360
aacacgcgga agtcgctcgc ggccgtgaag atctcgtccg cgcacgcctc cacgctcgcg  108420
aagcgcccag gcgagacgcc gtcgtgcgag cggaacccga actccgaggc cgccaccgcc  108480
gcgcccttga agagcacgca cgccacttc ttgcgcacgt cgaaggcctc gtcgttgggg   108540
tcgaacacgc gccggtccac gcgcgggccg cccgccgtgc gcgcgaactc cagcgccgcg  108600
ttcgccgcgt tgaactcgcg gatgttgtcg tagttctcgt agacgcccca gagctgcagc  108660
gccacgaaca tggcggccgc cgccgcgagg gccacgcaga gcgcggacac cgcgtccatc  108720
ttttatgtgc agaattattc gttggcgcgg agctcgcgca gctccgcggc gcgcagccgc  108780
gcgaaggctg ctttgagcgc gcgcagcagc tcctcggtgt ccgcgcgcag catgtcgaag  108840
cggtggtagc tgtccaggcg cgcgcggcag ccgaagaagc gtgcgacgca cgcggtgacg  108900
atgtcgttca cgtagagcac gcccgaggcc gtgcagtaca cggagcgcgg ctcgcgcggg  108960
tccggcggca cgtccacggc gaccgcgtgc gcggccacgt cctcgagcac cttgcgctcg  109020
agcacggcga ggaagtcgcg cagctggcgg cggttgtcca gccaggcgta ggtggtcgcg  109080
aagagcgtga gccgcccgcg cggcgcgatc gcggtgtagg gcgcgtaccc gcggaactcc  109140
cgggggtgca cgaccttgac gttctcgtgc tcgcgacgga aggcctcggt gtcgagcagc  109200
gccgcgagcg cgtccacgag cttgtcgag acctccacgc ccgcgccgaa ggcgatgagc    109260
tcgatcttct gctcgctctt ggggcggaag tcgtggaagg tgtgcagcag catctcgcgg  109320
agctgcggcg gcttctcgac ggcctcgagc gcgtcgccgc ggacgaggaa gtagtcgagg  109380
tcgtgcagcg agacgtgctg cccggcggcg ctctgcacaa acttgaggaa gacgcagagg  109440
cccgcgcggc gctcgagcac gtcctcgacg tgcgcgtgga atacgtgccg cgagggcatg  109500
gcctcgatcg cggagagcca ctcctcgttg acgcaggtgg tggtgttctc cagcaccacg  109560
ccctgcgtga gcgcgggcca ctgcaggtgg aaggcgaact cgtgcttgat gagcgaggcc  109620
acggccgggt ccaggtccac ggccagcgcg gcctcgccga cgaggggagc gtccgccatc  109680
acgcggagga cgcctggccc atctccttt tcgccttttt attcaggatc attattcttt    109740
cgttgacgag gtccatgagc atcttgatgg cggcggccgc ggccgccgcg tcgccgccgc  109800
acatctgcgc gatgcgcgtg agcatgtgca gcagcgcggc ctcgtttagg tcctcctcca  109860
tttagaggcc gtgagggcgc gcgtcgtcgc gacgagggga cgcctcccgc ggcagcgtgg  109920
tgcgcacggc gaaggcgagc agcgcgccgg cgcactgcgt gagcacacac tccgcgagcg  109980
cgacgaggag ctcggagggc gcgagcacca tttagaggcg cgcgcgggtt taattgccgc  110040
cgtcagagtc ggcatcatcg cccttgtcgc cgccgtcctt gcagtcgccc ttggtctcgg  110100
cgtcgacgat gtcggcgagc cgcgtcttca tgtgcgagaa ctgcgcgagc aggatgccgg  110160
```

```
ggtcgagaca gcgcttgacg acgctctcgt cggcgaagtc gtagcagatg cgctcctggt 110220
tctggcagaa caccgagtct tcgatgatca acaccctcct ggtcccggcc gaccgcatga 110280
tggccatggc ccggatgagc ctcttcttcg atccgcgtat ggacatggac cggagcacgt 110340
tctccacgtc ggagtcggag acgttgcagc agcagaggtg cgtgatgctg gcgcgcccgt 110400
tgacggggat gtgcttgtag gtctggcaga gcagcaccag cgacacgttg atgtgccgcc 110460
cgtagttcat gaggcccaag agtgtgggcg accgcgtctg cgtgtcgccc atatcgtcga 110520
gaatgatgag gaacttctgc ttcttcgtct gcgcgtgccg ctcgatcttg cgcttggcga 110580
ccgagaggtt gtactcgagc tcctcgtgcg tggtgacctt gtggatgtgg tccggccaca 110640
cgaagccgtc gtaggcggcg ttgtagacgg gcgtgaagag caggatgtgc ttgaagcggc 110700
gcacgagcgt gcggaagagc gagagcaggt aggcggtctt gccggagccg agccgccga 110760 cgagcgccat cctgaagggc gcctcgatga gactctcccg cttgaagcgc acctcctgca 110820
cgacatccat cgtatattta ctgtcactaa attaccggct ccgagaaata tagaaattag 110880
agcctcctag agcacaccga ggcgcatcgg caagatggca cataacacgt tcgaaaacga 110940
tagcgagtcg gcagctaaca accagtacgt ggcgtcagtc aagcgccaga aaatgattcg 111000
gcgatacatt aagatgttct tccggttcgt tacggcgata gctatcattg tcctggctat 111060
tctagttgtg attctgtcgc tatctctaga cgaatgtctg cacagagaac acctcatga 111120 ctattcacat gtacaaaatt caacatgcga cggcattact ttaggtggtg aaaagtgtct 111180
cagacttaat ttgccagcaa cgtgggaaga tgctaataga caatgtggta atcttgggtt 111240
ttacctacca tctactggcc ttgaaaagaa atttccttgg cttgtgacct atctcgacgg 111300
aacttgggga aacactcaga actccgtatt tggaccaacc ggtgacttgc agaatgtcat 111360
aggaccgaaa gaatacaaat attttgtgt gtccgattag atgattataa tctaataaat 111420
gggttgctgt aaggtcccta accgccagtc tataaggact ttgaaaaagg cgtcctgtcc 111480
ggtcgccagt ctcgtcacca ttctctccct agtcaccagc ctcggtgcga tagtcagata 111540
caccaatttt tttctaaaag aagcatgtga cgaaggatgg atgcccataa aaaacatatg 111600
cattttaaac acgcactttg aagccaccaa tgacgatgcc cacaggatat gtgaaaacct 111660
agacggaaag ccgccggcca tccctaaccc tactctgtta aagggtgtca cagttctcac 111720
cggcgaaaag aaattttgga tgacccatca cgaagactat actactgtgt ttgagcatat 111780
agacgatagg acgactccta aaaacacaga ctatgacagt aaaaaacaca cttgtttgat 111840
gagcgaggac ggattgatac accataactg catgatgaac gtgactgtgg tatgcatgaa 111900
ggagatgcac ggataactga aaatatactg tttgaacgca aagacgccat gtcgcgactt 111960
caaatactga cctcatttgg acaaatcttc gcacccgacg aagctcggct gcgcgagatc 112020
gcgcgtgatt tgggaatatg caccataaaa cgcgcattcg gcgacatgct gtacggcttt 112080
atagacttcg acccggtgcc cctgacccaa gtaaacatgc tcatgtccaa ctgctacttc 112140
gcggtcaacg gcaacctgct tccgtgcacg gaggacttcc ggctcagact cccggcaacg 112200
gagatctctg cggcctacct gacgagaacg ggacggacga tcctgtgcgg caaagacttc 112260
aacatagtag cgccgtcggg gttcaagccg tccatgcggc tgcgcgacct cagtcacgtg 112320
tctgcgcttg tagagatcct ggaagtctac gacgagtccg gggagtacca attcgtgctc 112380 ggcccccagcg cgcagttcat gctgcggctg atggagaagg agaacgtctg tctgttcggc 112440
agcgggtggt gcatagtgga cctgcgcaag ctggacgtac ccatataatc agcatccttg 112500
tttttatcct gtcttttat cagttttta gctagttaaa acataaatag taaagctaaa 112560
```

```
aagaggagtt ctggagtctt gcaacaacca ggatgaaggc ggtgttgttg ctggcgttac  112620
tgggagcgtt caccaacgca gcgcctttgt tagaaagcca gcgttctaac agtgaggaaa  112680
aagcaaattt ctgctcgacg cataatgatg aagtgtacgc caggttcagg cttcagatgc  112740
gcgtgggtgt acgacacagt ccgctctaca ctcccagcaa catgtgcatg ctggacatag  112800
aagactccgt tgaggacata aagagtcca cagaaaaaga atacgcgtct acggccacgg  112860
gtgaggcggc cggagtgaac gtgtcagtgg cactagtggg agaaggcgtg agcataccgt  112920
ttagttacat aggccttgga ttcaacccgt cgcttgaaga tagctacctg tacgtcaacg  112980
tctcgtcacg agctccttgg gttaaacaga cttcggacct atccgcgaac ggcggctggg  113040
gtatcaaaca ggttctagaa aaagagttac tggccatcca aataggtgc gacaaccaaa  113100 aatttcccga agaacccaca actacacccc cctcacctgt cactacaacg ctttcctcaa  113160
caactccaga tctgaatgaa gaaaacacag aaaatacgcc gacgaccacc ggcgccagtg  113220
tagacagaaa gcgcaatcca gctgacattg acttctcgct gctcgtggac ccccgatgcg  113280
tgacctctgt agacctgcac gtcgagctca gggacgcgtg catagactac aaacaagagt  113340
cgccgttgtc gctgaagggg aaatatgag acggcgaact agtaaaaaag gagattaaag  113400
acgtgggaaa gaatcacaat atgtgcagtc ttaacctcaa ccctggcaat tgagctgttt  113460
ttattcggca atataatagg tgattattga acattaaaca aaacttatcc cacaacgccg  113520
caacaatgga agtgctggtg atcatctcta ttatcgtcgc cgtaatatgc ttgaccggag  113580
cggtaatgta cctccttatt gaactcggct tagccgccga gcgcgctaac aaacgcgcgc  113640
gcgtgaagaa aaatatgcgc aaattagcca ctcaattggg aaatggatct gtcgactccg  113700
gcataggcat aggcccgtgc ataatgtcgc gcaccatgga ctctggaccc agtcgctggg  113760
acagcgacag tgaggatgac ggggacagcc tgtccacgac gtccaccagc ggagggggga  113820
ctctcacccg agtgtgggtt gggagcgccg ggcctatgta cgaaaacttc tgcgggaacg  113880
gcacccgcca ctcccccacc aacgaccctg gctaccactc gcgggagact ctctgcagcg  113940
gacctccccg tcaggcgccg gcgctaccgc ccaccccgaa gcccgacgag gtaacggtgg  114000
acgtggggcc cggtcccgac gaccaacacg gtccgtacga ggaacctgat cccattcccc  114060
cgcaggaacc cgagccgccg gtgcagattg aggtaaccat caacgggccc ggtggagaag  114120
gcgaggcgga aggagaattt ttctacgacg agtagccgcc aaaactgaat aactatcggg  114180
cttcgtaaac gcgcagacat gccgctgttc cggaagctca tggtttcgcg ctccctggtc  114240
aaggaatgtc tgactctgga cttccggcag ggcgagcgtc tccctacgcg atgcttcctc  114300
ccggtgcccg cggggacgac attccacaga gtctgcgaca cctcgccgct gacggacgaa  114360
gtctcccggc acgtgcagga gcccgtcatg gcaccggac gggtccagta ctactactc  114420 gagagcggcc agggcatgat cggcgacaac gcgggcatgg cgcgcatgct cgtgtgcacg  114480
cggtcggcgt acaacggcgg cgacgtcgtc gtgcggtcca cgcggagcag agcagacaag  114540
accgtggtcg cgccctgcca gggcatggcg ctgctgctga gccccttctg cgccttcgac  114600
atcacgccgg tcgagagcgg ctccgcgata ttcgcggagg tcatcgtcac cgcgcccagc  114660
atggactacg tcgaggcggt caccggcacg ggcgaggcg ccgtgcggat attcaactcg  114720
caccacccgc tctggccgcg acacggctcg aacgtctgct tcgcgctgcg gttgctgcga  114780
gacgtgcgca cgggcgagcg cgtggtcgag cagatgttca tggacgggcg ctggcacacc  114840
gtgctgagga cgtcctgcgg caacaaggtc tgcgtgcccg ccgacctcgt gggccagacg  114900
```

```
aacctcgagg aggtgcccct ctgcgacgtg acgcccgaga tcatgcgccg cgcgctggcg   114960
atcgacccgc cgtacgaggc cgtggcgcac ccgcaccgct gcgtgtacgg cgccatggac   115020
gtccggtgcg cgaacgagta cctcgtgtac tgcaccttca agacggagcc gacacggcgc   115080
agcacgtcct cgccgggccc ggacagcccg ctgtcgcccg cgactccgtc gacctcgcgg   115140
gccgcggccg cgcgcgtccc cacgacgccg caggaagtgg cctcgccgac cacgaggctc   115200
ctggagacct gtctgcgcga cgccctcgac ggactctgac ccgaaggacc caccgtccac   115260
tcacattcca ctgccagaca actcaagctt tttctgcatc tacctcgcta ataattgaat   115320
tgttatagga caaacaggcg cactcgagca caatggcgtg ttttatcgaa ttgttagact   115380
ccatcttcaa ccgacgccac cgtaatttcg ggccggagga catgtacagg ccctctgacg   115440
ccccgccccc caaatcgcac acgcctcgca ctccccgcac cccgcggacc cagtgtcccg   115500
gacacccgcg gcgacaaagc tcctctccca tctacggcgc ttatgtggac tccctgccga   115560
ggaacagaaa gcggttccag aatcaacaca gttgtcccgg agattacgag cggtgtcaac   115620
tctcggacac catcagcctg gatgcgacgc tactcacggt tacagtgacg tccatctcca   115680
gcatatccag ctctagtagc tcagactcta tctctctggg gcagtgcaga ctgtccatgg   115740
tgtccgcaac atcaacctcc acctccacaa ccttctcctc ctcggaatga cgccacact   115800 tattttgta taatagtttg tattgaacct tagagacatc cacaaatagt taggaagcat   115860
gagtagttca agtagcgaga ccaccccctaa gcccaagccc atccctgctc ctcccatgac   115920
tcaggaggag tttaacaaag aagtgaagaa acgaaaagaa cagaaaaagg aaaaatctag   115980
aaccgttgaa cgtgagtcag aaaccgtaac tgtatcttcc gacggatcag agataaaaaa   116040
gacttacgag cgcgagtctg agagaacaac cgaaacagaa aagaacaaca cgtcaaccga   116100
tgataataag cagaacaccc ctgtagagaa accagaggaa accaagcctg cttctactcc   116160
tgaaggtgtg aagccagccg agactcctgc cccgactact gacccccaac ctactacaca   116220 accaccccgca gaatcaaacc ctggaagtca acccgcacct gcttcagaac caaccccgc   116280 acctgagcct gcaccggaac ccactcagcc tgcatcagta actcaacccg ctccaacacc   116340
agagccaagt ccagccccta agcctactcc ggcttctgaa ccaaccccag catctgagcc   116400
tacttctgct ccagaaccta caccatccgc agaaccaact cctcaaccaa ctgtagaaac   116460
accaccatct gctccagcac caactcccga ggcccaacca cccgccaaca gcaatccac   116520 tactgaaact accactggta ccagcacctc ctaagtgagt acgtaagcat ttcggagtaa   116580
cgtcgtagca agcgctagtc cgccgcgagc ggttctcgca agttttttcg ggtaaaaagc   116640
gtacaccgtc gccttgtcgc ggcggtgtac gcttttttca cgccctttt gcaaaattta   116700 aattgtaccc gcgccggctc taggaaagat ggcgtgcctc agagtgttcc tggcggtgct   116760
cgcgctgtgc gggagcgtgc actcggcgca atggatcggc gagcgcgact tctgcacggc   116820
ccacgcgcag gacgtcttcg cgcggctgca ggtgtggatg cgcattgacc ggaacgtgac   116880
cgccgcggac aacagctcgg cctgcgcgct ggcgatagac acgccgccga gcaacttcga   116940
cgcggacgtc tacgtcgccg cggccggcat aaacgtcagc gtgtccgcga tcaactgcgg   117000
cttcttcaac atgcgccagg tagagacgac gtacaacacg gcacgccggc agatgtacgt   117060
gtacatggac tcctgggacc cttgggtgat cgacgacccc cagccgctct tcagccagga   117120
gtacgaaaac gaaacgcttc cgtacctgct ggaggttctg gagctagcga ggctgtacat   117180
tcgcgtgggc tgcacggtgc ccggagagca gcccttcgag gtgatcccgg ggatcgacta   117240
cccgcacacc ggcatggagt ttctccagca cgttctacgg ccgaaccgcc ggttcgctcc   117300
```

```
ggcgaagctg cacatggacc tcgaggtgga ccaccggtgc gtgagcgccg tccacgtgaa  117360
ggcgttcctg caggacgcct gtagcgcccg caaggcgcgg acgccactct acttcgcggg  117420
gcatggctgc aaccatccag atcgccggcc aaaaaaccca gtaccgcgcc ctcagcacgt  117480
atcgtcgccg atctccagga agtgcagcat gcagacggcg cgctaagggc gctcaccgcg  117540
ctgacggcgg ccgtggtgtg cgcgatcgcc atcgcgctcg agcgcggggc ggaggccgac  117600
gccgtggacc ttatccttat aaaatttcta atgatatgct agtttttatg cgaccttcct  117660
tagaaaattc ggaattcaaa atgaaataa  acggcgtttt agcacgcata ttattaatac  117720
cgaccaccat ggcaggcgtc cgcagctgcc agaagaaagt cccttctact gcgggctcca  117780
tgtcatttca acgggcaacc ggagcatcca gccggcgat  gtccgaggcg ttgcagaatg  117840
atttcagcta caacccgcga ccgcctccgc cgagcgcaga agagattgac ttcttctgcg  117900
tggacatgcg caaagtactg atggaaattg aggccaagcc cagcagctcc aagtaccccg  117960
atttcatcca cccggttgac agcagcccgc cgtgcacgcc ggcgcgcaag cgcaacggct  118020
tcggccgcaa ggcactgaac aaaacccagg tgccgcagca ggccaagcgt gacggctact  118080
cccgctaatg cagtccacac acttcacaca ctacatcagc actcaagctt ataatcacta  118140
cacaatgaat cagcccacca cgtgcgaagc acacacataa aatcacccac ctgtcctgat  118200
cgttcccaat actcccaatc accgtgcttt acacgcacgt taatcaccct ttccttcctt  118260
catgcgttcc tgatcgttcc tcctccttaa tcacacacac accccgtaat tttgtacttt  118320
tgtactttaa tttgtacact ttacacactg actttgtact gcctttgtac tttatttttg  118380
tactgaaatt ggacgatact tatctttgta ttcacatcca agttttgcaa attccacagc  118440
cggtagcgaa aagtgaaatc gtaccgtttt aggcttcgat ccccctcccg cgcgaagact  118500
cgccagcatg gactctcgta ggctcgctct tgccgtcgcc ttcggaggcg tcctcgccag  118560
catgacacag cgccgccgcc tggcttctct catcgccagc atcggccaac ggctgatggg  118620
cggcgacggc atgcgtcgcg tcgccgttcg gttgatcgac cagctcatgg ccggaccccc  118680
ggacatcaac gacgaggcct tccagcgcga gatccgcgtg ggcgagctct tccaggcgct  118740
ccaccgcgtg gtcgagcagg cacgccgaga gaagtacttc gaggtctgcg gcgccggcaa  118800
cgacgccgac gcgcccgtcg tcgagatgga caccgcggcc gcaccccgc  agccccagcc  118860
cgcgcccctc gtggtcacgc cgcagaacgc gttcatgttc gtgccgcaag gcagccacgt  118920
gcacgtggac gagagcgtgg acccgttctt cggcatgagc ccctccatct tcgggcgcga  118980
cctccccccct cagccgcccg aggagctgct gagcgactac gacccgctca tgagccaggc  119040
cggcgagccg ccgagcccgc ggtcgccctg cgaggccgac ctctggtgct tcgagacgct  119100
cggcgacagc gacagcgatt gagaccgcac cacaccctac ctcacccacc ccacactcca  119160
cctcacctca ccctaacacc cgacacccaa cacttcaacc ggacaatgaa ggagtcccac  119220
atttcactga aggacgcgga tgaagccgca ctcccccaca tgaaggattg caacggtca   119280
aacatttcac ctgcaatgaa ggacgatgcg cggtcgcatt ggcctgcgac cgacatcgca  119340
cacatgaagg acacaattgg tttgttaatc cggacaatga aggacaaatt gttttttgtta  119400
atcaggacaa ttagaacaca atcaaatttt tgtacgatca taaaatcgat atttgatgca  119460
catatattag taagtatatt agactaaatt ctccggggag gcaagcagtt ggatacggcg  119520
gggcggggca cgacgtgcac ggagagttcg ggcgggtccc ccttccccccc accccacgg   119580
caccacgatg cgcctaatct tagcgctcgt ggcctgcttg ttggcggcgc cgatgccgtt  119640
```

```
atcgggtcgt tcgacaagca ctccaaacac gtcccctcc gcactcggct cgacgagttc   119700
ggaaccaagc tcggaagacg ctgtggcttc gagcacaacg acaagcacac tcacaagcac   119760
tacaagcaca ctcactatgt ccacaagtgt ggacaccact actacctcgg gcgctacaac   119820
gtccgcaaac agcactcctg cagcgagtgt gagctcctcc acaccgcaa ctaccgaggc   119880 atcgacggca ccaacgacgc cgtcgacgcc gacgacagtg aaggtaacga agggcaagga   119940
agacacgaag gcgtctgcct acctcgtttt actaatcacg ttcatggtca tgaccacgct   120000
cgtgatggtc gtggtcgtgg tcgtggtcgt gtacaaacag ggactctgta actgctgctg   120060
taagtttccc ctgctgcaaa gagctcaagg actacctcga cgaggaggag agcgccgggc   120120
tgtacgacgc cttgacgtgg agccactcag actccggcct ccggctcgtc gtgcgcgcgg   120180
accccagatg atgaggatcg gataagatcg gcgtgttttt cccgcccgtc gcgaacatta   120240
tgcctctaaa tgccgagaat taactgaaat tcaaacacgc tttgggactc aactccgtga   120300
cccacactca accatggctg gcttcctagg cgcattcaga ggcgtgtgct ccgacttatg   120360
gcagtcgctc cgtggacacg acaccactc ttccagctgc ccgcgacgac gcgccaacag   120420
catggacgac cgcgaccggc gccgacaccg ccaccgcgag atccccaaca gctcggcgtc   120480
gctgaacagc gacccgatgc cgcaacgcag tgcgggtgcg cgccggcact acgactgccg   120540
cccctcggaa aagagcagac actcctccga caagcaccac tcggcggacc gacaccactc   120600
ggcggaccga caccaatcgg cggacaggga cagacaccgt cgcagtcgca agaactacga   120660
ctcgcacccg tcgcgcagga accgcaacta cgagcgggcg gactaccaga gacacccctc   120720
acaaacccac ccagacgccc ccgcgcagac ctcgacgctc aaggtgacct ccctaagcac   120780
cagctgcagc accctgtccc aacatcacta cgagacccc gaccacatct acgacatccc   120840
ggaagacagt cgcggggcgt cggctccccc tcgcgcggac ctcgcgctcc cccgctcgc   120900 catgcccaaa tccaagccgc gtcgcacgcg cccggcgtcc atgaacgact gcctgatgaa   120960
gcactgcggc gccggcagac ccaacctcca agacgacata tgcacactat gtactgatat   121020
agagacacag ctgagcgcac tagagaagtc tctggagtca gagctcaact tctatcgtcg   121080
ctacatacaa gacactaaga cattgctcgc cacgcgagca gcaaacatcg gcagcaaagc   121140
tctgatctac accgacgact acaacggcag tggcgacgtc ggcgaaaagg agcactgctc   121200
ggaggagtgc tgcaaagtgg aggaagttct gtgagaaagt gcgttttct gtaatgtgaa   121260 ataagatagc cttatgtgtg cacagacatg gcgaacaggc tcgtgtttt cgaccccgag   121320 accctagccg aggccgacgg catccccggc tatggggtgt tcgagcccgg caagaagaaa   121380
tgcatcttca caaagatccg caccagcgtc gcactcgcgt gccggtacgc cgtctcggac   121440
ggcggcctca tcgacgagtt cgtcatggct acatacggga ccagacgcgc gtgccggctc   121500
gtccggcacc tgacgatagg cgcggagggc gtgatgaccc ggcccgccag caactgcgcg   121560
ccgcacatgg tgctcatctg cctcagaggc gtggccgccg tgtccagcga ggacatgggc   121620
ttcggtcgct gcatcatgga gcgcggcacc atgttcatgg tcaagtccgc gcacagcgcc   121680
gtcgtctgcg gcaaccccgc ctgcgagctg ctcgtcctct tctacgacta cttcaccccc   121740 atccccggc cgctctccgg agacgaggtg ctgttcaccc gcgacctcgc gcacgtggac   121800
tacgcccccg agtcggcggt cgtcttcaag atggattaca acctcgagac cgacgtggcc   121860
acgctgtttg tcgggggta catattccgc gccaagggcc tgatgatgga gacgcgcgaa   121920
caagtgggcg acgagtgcga ctgctgccgc cacagctcgc cggtgctcgt catggatcgc   121980
gagaagatga tgtcgtcgct gcgcatgatc cccagcatcg tgcccggcca gcgggagatt   122040
```

```
tggcttcgcg agcgcggctg ggccgtcctc gagacggacg cccgcggaca ctgcgagccc   122100
ggcgtcctga ggctggcgct cgccggcctg cggctgttcg caggatgcct gcgctccgtc   122160
gtggggcggc gcgagctgtc gctgttctgc tacggcgtcg ctcccaagtt cggcggggag   122220
ttcgaggacg cgccgcgccc catggagatc gacggttagt tgtttttatc cctgtacata   122280
cgccgcaaac tgaaacttta gggcaccgcg taatagtgca cgaacgccca gtggaccgct   122340
tccgcagcca tggaaaacaa cgacggcaac gaacgcaaca acgaacaccc gcacgttcga   122400
gaattcaagg aggcgtccct gtacgggttt ctggtggcgg ccgcggacgt gaccgtcgaa   122460
gacgtgcacc ggtaccttca gttcggcgcg gacgtgaact acaggggcgc gtacctgtgc   122520
acgccgctgc acgcgtacct gcagtccggc tgcgaaaagc gcctagacgt cgtggacgcg   122580
ctgctggacg ccggcgcaga catcaacgcc aaggagatct gcggtctcac gcccgtgcac   122640
ctgtacgcga gctacgcgga cgtggacgta gagttcatgc gcgggctcat cgagcgcggc   122700
gcgagcgtgt gcggcgagag ctcggtcacg ggctgcctgt actcgtacct gtacacacac   122760
agcgtggacg gcggcgcgcg cctggacgtg gtcgagctgc tcgtgcaggc gggcgcggac   122820
gtgaacgtcc gcggcgaggc gcgcaagacg ccgctgcacg tgcactgcgc gggcttcgag   122880
gtggattcgg acatcgtgga tctgctgctg cgcgcgggcg cggaccccga ggcgctcgac   122940
gaacacgggc tcacgcccgc ggacgtgctc gtgaagtccg tgggcgccaa cgtggagacg   123000
ctgcggctct tcctcgacgc gggcgtgagc gtggccacgt cgccgacgc gcgcggacgc   123060 acgccgctgc accaccacgc agactccttc cgggcgagtg cgggcatcgt gcgcgaactg   123120
ctcgccgccg gctgcgacgc ggcggccgcc gacgacctcg gaaacacgcc cctgcacagc   123180
ctcgccacct tctgctcgtg ccggcgctcg gtgctcgacc agctcatcgc cggcggcgcg   123240
gacatcaacg cccgcaacca ctacggccac acctgtctgt actacgcgtc catctacaac   123300
ccctccgtct gctcgcggct catcgccgcg ggtgcggacg tgaccgcgcg cacgccggac   123360
ggacgcacgc cgctctcggg catgatcatg cgcaagcaca cgcgcgccgt gcgcgccgcc   123420
ctggcgacgc ggcctcccgc ggacgccgtc gccgcgtcgc tggacgtcgc agtacagccc   123480
gagcccacgg acgccactcg cgcgtgcgtg cggtacgtgg tgctctgcgg cggcacgctc   123540
tcggcgcgcg tgcggtcgcg acacgcggac ttcgtgcgag agtgcgaaag cgaggtggtc   123600
gtgctcagaa ccaccgtggt ggggctgccc ggcacctcgc tgctggacat cgtgcgtgcg   123660
gcgcagccgc cgccggtact gctctccccg cgcgtgcacc acgtgctgca gaagctgtgc   123720
gtgtacgcgg agttggtgga cgcgcggctg cgcgagatgc ggcacaagac caacctcgtg   123780
gacgcggtgt cgcggctcgt gtgtccgtgc gcgctgccgc cggaggtggt gcgcggcatc   123840
ctcgtgcacg tgccgataga cagcctgcgg cacacgttga ccctcggcgt ggcgcaggcc   123900
tcgcgttccc ttccctcgca taaatgaaat attattttt gtggtagacc ggatctcccc   123960
gatggacccc gccggacaac gactgcgcgc gccagggccg tggcgcctga acccgccgac   124020
cgcggccgcg ctggaaagcg cgctgctgcg gcccgcggcg tcggcgggcg ccgaccgctg   124080
cgcgaacgcg cacgtggacc gccgcaacat gggcgtcggc gagggccgcg aggtgccgc   124140 ggacgtcgag gggctcatga ccgagatcca cctgcggtac ggaatgacgc gcgtccaccg   124200
gaacgttcac ttcgtgcagt tctggcacgg cgagcacgtg cgccggcgcc ccgcgcgaca   124260
cgtgttcacg gtctggatct gcctcagcgg cgaggtgcgc atctacgcag agtgctgcca   124320
ggcggggcac ggcttcgtgc tctgccgaca gatggcggca gggtacatgt tcgtgaccga   124380
```

```
acccacggac tcggtcacgg tctcggtgcc gcaccgactg cgcaactcgc ggtcgccggt   124440
gtggctggcg gcggtcttcg ccacgcggca cttcgagccg ctgccgccgc ccatgtacgc   124500
cgtgcccggg cacgtggtgc tcgcgcgcag cgcctccatg ctctgcgact gctggccgtc   124560
ggacccgcgg cgccgcaacg tgatcttcta catgcggctg tcgggcgcga tggtgcgcgt   124620
ggtcgtgccg ggcgcggagc tcgagatcga gtgcacctcg gggttccggc cggaccactt   124680
ctccatcaac gacgagtgcg tgtgctgcga gcgtccgcac gtcgcgcgaa ccgcggtgtg   124740
gacgctggcg gagatttgcc gcggcgccac ggtggtgctc gcgccgccac tgccccgcga   124800
ccgcgccgcg gggctgctcg cggagatccg cctggcctcg ctgcgatggg tgcgcgtgcg   124860
tgcggtccgc agcggcagag aaagcgtggg cccgttcccc tcggtggtgt gggcggcggt   124920
cttctccgcc gttcggctct tcctggacgg aaccgtgcct gccttcccgg cgtgtgtgga   124980
gaatggacgc gcggcgtacg gcatggtgta cgtgcccccg gaggagccgc ggatggacgg   125040
gctctgtgtg ttcccgacgc ccgccgagcc ggcggcgctc ttcgtccgcg gagaccaggt   125100
gcttgaggcc ggcgcggccg ccgccataat cgcggccgct gagaagcgcg tccaggccgc   125160
caatgggtct cctgctgccg cggaggagga cataggtgcg gcggccgatg ccgccgcaga   125220
gagcgtggag caggaccagc gcgtcgagtt cgaccttggg cctgggcctg accccagcca   125280
agaagcgccc gcggacgcgc agcgtgccga ttcggacgac gacaccggct ccgagaccga   125340
gaccggcgac gagagtgtgg gcggcgagga tgacagcgac tcctcctcct cttactcggt   125400
gatgtcggac gacgaaaacg acagcggcga cgagggctgg ggcgactcta gcgactccgg   125460
catcgaggac gacgacggcg gtgtcgccag gccgccgagg aagaagagga ggaagagcgc   125520
gacgtcctcg gcgcagcggc ccagatgctc ggagactgac cggtggtgaa acataaaaa   125580 taaactgttc aacacttgta ctccgggcac caacactact atccatcccc accctccctc   125640
cacacactac aatggcaaac agagaagaga ttgacgcctc cgccgtcatg gctgcctacc   125700
tcgcgagaga gtacgcggcg gctgtagaag aacagctgac gccgcgcgag cgcgatgcgc   125760
tcgaagccct tcgcgtttcc ggcgaggagg tccggtcgcc gctgctgcaa gaactctcga   125820
acgcgggcga gcaccgcgcc aaccccgaaa actcgcacat ccccgccgcc ctcgtctccg   125880
cgcttctcga agcccccacc tcccccggcc gcatggtcac tgcgattgag ctctgcgcgc   125940
agatgggccg ggtatggacg cgcggccgcc agctcgtcga attcatgcgg gtcgtgtacg   126000
tgctcctaga ccgtctgccg cccacggccg acgaggacct cagcacctgg ctgcaggccg   126060
tcgcgcgcgt gcacgcacg cggcgccgcc tgcaccgcgt tctcggcgtc ggggccgtca   126120
tggcaggcgt cggtatgctg ctgctcggcg tgcgcgtgtt gcggcgcaca taacttttta   126180
tctcggctca aactgaaata cgacattgga ctacgaaacc tatgattttg ctcacggccg   126240
cgcgagatag gataataaat aacctttgag caactaacat ggccgatgag agagaggccg   126300
acggcgcgct gttccggtac ctggagagcg aggaccgtcc ggacgtggag cacatgcgcc   126360
ggctgctgga cgagggtgcg gacgtgaact acgcgggccc gcgcgggtac gcgccgctgc   126420
acatgctcat gcgcggcaac ccgctagacc ccgacgcggt gcgactgctg ctcgccgcgg   126480
gcgcggacgt gaacgcgaca tcgctctgcg ggttcacgcc gctgcactcc tacatgtgct   126540
tcgggaccgt gacgccagac acgctgcgtg cgctcatgcg ccacggcgcg agcgtcagcg   126600
acctcgagcg caacatcaac gcgctgatcg agtacttcaa ccgcgacggc tgcatgggcg   126660
gcgcggaggc gaccgtgatc gcactgctgg tggagcacgg cgcgcacgtg aacgccaaag   126720
acgaccttgg acgaacgccg ctgcacatct acctgtccgg cttcttcgtg tcggcaccgg   126780
```

```
tggcgctcgc gctgatcgcg ctcggcgcga acccgaacgc cacggacgcg tacgggcgca  126840
cgccactgca cgccttcctg cgctcccgcg acgtggaccc cgctgtgctg aagacgctca  126900
tcgccgcggg cgcagacccg ctcgcgcgcg acatcatccg gcgcacggcg ctgcactacc  126960
actgcgagtc cttcaagacg cgcgctagtg ttatagagac gctggtggcc gccggctgcg  127020
accccgcgag cacagacctg ctcgacaaca cggcgctgca cagcatggcc atgggcagct  127080
cctgccgcgc ctcgctgatc cgcccgctgc tggccgcggg cgtgtccgtg aacgcgcgca  127140
acgcgcggct gcagacgccg ctgcacctcg cggccgtgtt caacccgccg gcctgcgcgc  127200
ggctgctggc cgcgggcgcg accccgcgc tcgcggacct ggacgagaca acgccgctgc  127260
tgagcatggt gcggcacaac tgcgcacgcg cgctgcgcac ggcgctgccc ttggcgccgg  127320
acgcgctggt ggccggcgcg gtgaaccgcg tgaacgcgcg cacgccgagc gcggccacgc  127380
gagagtgcgt gatggcgctg gcgctgcgcg gcgcgctgga cctgctgagc gcggagagcg  127440
ttgccaccca cgcggccgcg atccgcgcct gcgaggcgga ggtcgcgctg ctgcggagca  127500
cgcgcctggg cgcgccgccg acgacgctct tcgcgctgct gacaggacga ccgaacacgc  127560
tggtttccgc gaaggcggcg cgacgcgcga tggcggacgt gtgtgtctac cgcgcggcgc  127620
tggccgcgcg cgtggagcgc gtgcgccgca agtcctcgct ggtcgagcgc ctcaccgcca  127680
tggtgtgtcc gtgcgctctg ccgccagagc tagtgacgcg catcctgcgc ctcctgaccg  127740
tggaggaact cgcttgcgca atgcgcaaat aataatgaac tataactagg cttattagag  127800
gcactatttg tgcagagtcg ttagttatag ttagtgtact taccattgga atgtcgaaga  127860
acaaaattct ggtgtgtttg gtaattattc ttacttatac attatacaca gatgcgtatt  127920
gtgttgagta tgaggaaagt gaggaagata acaacagtg cggtagtagt agtaattttc  127980
ctgcgagttt accgcacatg cttagagaac tcagggcagc gttcggaaag gtaaaaactt  128040
tcttccagat gaaagaccaa ctgaacagta tgctactcac acagtcgctc tcgacgact  128100 tcaaaggcta cctcgggtgt caggcacttt ctgagatgat acagttttac ttggaagagg  128160
tgatgccgca ggcggaaaat cacgggccgg acatcaaaga gcacgttaac tcgctgggag  128220
aaaaactcaa aacgctgcgt cttcgactgc gtcgctgcca ccgcttcctg ccgtgtgaga  128280
acaagagtaa ggccgtggag caagtcaaac gtgtgttcaa catgctgcag gaacgaggtg  128340
tttacaaggc catgagcgag ttcgacatat tcatcaacta catagaatca tacatgacta  128400
ctaaaatgta aaaatgtata caacttttag ttatcgttcg gattctcgta tcgttctgca  128460
tactatgtat ataaaatgta tattaacata gttacagtta cagttacagc tatatttta  128520 tgctcacaag atgctatata attgaaagga aattgttcac tctctgtcag ggcgccatgg  128580
actttctagg cgccgcgctt cacgactacg ttgccgatgc gcccaaggtc tgcgccgagg  128640
aggtgcggcg gctgctggcc gcaggcgcct ctgtggagta cgcgggcgag ttcgggaaga  128700
ccgcgctgca ccagtacatg ggccgttccg gcgcggaccc cgccgtcgtg cgcgcgctgc  128760
tggacgccgg cgcgcgcgtg gacctcccgg agacctgctg cggctgcacg cccgtgcacc  128820
tctgcctcat ggccgccaat atcgacgtgg aggttctccg catgctcgtc cacgagggcc  128880
gcgtcgagga ctgcggccgc gccgagctcg cctccgtggt gctcaaggag ttcgtggtga  128940
accgcgcctt cgacgagaac gtcagcgagc gagtgatgcg cgttcttgtg gccgcgggcg  129000
cggacgtgaa cgccgccagc gtggtcgacc gcacgccgct gcacgtctgc ctcacgggca  129060
tgtccacgca cccgggcacc atcgccgcgc tgctgcgctt cggcgcggac gtgaacgccg  129120
```

```
tggacctctg cggcatgtcg ccgctggcgg tgctcgtgcg ctcgcgcgcg gcgaccgcag   129180
agctggtgcg catgctgctc gacgcgggcg cagacgcaca cgctgtcgac agtcgcctgg   129240
actcgctgct gcaccagcac tttcagtccg cgcgcccgcg gccggaggtg gtgcgcgagc   129300
tcatccgcca cggctgctcg ccgcgggcgc ggaaccgaat cggcaacacg ccgctgcacg   129360
aggccgcaaa acactcctcc tgcaaacact cgctggtggg gccgctgctg gctgccggcg   129420
cgagcgtgga cgcgcgaaat aacacgggca ggacgccgct ccacttggcg gtggcgtcca   129480
acccgcgcgc gtgccgccgg ctgatcgcgc ttggggcgga cgtggtcgcg cgcagttacg   129540
cgggcgtcac gccgctggcg cagctgatcg cggacaataa ctccgcgctg gtgaccgcgg   129600
cgctgaacac gcagcccgag ccgcgggccg tggcagagtc gctgcgagcg accacgcccg   129660
tcggcgagac agcgtgctcg cggctctgtg tggcgtacgt ggtggcgcgc gcgccgagcg   129720
aggtcctcgg cgagcccgag cgcgccctgc acgcggcctt cgtggcggag tgcttagcgg   129780
aggtagcggc catacacgcc gtgcgctgcg gcacacctcc ggtctcgctg ctggagatcc   129840
tggtggccgc gcgcccgccg cggagcctgc tctcgcgccg cgcgtggcgg ctggccagcc   129900
ggacgacagt ttaccgcgcg ccgctccgtg cacgcatcgc ggccatgcgc catcgctcgc   129960
gactggtgga gcgcgcgctg cgcacgctgc gcggctgcgt gctcccgcgc gaggtgctgg   130020
agcgcgtgct gcggtgtctg tccacacagg acctgcgggc ctccggactg gccgagtagc   130080
tttttctgag ataagtgaat aaacatggtg ggattcgatc ggcgccgcca acgccacgcc   130140
atggacgccg ccgagatgga ggatctcgac atcaacgcgg agtcggcgct gtacgactac   130200
ttcatcctga acgcggacag agcccgcgtg ggcgaggtgg ttatgcttct cgcacagggc   130260
gcggaaataa actacgcgga cagcttcgac aagacgccgc tgcacctgta cttgcacacg   130320
cgacacccgc gctcggacgt gattctggcg ctgatggagg cgggcgcggt cgtggacacg   130380
ccggagcgct gctgcggcgc gaccgcggcg cacctgtaca tcctcaacgc ggccaaggtc   130440
gacctgtcgg tgctggaggc catgctgacc tggggcgtgc gccagaacga ccagcactcg   130500
gagcgggtgc tctcgagctt gttgcgcgag tacgtggtga cccgcgccta ctcggatcag   130560
accgagccga tcatggactt gctcatcggc atgggcgccg acgtggacat gccggtcggc   130620
gtgagtcgca cggggctgca cgcctgcctt acgggcctga acgcgaaccc gtgcatgatt   130680
cgcgcgctgt tcggcgcgg cgccagcgtg accgcaaaag acacctacga gatgacgccg   130740
ctggcggtgc tgctgaagtc cgcgagcgcg acgccggagc tcgtgcgcat cctcgtggag   130800
gcaggctccg acgtgagcgc caccgacttc cgcctcaacg gcatgctgca ccagcacgcg   130860
cagtccacgc gcccgcgcgc gagcgtcatg cgcgagctca tccggctggg gtgcagccca   130920
gcggccaaaa acatgtttgg gaacacgccg atgcacatgc tggccatgga aagctcctgc   130980
cgccgctcac tgatcctccc gctgctggag gcagggcttt ccgtgaacga ggagaacccg   131040
cactacggca ccgtgcctct gcacgtggcc tcggggtacg acaacacgca gggctgcctc   131100
aagctcctcc gggatggagg agaccccacc gtcgtgtcgg ccgccggacg cacgccgctc   131160
tcgaacatgc tcgtcaaacg caaccacgtg gcggtcgccg gcgcgctgtc gacgcacccg   131220
agcgcggcag tagtcgtgca ggctctcgag caggctctcg agaacgtgct gaacgccggg   131280
cccagcgagg cctcgcggct cgccgtggcc tttgtggtgg cgcgcgccgg cgcatccgcg   131340
ctaccggagg ccgtgcgccg tctgcacgag ggctttgtcg ccgactgcga gcgcgaagtc   131400
gagctgcttt cccgcaccat gctcggcaca ccggccgtga gcgcgctggt cgtgctggtc   131460
agcaaggagg tctttggcac tgttatctcc tcgcgtgcgc tgcgcgtcgt gcgggaggtc   131520
```

```
cgcgtgtacg caaggccgct ccgcgaggcg ctcataaatc tgcgccacaa atgccgctta 131580
gtttccagcc ttaaaaggca ggtgggacct tgctcgctgc ccggcgaact ggtggagcgc 131640
gtgctcgcga ccgtgccact gaccgacttg cgccgctcgt gcggccgccg cgcgcccgag 131700
taactgcccg tcccgttgct acgcgactcg agactgcccg ctgttttttct ttccccgttt 131760
cttcttatta ggagttgttg cccgcctcca tgatcctcgc acgcgccggc gggcaacctc 131820
gcacgcccgc ggcggccgcg ggcgccgccg aggacggcga gcacagtgat cgccggaagc 131880
gcaagcgcaa gacgcccaac tgcgaagacg ccgacaactc cgacgacgag ctagcgcaga 131940
cgccgtgcga ccgcgagtgg ccggactgtc gcgcgagctc gatcacgagc tccgactcgg 132000
tctctctcgg cgacgagatc tacctgcgat acgtggcctc gcaggtggac ttcgcgcaga 132060
cctgggcccc gccagtgcgg ctgctgcgct ccttcgggaa cttctcgaag gaaacgctca 132120
accgcatgtc gcggcgcggg tacgtgaacc gctcctactt ccagatggcg cacgcgcgct 132180
tctcgcccac caacgacgac atgtaccaca tggccacggg cggtacggc atcgtgttcc 132240
gcttcgaccg ctacgtggtt aagtacgtct tcgagcaccg caacggcatg tccgagatgg 132300
acgcctctac ggagtacacg gtgccgcggt tcctgcgcaa taacctcaag ggcgacgagc 132360
gcgagttcgt ggtctgcgcg ctgcccatgg ggctgaacta ccggctgggc ttcctgcact 132420
cgctgtaccg gcgcgtgctg cacacgctgc tgctgctcat gcgcgtggag gaaggccagc 132480
ggccctcggt ggagatgtcc aagaagccgc tgctgcgctg gttcgaggcg cgcaaggaca 132540
gcgagtcctt cgtgcgcctg atctcgtact tctaccccte ggccgtgcag agcaacgtga 132600
acctgatcaa caacttccac cacctggtgc acttcttcga gcacgagaag cgcgcgcggt 132660
acgtgttcga ccgcggggcc gtgatcgtgt tccctctggc gcgcgggtcc gcggactcga 132720
tctcgccgga ggcggcggcg gcgctgggct tcgcgccgca ctcggagttc ctcaagttcg 132780
tgttcctgca gatcgcgctg ctgtacctga agatctacga gctcccgggc tgcacgaact 132840
tcctgcacgt ggacctgaag cccgacaacg tgctcatctt cgacagtgcg cgcgcgctca 132900
gcgtgaccgc ggccggcgcg actttccgct tcgaggagcc cgtgcgcgcg cgctgaacg 132960
acttcgactt cgcgcgcgtg gccaccatcg agaaccgcaa gatcgcgggc agcgtccgcg 133020
tgccgcagaa ctggtactac gacttccact tcttcgcgca cacgctgctg cgcgcgtacc 133080
cgcacatcgc cgcggaggac ccgggcttcc acgcgctgct ctcggagctc acggtctcgt 133140
gctcgcgcgg gacctgcgac cgcttccggc tgcgcgtgtc ctcgccgcac cccatcgagc 133200
acctcgcgcg gctggtgcgc cgcgacgtct tctcccgctg gataaatgcc gccgcggacg 133260
cccccgacgc cgccgcactc tcctgagccc acgcccgcgg cgccgggctc gctgtacgac 133320
gtcttcctcg cgcgcttcct gcgccggctg ccgcgcgcg cggcgccggc ctcggccgcc 133380
tgcgccgtgc gcgtgggtgc ggtgcgcggc cgcctgcgga actgcgagct agtggtgctg 133440
aaccgctgcc acgcggacgc ggccggcgcg ctcgcgctag cctccgcggc gctcgccgag 133500
acgctggcgg agctcccgcg cgcggacaag ctcgccgtcg cgctcgagct gggcgtggac 133560
cccgagcacc cggagctgac gccggacccc gcctgcgcag gcgagagcgc actcgcacag 133620
aacatcgaca tccagacgct ggacctgggc gactgcggag accccaaagg ccgccgactg 133680
cgcgtggcgc tggtgaacag cggccacgcg gccgcgaact gcgcgctcgc gcgcgtggcg 133740
accgcgctga cgcgccgcgt gcccgcgagc cggcacggcc tcgcggaggg cggcacgccg 133800
ccgtggacgc tgctgctggc ggtggccgcg gtgacggtgc tcggcgtggt ggcggtttca 133860
```

```
ctgctgcggc gcgcgctgcg ggtacgctac cgcttcgcgc ggccggccgc gctgcgcgcg   133920
tagccgcgca aaatgtaaat tataacgccc aacttttaag ggtgaggcgc catgaagttg   133980
ctcgtcggca tactagtagc cgtgtgcttg caccagtatc tgctgaacgc ggacagcaac   134040
acgaaaggat ggtccgaagt gctgaaaggc agcgagtgca agcctaggcc gattgttgtt   134100
cctgtaagcg agacgcaccc agagctgact tctcagcggt tcaacccgcc gtgtgtcacg   134160
ttgatgcgat gcggcgggtg ctgcaacgac gagagcttgg aatgcgtccc cacgaagaa    134220 gtaaacgtga cgatggaact cctgggggcg tcgggctccg gtagtaacgg gatgcaacgt   134280
ctgagcttcg tagagcataa gaaatgcgat tgtagaccac gattcacaac cacgccaccg   134340
acgaccacaa ggccgcccag aagacgccgc tagaactttt tatggaccgc agatccaaac   134400
gatgatgcga tcaggtcatg cggaagaagg cgccacggag caaagtgaaa aaggaccgcc   134460
tagcagtcga gaccctcccg ccgcagccgc ggacacccca cacccgcctt ccacccgcca   134520
gacgccaaca ccgcagccaa caagcatgca cccctcgccg cgcaggctgc tcggcgcgct   134580
cgcgctggtg gcgctgggct tcctcctcgg cgggctcttc cgccccgcgg cgccgccgct   134640
gccggccgcc ctcgtggagg cgggccccgt ccgcgcgaac ggctccgcct cggtgacctg   134700
cctgaccgtc ggcggcgacg ggcggcacat ggcggtggtc gcgcacggcg gcgggacgct   134760
ctcgccggtg tacccgctcg ccgccggcat gcacgcgacc ttcgcctcgc tgcgcaaggg   134820
cgcgctgctg ctgaacgtcg cgaccgtgca catctacgac gtgcgcgcgc tcgggccgga   134880
gttcgagctg acctgcgtcg cggtggcggg cggctacaac gcggcctggg cggccgcgcg   134940
gcccgcggcc gagtggcgcc gccagctggc gcggatgcac cgctcggagc tgtgaccctc   135000
tccctcccgg tctcccatcc gtttttgtaa tcggccttag tagattagac cagcatcccg   135060
cgcccttgtc cgagaacaag taacagtaac cgttacctca ctcgccactc ctcggaataa   135120
tagaacgaga gaacgagaga acgagttaac cgttgctcac tcgctcactc ggtgtgagag   135180
aacaagtaac gttgctcact cgctcactcg gtgtgagaga acaagagaac gagtagctgt   135240
tgctaactca atcaccccct cggagtaagag aacaagagca gtcaactacc cactcagtct   135300
tggatgagag gcagaggacg agttgacgag ttgaacagtt aatcctcact cactcagagc   135360
gagagagcga gagagtggag gacgagttaa caagtcaatc ctcactcaga gtgagagagt   135420
gagagagtgg aggacgagtt aatggttaac agttatcacc actcagagtg agagcggagg   135480
acgagtcaac cactcgctcg cccactccga gttagagagg gaaccagtgc gagttaacgc   135540
gcacacgagc gagagaacgt aaactcgctc gcgcgctcgc tcggctaacc gtcggcctct   135600
cccaaaactc ttcgtaaaac tttcccgatg acagttcacc ctccaaaact ttgtaaaact   135660
aaactgttcg gaggtcggtc tgctgcctct ctaactctcc gtaaaacgtt tgtaaactgt   135720
cggaggtcgg tgacccgctc aaccgtccgc gaaaactttt cgcaggcagt gtctgcctct   135780
ctcggactct ccgcaaacac tttgcggaa cctcggaggg tggtcgacct ctctccaaac   135840
tcttgcaaaa cttttcgcg gaaccgttgg aggccagtcc tccctccaaa ctctttgtaa   135900
aatcttttcg aggccagtcc tcctctccaa aacgttccgc aaaatctttg ggaggtcggc   135960
ctctcctctc cagaacgttc cgtaaaactc tggaggccg cccgcggcac gcgaggcgga   136020
ggatccgagg tgtcgacctc cctcaaaaac tttgtaaaaa cttttttataa aactttccgc   136080 ggaacctcgg agagtaggtc gacctctctc aaaactctta taaaactttt ccgcggaacc   136140
gttggaaggt aggtcgacct ctctcaaaac tcttataaaa cttttcgcg gaaccgttgg   136200 aaggtaggtc gacctctctc aaaactctta taaaactttt ccgcggaacc gttggaggca   136260
```

```
ggtcggcctc tcaaactctt tgcgagaact cttcgcgaga actcttcgat aactttagga    136320
ggtcaggtcg acctcccaaa acttttgcga gaactctctg taaaacttta ggaggtcggt    136380
acctccctca aaacttttta taaaactttt cgcggaacct ccggagacgg gccgccgccg    136440
cgaccgcggg agcggagagg ccgacctccc gagacgttcc gcgttaccgt cggggtaggc    136500
gtcctctcga gaacgccaaa agacttcgtg caaaaacttt tcggaggggc gcggagggcg    136560
ggtcagctcc cgcgaactcc cgcagaacct tttcgcgcga ccgcgaaggc cggccgcctc    136620
tcccacactc tcaagagctt ttcggaggag aggaagggca ggtcgccccc acctccgacg    136680
ctttgtaaaa acgtttacgc ggaacctcgg aggcaggtcg cctccctcga aaactcctcg    136740
cgaaaccttt aaaaacttt tgcgaaaact tttcggagga tgtcggaggg cgggcggctc    136800
ttccaaacct ccgcagaacc ttttcgcgca accgttggaa acaggtcgg cctctctcga    136860 aaactttaa aactttgtaa acgcgttggc gggaccgtcg cgggagagcg gccgcccgcg    136920
gcacgcgaga ggaggaaccg ttggaaggca gtcggcctct cccgaaaact ttttataaaa    136980
acttttccgc ggaaccgttg gaggcaggtc ggcctctctc agagtctaaa aacttttgc    137040 gggactcgga cggcgcggtc acccgaccac ctgactcctg tctcacccgt actacttgga    137100 cttctgttc cctgactccc gactccctga cctcccgact cctgactcc cgactccctg    137160 actcccgact cctgactcc cgactccctg actcccgact cctgactcc cgactccctg    137220 actcccgact cctgactcc cgactccctg actcccgact cctgactcc cgactccctg    137280 actcccgact cctgactcc cgactccctg actcccgact cctgactcc cgactccctg    137340 actcccgact cctgactcc ctgactccag agcgaggtct cgcggctgcg gggtgccgcc    137400
tccgcggagt cgcgttcccg cggacgcccg tcctcgaaag cattcagcag ttccagcctc    137460
tgccgtagct cctcccgcag gaactcctgg tccgcgttcg tcgcggcacc gcggctcagc    137520
cgccgcggga gccggccgcc gcccgcgaag ccgcggatcc                           137560
```

```
<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
attacagtga tgcctacatg ccg                                             23

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
gctgtagtcg tggtccggc                                                  19

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
```
cttcctaggc ttctaccgca cg                                22

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
cggtttacgt tgaaatgtcc cat                               23

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
ctggccaacg acgccttc                                     18

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
tctggtaccc cttgccgg                                     18

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
gaacccgctc tcgctcga                                     18

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
gccgggcaag tgtctggtc                                    19

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
ctcgaagtag ctgatgtcgc g                                 21

<210> SEQ ID NO 11
<211> LENGTH: 28
<212> TYPE: DNA
<213> ORGANISM: Artificial Sequence

```
<220> FEATURE:
<223> OTHER INFORMATION: Primer

<400> SEQUENCE: 11
agagctttac gtagactctc caagtgtc                                            28

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
atacggaacg ggactatgga cg                                                  22

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
gcggtggcca tgtacgtg                                                       18

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
ggttgtggcg atggtcgg                                                       18

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
cttgatgagc cggacgca                                                       18

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
ccgagttgga gaggaaggag c                                                   21

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
ctgttggagg atgaggtcaa gga                                                 23
```

```
<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
cgtgctcatg cctgtggac                                                   19

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
cgacatcctc acctgcaaga ag                                               22

<210> SEQ ID NO 20
<211> LENGTH: 18
<212> TYPE: DNA
<213> ORGANISM: Artificial Sequence
<220> FEATURE:
<223> OTHER INFORMATION: Primer

<400> SEQUENCE: 20
tacaggcagc ccgtgacc                                                    18

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gccgtgtgtc acgttgatgc                                                  20

<210> SEQ ID NO 22
<211> LENGTH: 6
<212> TYPE: PRT
<213> ORGANISM: Artificial Sequence
<220> FEATURE:
<223> OTHER INFORMATION: Synthetic construct

<400> SEQUENCE: 22

Ile Arg Gly Phe Ala Gly
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic construct

<400> SEQUENCE: 23

Pro Gln Lys Val Phe Arg Leu
1               5

<210> SEQ ID NO 24
<211> LENGTH: 7
<212> TYPE: PRT
<213> ORGANISM: Artificial Sequence
```

```
<220> FEATURE:
<223> OTHER INFORMATION: Synthetic construct

<400> SEQUENCE: 24

Met Ser Glu Gly Gly Arg Leu
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic construct

<400> SEQUENCE: 25

Leu Leu Gly Leu Leu Phe Pro
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic construct

<400> SEQUENCE: 26

Met Thr Val His Pro Pro Lys
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic construct

<400> SEQUENCE: 27

Val Leu Pro Pro Asn Ser Leu
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic construct

<400> SEQUENCE: 28

Met His Pro Ser Pro Arg Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic construct

<400> SEQUENCE: 29

Pro Val Ser His Pro Phe Leu
1               5

<210> SEQ ID NO 30
<211> LENGTH: 7
<212> TYPE: PRT
<213> ORGANISM: Artificial Sequence
<220> FEATURE:
```

```
<223> OTHER INFORMATION: Synthetic construct

<400> SEQUENCE: 30

Met Gly Asp Arg Glu Gly Glu
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic construct

<400> SEQUENCE: 31

Phe Glu Asp Gly Val Lys Cys
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic construct

<400> SEQUENCE: 32

Met Cys Thr Val Ala Thr Phe
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic construct

<400> SEQUENCE: 33

Gly Ala Pro Arg Ala Gly Trp
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic construct

<400> SEQUENCE: 34

Met Thr Pro Thr Ser Arg Glu
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic construct

<400> SEQUENCE: 35

Ala Arg Thr Ala Pro Pro Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic construct
```

<400> SEQUENCE: 36

Met Pro Gly Glu Gly Gln Tyr
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic construct

<400> SEQUENCE: 37

Asn Gly Gly Leu Gly Lys Ile
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic construct

<400> SEQUENCE: 38

Met Glu Phe Cys His Thr Glu
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic construct

<400> SEQUENCE: 39

Asp Thr Ala Trp Tyr Ile Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic construct

<400> SEQUENCE: 40

Met Leu Ser Arg Glu Ser Val
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic construct

<400> SEQUENCE: 41

Arg Ala Met Leu Thr Arg Pro
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 42

Met Phe Phe Trp Phe Trp Cys
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic construct

<400> SEQUENCE: 43

Ser Gly Glu Gly Val Pro Val
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic construct

<400> SEQUENCE: 44

Met Leu Gly Phe Trp Gly Lys
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic construct

<400> SEQUENCE: 45

Val Leu Pro Ser Val Ser Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic construct

<400> SEQUENCE: 46

Met Trp Pro Phe Ser Ser Ile
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic construct

<400> SEQUENCE: 47

Glu Phe Cys Lys Pro Ile Asn
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic construct

<400> SEQUENCE: 48
```

```
Met Leu Ile Tyr Gly Pro Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic construct

<400> SEQUENCE: 49

Arg Leu Leu Lys Asp Phe Pro
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic construct

<400> SEQUENCE: 50

Met Gly Val Val Met Cys Gly
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic construct

<400> SEQUENCE: 51

Ala Pro Ala Gly Val Thr Glu
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic construct

<400> SEQUENCE: 52

Met Pro Val Lys Val Lys Gln
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic construct

<400> SEQUENCE: 53

Ala Ser Arg Glu Phe Ile Val
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic construct

<400> SEQUENCE: 54
```

```
Met Glu Glu Glu Leu Thr Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic construct

<400> SEQUENCE: 55

Ser Pro Met Val Val Phe Asn
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic construct

<400> SEQUENCE: 56

Met Ile Arg Ile Gly Gly Gly
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic construct

<400> SEQUENCE: 57

Asp Asn Met Arg Val Asp Asp
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic construct

<400> SEQUENCE: 58

Met Asp Gly Gly Val His Lys
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic construct

<400> SEQUENCE: 59

Glu Gln Met Cys Arg Arg Gln
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic construct

<400> SEQUENCE: 60

Met Ala Pro Pro Val Ile Glu
```

```
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic construct

<400> SEQUENCE: 61

Ala Lys Asn Val Ile Thr His
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic construct

<400> SEQUENCE: 62

Met Leu Gln Leu Leu Lys Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic construct

<400> SEQUENCE: 63

Asn Asn Arg Gly Phe Arg Lys
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic construct

<400> SEQUENCE: 64

Met Ala Cys Glu Cys Ala Ser
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic construct

<400> SEQUENCE: 65

Asn Asn Cys Gly Ile Ser Phe
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic construct

<400> SEQUENCE: 66

Met Asp Glu Asp Arg Leu Arg
1               5
```

```
<210> SEQ ID NO 67
<211> LENGTH: 7
<212> TYPE: PRT
<213> ORGANISM: Artificial Sequence
<220> FEATURE:
<223> OTHER INFORMATION: Synthetic construct

<400> SEQUENCE: 67

Lys Lys Gly Lys Pro Lys Ser
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic construct

<400> SEQUENCE: 68

Met Asp Phe Val Arg Arg Lys
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic construct

<400> SEQUENCE: 69

Val Val Leu Gln Gly Arg Ala
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic construct

<400> SEQUENCE: 70

Met Val Asp Ser Gly Thr His
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic construct

<400> SEQUENCE: 71

Pro Glu Asn Val Val Leu Leu
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic construct

<400> SEQUENCE: 72

Met Ala Ser Tyr Ile Ser Gly
1               5
```

<210> SEQ ID NO 73
<211> LENGTH: 7
<212> TYPE: PRT
<213> ORGANISM: Artificial Sequence
<220> FEATURE:
<223> OTHER INFORMATION: Synthetic construct

<400> SEQUENCE: 73

Arg Thr His Thr Val Tyr Val
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic construct

<400> SEQUENCE: 74

Met Leu Phe Glu Met Glu Leu
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic construct

<400> SEQUENCE: 75

Ser Lys Pro Val Phe Thr Gly
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic construct

<400> SEQUENCE: 76

Met Glu Pro Arg Phe Trp Gly
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic construct

<400> SEQUENCE: 77

Ala Lys Val Arg Pro Leu Val
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic construct

<400> SEQUENCE: 78

Met Glu Ala Ile Asn Val Phe
1               5

```
<210> SEQ ID NO 79
<211> LENGTH: 7
<212> TYPE: PRT
<213> ORGANISM: Artificial Sequence
<220> FEATURE:
<223> OTHER INFORMATION: Synthetic construct

<400> SEQUENCE: 79

Arg Ala Tyr Glu Gly Met Leu
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic construct

<400> SEQUENCE: 80

Met Leu Leu Tyr Pro Lys Lys
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic construct

<400> SEQUENCE: 81

Leu Leu Gly Asp Gly Gly Asp
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic construct

<400> SEQUENCE: 82

Met Leu Ile Arg Thr Thr Asp
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic construct

<400> SEQUENCE: 83

Glu Ala Gln Asn Met Gln Asn
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic construct

<400> SEQUENCE: 84

Met Glu Asp Glu Arg Leu Ile
1               5

<210> SEQ ID NO 85
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 85

Pro Ser Pro Cys Gly Gly Glu
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic construct

<400> SEQUENCE: 86

Met Asp Lys Leu Tyr Thr Gly
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic construct

<400> SEQUENCE: 87

Phe His Tyr Leu Lys Leu Val
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic construct

<400> SEQUENCE: 88

Met Lys Arg Ala Val Ser Lys
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic construct

<400> SEQUENCE: 89

Leu Glu Ala Pro Phe Asn Ile
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic construct

<400> SEQUENCE: 90

Met Glu Ser Arg Asp Leu Gly
1               5

<210> SEQ ID NO 91
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 91

Leu Asn Ala Arg Arg Gln Asn
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic construct

<400> SEQUENCE: 92

Met Asn His Phe Phe Lys Gln
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic construct

<400> SEQUENCE: 93

Arg Ser Leu Tyr Thr Val Leu
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic construct

<400> SEQUENCE: 94

Met Asp Lys Tyr Thr Asp Leu
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic construct

<400> SEQUENCE: 95

Pro Glu Lys Pro Ala Ala Pro
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic construct

<400> SEQUENCE: 96

Met Glu Asn His Leu Pro Asp
1               5

<210> SEQ ID NO 97
<211> LENGTH: 7
<212> TYPE: PRT
```

<213> ORGANISM: Artificial Sequence
<220> FEATURE:
<223> OTHER INFORMATION: Synthetic construct

<400> SEQUENCE: 97

Ile Glu Ala Glu Pro Pro Phe
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic construct

<400> SEQUENCE: 98

Met Ile Val Leu Glu Asn Gly
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic construct

<400> SEQUENCE: 99

Arg Met Gly Ala Arg Pro Arg
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic construct

<400> SEQUENCE: 100

Met Thr Phe Arg Glu Leu Ile
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic construct

<400> SEQUENCE: 101

Asp Ser Met Ala Ser Arg Ser
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic construct

<400> SEQUENCE: 102

Met Arg Gly His Pro Ala His
1               5

<210> SEQ ID NO 103
<211> LENGTH: 7
<212> TYPE: PRT
<213> ORGANISM: Artificial Sequence

```
<220> FEATURE:
<223> OTHER INFORMATION: Synthetic construct

<400> SEQUENCE: 103

Val Ala Pro Arg Glu Glu Leu
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic construct

<400> SEQUENCE: 104

Met Ala Ser Asp Ala Ser Pro
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic construct

<400> SEQUENCE: 105

Gln Pro Ser Ser Ser Arg Arg
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic construct

<400> SEQUENCE: 106

Met Gly Ile Lys Asn Leu Lys
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic construct

<400> SEQUENCE: 107

Pro Arg Leu Leu Lys Leu Arg
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic construct

<400> SEQUENCE: 108

Met Val Phe Pro Ile Val Cys
1               5

<210> SEQ ID NO 109
<211> LENGTH: 7
<212> TYPE: PRT
<213> ORGANISM: Artificial Sequence
<220> FEATURE:
```

```
<223> OTHER INFORMATION: Synthetic construct

<400> SEQUENCE: 109

Leu Pro Met Leu Asp Ile Ser
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic construct

<400> SEQUENCE: 110

Met Arg Glu Phe Gly Leu Ala
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic construct

<400> SEQUENCE: 111

Ala Glu Pro Pro Trp Leu Val
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic construct

<400> SEQUENCE: 112

Met Glu Ser Ser Lys Gln Ala
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic construct

<400> SEQUENCE: 113

Thr Arg Ala Pro Pro Leu Phe
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic construct

<400> SEQUENCE: 114

Met Thr Leu Arg Ile Lys Leu
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 115

Asp Arg Ser Leu Ser Cys Asp
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic construct

<400> SEQUENCE: 116

Met Gly Gly Ser Val Ser Leu
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic construct

<400> SEQUENCE: 117

Tyr Leu Leu Ile Val Trp Leu
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic construct

<400> SEQUENCE: 118

Met Gly Ala Ala Ala Ser Ile
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic construct

<400> SEQUENCE: 119

Thr Glu Phe Pro Pro Ser Val
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic construct

<400> SEQUENCE: 120

Met Val Arg Arg Val Leu Leu
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 121

Leu Cys Leu Phe Ser Met Asp
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic construct

<400> SEQUENCE: 122

Met Glu Glu Lys Arg Gly Arg
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic construct

<400> SEQUENCE: 123

Ala Arg Ala Met Val Cys Leu
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic construct

<400> SEQUENCE: 124

Met Thr Asn Leu Leu Ser Leu
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic construct

<400> SEQUENCE: 125

Thr Gly Ala Glu Ala Ala Pro
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic construct

<400> SEQUENCE: 126

Met Ala Ala Pro Thr Thr Pro
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic construct

<400> SEQUENCE: 127
```

Val Asp Val Leu Gly Gly Arg
1               5

<210> SEQ ID NO 128
<211> LENGTH: 7
<212> TYPE: PRT
<213> ORGANISM: Artificial Sequence
<220> FEATURE:
<223> OTHER INFORMATION: Synthetic construct

<400> SEQUENCE: 128

Met Asp His Glu Lys Tyr Val
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic construct

<400> SEQUENCE: 129

Ala Thr Leu Ser Pro Gly Leu
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic construct

<400> SEQUENCE: 130

Met Glu Gly Val Glu Met Asp
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic construct

<400> SEQUENCE: 131

Arg Pro Leu Arg Gly Gly Lys
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic construct

<400> SEQUENCE: 132

Met Asn Arg His Asn Thr Arg
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic construct

<400> SEQUENCE: 133

Ser Val Ser Val Val Leu Asp
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetic construct

<400> SEQUENCE: 134

Met Phe Phe Arg Arg Arg Ala
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic construct

<400> SEQUENCE: 135

Gly Arg Arg Pro Pro Arg Pro
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic construct

<400> SEQUENCE: 136

Met Ser Val Val Ala Arg Val
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic construct

<400> SEQUENCE: 137

Glu Ala Ala Glu Glu Glu Phe
1               5

<210> SEQ ID NO 138
<211> LENGTH: 7
<212> TYPE: PRT
<213> ORGANISM: Artificial Sequence
<220> FEATURE:
<223> OTHER INFORMATION: Synthetic construct

<400> SEQUENCE: 138

Met Gly Asp Lys Ser Glu Trp
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic construct

<400> SEQUENCE: 139

Phe Val Cys Asp Ser Pro Ser

```
1               5
```

<210> SEQ ID NO 140
<211> LENGTH: 7
<212> TYPE: PRT
<213> ORGANISM: Artificial Sequence
<220> FEATURE:
<223> OTHER INFORMATION: Synthetic construct

<400> SEQUENCE: 140

```
Met Ala Ala Ala Pro Leu Arg
1               5
```

<210> SEQ ID NO 141
<211> LENGTH: 7
<212> TYPE: PRT
<213> ORGANISM: Artificial Sequence
<220> FEATURE:
<223> OTHER INFORMATION: Synthetic construct

<400> SEQUENCE: 141

```
Ala Thr Ser Gly Val Leu Thr
1               5
```

<210> SEQ ID NO 142
<211> LENGTH: 7
<212> TYPE: PRT
<213> ORGANISM: Artificial Sequence
<220> FEATURE:
<223> OTHER INFORMATION: Synthetic construct

<400> SEQUENCE: 142

```
Met Asp Pro Pro Glu Ile Thr
1               5
```

<210> SEQ ID NO 143
<211> LENGTH: 7
<212> TYPE: PRT
<213> ORGANISM: Artificial Sequence
<220> FEATURE:
<223> OTHER INFORMATION: Synthetic construct

<400> SEQUENCE: 143

```
Leu Leu Val Thr Ala Ile Val
1               5
```

<210> SEQ ID NO 144
<211> LENGTH: 7
<212> TYPE: PRT
<213> ORGANISM: Artificial Sequence
<220> FEATURE:
<223> OTHER INFORMATION: Synthetic construct

<400> SEQUENCE: 144

```
Met Asp Ser Arg Glu Ser Ile
1               5
```

<210> SEQ ID NO 145
<211> LENGTH: 7
<212> TYPE: PRT
<213> ORGANISM: Artificial Sequence
<220> FEATURE:
<223> OTHER INFORMATION: Synthetic construct

<400> SEQUENCE: 145

```
Tyr Met Ile Asn Phe Asn Asn
1               5
```

<210> SEQ ID NO 146
<211> LENGTH: 7
<212> TYPE: PRT
<213> ORGANISM: Artificial Sequence
<220> FEATURE:
<223> OTHER INFORMATION: Synthetic construct

<400> SEQUENCE: 146

Met Ser Ser Trp Arg Leu Lys
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic construct

<400> SEQUENCE: 147

Lys Ala Ala Ala Cys Lys Lys
1               5

<210> SEQ ID NO 148
<211> LENGTH: 7
<212> TYPE: PRT
<213> ORGANISM: Artificial Sequence
<220> FEATURE:
<223> OTHER INFORMATION: Synthetic construct

<400> SEQUENCE: 148

Met Arg Ala Leu His Leu Ser
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic construct

<400> SEQUENCE: 149

Asn Ser Glu Gln Val Asn Gly
1               5

<210> SEQ ID NO 150
<211> LENGTH: 7
<212> TYPE: PRT
<213> ORGANISM: Artificial Sequence
<220> FEATURE:
<223> OTHER INFORMATION: Synthetic construct

<400> SEQUENCE: 150

Met Asp Glu Ala Leu Arg Val
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic construct

<400> SEQUENCE: 151

Phe Ile Arg Ala Ala Val Ala
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic construct

<400> SEQUENCE: 152

Met Asp Ala Pro Ser Leu Asp
1               5

<210> SEQ ID NO 153
<211> LENGTH: 7
<212> TYPE: PRT
<213> ORGANISM: Artificial Sequence
<220> FEATURE:
<223> OTHER INFORMATION: Synthetic construct

<400> SEQUENCE: 153

Leu Tyr Val Phe Ser Lys Arg
1               5

<210> SEQ ID NO 154
<211> LENGTH: 7
<212> TYPE: PRT
<213> ORGANISM: Artificial Sequence
<220> FEATURE:
<223> OTHER INFORMATION: Synthetic construct

<400> SEQUENCE: 154

Met Glu Pro Ser Ala Met Arg
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic construct

<400> SEQUENCE: 155

Asp Val Gln His Val Asp Leu
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic construct

<400> SEQUENCE: 156

Met Ala Gly Phe Ser Gln Ser
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic construct

<400> SEQUENCE: 157

Thr Thr Cys Val Pro Pro Gln
1               5

```
<210> SEQ ID NO 158
<211> LENGTH: 7
<212> TYPE: PRT
<213> ORGANISM: Artificial Sequence
<220> FEATURE:
<223> OTHER INFORMATION: Synthetic construct

<400> SEQUENCE: 158

Met Ala Thr Pro Ala Asn Ala
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic construct

<400> SEQUENCE: 159

Phe Ser Phe Tyr Ser Glu Asn
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic construct

<400> SEQUENCE: 160

Met Ala Ala Pro Ile Cys Asp
1               5

<210> SEQ ID NO 161
<211> LENGTH: 7
<212> TYPE: PRT
<213> ORGANISM: Artificial Sequence
<220> FEATURE:
<223> OTHER INFORMATION: Synthetic construct

<400> SEQUENCE: 161

Ile Glu Asp Val Glu Asn Lys
1               5

<210> SEQ ID NO 162
<211> LENGTH: 7
<212> TYPE: PRT
<213> ORGANISM: Artificial Sequence
<220> FEATURE:
<223> OTHER INFORMATION: Synthetic construct

<400> SEQUENCE: 162

Met Asn Ser Asp Val Ile Lys
1               5

<210> SEQ ID NO 163
<211> LENGTH: 7
<212> TYPE: PRT
<213> ORGANISM: Artificial Sequence
<220> FEATURE:
<223> OTHER INFORMATION: Synthetic construct

<400> SEQUENCE: 163

Glu Val Ser Val Val Asn Ile
1               5

<210> SEQ ID NO 164
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 164

Met Ser Thr Phe Arg Gln Thr
1               5

<210> SEQ ID NO 165
<211> LENGTH: 7
<212> TYPE: PRT
<213> ORGANISM: Artificial Sequence
<220> FEATURE:
<223> OTHER INFORMATION: Synthetic construct

<400> SEQUENCE: 165

Ala Ser Pro Ala Ala Lys Asn
1               5

<210> SEQ ID NO 166
<211> LENGTH: 7
<212> TYPE: PRT
<213> ORGANISM: Artificial Sequence
<220> FEATURE:
<223> OTHER INFORMATION: Synthetic construct

<400> SEQUENCE: 166

Met Arg Thr Tyr Thr Ser Leu
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic construct

<400> SEQUENCE: 167

Trp Gly Ala Ala Val Thr Arg
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic construct

<400> SEQUENCE: 168

Met Thr Ser Ala His Ala Ala
1               5

<210> SEQ ID NO 169
<211> LENGTH: 7
<212> TYPE: PRT
<213> ORGANISM: Artificial Sequence
<220> FEATURE:
<223> OTHER INFORMATION: Synthetic construct

<400> SEQUENCE: 169

Val Asp Pro Ala Ser Ile Ala
1               5

<210> SEQ ID NO 170
<211> LENGTH: 7
```

```
<212> TYPE: PRT
<213> ORGANISM: Artificial Sequence
<220> FEATURE:
<223> OTHER INFORMATION: Synthetic construct

<400> SEQUENCE: 170

Met Glu Gly Arg Ala Arg Phe
1               5

<210> SEQ ID NO 171
<211> LENGTH: 7
<212> TYPE: PRT
<213> ORGANISM: Artificial Sequence
<220> FEATURE:
<223> OTHER INFORMATION: Synthetic construct

<400> SEQUENCE: 171

Arg Phe Cys Asn Tyr Cys Pro
1               5

<210> SEQ ID NO 172
<211> LENGTH: 7
<212> TYPE: PRT
<213> ORGANISM: Artificial Sequence
<220> FEATURE:
<223> OTHER INFORMATION: Synthetic construct

<400> SEQUENCE: 172

Met Lys Thr Asp Cys Ala Ser
1               5

<210> SEQ ID NO 173
<211> LENGTH: 7
<212> TYPE: PRT
<213> ORGANISM: Artificial Sequence
<220> FEATURE:
<223> OTHER INFORMATION: Synthetic construct

<400> SEQUENCE: 173

Lys Leu Lys Leu Leu Leu Gln
1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic construct

<400> SEQUENCE: 174

Met Asn Asn Ser Val Val Ser
1               5

<210> SEQ ID NO 175
<211> LENGTH: 7
<212> TYPE: PRT
<213> ORGANISM: Artificial Sequence
<220> FEATURE:
<223> OTHER INFORMATION: Synthetic construct

<400> SEQUENCE: 175

Ala Glu Lys Val Thr Ala Gln
1               5

<210> SEQ ID NO 176
<211> LENGTH: 7
<212> TYPE: PRT
```

```
<213> ORGANISM: Artificial Sequence
<220> FEATURE:
<223> OTHER INFORMATION: Synthetic construct

<400> SEQUENCE: 176

Met Lys Arg Ile Ala Leu Ser
1               5

<210> SEQ ID NO 177
<211> LENGTH: 7
<212> TYPE: PRT
<213> ORGANISM: Artificial Sequence
<220> FEATURE:
<223> OTHER INFORMATION: Synthetic construct

<400> SEQUENCE: 177

Met Ala Leu Lys Ser Leu Ile
1               5

<210> SEQ ID NO 178
<211> LENGTH: 7
<212> TYPE: PRT
<213> ORGANISM: Artificial Sequence
<220> FEATURE:
<223> OTHER INFORMATION: Synthetic construct

<400> SEQUENCE: 178

Met Asn Leu Arg Met Cys Gly
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic construct

<400> SEQUENCE: 179

Ala Ala Cys Ser Leu Asp Leu
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic construct

<400> SEQUENCE: 180

Met Gly Asp Asn Val Trp Phe
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic construct

<400> SEQUENCE: 181

Val Leu Gly Leu Glu Gln Ala
1               5

<210> SEQ ID NO 182
<211> LENGTH: 7
<212> TYPE: PRT
<213> ORGANISM: Artificial Sequence
```

```
<220> FEATURE:
<223> OTHER INFORMATION: Synthetic construct

<400> SEQUENCE: 182

Met Glu Ser Pro Ala Cys Ala
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic construct

<400> SEQUENCE: 183

Asn Met Cys Asp Val Leu Cys
1               5

<210> SEQ ID NO 184
<211> LENGTH: 7
<212> TYPE: PRT
<213> ORGANISM: Artificial Sequence
<220> FEATURE:
<223> OTHER INFORMATION: Synthetic construct

<400> SEQUENCE: 184

Met Asp Leu Arg Arg Arg Phe
1               5

<210> SEQ ID NO 185
<211> LENGTH: 7
<212> TYPE: PRT
<213> ORGANISM: Artificial Sequence
<220> FEATURE:
<223> OTHER INFORMATION: Synthetic construct

<400> SEQUENCE: 185

Val Asp Asn Thr Gly Thr Ser
1               5

<210> SEQ ID NO 186
<211> LENGTH: 7
<212> TYPE: PRT
<213> ORGANISM: Artificial Sequence
<220> FEATURE:
<223> OTHER INFORMATION: Synthetic construct

<400> SEQUENCE: 186

Met Glu Glu Ser Val Ala Val
1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic construct

<400> SEQUENCE: 187

Leu Leu Asn Tyr Gly Cys Gly
1               5

<210> SEQ ID NO 188
<211> LENGTH: 7
<212> TYPE: PRT
<213> ORGANISM: Artificial Sequence
<220> FEATURE:
```

<223> OTHER INFORMATION: Synthetic construct

<400> SEQUENCE: 188

Met Asp Arg Leu Arg Thr Cys
1               5

<210> SEQ ID NO 189
<211> LENGTH: 7
<212> TYPE: PRT
<213> ORGANISM: Artificial Sequence
<220> FEATURE:
<223> OTHER INFORMATION: Synthetic construct

<400> SEQUENCE: 189

Ala Glu Ala Ala Glu Ser Ala
1               5

<210> SEQ ID NO 190
<211> LENGTH: 7
<212> TYPE: PRT
<213> ORGANISM: Artificial Sequence
<220> FEATURE:
<223> OTHER INFORMATION: Synthetic construct

<400> SEQUENCE: 190

Met Val Ser Val Met Arg Lys
1               5

<210> SEQ ID NO 191
<211> LENGTH: 7
<212> TYPE: PRT
<213> ORGANISM: Artificial Sequence
<220> FEATURE:
<223> OTHER INFORMATION: Synthetic construct

<400> SEQUENCE: 191

Gln Glu Phe Tyr Pro Gln Pro
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic construct

<400> SEQUENCE: 192

Met Phe Gln Pro Val Pro Asp
1               5

<210> SEQ ID NO 193
<211> LENGTH: 7
<212> TYPE: PRT
<213> ORGANISM: Artificial Sequence
<220> FEATURE:
<223> OTHER INFORMATION: Synthetic construct

<400> SEQUENCE: 193

Ser Ala Cys Arg Ala Ser Pro
1               5

<210> SEQ ID NO 194
<211> LENGTH: 7
<212> TYPE: PRT
<213> ORGANISM: Artificial Sequence
<220> FEATURE:
<223> OTHER INFORMATION: Synthetic construct

<400> SEQUENCE: 194

Met Arg Pro Cys Tyr Val Thr
1               5

<210> SEQ ID NO 195
<211> LENGTH: 7
<212> TYPE: PRT
<213> ORGANISM: Artificial Sequence
<220> FEATURE:
<223> OTHER INFORMATION: Synthetic construct

<400> SEQUENCE: 195

Thr Arg Gly Thr Gln Thr Gly
1               5

<210> SEQ ID NO 196
<211> LENGTH: 7
<212> TYPE: PRT
<213> ORGANISM: Artificial Sequence
<220> FEATURE:
<223> OTHER INFORMATION: Synthetic construct

<400> SEQUENCE: 196

Met Thr Ala Pro Asn Val His
1               5

<210> SEQ ID NO 197
<211> LENGTH: 7
<212> TYPE: PRT
<213> ORGANISM: Artificial Sequence
<220> FEATURE:
<223> OTHER INFORMATION: Synthetic construct

<400> SEQUENCE: 197

Ala Val Ser Phe Asp Ser Glu
1               5

<210> SEQ ID NO 198
<211> LENGTH: 7
<212> TYPE: PRT
<213> ORGANISM: Artificial Sequence
<220> FEATURE:
<223> OTHER INFORMATION: Synthetic construct

<400> SEQUENCE: 198

Met Thr Ala Val Pro Val Thr
1               5

<210> SEQ ID NO 199
<211> LENGTH: 7
<212> TYPE: PRT
<213> ORGANISM: Artificial Sequence
<220> FEATURE:
<223> OTHER INFORMATION: Synthetic construct

<400> SEQUENCE: 199

Val Arg Lys Leu Asn Leu Ile
1               5

<210> SEQ ID NO 200
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 200

Met Ala Ser Glu Lys Met Ala
1               5

<210> SEQ ID NO 201
<211> LENGTH: 7
<212> TYPE: PRT
<213> ORGANISM: Artificial Sequence
<220> FEATURE:
<223> OTHER INFORMATION: Synthetic construct

<400> SEQUENCE: 201

Asp Leu Asp Gly Gly Met Cys
1               5

<210> SEQ ID NO 202
<211> LENGTH: 7
<212> TYPE: PRT
<213> ORGANISM: Artificial Sequence
<220> FEATURE:
<223> OTHER INFORMATION: Synthetic construct

<400> SEQUENCE: 202

Met Gly Leu Leu Asp Ala Leu
1               5

<210> SEQ ID NO 203
<211> LENGTH: 7
<212> TYPE: PRT
<213> ORGANISM: Artificial Sequence
<220> FEATURE:
<223> OTHER INFORMATION: Synthetic construct

<400> SEQUENCE: 203

Arg Phe Ser Ala Ala Ser Ser
1               5

<210> SEQ ID NO 204
<211> LENGTH: 7
<212> TYPE: PRT
<213> ORGANISM: Artificial Sequence
<220> FEATURE:
<223> OTHER INFORMATION: Synthetic construct

<400> SEQUENCE: 204

Met Asp Ile Phe Glu Thr Leu
1               5

<210> SEQ ID NO 205
<211> LENGTH: 7
<212> TYPE: PRT
<213> ORGANISM: Artificial Sequence
<220> FEATURE:
<223> OTHER INFORMATION: Synthetic construct

<400> SEQUENCE: 205

Asp Ile Glu Leu Thr Ala Arg
1               5

<210> SEQ ID NO 206
<211> LENGTH: 7
<212> TYPE: PRT
<213> ORGANISM: Artificial Sequence
<220> FEATURE:
<223> OTHER INFORMATION: Synthetic construct

<400> SEQUENCE: 206
```

```
Met Val Ser Asp Tyr Asp Pro
1               5

<210> SEQ ID NO 207
<211> LENGTH: 7
<212> TYPE: PRT
<213> ORGANISM: Artificial Sequence
<220> FEATURE:
<223> OTHER INFORMATION: Synthetic construct

<400> SEQUENCE: 207

His Phe Val His Ser Val Ile
1               5

<210> SEQ ID NO 208
<211> LENGTH: 7
<212> TYPE: PRT
<213> ORGANISM: Artificial Sequence
<220> FEATURE:
<223> OTHER INFORMATION: Synthetic construct

<400> SEQUENCE: 208

Met Phe Leu Asp Ser Asp Thr
1               5

<210> SEQ ID NO 209
<211> LENGTH: 7
<212> TYPE: PRT
<213> ORGANISM: Artificial Sequence
<220> FEATURE:
<223> OTHER INFORMATION: Synthetic construct

<400> SEQUENCE: 209

Asp Met Pro Phe Ser Val Val
1               5

<210> SEQ ID NO 210
<211> LENGTH: 7
<212> TYPE: PRT
<213> ORGANISM: Artificial Sequence
<220> FEATURE:
<223> OTHER INFORMATION: Synthetic construct

<400> SEQUENCE: 210

Met Gly Asp Thr Val Ser Lys
1               5

<210> SEQ ID NO 211
<211> LENGTH: 7
<212> TYPE: PRT
<213> ORGANISM: Artificial Sequence
<220> FEATURE:
<223> OTHER INFORMATION: Synthetic construct

<400> SEQUENCE: 211

Lys Thr Ile Asn Val Ser Arg
1               5

<210> SEQ ID NO 212
<211> LENGTH: 7
<212> TYPE: PRT
<213> ORGANISM: Artificial Sequence
<220> FEATURE:
<223> OTHER INFORMATION: Synthetic construct

<400> SEQUENCE: 212
```

```
Met Glu Ser Tyr Phe Ser Tyr
1               5

<210> SEQ ID NO 213
<211> LENGTH: 7
<212> TYPE: PRT
<213> ORGANISM: Artificial Sequence
<220> FEATURE:
<223> OTHER INFORMATION: Synthetic construct

<400> SEQUENCE: 213

Glu Asp Leu Phe Phe Ala Glu
1               5

<210> SEQ ID NO 214
<211> LENGTH: 7
<212> TYPE: PRT
<213> ORGANISM: Artificial Sequence
<220> FEATURE:
<223> OTHER INFORMATION: Synthetic construct

<400> SEQUENCE: 214

Met Phe Gly Gly Val Gln Val
1               5

<210> SEQ ID NO 215
<211> LENGTH: 7
<212> TYPE: PRT
<213> ORGANISM: Artificial Sequence
<220> FEATURE:
<223> OTHER INFORMATION: Synthetic construct

<400> SEQUENCE: 215

Gly Arg Asp Leu Ala Ala Val
1               5

<210> SEQ ID NO 216
<211> LENGTH: 7
<212> TYPE: PRT
<213> ORGANISM: Artificial Sequence
<220> FEATURE:
<223> OTHER INFORMATION: Synthetic construct

<400> SEQUENCE: 216

Met Ser Ala Val Lys Ala Lys
1               5

<210> SEQ ID NO 217
<211> LENGTH: 7
<212> TYPE: PRT
<213> ORGANISM: Artificial Sequence
<220> FEATURE:
<223> OTHER INFORMATION: Synthetic construct

<400> SEQUENCE: 217

Pro Leu Arg Asp Leu Ala Arg
1               5

<210> SEQ ID NO 218
<211> LENGTH: 7
<212> TYPE: PRT
<213> ORGANISM: Artificial Sequence
<220> FEATURE:
<223> OTHER INFORMATION: Synthetic construct

<400> SEQUENCE: 218

Met Thr Ser Glu Ser Asp Leu
```

```
1               5

<210> SEQ ID NO 219
<211> LENGTH: 7
<212> TYPE: PRT
<213> ORGANISM: Artificial Sequence
<220> FEATURE:
<223> OTHER INFORMATION: Synthetic construct

<400> SEQUENCE: 219

Ala Ile Ala Arg Ala Gln Pro
1               5

<210> SEQ ID NO 220
<211> LENGTH: 7
<212> TYPE: PRT
<213> ORGANISM: Artificial Sequence
<220> FEATURE:
<223> OTHER INFORMATION: Synthetic construct

<400> SEQUENCE: 220

Met Ile Val Ala Ala Phe Asp
1               5

<210> SEQ ID NO 221
<211> LENGTH: 7
<212> TYPE: PRT
<213> ORGANISM: Artificial Sequence
<220> FEATURE:
<223> OTHER INFORMATION: Synthetic construct

<400> SEQUENCE: 221

Asn Tyr Val Leu Arg Thr Asn
1               5

<210> SEQ ID NO 222
<211> LENGTH: 7
<212> TYPE: PRT
<213> ORGANISM: Artificial Sequence
<220> FEATURE:
<223> OTHER INFORMATION: Synthetic construct

<400> SEQUENCE: 222

Met Leu Ala Leu Phe Glu Phe
1               5

<210> SEQ ID NO 223
<211> LENGTH: 7
<212> TYPE: PRT
<213> ORGANISM: Artificial Sequence
<220> FEATURE:
<223> OTHER INFORMATION: Synthetic construct

<400> SEQUENCE: 223

Leu Lys Glu Leu Leu Gly Pro
1               5

<210> SEQ ID NO 224
<211> LENGTH: 7
<212> TYPE: PRT
<213> ORGANISM: Artificial Sequence
<220> FEATURE:
<223> OTHER INFORMATION: Synthetic construct

<400> SEQUENCE: 224

Met Glu Gln Ala Leu Gly Tyr
1               5
```

<210> SEQ ID NO 225
<211> LENGTH: 7
<212> TYPE: PRT
<213> ORGANISM: Artificial Sequence
<220> FEATURE:
<223> OTHER INFORMATION: Synthetic construct

<400> SEQUENCE: 225

Ser Leu Phe Ser Pro Glu Asp
1               5

<210> SEQ ID NO 226
<211> LENGTH: 7
<212> TYPE: PRT
<213> ORGANISM: Artificial Sequence
<220> FEATURE:
<223> OTHER INFORMATION: Synthetic construct

<400> SEQUENCE: 226

Met Glu Ser Asp Asn Ala Leu
1               5

<210> SEQ ID NO 227
<211> LENGTH: 7
<212> TYPE: PRT
<213> ORGANISM: Artificial Sequence
<220> FEATURE:
<223> OTHER INFORMATION: Synthetic construct

<400> SEQUENCE: 227

Gly Gln His Ala Ala Ile Trp
1               5

<210> SEQ ID NO 228
<211> LENGTH: 7
<212> TYPE: PRT
<213> ORGANISM: Artificial Sequence
<220> FEATURE:
<223> OTHER INFORMATION: Synthetic construct

<400> SEQUENCE: 228

Met Glu Lys Leu Val Ser Asp
1               5

<210> SEQ ID NO 229
<211> LENGTH: 7
<212> TYPE: PRT
<213> ORGANISM: Artificial Sequence
<220> FEATURE:
<223> OTHER INFORMATION: Synthetic construct

<400> SEQUENCE: 229

Gly Arg Ser Gly Ala Ile Trp
1               5

<210> SEQ ID NO 230
<211> LENGTH: 7
<212> TYPE: PRT
<213> ORGANISM: Artificial Sequence
<220> FEATURE:
<223> OTHER INFORMATION: Synthetic construct

<400> SEQUENCE: 230

Met Asp Glu Asn Asp Gly Glu
1               5

```
<210> SEQ ID NO 231
<211> LENGTH: 7
<212> TYPE: PRT
<213> ORGANISM: Artificial Sequence
<220> FEATURE:
<223> OTHER INFORMATION: Synthetic construct

<400> SEQUENCE: 231

Gln Thr Gly Tyr Ser Arg Tyr
1               5

<210> SEQ ID NO 232
<211> LENGTH: 7
<212> TYPE: PRT
<213> ORGANISM: Artificial Sequence
<220> FEATURE:
<223> OTHER INFORMATION: Synthetic construct

<400> SEQUENCE: 232

Met Asp Ala Val Ser Ala Leu
1               5

<210> SEQ ID NO 233
<211> LENGTH: 7
<212> TYPE: PRT
<213> ORGANISM: Artificial Sequence
<220> FEATURE:
<223> OTHER INFORMATION: Synthetic construct

<400> SEQUENCE: 233

Leu Phe Leu Lys Ser Ile Leu
1               5

<210> SEQ ID NO 234
<211> LENGTH: 7
<212> TYPE: PRT
<213> ORGANISM: Artificial Sequence
<220> FEATURE:
<223> OTHER INFORMATION: Synthetic construct

<400> SEQUENCE: 234

Met Ala Asp Ala Pro Leu Val
1               5

<210> SEQ ID NO 235
<211> LENGTH: 7
<212> TYPE: PRT
<213> ORGANISM: Artificial Sequence
<220> FEATURE:
<223> OTHER INFORMATION: Synthetic construct

<400> SEQUENCE: 235

Arg Glu Leu Arg Ala Asn Glu
1               5

<210> SEQ ID NO 236
<211> LENGTH: 7
<212> TYPE: PRT
<213> ORGANISM: Artificial Sequence
<220> FEATURE:
<223> OTHER INFORMATION: Synthetic construct

<400> SEQUENCE: 236

Met Glu Glu Asp Leu Asn Glu
1               5
```

```
<210> SEQ ID NO 237
<211> LENGTH: 7
<212> TYPE: PRT
<213> ORGANISM: Artificial Sequence
<220> FEATURE:
<223> OTHER INFORMATION: Synthetic construct

<400> SEQUENCE: 237

Met Gly Gln Ala Ser Ser Ala
1               5

<210> SEQ ID NO 238
<211> LENGTH: 7
<212> TYPE: PRT
<213> ORGANISM: Artificial Sequence
<220> FEATURE:
<223> OTHER INFORMATION: Synthetic construct

<400> SEQUENCE: 238

Met Asp Val Val Gln Glu Val
1               5

<210> SEQ ID NO 239
<211> LENGTH: 7
<212> TYPE: PRT
<213> ORGANISM: Artificial Sequence
<220> FEATURE:
<223> OTHER INFORMATION: Synthetic construct

<400> SEQUENCE: 239

Ala Asp Ser Asp Gly Gly Asn
1               5

<210> SEQ ID NO 240
<211> LENGTH: 7
<212> TYPE: PRT
<213> ORGANISM: Artificial Sequence
<220> FEATURE:
<223> OTHER INFORMATION: Synthetic construct

<400> SEQUENCE: 240

Met Arg Ser Trp Phe Trp Gln
1               5

<210> SEQ ID NO 241
<211> LENGTH: 7
<212> TYPE: PRT
<213> ORGANISM: Artificial Sequence
<220> FEATURE:
<223> OTHER INFORMATION: Synthetic construct

<400> SEQUENCE: 241

Pro Leu Thr Gly Met Cys Leu
1               5

<210> SEQ ID NO 242
<211> LENGTH: 7
<212> TYPE: PRT
<213> ORGANISM: Artificial Sequence
<220> FEATURE:
<223> OTHER INFORMATION: Synthetic construct

<400> SEQUENCE: 242

Met Arg Pro Lys Ser Val Gly
1               5

<210> SEQ ID NO 243
```

```
<211> LENGTH: 7
<212> TYPE: PRT
<213> ORGANISM: Artificial Sequence
<220> FEATURE:
<223> OTHER INFORMATION: Synthetic construct

<400> SEQUENCE: 243

Ser Gly His Thr Lys Pro Ser
1               5

<210> SEQ ID NO 244
<211> LENGTH: 7
<212> TYPE: PRT
<213> ORGANISM: Artificial Sequence
<220> FEATURE:
<223> OTHER INFORMATION: Synthetic construct

<400> SEQUENCE: 244

Met Ala His Asn Thr Phe Glu
1               5

<210> SEQ ID NO 245
<211> LENGTH: 7
<212> TYPE: PRT
<213> ORGANISM: Artificial Sequence
<220> FEATURE:
<223> OTHER INFORMATION: Synthetic construct

<400> SEQUENCE: 245

Lys Tyr Phe Cys Val Ser Asp
1               5

<210> SEQ ID NO 246
<211> LENGTH: 7
<212> TYPE: PRT
<213> ORGANISM: Artificial Sequence
<220> FEATURE:
<223> OTHER INFORMATION: Synthetic construct

<400> SEQUENCE: 246

Met Gly Cys Cys Lys Val Pro
1               5

<210> SEQ ID NO 247
<211> LENGTH: 7
<212> TYPE: PRT
<213> ORGANISM: Artificial Sequence
<220> FEATURE:
<223> OTHER INFORMATION: Synthetic construct

<400> SEQUENCE: 247

Cys Met Lys Glu Met His Gly
1               5

<210> SEQ ID NO 248
<211> LENGTH: 7
<212> TYPE: PRT
<213> ORGANISM: Artificial Sequence
<220> FEATURE:
<223> OTHER INFORMATION: Synthetic construct

<400> SEQUENCE: 248

Met Ser Arg Leu Gln Ile Leu
1               5

<210> SEQ ID NO 249
<211> LENGTH: 7
```

<212> TYPE: PRT
<213> ORGANISM: Artificial Sequence
<220> FEATURE:
<223> OTHER INFORMATION: Synthetic construct

<400> SEQUENCE: 249

Arg Lys Leu Asp Val Pro Ile
1               5

<210> SEQ ID NO 250
<211> LENGTH: 7
<212> TYPE: PRT
<213> ORGANISM: Artificial Sequence
<220> FEATURE:
<223> OTHER INFORMATION: Synthetic construct

<400> SEQUENCE: 250

Met Lys Ala Val Leu Leu Leu
1               5

<210> SEQ ID NO 251
<211> LENGTH: 7
<212> TYPE: PRT
<213> ORGANISM: Artificial Sequence
<220> FEATURE:
<223> OTHER INFORMATION: Synthetic construct

<400> SEQUENCE: 251

Leu Asn Leu Asn Pro Gly Asn
1               5

<210> SEQ ID NO 252
<211> LENGTH: 7
<212> TYPE: PRT
<213> ORGANISM: Artificial Sequence
<220> FEATURE:
<223> OTHER INFORMATION: Synthetic construct

<400> SEQUENCE: 252

Met His Ala Ser Leu Ser Ser
1               5

<210> SEQ ID NO 253
<211> LENGTH: 7
<212> TYPE: PRT
<213> ORGANISM: Artificial Sequence
<220> FEATURE:
<223> OTHER INFORMATION: Synthetic construct

<400> SEQUENCE: 253

Asp Glu Thr Leu Thr Tyr Arg
1               5

<210> SEQ ID NO 254
<211> LENGTH: 7
<212> TYPE: PRT
<213> ORGANISM: Artificial Sequence
<220> FEATURE:
<223> OTHER INFORMATION: Synthetic construct

<400> SEQUENCE: 254

Met Glu Val Leu Val Ile Ile
1               5

<210> SEQ ID NO 255
<211> LENGTH: 7
<212> TYPE: PRT

<213> ORGANISM: Artificial Sequence
<220> FEATURE:
<223> OTHER INFORMATION: Synthetic construct

<400> SEQUENCE: 255

Gly Glu Phe Phe Tyr Asp Glu
1               5

<210> SEQ ID NO 256
<211> LENGTH: 7
<212> TYPE: PRT
<213> ORGANISM: Artificial Sequence
<220> FEATURE:
<223> OTHER INFORMATION: Synthetic construct

<400> SEQUENCE: 256

Met Pro Leu Phe Arg Lys Leu
1               5

<210> SEQ ID NO 257
<211> LENGTH: 7
<212> TYPE: PRT
<213> ORGANISM: Artificial Sequence
<220> FEATURE:
<223> OTHER INFORMATION: Synthetic construct

<400> SEQUENCE: 257

Arg Asp Ala Leu Asp Gly Leu
1               5

<210> SEQ ID NO 258
<211> LENGTH: 7
<212> TYPE: PRT
<213> ORGANISM: Artificial Sequence
<220> FEATURE:
<223> OTHER INFORMATION: Synthetic construct

<400> SEQUENCE: 258

Met Ala Cys Phe Ile Glu Leu
1               5

<210> SEQ ID NO 259
<211> LENGTH: 7
<212> TYPE: PRT
<213> ORGANISM: Artificial Sequence
<220> FEATURE:
<223> OTHER INFORMATION: Synthetic construct

<400> SEQUENCE: 259

Thr Thr Phe Ser Ser Ser Glu
1               5

<210> SEQ ID NO 260
<211> LENGTH: 9
<212> TYPE: PRT
<213> ORGANISM: Artificial Sequence
<220> FEATURE:
<223> OTHER INFORMATION: Synthetic construct

<400> SEQUENCE: 260

Met Ser Ser Ser Ser Ser Glu Thr Thr
1               5

<210> SEQ ID NO 261
<211> LENGTH: 7
<212> TYPE: PRT
<213> ORGANISM: Artificial Sequence

```
<220> FEATURE:
<223> OTHER INFORMATION: Synthetic construct

<400> SEQUENCE: 261

Thr Thr Gly Thr Ser Thr Ser
1               5

<210> SEQ ID NO 262
<211> LENGTH: 7
<212> TYPE: PRT
<213> ORGANISM: Artificial Sequence
<220> FEATURE:
<223> OTHER INFORMATION: Synthetic construct

<400> SEQUENCE: 262

Met Ala Cys Leu Arg Val Phe
1               5

<210> SEQ ID NO 263
<211> LENGTH: 7
<212> TYPE: PRT
<213> ORGANISM: Artificial Sequence
<220> FEATURE:
<223> OTHER INFORMATION: Synthetic construct

<400> SEQUENCE: 263

Cys Ser Met Gln Thr Ala Arg
1               5

<210> SEQ ID NO 264
<211> LENGTH: 7
<212> TYPE: PRT
<213> ORGANISM: Artificial Sequence
<220> FEATURE:
<223> OTHER INFORMATION: Synthetic construct

<400> SEQUENCE: 264

Met Ala Ile Ala His Thr Thr
1               5

<210> SEQ ID NO 265
<211> LENGTH: 7
<212> TYPE: PRT
<213> ORGANISM: Artificial Sequence
<220> FEATURE:
<223> OTHER INFORMATION: Synthetic construct

<400> SEQUENCE: 265

Phe Arg Phe Arg Thr Pro Gly
1               5

<210> SEQ ID NO 266
<211> LENGTH: 7
<212> TYPE: PRT
<213> ORGANISM: Artificial Sequence
<220> FEATURE:
<223> OTHER INFORMATION: Synthetic construct

<400> SEQUENCE: 266

Met Ala Ala Thr Ile Gln Ile
1               5

<210> SEQ ID NO 267
<211> LENGTH: 7
<212> TYPE: PRT
<213> ORGANISM: Artificial Sequence
<220> FEATURE:
```

```
<223> OTHER INFORMATION: Synthetic construct

<400> SEQUENCE: 267

Lys Arg Asp Gly Tyr Ser Arg
1               5

<210> SEQ ID NO 268
<211> LENGTH: 7
<212> TYPE: PRT
<213> ORGANISM: Artificial Sequence
<220> FEATURE:
<223> OTHER INFORMATION: Synthetic construct

<400> SEQUENCE: 268

Met Glu Gly Leu Met Pro Lys
1               5

<210> SEQ ID NO 269
<211> LENGTH: 7
<212> TYPE: PRT
<213> ORGANISM: Artificial Sequence
<220> FEATURE:
<223> OTHER INFORMATION: Synthetic construct

<400> SEQUENCE: 269

Arg Pro Ile Ser Val Gln Lys
1               5

<210> SEQ ID NO 270
<211> LENGTH: 7
<212> TYPE: PRT
<213> ORGANISM: Artificial Sequence
<220> FEATURE:
<223> OTHER INFORMATION: Synthetic construct

<400> SEQUENCE: 270

Met Asp Ser Arg Arg Leu Ala
1               5

<210> SEQ ID NO 271
<211> LENGTH: 7
<212> TYPE: PRT
<213> ORGANISM: Artificial Sequence
<220> FEATURE:
<223> OTHER INFORMATION: Synthetic construct

<400> SEQUENCE: 271

Leu Gly Asp Ser Asp Ser Asp
1               5

<210> SEQ ID NO 272
<211> LENGTH: 7
<212> TYPE: PRT
<213> ORGANISM: Artificial Sequence
<220> FEATURE:
<223> OTHER INFORMATION: Synthetic construct

<400> SEQUENCE: 272

Met Arg Leu Ile Leu Ala Leu
1               5

<210> SEQ ID NO 273
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 273

Pro Gln Met Met Arg Ile Gly
1               5

<210> SEQ ID NO 274
<211> LENGTH: 7
<212> TYPE: PRT
<213> ORGANISM: Artificial Sequence
<220> FEATURE:
<223> OTHER INFORMATION: Synthetic construct

<400> SEQUENCE: 274

Met Ala Gly Phe Leu Gly Ala
1               5

<210> SEQ ID NO 275
<211> LENGTH: 7
<212> TYPE: PRT
<213> ORGANISM: Artificial Sequence
<220> FEATURE:
<223> OTHER INFORMATION: Synthetic construct

<400> SEQUENCE: 275

Cys Lys Val Glu Glu Val Leu
1               5

<210> SEQ ID NO 276
<211> LENGTH: 7
<212> TYPE: PRT
<213> ORGANISM: Artificial Sequence
<220> FEATURE:
<223> OTHER INFORMATION: Synthetic construct

<400> SEQUENCE: 276

Met His Leu His Lys Asp Pro
1               5

<210> SEQ ID NO 277
<211> LENGTH: 7
<212> TYPE: PRT
<213> ORGANISM: Artificial Sequence
<220> FEATURE:
<223> OTHER INFORMATION: Synthetic construct

<400> SEQUENCE: 277

Leu Ala Phe Pro Ser Leu Ala
1               5

<210> SEQ ID NO 278
<211> LENGTH: 7
<212> TYPE: PRT
<213> ORGANISM: Artificial Sequence
<220> FEATURE:
<223> OTHER INFORMATION: Synthetic construct

<400> SEQUENCE: 278

Met Ala Asn Arg Leu Val Phe
1               5

<210> SEQ ID NO 279
<211> LENGTH: 7
<212> TYPE: PRT
<213> ORGANISM: Artificial Sequence
<220> FEATURE:
<223> OTHER INFORMATION: Synthetic construct
```

```
<400> SEQUENCE: 279

Arg Pro Met Glu Ile Asp Gly
1               5

<210> SEQ ID NO 280
<211> LENGTH: 7
<212> TYPE: PRT
<213> ORGANISM: Artificial Sequence
<220> FEATURE:
<223> OTHER INFORMATION: Synthetic construct

<400> SEQUENCE: 280

Met Glu Asn Asn Asp Gly Asn
1               5

<210> SEQ ID NO 281
<211> LENGTH: 7
<212> TYPE: PRT
<213> ORGANISM: Artificial Sequence
<220> FEATURE:
<223> OTHER INFORMATION: Synthetic construct

<400> SEQUENCE: 281

Arg Phe Leu Pro Ser His Lys
1               5

<210> SEQ ID NO 282
<211> LENGTH: 7
<212> TYPE: PRT
<213> ORGANISM: Artificial Sequence
<220> FEATURE:
<223> OTHER INFORMATION: Synthetic construct

<400> SEQUENCE: 282

Met Asp Pro Ala Gly Gln Arg
1               5

<210> SEQ ID NO 283
<211> LENGTH: 7
<212> TYPE: PRT
<213> ORGANISM: Artificial Sequence
<220> FEATURE:
<223> OTHER INFORMATION: Synthetic construct

<400> SEQUENCE: 283

Cys Ser Glu Thr Asp Arg Trp
1               5

<210> SEQ ID NO 284
<211> LENGTH: 7
<212> TYPE: PRT
<213> ORGANISM: Artificial Sequence
<220> FEATURE:
<223> OTHER INFORMATION: Synthetic construct

<400> SEQUENCE: 284

Met Ser Ser Ser Ala Ala Ala
1               5

<210> SEQ ID NO 285
<211> LENGTH: 7
<212> TYPE: PRT
<213> ORGANISM: Artificial Sequence
<220> FEATURE:
<223> OTHER INFORMATION: Synthetic construct

<400> SEQUENCE: 285
```

```
Ile Ala Pro Asp Ser Arg Met
1               5

<210> SEQ ID NO 286
<211> LENGTH: 7
<212> TYPE: PRT
<213> ORGANISM: Artificial Sequence
<220> FEATURE:
<223> OTHER INFORMATION: Synthetic construct

<400> SEQUENCE: 286

Met Thr Ala Glu Ala Ser Ile
1               5

<210> SEQ ID NO 287
<211> LENGTH: 7
<212> TYPE: PRT
<213> ORGANISM: Artificial Sequence
<220> FEATURE:
<223> OTHER INFORMATION: Synthetic construct

<400> SEQUENCE: 287

Asp Pro Val Tyr His Lys Lys
1               5

<210> SEQ ID NO 288
<211> LENGTH: 7
<212> TYPE: PRT
<213> ORGANISM: Artificial Sequence
<220> FEATURE:
<223> OTHER INFORMATION: Synthetic construct

<400> SEQUENCE: 288

Met Pro Arg Thr Thr Ser Gly
1               5

<210> SEQ ID NO 289
<211> LENGTH: 7
<212> TYPE: PRT
<213> ORGANISM: Artificial Sequence
<220> FEATURE:
<223> OTHER INFORMATION: Synthetic construct

<400> SEQUENCE: 289

Arg Glu Gln Thr Glu Gly Leu
1               5

<210> SEQ ID NO 290
<211> LENGTH: 7
<212> TYPE: PRT
<213> ORGANISM: Artificial Sequence
<220> FEATURE:
<223> OTHER INFORMATION: Synthetic construct

<400> SEQUENCE: 290

Met Ala Asn Arg Glu Glu Ile
1               5

<210> SEQ ID NO 291
<211> LENGTH: 7
<212> TYPE: PRT
<213> ORGANISM: Artificial Sequence
<220> FEATURE:
<223> OTHER INFORMATION: Synthetic construct

<400> SEQUENCE: 291
```

Val Arg Val Leu Arg Arg Thr
1               5

<210> SEQ ID NO 292
<211> LENGTH: 7
<212> TYPE: PRT
<213> ORGANISM: Artificial Sequence
<220> FEATURE:
<223> OTHER INFORMATION: Synthetic construct

<400> SEQUENCE: 292

Met Thr Ala Pro Thr Pro Arg
1               5

<210> SEQ ID NO 293
<211> LENGTH: 7
<212> TYPE: PRT
<213> ORGANISM: Artificial Sequence
<220> FEATURE:
<223> OTHER INFORMATION: Synthetic construct

<400> SEQUENCE: 293

Ala Ala Tyr Ser Leu Ala Arg
1               5

<210> SEQ ID NO 294
<211> LENGTH: 7
<212> TYPE: PRT
<213> ORGANISM: Artificial Sequence
<220> FEATURE:
<223> OTHER INFORMATION: Synthetic construct

<400> SEQUENCE: 294

Met Ala Asp Glu Arg Glu Ala
1               5

<210> SEQ ID NO 295
<211> LENGTH: 7
<212> TYPE: PRT
<213> ORGANISM: Artificial Sequence
<220> FEATURE:
<223> OTHER INFORMATION: Synthetic construct

<400> SEQUENCE: 295

Leu Ala Cys Ala Met Arg Lys
1               5

<210> SEQ ID NO 296
<211> LENGTH: 7
<212> TYPE: PRT
<213> ORGANISM: Artificial Sequence
<220> FEATURE:
<223> OTHER INFORMATION: Synthetic construct

<400> SEQUENCE: 296

Met Ser Lys Asn Lys Ile Leu
1               5

<210> SEQ ID NO 297
<211> LENGTH: 7
<212> TYPE: PRT
<213> ORGANISM: Artificial Sequence
<220> FEATURE:
<223> OTHER INFORMATION: Synthetic construct

<400> SEQUENCE: 297

Ser Tyr Met Thr Thr Lys Met

```
1               5

<210> SEQ ID NO 298
<211> LENGTH: 7
<212> TYPE: PRT
<213> ORGANISM: Artificial Sequence
<220> FEATURE:
<223> OTHER INFORMATION: Synthetic construct

<400> SEQUENCE: 298

Met Leu Thr Arg Cys Tyr Ile
1               5

<210> SEQ ID NO 299
<211> LENGTH: 7
<212> TYPE: PRT
<213> ORGANISM: Artificial Sequence
<220> FEATURE:
<223> OTHER INFORMATION: Synthetic construct

<400> SEQUENCE: 299

Arg Ala Ser Gly Leu Ala Glu
1               5

<210> SEQ ID NO 300
<211> LENGTH: 7
<212> TYPE: PRT
<213> ORGANISM: Artificial Sequence
<220> FEATURE:
<223> OTHER INFORMATION: Synthetic construct

<400> SEQUENCE: 300

Met Val Gly Phe Asp Arg Arg
1               5

<210> SEQ ID NO 301
<211> LENGTH: 7
<212> TYPE: PRT
<213> ORGANISM: Artificial Sequence
<220> FEATURE:
<223> OTHER INFORMATION: Synthetic construct

<400> SEQUENCE: 301

Cys Gly Arg Arg Ala Pro Glu
1               5

<210> SEQ ID NO 302
<211> LENGTH: 7
<212> TYPE: PRT
<213> ORGANISM: Artificial Sequence
<220> FEATURE:
<223> OTHER INFORMATION: Synthetic construct

<400> SEQUENCE: 302

Met Ile Leu Ala Arg Ala Gly
1               5

<210> SEQ ID NO 303
<211> LENGTH: 7
<212> TYPE: PRT
<213> ORGANISM: Artificial Sequence
<220> FEATURE:
<223> OTHER INFORMATION: Synthetic construct

<400> SEQUENCE: 303

Pro Asp Ala Ala Ala Leu Ser
1               5
```

```
<210> SEQ ID NO 304
<211> LENGTH: 7
<212> TYPE: PRT
<213> ORGANISM: Artificial Sequence
<220> FEATURE:
<223> OTHER INFORMATION: Synthetic construct

<400> SEQUENCE: 304

Met Pro Pro Arg Thr Pro Pro
1               5

<210> SEQ ID NO 305
<211> LENGTH: 7
<212> TYPE: PRT
<213> ORGANISM: Artificial Sequence
<220> FEATURE:
<223> OTHER INFORMATION: Synthetic construct

<400> SEQUENCE: 305

Arg Pro Ala Ala Leu Arg Ala
1               5

<210> SEQ ID NO 306
<211> LENGTH: 7
<212> TYPE: PRT
<213> ORGANISM: Artificial Sequence
<220> FEATURE:
<223> OTHER INFORMATION: Synthetic construct

<400> SEQUENCE: 306

Met Lys Leu Leu Val Gly Ile
1               5

<210> SEQ ID NO 307
<211> LENGTH: 7
<212> TYPE: PRT
<213> ORGANISM: Artificial Sequence
<220> FEATURE:
<223> OTHER INFORMATION: Synthetic construct

<400> SEQUENCE: 307

Arg Pro Pro Arg Arg Arg Arg
1               5

<210> SEQ ID NO 308
<211> LENGTH: 7
<212> TYPE: PRT
<213> ORGANISM: Artificial Sequence
<220> FEATURE:
<223> OTHER INFORMATION: Synthetic construct

<400> SEQUENCE: 308

Met Arg Lys Lys Ala Pro Arg
1               5

<210> SEQ ID NO 309
<211> LENGTH: 7
<212> TYPE: PRT
<213> ORGANISM: Artificial Sequence
<220> FEATURE:
<223> OTHER INFORMATION: Synthetic construct

<400> SEQUENCE: 309

Ala Arg Thr Ala Pro Pro Arg
1               5
```

<210> SEQ ID NO 310
<211> LENGTH: 7
<212> TYPE: PRT
<213> ORGANISM: Artificial Sequence
<220> FEATURE:
<223> OTHER INFORMATION: Synthetic construct

<400> SEQUENCE: 310

Met Met Arg Ser Gly His Ala
1               5

<210> SEQ ID NO 311
<211> LENGTH: 7
<212> TYPE: PRT
<213> ORGANISM: Artificial Sequence
<220> FEATURE:
<223> OTHER INFORMATION: Synthetic construct

<400> SEQUENCE: 311

Arg Met His Arg Ser Glu Leu
1               5

<210> SEQ ID NO 312
<211> LENGTH: 7
<212> TYPE: PRT
<213> ORGANISM: Artificial Sequence
<220> FEATURE:
<223> OTHER INFORMATION: Synthetic construct

<400> SEQUENCE: 312

Met Cys Thr Val Ala Thr Phe
1               5

<210> SEQ ID NO 313
<211> LENGTH: 7
<212> TYPE: PRT
<213> ORGANISM: Artificial Sequence
<220> FEATURE:
<223> OTHER INFORMATION: Synthetic construct

<400> SEQUENCE: 313

Ser Val Ala Pro Ser Ser Ala
1               5

<210> SEQ ID NO 314
<211> LENGTH: 7
<212> TYPE: PRT
<213> ORGANISM: Artificial Sequence
<220> FEATURE:
<223> OTHER INFORMATION: Synthetic construct

<400> SEQUENCE: 314

Met Thr Val His Pro Pro Lys
1               5

<210> SEQ ID NO 315
<211> LENGTH: 7
<212> TYPE: PRT
<213> ORGANISM: Artificial Sequence
<220> FEATURE:
<223> OTHER INFORMATION: Synthetic construct

<400> SEQUENCE: 315

Val Leu Pro Pro Asn Ser Leu
1               5

```
<210> SEQ ID NO 316
<211> LENGTH: 7
<212> TYPE: PRT
<213> ORGANISM: Artificial Sequence
<220> FEATURE:
<223> OTHER INFORMATION: Synthetic construct

<400> SEQUENCE: 316

Met Ser Glu Gly Gly Arg Leu
1               5

<210> SEQ ID NO 317
<211> LENGTH: 7
<212> TYPE: PRT
<213> ORGANISM: Artificial Sequence
<220> FEATURE:
<223> OTHER INFORMATION: Synthetic construct

<400> SEQUENCE: 317

Leu Leu Gly Leu Leu Phe Pro
1               5

<210> SEQ ID NO 318
<211> LENGTH: 7
<212> TYPE: PRT
<213> ORGANISM: Artificial Sequence
<220> FEATURE:
<223> OTHER INFORMATION: Synthetic construct

<400> SEQUENCE: 318

Ile Arg Gly Phe Ala Gly Gly
1               5

<210> SEQ ID NO 319
<211> LENGTH: 7
<212> TYPE: PRT
<213> ORGANISM: Artificial Sequence
<220> FEATURE:
<223> OTHER INFORMATION: Synthetic construct

<400> SEQUENCE: 319

Pro Gln Lys Val Phe Arg Leu
1               5

<210> SEQ ID NO 320
<211> LENGTH: 8
<212> TYPE: PRT
<213> ORGANISM: Artificial Sequence
<220> FEATURE:
<223> OTHER INFORMATION: Synthetic construct

<400> SEQUENCE: 320

Ser Ile Ile Asn Phe Glu Lys Leu
1               5
```